(12) United States Patent
Soto-Moreno et al.

(10) Patent No.: US 11,311,882 B2
(45) Date of Patent: Apr. 26, 2022

(54) DIGITAL MICROFLUIDICS DEVICES AND METHODS OF USING THEM

(71) Applicant: mirOculus Inc., San Francisco, CA (US)

(72) Inventors: Jorge Abraham Soto-Moreno, San Francisco, CA (US); Ik Pyo Hong, Toronto (CA); Jair Giovanny Beltran-Vera, Bogota (CO); Juan Matias DeCarli, San Francisco, CA (US); Jobelo Andres Quintero Rodriguez, San Francisco, CA (US); Rodolfo Wilhelmy-Preciado, San Francisco, CA (US); Mais Jehan Jebrail, Toronto (CA); Gregory Ray, San Francisco, CA (US); Mathieu Gabriel-Emmanuel Chauleau, San Francisco, CA (US); Paul Mathew Lundquist, Emeryville, CA (US); Alejandro Tocigl, Mountain View, CA (US); John Peter Cannistraro, San Francisco, CA (US); Gareth Scott, San Francisco, CA (US); Spencer Seiler, San Francisco, CA (US); Rohit Lal, San Francisco, CA (US); Eugenia Carvajal, San Francisco, CA (US); Eduardo Cervantes, San Francisco, CA (US); Nikolay Sergeev, San Francisco, CA (US); Yu-Hung Chen, San Francisco, CA (US); Poornasree Kumar, San Francisco, CA (US); Foteini Christodoulou, San Francisco, CA (US)

(73) Assignee: mirOculus Inc., San Francisco, CA (US)

( * ) Notice: Subject to any disclaimer, the term of this patent is extended or adjusted under 35 U.S.C. 154(b) by 0 days.

(21) Appl. No.: 16/259,984

(22) Filed: Jan. 28, 2019

(65) Prior Publication Data

US 2019/0168223 A1 Jun. 6, 2019

Related U.S. Application Data

(63) Continuation of application No. PCT/US2018/049415, filed on Sep. 4, 2018.
(Continued)

(51) Int. Cl.
*B01L 3/00* (2006.01)
*C12M 3/06* (2006.01)
(Continued)

(52) U.S. Cl.
CPC ........ *B01L 3/502792* (2013.01); *C12M 1/00* (2013.01); *C12M 23/16* (2013.01);
(Continued)

(58) Field of Classification Search
CPC ........ B01L 3/502792; B01L 3/502715; B01L 2200/0605; B01L 2200/142;
(Continued)

(56) References Cited

U.S. PATENT DOCUMENTS 4,469,863 A 9/1984 Ts'o et al.
4,569,575 A 2/1986 Le Pesant et al.
(Continued)

FOREIGN PATENT DOCUMENTS

CA 2470847 A1 7/2003
CA 2740113 A1 4/2010
(Continued)

OTHER PUBLICATIONS

Shih, Steve CC, et al. "Dried blood spot analysis by digital microfluidics coupled to nanoelectrospray ionization mass spectrometry." Analytical chemistry 84.8 (2012): 3731-3738.*
(Continued)

Page 2

Primary Examiner — Robert J Eom
(74) *Attorney, Agent, or Firm* — Shay Glenn LLP

(57) ABSTRACT

Digital microfluidic (DMF) methods and apparatuses (including devices, systems, cartridges, DMF readers, etc.), and in particular DMF apparatuses and methods adapted for large volume. For example, described herein are methods and apparatuses for DMF using an air gap having a width of the gap that may be between 0.3 mm and 3 mm. Also described herein are DMF readers for use with a DMF cartridges, including those adapted for use with large air gap/large volume, although smaller volumes may be used as well.

31 Claims, 59 Drawing Sheets

Related U.S. Application Data

(60) Provisional application No. 62/553,743, filed on Sep. 1, 2017, provisional application No. 62/557,714, filed on Sep. 12, 2017.

(51) Int. Cl.
*C12M 1/00* (2006.01)
*H01L 21/768* (2006.01)

(52) U.S. Cl.
CPC ............ *C12M 23/40* (2013.01); *H01L 21/768* (2013.01); *B01L 3/502715* (2013.01); *B01L 2200/027* (2013.01); *B01L 2200/04* (2013.01); *B01L 2200/0605* (2013.01); *B01L 2200/142* (2013.01); *B01L 2300/023* (2013.01); *B01L 2300/0867* (2013.01); *B01L 2300/0883* (2013.01); *B01L 2300/0887* (2013.01); *B01L 2300/123* (2013.01); *B01L 2300/161* (2013.01); *B01L 2300/1822* (2013.01); *B01L 2300/1827* (2013.01); *B01L 2400/043* (2013.01); *B01L 2400/049* (2013.01); *B01L 2400/0487* (2013.01)

(58) Field of Classification Search
CPC ....... B01L 2300/023; B01L 2300/0867; B01L 2300/0883; B01L 2300/0887; B01L 2300/123; B01L 2300/161; B01L 2300/1822; B01L 2300/1827; B01L 2400/043; B01L 2400/0487; B01L 2400/049; C12M 1/00; C12M 23/16; C12M 23/40; H01L 21/768
See application file for complete search history.

(56) References Cited

U.S. PATENT DOCUMENTS

| | | |
|---|---|---|
| 4,636,785 A | 1/1987 | Le Pesant |
| 4,818,052 A | 4/1989 | Le Pesant et al. |
| 5,034,506 A | 7/1991 | Summerton et al. |
| 5,130,238 A | 7/1992 | Malek et al. |
| 5,216,141 A | 6/1993 | Benner |
| 5,235,033 A | 8/1993 | Summerton et al. |
| 5,270,185 A | 12/1993 | Margolskee |
| 5,386,023 A | 1/1995 | Sanghvi et al. |
| 5,399,491 A | 3/1995 | Kacian et al. |
| 5,409,818 A | 4/1995 | Davey et al. |
| 5,411,876 A | 5/1995 | Bloch et al. |
| 5,455,166 A | 10/1995 | Walker |
| 5,486,337 A | 1/1996 | Ohkawa |
| 5,602,240 A | 2/1997 | De Mesmaeker et al. |
| 5,637,684 A | 6/1997 | Cook et al. |
| 5,644,048 A | 7/1997 | Yau |
| 5,681,702 A | 10/1997 | Collins et al. |
| 5,705,365 A | 1/1998 | Ryder et al. |
| 5,710,029 A | 1/1998 | Ryder et al. |
| 5,888,779 A | 3/1999 | Kacian et al. |
| 6,007,690 A | 12/1999 | Nelson et al. |
| 6,074,725 A | 6/2000 | Kennedy |
| 6,294,063 B1 | 9/2001 | Becker et al. |
| 6,352,838 B1 | 3/2002 | Krulevitch et al. |
| 6,401,552 B1 | 6/2002 | Elkins |
| 6,565,727 B1 | 5/2003 | Shenderov |
| 6,596,988 B2 | 7/2003 | Corso et al. |
| 6,723,985 B2 | 4/2004 | Schultz et al. |
| 6,773,566 B2 | 8/2004 | Shenderov |
| 6,787,111 B2 | 9/2004 | Roach et al. |
| 6,887,384 B1 | 5/2005 | Frechet et al. |
| 6,911,132 B2 | 6/2005 | Pamula et al. |
| 6,989,234 B2 | 1/2006 | Kolar et al. |
| 7,147,763 B2 | 12/2006 | Elrod et al. |
| 7,163,612 B2 | 1/2007 | Sterling et al. |
| 7,214,302 B1 | 5/2007 | Reihs et al. |
| 7,323,345 B1 | 1/2008 | Stjernstrom |
| 7,328,979 B2 | 2/2008 | Decre et al. |
| 7,329,545 B2 | 2/2008 | Pamula et al. |
| 7,349,014 B2 | 3/2008 | Higashihara |
| 7,390,463 B2 | 6/2008 | He et al. |
| 7,391,020 B2 | 6/2008 | Bousse et al. |
| 7,439,014 B2 | 10/2008 | Pamula et al. |
| 7,445,926 B2 | 11/2008 | Mathies et al. |
| 7,531,120 B2 | 5/2009 | Van Rijn et al. |
| D599,832 S | 9/2009 | Chapin et al. |
| 7,713,456 B2 | 5/2010 | Dodd et al. |
| 7,727,723 B2 | 6/2010 | Pollack et al. |
| 7,745,207 B2 | 6/2010 | Jovanovich et al. |
| 7,763,471 B2 | 7/2010 | Pamula et al. |
| 7,815,871 B2 | 10/2010 | Pamula et al. |
| 7,816,121 B2 | 10/2010 | Pollack et al. |
| 7,822,510 B2 | 10/2010 | Paik et al. |
| 7,851,184 B2 | 12/2010 | Pollack et al. |
| 7,901,947 B2 | 3/2011 | Pollack et al. |
| 7,919,330 B2 | 4/2011 | de Guzman et al. |
| 7,939,021 B2 | 5/2011 | Smith et al. |
| 7,998,436 B2 | 8/2011 | Pollack et al. |
| 8,007,739 B2 | 8/2011 | Pollack et al. |
| 8,041,463 B2 | 10/2011 | Pollack et al. |
| 8,053,239 B2 | 11/2011 | Wheeler et al. |
| 8,088,578 B2 | 1/2012 | Hua et al. |
| 8,093,062 B2 | 1/2012 | Winger |
| 8,137,917 B2 | 3/2012 | Pollack et al. |
| 8,187,864 B2 | 5/2012 | Wheeler et al. |
| 8,190,371 B2 | 5/2012 | Allawi et al. |
| 8,202,686 B2 | 6/2012 | Pamula et al. |
| 8,202,736 B2 | 6/2012 | Mousa et al. |
| 8,208,146 B2 | 6/2012 | Srinivasan et al. |
| 8,268,246 B2 | 9/2012 | Srinivasan et al. |
| 8,304,253 B2 | 11/2012 | Yi et al. |
| 8,317,990 B2 | 11/2012 | Pamula et al. |
| 8,349,276 B2 | 1/2013 | Pamula et al. |
| 8,364,315 B2 | 1/2013 | Sturmer et al. |
| 8,389,297 B2 | 3/2013 | Pamula et al. |
| 8,394,641 B2 | 3/2013 | Winger |
| 8,399,222 B2 | 3/2013 | Siva et al. |
| 8,426,213 B2 | 4/2013 | Eckhardt et al. |
| 8,440,392 B2 | 5/2013 | Pamula et al. |
| 8,454,905 B2 | 6/2013 | Pope et al. |
| 8,460,528 B2 | 6/2013 | Pollack et al. |
| 8,470,153 B2 | 6/2013 | Feiglin et al. |
| 8,470,606 B2 | 6/2013 | Srinivasan et al. |
| 8,481,125 B2 | 7/2013 | Yi et al. |
| 8,492,168 B2 | 7/2013 | Srinivasan et al. |
| 8,562,807 B2 | 10/2013 | Srinivasan et al. |
| 8,591,830 B2 | 11/2013 | Sudarsan et al. |
| 8,592,217 B2 | 11/2013 | Eckhardt |
| 8,613,889 B2 | 12/2013 | Pollack et al. |
| 8,637,317 B2 | 1/2014 | Pamula et al. |
| 8,637,324 B2 | 1/2014 | Pollack et al. |
| 8,658,111 B2 | 2/2014 | Srinivasan et al. |

(56) References Cited

U.S. PATENT DOCUMENTS

| | | |
|---|---|---|
| 8,685,344 B2 | 4/2014 | Sudarsan et al. |
| 8,685,754 B2 | 4/2014 | Pollack et al. |
| 8,702,938 B2 | 4/2014 | Srinivasan et al. |
| 8,716,015 B2 | 5/2014 | Pollack et al. |
| 8,809,068 B2 | 8/2014 | Sista et al. |
| 8,821,705 B2 | 9/2014 | Bjornson et al. |
| 8,845,872 B2 | 9/2014 | Pollack et al. |
| 8,846,414 B2 | 9/2014 | Sista et al. |
| 8,852,952 B2 | 10/2014 | Pollack et al. |
| 8,872,527 B2 | 10/2014 | Sturmer et al. |
| 8,877,512 B2 | 11/2014 | Srinivasan et al. |
| 8,888,969 B2 | 11/2014 | Soleymani et al. |
| 8,901,043 B2 | 12/2014 | Eckhardt et al. |
| 8,926,065 B2 | 1/2015 | Winger |
| 8,927,296 B2 | 1/2015 | Sista et al. |
| 8,936,708 B2 | 1/2015 | Feiglin et al. |
| 8,951,732 B2 | 2/2015 | Pollack et al. |
| 8,980,198 B2 | 3/2015 | Srinivasan et al. |
| 9,005,544 B2 | 4/2015 | Van Dam et al. |
| 9,011,662 B2 | 4/2015 | Wang et al. |
| 9,039,973 B2 | 5/2015 | Watson et al. |
| 9,046,514 B2 | 6/2015 | Sista et al. |
| 9,091,649 B2 | 7/2015 | Pollack et al. |
| 9,140,635 B2 | 9/2015 | Graham et al. |
| 9,188,615 B2 | 11/2015 | Sturmer et al. |
| 9,223,317 B2 | 12/2015 | Winger |
| 9,238,222 B2 | 1/2016 | Delattre et al. |
| 9,248,450 B2 | 2/2016 | Bauer |
| 9,377,439 B2 | 6/2016 | Lee et al. |
| 9,435,765 B2 | 9/2016 | Reimitz et al. |
| 9,442,404 B1 | 9/2016 | Bauer et al. |
| 9,476,811 B2 | 10/2016 | Mudrik et al. |
| 9,476,856 B2 | 10/2016 | Pamula et al. |
| 9,513,253 B2 | 12/2016 | Winger |
| 9,517,469 B2 | 12/2016 | Shenderov et al. |
| 9,594,056 B2 | 3/2017 | Fobel et al. |
| 9,851,365 B2 | 12/2017 | Mousa et al. |
| 10,232,374 B2 | 3/2019 | Jebrai et al. |
| 2002/0150683 A1 | 10/2002 | Troian et al. |
| 2003/0017551 A1 | 1/2003 | Parthasarathy et al. |
| 2003/0136451 A1 | 7/2003 | Beebe et al. |
| 2003/0194716 A1 | 10/2003 | Knoll |
| 2004/0171169 A1 | 9/2004 | Kallury et al. |
| 2004/0211659 A1 | 10/2004 | Velev |
| 2005/0115836 A1 | 6/2005 | Reihs |
| 2005/0133370 A1 | 6/2005 | Park et al. |
| 2005/0148091 A1 | 7/2005 | Kitaguchi et al. |
| 2005/0191759 A1 | 9/2005 | Pedersen Bjergaard et al. |
| 2005/0220675 A1 | 10/2005 | Reed et al. |
| 2006/0091015 A1 | 5/2006 | Lau |
| 2006/0132542 A1 | 6/2006 | Bruker et al. |
| 2006/0231398 A1 | 10/2006 | Sarrut et al. |
| 2006/0272942 A1 | 12/2006 | Sirringhaus |
| 2007/0023292 A1 | 2/2007 | Kim et al. |
| 2007/0095407 A1 | 5/2007 | Chen et al. |
| 2007/0148763 A1 | 6/2007 | Huh et al. |
| 2007/0269825 A1 | 11/2007 | Wang et al. |
| 2008/0110753 A1 | 5/2008 | Fourrier et al. |
| 2008/0131904 A1 | 6/2008 | Parce et al. |
| 2008/0156983 A1 | 7/2008 | Fourrier et al. |
| 2008/0169197 A1 | 7/2008 | McRuer et al. |
| 2008/0185339 A1 | 8/2008 | Delapierre et al. |
| 2008/0210558 A1 | 9/2008 | Sauter-Starace et al. |
| 2008/0241831 A1 | 10/2008 | Fan et al. |
| 2008/0293051 A1 | 11/2008 | Levy et al. |
| 2009/0017197 A1 | 1/2009 | Zhang et al. |
| 2009/0017453 A1 | 1/2009 | Maples et al. |
| 2009/0203063 A1 | 8/2009 | Wheeler et al. |
| 2010/0025250 A1 | 2/2010 | Pamula et al. |
| 2010/0032293 A1 | 2/2010 | Pollack et al. |
| 2010/0048410 A1 | 2/2010 | Shenderov et al. |
| 2010/0087012 A1 | 4/2010 | Shenderov |
| 2010/0120130 A1 | 5/2010 | Srinivasan et al. |
| 2010/0130369 A1 | 5/2010 | Shenderov et al. |
| 2010/0136544 A1 | 6/2010 | Agresti et al. |
| 2010/0206094 A1 | 8/2010 | Shenderov |
| 2010/0236927 A1 | 9/2010 | Pope et al. |
| 2010/0236928 A1 | 9/2010 | Srinivasan et al. |
| 2010/0236929 A1 | 9/2010 | Pollack et al. |
| 2010/0270156 A1 | 10/2010 | Srinivasan et al. |
| 2010/0288368 A1 | 11/2010 | Beebe et al. |
| 2010/0311599 A1 | 12/2010 | Wheeler et al. |
| 2011/0024793 A1 | 2/2011 | Jeon |
| 2011/0076685 A1 | 3/2011 | Moeller et al. |
| 2011/0097763 A1 | 4/2011 | Pollack et al. |
| 2011/0104725 A1 | 5/2011 | Pamula et al. |
| 2011/0104747 A1 | 5/2011 | Pollack et al. |
| 2011/0107822 A1 | 5/2011 | Bunner et al. |
| 2011/0147216 A1 | 6/2011 | Fan et al. |
| 2011/0240471 A1 | 10/2011 | Wheeler et al. |
| 2011/0247934 A1 | 10/2011 | Wang et al. |
| 2011/0293851 A1 | 12/2011 | Bollström et al. |
| 2011/0303542 A1 | 12/2011 | Srinivasan et al. |
| 2011/0311980 A1 | 12/2011 | Pollack et al. |
| 2012/0000777 A1 | 1/2012 | Garrell et al. |
| 2012/0045748 A1 | 2/2012 | Willson et al. |
| 2012/0045768 A1 | 2/2012 | Arunachalam et al. |
| 2012/0149018 A1 | 6/2012 | Dahlberg et al. |
| 2012/0190027 A1 | 7/2012 | Loeffert et al. |
| 2012/0259233 A1 | 10/2012 | Chan et al. |
| 2012/0261264 A1 | 10/2012 | Srinivasan et al. |
| 2012/0289581 A1 | 11/2012 | Chang et al. |
| 2012/0325665 A1 | 12/2012 | Chiou et al. |
| 2013/0017544 A1 | 1/2013 | Eckhardt et al. |
| 2013/0018611 A1 | 1/2013 | Sturmer |
| 2013/0062205 A1 | 3/2013 | Hadwen et al. |
| 2013/0105318 A1 | 5/2013 | Bhattacharya et al. |
| 2013/0123979 A1 | 5/2013 | Elliot et al. |
| 2013/0157259 A1 | 6/2013 | Choi et al. |
| 2013/0168250 A1 | 7/2013 | Fogleman et al. |
| 2013/0171546 A1 | 7/2013 | White et al. |
| 2013/0177915 A1 | 7/2013 | Too et al. |
| 2013/0203606 A1 | 8/2013 | Pollack et al. |
| 2013/0215492 A1 | 8/2013 | Steckl et al. |
| 2013/0217113 A1 | 8/2013 | Srinivasan et al. |
| 2013/0225450 A1 | 8/2013 | Pollack et al. |
| 2013/0270114 A1 | 10/2013 | Feiglin |
| 2013/0284956 A1 | 10/2013 | Kwon |
| 2013/0288254 A1 | 10/2013 | Pollack et al. |
| 2013/0293246 A1 | 11/2013 | Pollack et al. |
| 2013/0306480 A1 | 11/2013 | Chang et al. |
| 2014/0005066 A1 | 1/2014 | Boles et al. |
| 2014/0054174 A1 | 2/2014 | Wang |
| 2014/0124037 A1 | 5/2014 | Foley |
| 2014/0141409 A1 | 5/2014 | Foley et al. |
| 2014/0161686 A1 | 6/2014 | Bort et al. |
| 2014/0174926 A1 | 6/2014 | Bort et al. |
| 2014/0179539 A1 | 6/2014 | Lohman et al. |
| 2014/0194305 A1 | 7/2014 | Kayyem et al. |
| 2014/0216559 A1 | 8/2014 | Foley |
| 2014/0273100 A1 | 9/2014 | Saito et al. |
| 2014/0335069 A1 | 11/2014 | Graham et al. |
| 2015/0001078 A1 | 1/2015 | Feiglin |
| 2015/0021182 A1 | 1/2015 | Rival et al. |
| 2015/0075986 A1 | 3/2015 | Cyril et al. |
| 2015/0111237 A1 | 4/2015 | Graham et al. |
| 2015/0144489 A1 | 5/2015 | Hoffmeyer et al. |
| 2015/0205272 A1 | 7/2015 | Yi et al. |
| 2015/0212043 A1 | 7/2015 | Pollack |
| 2015/0258520 A1 | 9/2015 | Griffiths et al. |
| 2015/0267242 A1 | 9/2015 | Foegeding et al. |
| 2016/0068901 A1 | 3/2016 | Eckhardt et al. |
| 2016/0108432 A1 | 4/2016 | Punnamaraju et al. |
| 2016/0116438 A1 | 4/2016 | Pamula et al. |
| 2016/0129437 A1 | 5/2016 | Kayyem et al. |
| 2016/0161343 A1 | 6/2016 | Smith et al. |
| 2016/0175859 A1 | 6/2016 | Yi et al. |
| 2016/0199832 A1 | 7/2016 | Jamshidi et al. |
| 2016/0298173 A1 | 10/2016 | Wang et al. |
| 2016/0319354 A1 | 11/2016 | Tocigl et al. |
| 2016/0370317 A9 | 12/2016 | Sudarsan et al. |
| 2017/0315090 A1 | 11/2017 | Wheeler et al. |
| 2017/0354973 A1 | 12/2017 | Sustarich et al. |
| 2018/0001286 A1 | 1/2018 | Wu |

(56) References Cited

U.S. PATENT DOCUMENTS

| | | |
|---|---|---|
| 2018/0095067 A1 | 4/2018 | Huff et al. |
| 2018/0099275 A1 | 4/2018 | Wu et al. |
| 2018/0120335 A1 | 5/2018 | Mousa et al. |
| 2018/0141049 A1 | 5/2018 | Jebrail et al. |
| 2018/0178217 A1 | 6/2018 | Jebrail et al. |
| 2018/0250672 A1 | 9/2018 | Jamshidi et al. |
| 2019/0210026 A1 | 7/2019 | Jebrai et al. |
| 2020/0324290 A1 | 10/2020 | Jebrail et al. |

FOREIGN PATENT DOCUMENTS

| | | |
|---|---|---|
| CN | 1668527 A | 9/2005 |
| CN | 101609063 A | 12/2009 |
| CN | 102549804 A | 7/2012 |
| CN | 102719526 A | 10/2012 |
| CN | 103014148 A | 4/2013 |
| CN | 103170383 A | 6/2013 |
| CN | 106092865 A | 11/2016 |
| EP | 2111554 B1 | 5/2013 |
| GB | 2533952 A | 7/2016 |
| JP | 2002321449 A | 11/2002 |
| JP | 2006220606 A | 8/2006 |
| JP | 2010098133 A | 4/2010 |
| JP | 2010515877 A | 5/2010 |
| JP | 2010180222 A | 8/2010 |
| JP | 2012525687 A | 10/2012 |
| WO | WO2000/067907 A2 | 11/2000 |
| WO | WO2001/025137 A1 | 4/2001 |
| WO | WO2003/045556 A2 | 6/2003 |
| WO | WO2004/074169 A1 | 9/2004 |
| WO | WO2005/068993 A1 | 7/2005 |
| WO | WO2005/118129 A1 | 12/2005 |
| WO | WO2006/000828 A1 | 1/2006 |
| WO | WO2006/102309 A2 | 9/2006 |
| WO | WO2007/120240 A2 | 10/2007 |
| WO | WO2007/123908 A2 | 11/2007 |
| WO | WO2007/130294 A2 | 11/2007 |
| WO | WO2007/136386 A2 | 11/2007 |
| WO | WO2008/066828 A2 | 6/2008 |
| WO | WO2009/026339 A2 | 2/2009 |
| WO | WO2009/052348 A2 | 4/2009 |
| WO | WO2009/111723 A1 | 9/2009 |
| WO | WO2009/111769 A2 | 9/2009 |
| WO | WO2009/140671 A2 | 11/2009 |
| WO | WO2010/003188 A1 | 1/2010 |
| WO | WO2010/006166 A2 | 1/2010 |
| WO | WO2010/027894 A2 | 3/2010 |
| WO | WO2010/042637 A2 | 4/2010 |
| WO | WO2010/069977 A1 | 6/2010 |
| WO | WO2010/091334 A2 | 8/2010 |
| WO | WO2010/111265 A1 | 9/2010 |
| WO | WO2011/002957 A2 | 1/2011 |
| WO | WO2011/062557 A1 | 5/2011 |
| WO | WO2012/172172 A1 | 12/2012 |
| WO | WO2013/006312 A2 | 1/2013 |
| WO | WO2013/040562 A2 | 3/2013 |
| WO | WO2013/090889 A1 | 6/2013 |
| WO | WO2013/096839 A1 | 6/2013 |
| WO | WO2013/116039 A1 | 8/2013 |
| WO | WO2013/176767 A1 | 11/2013 |
| WO | WO2014/078100 A1 | 5/2014 |
| WO | WO2014/100473 A1 | 6/2014 |
| WO | WO2014/106167 A1 | 7/2014 |
| WO | WO2014/108185 A1 | 7/2014 |
| WO | WO2014/183118 A1 | 11/2014 |
| WO | WO2015/023745 A1 | 2/2015 |
| WO | WO2015/172256 A1 | 11/2015 |
| WO | WO2016/128544 A1 | 8/2016 |
| WO | WO2016/182814 A2 | 11/2016 |
| WO | WO2016/197013 A1 | 12/2016 |
| WO | WO2016/197103 A1 | 12/2016 |
| WO | WO2017/223026 A1 | 12/2017 |
| WO | WO2018/119253 A1 | 6/2018 |
| WO | WO2018/126082 A1 | 7/2018 |
| WO | WO2018/187476 A1 | 10/2018 |
| WO | WO2019/023133 A1 | 1/2019 |
| WO | WO2019/046860 A1 | 3/2019 |
| WO | WO2019/075211 A1 | 4/2019 |
| WO | WO2019/226919 A1 | 11/2019 |

OTHER PUBLICATIONS

Dixon, Christopher, et al. "An inkjet printed, roll-coated digital microfluidic device for inexpensive, miniaturized diagnostic assays." Lab on a Chip 16.23 (2016): 4560-4568.*

Kim, Hanyoup, et al. "Automated digital microfluidic sample preparation for next-generation DNA sequencing." JALA: Journal of the Association for Laboratory Automation 16.6 (2011): 405-414. (Year: 2011).*

Faure et al.; Improved electrochemical detection of a transthyretin synthetic peptide in the nanomolar range with a two-electrode system integrated in a glass/PDMS microchip; Lab on a Chip; 14(15); pp. 2800-2805, Aug. 2014.

Tang et al.; Mechano-regulated surface for manipulating liquid droplets; Nature Communications; 10 pages; DOI: 10.1038/ncomms14831; ; Apr. 4, 2017.

Jebrail et al.; U.S. Appl. No. 16/523,876 entitled "Air-matrix digital microfluidics apparatuses and methods for limiting evaporation and surface fouling," filed Jul. 26, 2019.

Abdelgawad et al., All-terrain droplet actuation, Lab on a Chip, 8(5), pp. 672-677, May 2008.

Abdelgawad et al.; Low-cost, rapid-prototyping of digital microfluidics devices, Microfluidics and Nanofluidics, 4, pp. 349-355, Apr. 2008.

Abdelgawad et al.; Rapid prototyping in copper substrates for digital microfluidics, Adv. Mater., 19(1), pp. 133-137; Jan. 2007.

Abdelgawad et al.; Hybrid microfluidics: a digital-to-channel interface for in-line sample processing and chemical separations, Lab on a Chip, 9(8), pp. 1046-1051, Apr. 2009.

Abdelgawad; Digital Microfluidics for Integration of Lab-on-a-Chip Devices (Doctoral dissertation); University of Toronto; © 2009.

Albrecht et al.; Laboratory testing of gonadal steroids in children; Pediatric Endocrinology Reviews; 5(suppl 1); pp. 599-607; Oct. 2007.

Ankarberg-Lindren et al.; A purification step prior to commercial sensitive immunoassay is necessary to achieve clinical usefulness when quantifying serum 17 ?-estradiol in prepubertal children. Eur J Endocrinol, 158, pp. 117-124, Jan. 2008.

Armstrong et al.; A study of plasma free amino acid levels. II. Normal values for children and adults, Metabolism, 22(4), pp. 561-569, Apr. 1973.

Asiello et al.; Miniaturized isothermal nucleic acid amplification, a review; Lab Chip; 11(8); pp. 1420-1430; Apr. 2011.

Au et al., Integrated microbioreactor for culture and analysis of bacteria, algae and yeast, Biomedical Microdevices, 13(1), pp. 41-50, Feb. 2011.

Au et al.; A new angle on pluronic additives: Advancing droplets and understanding in digital microfluidics; Langmuir; 27; pp. 8586-8594; Jun. 2011.

Banatvala et al., Rubella, The Lancet, 363(9415), pp. 1127-1137, Apr. 2004.

Banér et al.; Signal amplification of padlock probes by rolling circle replication; Nuc. Acids Res.; 26(22); pp. 5073-5078; Nov. 1998.

Barany; Genetic disease detection and DNA amplification using cloned thermostable ligase; PNAS; 88(1); pp. 189-193; Jan. 1991.

Barbulovic-Nad et al., A microfluidic platform for complete mammalian cell culture, Lab on a Chip, 10(12), pp. 1536-1542; Jun. 2010.

Barbulovic-Nad et al.; Digital microfluidics for cell-based assays, Lab Chip, 8(4), pp. 519-526; Apr. 2008.

Beattie et al.; Endogenous sex hormones, breast cancer risk, and tamoxifen response: an ancillary study in the NSABP Breast Cancer Prevention Trial P-1, J Natl Cancer Inst, 98(2), pp. 110-115, Jan. 2006.

(56) References Cited

OTHER PUBLICATIONS

Beaucage et al., The Functionalization of Oligonucleotides Via Phosphoramidite Derivatives, Tetrahedron, 49(10), pp. 1925-1963, Mar. 1993.
Belanger et al.; Omental and subcutaneous adipose tissue steroid levels in obese men. Steroids, 71(8), pp. 674-682, Aug. 2006.
Bergkvist et al., Improved chip design for integrated solid-phase microextraction in on-line proteomic sample preparation, Proteomics, 2(4), pp. 422-429, Apr. 2002.
Bi et al.; Dumbbell probe-mediated cascade isothermal amplification: A novel strategy for label-free detection of microRNAs and its application to real sample assay; Analytica Chimica Acta; 760; pp. 69-74; Jan. 2013.
Blankenstein et al.; Intratumoral levels of estrogens in breast cancer. J Steroid Biochem Mol Biol, 69(1-6), pp. 293-297, Apr.-Jun. 1999.
Bodamer et al.; Expanded newborn screening in Europe, Journal of Inherited Metabolic Disease, 30(4), pp. 439-444, Aug. 2007.
Bohlen et al.; Fluorometric assay of proteins in the nanogram range, Archives of Biochemistry and Biophysics, 155(1), pp. 213-220, Mar. 1973.
Bollström et al.; A Multilayer Coated Fiber-Based Substrate Suitable For Printed Functionality; Organic Electronics; 10(5); pp. 1020-1023; Aug. 2009.
Bonneil et al., Integration of solid-phase extraction membranes for sample multiplexing: Application to rapid protein identification from gel-isolated protein extracts, Electrophoresis, 23(20), pp. 3589-3598, Oct. 2002.
Brassard et al.; Water-oil core-shell droplets for electrowetting-based digital microfluidic devices; Lab Chip; 8(8); pp. 1342-1349; Aug. 2008.
Brill et al., Synthesis of oligodeoxynucleoside phosphorodithioates via thioamidites, J. Am. Chern. Soc., 111(6), pp. 2321-2322, Mar. 1989.
Brivio et al.; Integrated microfluidic system enabling (bio)chemical reactions with on-line MALDI-TOF mass spectrometry, Anal. Chem., 74(16), pp. 3972-3976, Aug. 2002.
Burstein; Aromatase inhibitor-associated arthralgia syndrome. Breast, 16(3), pp. 223-234, Jun. 2007.
Carlsson et al., Screening for genetic mutations, Nature, 380(6571), pp. 207, Mar. 1996.
Chace et al.; A biochemical perspective on the use of tandem mass spectrometry for newborn screening and clinical testing, Clinical Biochemistry, 38(4), pp. 296-309; Apr. 2005.
Chace et al.; Rapid diagnosis of maple syrup urine disease in blood spots from newborns by tandem mass spectrometry, Clinical Chemistry, 41(1), pp. 62-68, Jan. 1995.
Chace et al.; Rapid diagnosis of phenylketonuria by quantitative analysis for phenylalanine and tyrosine in neonatal blood spots by tandem mass spectrometry, Clinical Chemistry, 39(1), pp. 66-71; Jan. 1993.
Chace et al.; Use of tandem mass spectrometry for multianalyte screening of dried blood specimens from newborns, Clinical Chemistry, 49(11), pp. 1797-1817, Nov. 2003.
Chace; Mass spectrometry in newborn and metabolic screening: historical perspective and future directions, Journal of Mass Spectrometry, 44(2), pp. 163-170, Feb. 2009.
Chang et al.; Integrated polymerase chain reaction chips utilizing digital microfluidics; Biomedical Microdevices; 8(3); pp. 215-225; Sep. 2006.
Chatterjee et al.; Droplet-based microfluidics with nonaqueous solvents and solutions, Lab Chip, 6(2), pp. 199-206, Feb. 2006.
Chen et al.; Selective Wettability Assisted Nanoliter Sample Generation Via Electrowetting-Based Transportation; Proceedings of the 5th International Conference on Nanochannels, Microchannels and Minichannels (ICNMM); Puebla, Mexico; Paper No. ICNMM2007-30184; pp. 147-153; Jun. 18-20, 2007.
Cheng et al., Paper-Based ELISA, Angewandte Chemie, 49(28), pp. 4771-4774, Jun. 2010.
Cheng et al.; Highly Sensitive Determination of microRNA Using Target-Primed and Branched Rolling-Circle Amplification; Angew. Chem.; 121(18); pp. 3318-3322; Apr. 2009.
Chetrite et al.; Estradiol inhibits the estrone sulfatase activity in normal and cancerous human breast tissues. Journal of Steroid Biochemistry and Molecular Biology, 104(3-5), pp. 289-292, May 2007.
Cho et al.; Creating, transporting, cutting, and merging liquid droplets by electrowetting-based actuation for digital microfluidic circuits, J. MEMS 2003, 12(1), pp. 70-80, Feb. 2003.
Choi et al., Automated digital microfluidic platform for magnetic-particle-based immunoassays with optimization by design of experiments, Anal. Chern., 85(20), pp. 9638-9646; Oct. 2013.
Choi et al., Digital Microfluidics, Annu. Rev. Anal. Chem., 5, pp. 413-440, (Epub) Apr. 2012.
Christiansen; Hormone Replacement Therapy and Osteoporosis; Maturitas, 23, Suppl. pp. S71-S76, May 1996.
Chuang et al.; Direct Handwriting Manipulation of Droplets By Self-Aligned Mirror-EWOO Across A Dielectric Sheet; 19th IEEE International Conf. on Micro Electro Mechanical Systems (MEMS); Instanbul, Turkey; pp. 538-541; Jan. 22-26, 2006.
Cipriano et al.; The cost-effectiveness of expanding newborn screening for up to 21 inherited metabolic disorders using tandem mass spectrometry: results from a decision-analytic model, Value in Health, 10(2), pp. 83-97, Mar.-Apr. 2007.
Cooney et al.; Electrowetting droplet microfluidics on a single planar surface, Microfluid. Nanofluid., 2(5), pp. 435-446; Sep. 2006.
COREGENOMICS; How do SPRI beads work; 31 pages; retrieved from the internet (http://core-genomics.blogspot.com/2012/04/how-do-spri-beads-work.html); Apr. 28, 2012.
Crabtree et al.; Microchip injection and separation anomalies due to pressure effects, Anal. Chem., 73(17), pp. 4079-4086, Sep. 2001.
Cunningham; Testosterone replacement therapy for late-onset hypogonadism. Nature Clinical Practice Urology, 3(5), pp. 260-267, May 2006.
Cuzick; Chemoprevention of breast cancer. Women's Health, 2(6), pp. 853-861, Nov. 2006.
Dahlin et al.; Poly(dimethylsiloxane)-based microchip for two-dimensional solid-phase extraction-capillary electrophoresis with an integrated electrospray emitter tip, Anal. Chem., 77(16), pp. 5356-5363, Aug. 2005.
Danton et al.; Porphyrin profiles in blood, urine and faeces by HPLC/electrospray ionization tandem mass spectrometry. Biomedical Chromatography, 20(6-7), pp. 612-621, Jun.-Jul. 2006.
De Mesmaeker et al.; Comparison of rigid and flexible backbones in antisense oligonucleotides; Bioorganic & Medicinal Chem. Lett; 4(3); pp. 395-398; Feb. 1994.
Deligeorgiev et al.; Intercalating Cyanine Dyes for Nucleic Acid Detection; Recent Pat Mat Sci; 2(1); pp. 1-26; Jan. 2006.
Dempcy et al., Synthesis of a thymidyl pentamer of deoxyribonucleic guanidine and binding studies with DNA homopolynucleotides, Proc. Natl. Acad. Sci., 92(13), pp. 6097-6101, Jun. 1995.
Deng et al.; Rapid determination of amino acids in neonatal blood samples based on derivatization with isobutyl chloroformate followed by solid-phase microextraction and gas chromatography/mass spectrometry. Rapid Communications in Mass Spectrometry, 18(1), pp. 2558-2564, Nov. 2004.
Denneulin et al.; Infra-red assisted sintering of inkjet printed silver tracks on paper substrates; J Nanopart Res; 13(9); pp. 3815-3823; Sep. 2011.
Dibbelt et al.; Determination of natural and synthetic estrogens by radioimmunoassay: Comparison of direct and extraction methods for quantification of estrone in human serum. Clinical Laboratory, 44(3), 137-143, Mar. 1998.
Dietzen et al.; National academy of clinical biochemistry laboratory medicine practice guidelines: follow-up testing for metabolic disease identified by expanded newborn screening using tandem mass spectrometry; executive summary, Clinical Chemistry, 55(9), pp. 1615-1626, Sep. 2009.
Diver et al.; Warning on plasma oestradiol measurement. Lancet, 330 (8567), p. 1097, Nov. 1987.

(56) References Cited

OTHER PUBLICATIONS

Divino Filho et al.; Simultaneous measurements of free amino acid patterns of plasma, muscle and erythrocytes in healthy human subjects, Clinical Nutrition, 16(6), pp. 299-305, Dec. 1997.
Djerassi; Chemical birth of the pill. American Journal of Obstetrics and Gynecology, 194(1), pp. 290-298, Jan. 2006.
Dobrowolski et al.; DNA microarray technology for neonatal screening, Acta Paediatrica Suppl, 88(432), pp. 61-64, Dec. 1999.
Dong et al.; Highly sensitive multiple microRNA detection based on flourescence quenching of graphene oxide and isothermal strand-displacement polymerase reaction; Anal Chem; 84; pp. 4587-4593; Apr. 2012.
Duffy et al.; Rapid prototyping of microfluidic systems in Poly (dimethylsiloxane), Anal. Chem., 70(23), pp. 4974-4984, Dec. 1998.
Edgar et al.; Capillary electrophoresis separation in the presence of an immiscible boundary for droplet analysis, Anal. Chem., 78(19), pp. 6948-6954 (author manuscript, 15 pgs.), Oct. 2006.
Egholm et al., PNA hybridizes to complementary oligonucleotides obeying the Watson-Crick hydrogen-bonding rules, Nature, 365(6446), pp. 566-568, Oct. 1993.
Egholm et al., Recognition of guanine and adenine in DNA by cytosine and thymine containing peptide nucleic acids (PNA), J. Am. Chem. Soc., 114(24), pp. 9677-9678; Nov. 1992.
Ehrmann; Polycystic ovary syndrome. New England Journal of Medicine; 352(12); pp. 1223-1236; Mar. 2005.
Ekstrom et al., Miniaturized solid-phase extraction and sample preparation for MALDI MS using a microfabricated integrated selective enrichment target, Journal of Proteome Research, 5(5), pp. 1071-1081, May 2006.
Ekstrom et al., Polymeric integrated selective enrichment target (ISET) for solid-phase-based sample preparation in MALDI-TOF MS, Journal of Mass Spectrometry, 42(11), pp. 1445-1452, Nov. 2007.
Ekstrom et al.,On-chip microextraction for proteomic sample preparation of in-gel digests, Proteomics, 2(4), pp. 413-421, Apr. 2002.
El-Ali et al.; Cells on chips; NATURE (2006) insight Review; 442(7101); pp. 403-411; Jul. 2006.
Fair; Digital microfluidics: Is a true lab-on-a-chip possible?; Microfuid. Nanofluid.; 3(3); pp. 245-281; Jun. 2007.
Falk et al.; Measurement of Sex Steroid Hormones in Breast Adipocytes: Methods and Implications; Cancer Epidemiol Biomarkers Prev; 17(8); pp. 1891-1895; Aug. 2008.
Fan et al.; Cross-scale electric manipulations of cells and droplets by frequency-modulated dielectrophoresis and electrowetting; Lab Chip; 8(8); pp. 1325-1331; Aug. 2008.
Fan et al.; Electrically Programmable Surfaces for Configurable Patterning of Cells; Advanced Materials; 20(8); pp. 1418-1423; Apr. 2008.
Fobel et al.; DropBot: An open-source digital microfluidic control system with precise control of electrostatic driving force and instantaneous drop velocity measurement; Applied Physics Letters; 102(19); 193513 (5 pgs.); May 2013.
Foote et al., Preconcentration of proteins on microfluidic devices using porous silica membranes, Analytical Chemistry, 77(1), pp. 57-63, Jan. 2005.
Freire et al.; A practical interface for microfluidics and nanoelectrospray mass spectrometry, Electrophoresis, 29(9), pp. 1836-1843, May 2008.
Fridley et al., Controlled release of dry reagents in porous media for tunable temporal and spatial distribution upon rehydration, Lab Chip, 12(21), pp. 4321-4327 (author manuscript, 14 pgs.), Nov. 2012.
Fu et al., Controlled Reagent Transport in Disposable 2D Paper Networks, Lab. Chip, 10(7), pp. 918-920 (author manuscript, 9 pgs.), Apr. 2010.
Gao et al.; Unusual conformation of a 3'-thioformacetal linkage in a DNA duplex; J. Biomol. NMR; 4(1); pp. 17-34; Jan. 1994.
Gentili et al.; Analysis of free estrogens and their conjugates in sewage and river waters by solid-phase extraction then liquid chromatography-electrospray-tandem mass spectrometry. Chromatographia 56(1), pp. 25-32, Jul. 2002.
Gerasimova et al.; Fluorometric method for phenylalanine microplate assay adapted for phenylketonuria screening, Clinical Chemistry, 35(10), pp. 2112-2115, Oct. 1989.
Gong et al., All-Electronic Droplet Generation On-Chip With Real-Time Feedback Control For EWOD Digital Microfluidics, Lab Chip, 8(6), pp. 898-906 (author manuscript, 20 pgs.), Jun. 2008.
Gong et al.; Portable digital microfluidics platform with active but disposable lab-on-chip; 17th IEEE International Conference on Micro Electro Mechanical Systems; Maastricht, Netherlands; pp. 355-358; Jan. 24-29, 2004.
Gong et al.; Two-dimensional digital microfluidic system by multilayer printed circuit board, 18th IEEE International Conference on Micro Electro Mechanical Systems (MEMS 2005); IEEE; pp. 726-729; Jan. 30-Feb. 3, 2005.
Goto et al.; Colorimetric detection of loop-mediated isothermal amplification reaction by using hydroxy naphthol blue; Biotechniques; 46(3); pp. 167-172; Mar. 2009.
Gottschlich et al.; Integrated microchip-device for the digestion, separation and postcolumn labeling of proteins and peptides, J. Chromatogr. B, 745(1), pp. 243-249, Aug. 2000.
Govindarajan et al., A low cost point-of-care viscous sample preparation device for molecular diagnosis in the developing world; an example of microfluidic origami, Lab Chip, 12(1), pp. 174-181, Jan. 2012.
Green et al.; Neonatal screening by DNA microarray: spots and chips, Nature Reviews Genetics, 6(2), pp. 147-151, Feb. 2005.
Hatch et al., Integrated preconcentration SDS-PAGE of proteins in microchips using photopatterned cross-linked polyacrylamide gels, Analytical Chemistry, 78(14), pp. 4976-4984, Jul. 2006.
Henderson et al.; Estrogens as a cause of human cancer: The Richard and Hinda Rosenthal Foundation award lecture. Cancer Res, 48(2), pp. 246-253, Jan. 1988.
Herdewijn et al.; 2'-5'-Oligoadenylates (2-5A) As Mediators of Interferon Action. Synthesis and Biological Activity of New 2-5A Analogues. E. De Clerq (ed.) Frontiers in Microbiology, 231-232, Springer, Dordrecht Jan. 1987.
Hertz et al.; Estrogen-progestogen combinations for contraception. Journal of the American Medical Association, 198(9), pp. 1000-1006, Nov. 1966.
Hong et al.; Three-dimensional digital microfluidic manipulation of droplets in oil medium; Scientific Reports; 5 (Article No. 10685); 5 pgs.; Jun. 2015.
Horn et al.; Oligonucleotides with alternating anionic and cationic phosphoramidate linkages: Synthesis and hybridization of stereo-uniform isomers; Tetrahedron Lett.; 37(6); pp. 743-746; Feb. 1996.
Hou et al.; Microfluidic devices for blood fractionation; Micromachines; 2(3); pp. 319-343; Jul. 20, 2011.
Huh et al.; Reversible Switching of High-Speed Air-Liquid Two-Phase Flows Using Electrowetting-Assisted Flow-Pattern Change, J. Am. Chem. Soc., 125, pp. 14678-14679; Dec. 2003.
Ihalainen et al.; Application of paper-supported printed gold electrodes for impedimetric immunosensor development; Biosensors; 3(1); pp. 1-17; Mar. 2013.
Jacobson et al.; High-Speed Separations on a Microchip, Anal. Chem., 66(7), pp. 1114-1118, Apr. 1994.
Jacobson et al.; Precolumn Reactions with Electrophoretic Analysis Integrated on a Microchip, Anal. Chem., 66(23), pp. 4127-4132, Dec. 1994.
Jebrail et al., Combinatorial Synthesis of Peptidomimetics Using Digital Microfluidics, J. Flow Chem., 2(3), pp. 103-107; (online) Aug. 2012.
Jebrail et al., Let's get digital: digitizing chemical biology with microfluidics, Curr. Opin. Chem. Biol., 14(5), 574-581, Oct. 2010.
Jebrail et al., Synchronized synthesis of peptide-based macrocycles by digital microfluidics, Angew. Chem. Int. Ed. Eng., 49(46), pp. 8625-8629, Nov. 2010.
Jebrail et al., World-to-digital-microfluidic interface enabling extraction and purification of RNA from human whole blood, Analytical Chemistry, 86(8), pp. 3856-3862, Apr. 2014.

(56) References Cited

OTHER PUBLICATIONS

Jebrail et al.; A Solvent Replenishment Solution for Managing Evaporation of Biochemical Reactions in Air-Matrix Digital Microfluidics Devices, Lab on a Chip, 15(1), pp. 151-158; Jan. 2015.
Jebrail et al.; Digital Microfluidic Method for Protein Extraction by Precipitation; Analytical Chemistry; 81(1); pp. 330-335; Jan. 2009.
Jebrail et al.; Digital Microfluidics for Automated Proteomic Processing, Journal of Visualized Experiments, 33 (e1603), 5 pgs., Nov. 2009.
Jebrail et al.; Digital microfluidics: a versatile tool for applications in chemistry, biology and medicine; Lab Chip; 12 (14); pp. 2452-2463; Jul. 2012.
Jemere et al., An integrated solid-phase extraction system for sub-picomolar detection, Electrophoresis, 23(20), pp. 3537-3544, Oct. 2002.
Jenkins et al., The biosynthesis of carbocyclic nucleosides; Chem. Soc. Rev.; 24(3); pp. 169-176; Jan. 1995.
Jessome et al.; Ion Suppression: A Major Concern in Mass Spectrometry. LC-GC North America, 24(5), pp. 498-510, May 2006.
Jia et al.; Ultrasensitive detection of microRNAs by exponential isothermal amplification; Angew. Chem. Int. Ed. Engl.; 49(32); pp. 5498-5501; Jul. 2010.
Jung et al.; Hybridization of Alternating Cationic/Anionic Oligonucleotides to RNA Segments; Nucleosides & Nucleotides; 13(6-7); pp. 1597-1605; Jul. 1994.
Kaaks et al.; Postmenopausal serum androgens, oestrogens and breast cancer risk: The European prospective investigation into cancer and nutrition. Endocrine-Related Cancer,12(4), pp. 1071-1082, Dec. 2005.
Keng et al., Micro-chemical synthesis of molecular probes on an electronic microfluidic device,PNAS, 109(3), pp. 690-695; Jan. 2012.
Kiedrowski et al., Parabolic Growth of a Self-Replicating Hexadeoxynucleotide Bearing a 3'-5'-Phosphoamidate Linkage; Angew. Chemie Intl. Ed.; 30(4); pp. 423-426; Apr. 1991.
Kim et al., A Microfluidic DNA Library Preparation Platform for Next-Generation Sequencing, PLoS ONE, 8(7), Article ID: e68988; 9 pgs., Jul. 2013.
Kim et al.; Microfabricated Monolithic Multinozzle Emitters for Nanoelectrospray Mass Spectrometry; Anal Chem; 79(10); pp. 3703-3707; May 2007.
Kralj et al.; Integrated continuous microfluidic liquid-liquid extraction. Lab on a Chip, 7(2), pp. 256-263, Feb. 2007.
Kutter et al., Solid phase extraction on microfluidic devices, Journal of Microcolumn Separations, 12(2), pp. 93-97, Jan. 2000.
Kutter et al., Solvent-Programmed Microchip Open-Channel Electrochromatography, Analytical Chemistry, 70(15), pp. 3291-3297, Aug. 1998.
Labrie et al., Androgen glucuronides, instead of testosterone, as the new markers of androgenic activity in women. The Journal of Steroid Biochemistry and Molecular Biology, 99(4-5), pp. 182-188, Jun. 2006.
Labrie; Intracrinology. Molecular and Cellular Endocrinology, 78(3), pp. C113-C118, Jul. 1991.
Lamar et al.; Serum sex hormones and breast cancer risk factors in postmenopausal women. Cancer Epidemiol Biomarkers Prev, 12(4), pp. 380-383, Apr. 2003.
Langevin et al., A rapid and unbiased method to produce strand-specific RNA-Seq libraries from small quantities of starting materiaRNA Biol., 10(4), pp. 502-515, (online) Apr. 2013.
Lawyer et al.; High-level expression, purification, and enzymatic characterization of full-length Thermus aquaticus DNA polymerase and a truncated form deficient in 5' to 3' exonuclease activity; Genome Res; 2(4); pp. 275-287; May 1993.
Lawyer et al.; Isolation, characterization, and expression in *Escherichia coli* of the DNA polymerase gene from Thermus aquaticus; J. Biol. Chem.; 264; pp. 6427-6437; Apr. 1989.

Lebrasseur et al.; Two-dimensional electrostatic actuation of droplets using a single electrode panel and development of disposable plastic film card; Sensors and Actuators A; 136(1); pp. 368-386; May 2007.
Lee et al.; Electrowetting and electrowetting-on-dielectric for microscale liquid handling, Sens. Actuators A, 95(2), pp. 259-268, Jan. 2002.
Lee et al.; Removal of bovine serum albumin using solid-phase extraction with in-situ polymerized stationary phase in a microfluidic device; Journal of Chromatography A; 1187(1-2); pp. 11-17; Apr. 2008.
Lee et al.; Surface-Tension-Driven Microactuation Based on Continuous Electrowetting; J. Microelectromechanical Systems; 9(2); pp. 171-180; Jun. 2000.
Letsinger et al., Cationic oligonucleotides, J. Am. Chem. Soc., 110(13), pp. 4470-4471, Jun. 1988.
Letsinger et al., Effects of pendant groups at phosphorus on binding properties of d-ApA analogues, Nucl. Acids Res., 14(8), pp. 3487-3499, Apr. 1986.
Letsinger et al., Phosphoramidate analogs of oligonucleotides, J. Org. Chem., 35(11), pp. 3800-3803, Nov. 1970.
Lettieri et al., A novel microfluidic concept for bioanalysis using freely moving beads trapped in recirculating flows, Lab on a Chip, 3(1), pp. 34-39, Feb. 2003.
Levy et al.; Genetic screening of newborns, Annual Review of Genomics and Human Genetics, 1, pp. 139-177, Sep. 2000.
Li et al., A perspective on paper-based microfluidics: Current status and future trends, Biomicrofluidics, 6(1), pp. 011301 (13 pgs), Mar. 2012.
Li et al., Application of microfluidic devices to proteomics research: identification of trace-level protein digests and affinity capture of target peptides, Molecular & cellular Proteomics, 16(2), pp. 157-168, Feb. 2002.
Li et al., Paper-based microfluidic devices by plasma treatment, Anal. Chem., 80(23), pp. 9131-9134, Nov. 2008.
Li et al.; One-step ultrasensitive detection of microRNAs with loop-mediated isothermal amplification (LAMP); Chem Commun; 47(9); pp. 2595-2597; Mar. 2011.
Li et al.; Test structure for characterizing low voltage coplanar EWOD system; IEEE Transaction on Semiconductor Manufacturing; IEEE Service Center; Piscataway, NJ.; 22(1); pp. 88-95; Feb. 4, 2009.
Liana et al.; Recent Advances in Paper-Based Sensors; Sensors; 12(9); pp. 11505-11526; Aug. 2012.
Link et al.; Electric Control of Droplets in Microfluidic Devices; Angew Chem Int Ed Engl; 45(16); pp. 2556-2560; Apr. 2006.
Liu et al., Three-dimensional paper microfluidic devices assembled using the principles of origami, JACS, 133(44), pp. 17564-17566, Nov. 2011.
Liu et al.; Attomolar ultrasensitive microRNA detection by DNA-scaffolded silver-nanocluster probe based on isothermal amplification; Anal Chem; 84(12); pp. 5165-5169; Jun. 2012.
Lizardi et al.; Mutation detection and single-molecule counting using isothermal rolling-circle amplification; Nat. Genet.; 19(3); pp. 225-232; Jul. 1998.
Locascio et al.; Surface chemistry in polymer microfluidic systems; in Lab-on-a-Chip; Elsevier Science; 1st Ed.; pp. 65-82; Oct. 2003.
Loeber; Neonatal screening in Europe; the situation in 2004, Journal of Inherited Metabolic Disease, 30(4), pp. 430-438, Aug. 2007.
Lohman et al.; Efficient DNA ligation in DNA-RNA hybrid helices by Chlorella virus DNA ligase; Nucleic Acids Research; 42(3); pp. 1831-1844; Nov. 2013.
Luk et al.; Pluronic Additives: A Solution to Sticky Problems in Digital Microfluidics, Langmuir, 24(12), pp. 6382-6389, Jun. 2008.
Luk et al; A digital microfluidic approach to proteomic sample processing; Analytical Chemistry; 81(11); pp. 4524-4530; Jun. 2009.
Mag et al., Synthesis and selective cleavage of an oligodeoxynucleotide containing a bridged internucleotide 5'-phosphorothioate linkage, Nucleic Acids Res., 19(7), pp. 1437-1441, Apr. 1991.
Mais et al.; A solvent replenishment solution for managing evaporation of biochemical reactions in air-matrix digital microfluidics devices; Lab on a Chip; 15(1); pp. 151-158; Jan. 2015.

(56) References Cited

OTHER PUBLICATIONS

Makamba et al.; Surface modification of poly(dimethylsiloxane) microchannels; Electrophoresis; 24(21); pp. 3607-3619; Nov. 2003.
Malloggi et al.; Electrowetting—A versatile tool for controlling microdrop generation, Eur. Phys. J. E, 26(1), pp. 91-96, May 2008.
Mandl et al.; Newborn screening program practices in the United States: notification, research, and consent, Pediatrics, 109(2), pp. 269-273, Feb. 2002.
Maroney et al.; A Rapid, quantitative assay for direct detection of microRNAs and other small RNAs using splinted ligation; RNA; 13(6); pp. 930R936; Jun. 2007.
Maroney et al.; Direct detection of small RNAs using splinted ligation; Nat. Protocols3(2); pp. 279-287; Jan. 2008.
Martinez et al., Simple Telemedicine for Developing Regions: Camera Phones and Paper-Based Microfluidic Devices for Real-Time, Off-Site Diagnosis, Anal. Chem., 80(10), pp. 3699-3707, May 2008.
Martinez et al., Three-dimensional microfluidic devices fabricated in layered paper and tape, PNAS, 105(50), pp. 19606-19611, Dec. 2008.
Martinez et al.; Patterned paper as a platform for inexpensive low-volume, portable bioassays, Angewandte Chemie, 46(8), pp. 1318-1320, Feb. 2007.
Martinez-Sanchez et al.; MicroRNA Target Identification—Experimental Approaches; Biology; 2; pp. 189-205; Jan. 2013.
Matern et al.; Reduction of the false-positive rate in newborn screening by implementation of MS/MS-based second-tier tests: the Mayo Clinic experience (2004-2007), Journal of Inherited Metabolic Disease, 30(4), pp. 585-592, Aug. 2007.
Mauney, Thermal Considerations for Surface Mount Layouts, in Texas Instruments Portable Power Supply Design Seminar, 16 pgs., 2006.
Mega; Heterogenous ion-exchange membranes RALEX; 3 pgs.; retrieved Mar. 1, 2016 from the internet: http://www.mega.cz/heterogenous-ion-exchange-membranes-ralex.html.
Meier et al., The photochemistry of stilbenoid compounds and their role in materials technology, Chern. Int. Ed. Engl., 31(11), pp. 1399-1420, Nov. 1992.
Mellors et al.; Fully Integrated Glass Microfluidic Device for Performing High-Efficiency Capillary Electrophoresis and Electrospray Ionization Mass Spectrometry, Analytical Chemistry, 80(18), pp. 6881-6887 (Author Manuscript, 18 pgs.), Sep. 2008.
Michigan Dept. of Community Health; Specimen collection procedure from Michigan Newborn Screening Program, 37 pgs., (retrieved Feb. 9, 2017 online: http://web.archive.org/web/20100715000000*/http://www.michigan.gov/documents/Bloodco2_60773_7.pdf) Jul. 2009.
Miller et al.; A digital microfluidic approach to homogeneous enzyme assays, Anal. Chem., 80(5), pp. 1614-1619, Mar. 2008.
Millington et al.; Digital Microfluidics: A Future Technology in the Newborn Screening Laboratory?, Seminars in Perinatology, 34(2), pp. 163-169 (Author Manuscript, 14 pgs.), Apr. 2010.
Millington et al.; Digital Microfluidics: A novel platform for multiplexed detection of LSDs with potential for newborn screening (conference presentation); Oak Ridge Conference; 15 pgs.; 2009.
Millington et al.; Tandem mass spectrometry: a new method for acylcarnitine profiling with potential for neonatal screening for inborn errors of metabolism, Journal of Inherited Metabolic Disease, 13(3), pp. 321ý324, May 1990.
Millington et al.; The Analysis Of Diagnostic Markers Of Genetic Disorders In Human Blood And Urine Using Tandem Mass Spectrometry With Liquid Secondary Ion Mass Spectrometry, International Journal of Mass Spectrometry, 111, pp. 211-228, Dec. 1991.
Miralles et al.; A Review of Heating and Temperature Control in Microfluidic Systems: Techniques and Applications; Diagnostics; 3; pp. 33-67; Jan. 2013.
Mitchell et al.; Circulating microRNAs as stable blood-based markers for cancer detection; Proc Nat Acad Sci; 105(30); pp. 10513-10518; Jul. 2008.

Moon et al.; An integrated digital microfluidic chip for multiplexed proteomic sample preparation and analysis by MALDI-MS. Lab Chip, 6(9), pp. 1213-1219, Sep. 2006.
Moqadam et al.; The Hunting of Targets: Challenge in miRNA Research; Leukemia; 27(1); pp. 16-23; Jan. 2013.
Mousa et al.; Droplet-scale estrogen assays in breast tissue, blood, and serum, Science Translational Medicine, 1(1), 6 pgs., Oct. 2009.
Murran et al.; Capacitance-based droplet position estimator for digital microfluidic devices; Lab Chip;12(11); pp. 2053-2059; May 2012.
Nakamura et al.; Simple and accurate determination of CYP2D6 gene copy number by a loop-mediated isothermal amplification method and an electrochemical DNA chip; Clinica Chimica Acta; 411(7-8); pp. 568-573; Apr. 2010.
Nelson et al., Incubated protein reduction and digestion on an EWOD digital microfluidic chip for MALDI-MS, Analytical Chemistry, 82(23), pp. 9932-9937, Dec. 2010.
Newborn Screening Ontario, The newborn screening ontario unsatisfactory sample indicator (educational resource), 3 pgs., retrieved online: https://www.newbornscreening.on.ca/en/health-care-providers/submitters/report-cards/nso_unsatisfatory_sample_indicator_jan_2017, (web address was available to applicant(s) at least as of Jan. 2010).
Ng et al., Digital microfluidic magnetic separation for particle-based immunoassays, Anal. Chem., 84(20), 8805-8812, Oct. 2012.
Nilsson et al.; RNA-templated DNA ligation fortranscript analysis; Nucl. Acid Res.; 29(2); pp. 578-581; Jan. 2001.
Njiru; Loop-Mediated Isothermal Amplification Technology: Towards Point of Care Diagnostics; PLoS; 6(6); pp. e1572 (4 pgs.); Jun. 2012.
Notomi et al.; Loop-mediated isothermal amplification of DNA; Nucleic Acid Research; 28(12); p. e63 (7 pgs.); Jun. 2000.
Okubo et al.; Liquid-liquid extraction for efficient synthesis and separation by utilizing micro spaces. Chemical Engineering Science, 63(16), pp. 4070-4077, Aug. 2008.
Oleschuk et al., Trapping of bead-based reagents within microfluidic systems: On-chip solid-phase extraction and electrochromatography, Analytical Chemistry, 72(3), pp. 585-590, Feb. 2000.
Padilla et al.; Newborn screening in the Asia Pacific region, Journal of Inherited Metabolic Disease, 30(4), pp. 490-506, Aug. 2007.
Paik et al., Coplanar digital microfluidics using standard printed circuit board processes, in Proceedings 9th Int'l Conf Miniaturized Systems for Chemistry and Life Sciences (MicroTAS 2005), Boston, MA, USA, pp. 566-568, Oct. 9-13, 2005.
Paneri et al.; Effect of change in ratio of electrode to total pitch length in EWOD based microfluidic system; InComputer Applications and Industrial Electronics (ICCAIE); 2010 International Conference; pp. 25-28; Dec. 5, 2010.
Parida et al.; Rapid detection and differentiation of Dengue virus serotypes by a real-time reverse transcription-loop-mediated isothermal amplification assay; J Clinical Microbiology; 43(6); pp. 2895-2903; Jun. 2005.
Pauwels et al., Biological-Activity of New 2-5a Analogs, Chemica Scripta, 26(1), pp. 141-145, Mar. 1986.
Peltonen et al.; Printed electrodes on tailored paper enable electrochemical functionalization of paper; TAPPI Nanotechnology Conference; Espoo, Finland; 20 pgs.; Sep. 2010.
Peterschmitt et al.; Reduction of false negative results in screening of newborns for homocystinuria, New England Journal of Medicine, 341(21), 1572-1576, Nov. 1999.
Petersen et al., On-chip electro membrane extraction, Microfluidics and Nanofluidics, 9(4), pp. 881-888, Oct. 2010.
Pitt et al.; Hormone replacement therapy for osteoporosis. Lancet, 335(8695), p. 978, Apr. 1990.
Pollack et al.; Electrowetting-based actuation of droplets for integrated microfluidics; Lab on a Chip; 2(2); pp. 96-101; May 2002.
Pollack et al.; Electrowetting-based actuation of liquid droplets for microfluidic applications, Appl. Phys. Lett., 77(11), pp. 1725-1726, Sep. 2000.
Provincial Health Services Authority (British Columbia Perinatal Health Program), Perinatal Services BC Neonatal Guideline 9: Newborn Screening, 29 pgs., (retrieved Feb. 9, 2017 online: http://

(56) References Cited

OTHER PUBLICATIONS www.perinatalservicesbc.ca/health-professionals/guidelines-standards/newborn) guideline revised: Dec. 2010.

Rahhal et al.; The impact of assay sensitivity in the assessment of diseases and disorders in children. Steroids, 73(13), pp. 1322-1327, Dec. 2008.

Rashad; Clinical applications of tandem mass spectrometry: ten years of diagnosis and screening for inherited metabolic diseases, Journal of Chromatography B: Biomedical Sciences and Applications, 758(1), pp. 27-48, Jul. 2001.

Rashed et al.; Diagnosis of inborn errors of metabolism from blood spots by acylcarnitines and amino acids profiling using automated electrospray tandem mass spectrometry, Pediatric Research, 38(3), 324-331, Sep. 1995.

Rawls, Optimistic About Antisense: Promising clinical results and chemical strategies for further improvements delight antisense drug researchers; Chemical & Engineering News; 75(22); pp. 35-39; Jun. 2, 1997.

Ren et al., Automated on-chip droplet dispensing with volume control by electro-wetting actuation and capacitance metering, Sens. Actuator B Chem., 98(2-3), pp. 319-327, Mar. 2004.

Ren et al.; Design and testing of an interpolating mixing architecture for electrowetting-based droplet-on-chip chemical dilution; 12th International Conference on TRANSDUCERS, Solid-State Sensors, Actuators and Microsystems; vol. 2; Boston, MA, USA; pp. 619-622; Jun. 8-12, 2003.

Ro et al.; Poly (dimethylsiloxane) microchip for precolumn reaction and micellar electrokinetic chromatography of biogenic amines, Electrophoresis, 23(7-8), pp. 1129-1137, Apr. 2002.

Roman et al.; Fully integrated microfluidic separations systems for biochemical analysis, J. Chromatogr. A, 1168(1-2), pp. 170-188, Oct. 2007.

Roman et al.; Sampling and Electrophoretic Analysis of Segmented Flow Streams in a Microfluidic Device, Anal. Chem., 80(21), pp. 8231-8238 (author manuscript, 19 pgs.), Nov. 2008.

Sabourin et al.; Interconnection blocks: a method for providing reusable, rapid, multiple, aligned and planar microfluidic interconnections; Journal of Micromechanics and Microengineering; 19(3); 10 pages; doi:10.1088/0960-1317/19/3/035021; Feb. 18, 2009.

Sadeghi et al.; On Chip Droplet Characterization: A Practical, High-Sensitivity Measurement of Droplet Impedance in Digital Microfluidics; Anal. Chem.; 84(4); pp. 1915-1923; Feb. 2012.

Sahai et al.; Newborn screening, Critical Reviews in Clinical Laboratory Sciences, 46(2), pp. 55-82, (online) Mar. 2009.

Samsi et al.; A Digital Microfluidic Electrochemical Immunoassay; Lab On A Chip; 14(3); pp. 547-554; Feb. 2014.

Sanghvi & Cook (Ed.); Carbohydrate Modifications in Antisense Research; Chapters 2 and 3, American Chemical Society, Washington DC; (207th National Meeting of the American Chemical Society Mar. 13-17, 1994, San Jose, CA); Dec. 1994.

Sanghvi & Cook (Ed.); Carbohydrate Modifications in Antisense Research; Chapters 6 and 7, American Chemical Society, Washington DC; (207th National Meeting of the American Chemical Society Mar. 13-17, 1994, San Jose, CA); Dec. 1994.

Santen et al.; Superiority of gas chromatography/tandem mass spectrometry assay (GC/MS/MS) for estradiol for monitoring of aromatase inhibitor therapy. Steroids. 72(8), pp. 666-671, Jul. 2007.

Sasano et al.; From Endocrinology to Intracrinology. Endocr Pathol, 9(1), pp. 9-20, Spring 1998.

Satoh et al.; Electrowetting-based valve for the control of the capillary flow, J. Appl. Phys., 103(3), 034903, Feb. 2008.

Satoh et al.; On-chip microfluidic transport and mixing using electrowetting and incorporation of sensing functions, Anal. Chem., 77(21), pp. 6857-6863, Nov. 2005.

Sawai et al., Synthesis and properties of oligoadenylic acids containing 2?-5? phosphoramide linkage, Chem. Lett., 13(5), pp. 805-808, May 1984.

Schertzer et al.; Using capacitance measurements in EWOD devices to identify fluid composition and control droplet mixing; Sens. Actuators B; 145(1); pp. 340-347; Mar. 2010.

Scriver_Commentary; A Simple Phenylalanine Method For Detecting Phenylketonuria In Large Populations Of Newborn Infants by Guthrie et al., Pediatrics, 32(3), 338-343, Sep. 1963.

Shah et al., On-demand droplet loading for automated organic chemistry on digital microfluidics, Lab Chip, 13(14), pp. 2785-2795, Jul. 2013.

Shamsi et al.; A digital microfluidic electrochemical immunoassay; Lab on a Chip; 14(3); pp. 547-554; (year of pub. sufficiently earlier than effective US filing date and any foreign priority date) 2014.

Shih et al., A feedback control system for high-fidelity digital microfluidics, Lab Chip, 11 (3), pp. 535-540, Feb. 2011.

Simpson et al.; Estrogen—the Good, the Bad, and the Unexpected. Endocr Rev, 26(3), pp. 322-330; May 2005.

Sinha et al., A Versatile Automated Platform for Micro-scale Cell Stimulation Experiments, J. Vis. Exp., e50597, 8 pgs., Aug. 2013.

Sinton et al.; Electroosmotic velocity profiles in microchannels, Colloids Surf. A, 222(1-3), pp. 273-283, Jul. 2003.

Skendzel, Rubella immunity: Defining the level of protective antibody, Am. J. Clin. Pathol., 106(2), 170-174, Aug. 1996.

Smith et al.; Diagnosis and Management of Female Infertility. Journal of the American Medical Association 290(13), pp. 1767-1770, Oct. 2003.

Sooknanan et al., Nucleic Acid Sequence-Based Amplification, Ch. 12; Molecular Methods for Virus Detection (1st Ed.), Academic Press, Inc., pp. 261-285; Jan. 1995.

Sprinzl et al., Enzymatic incorporation of ATP and CTP analogues into the 3' end of tRNA, Eur. J. Biochem., 81(3), pp. 579-589, Dec. 1977.

Srinivasan et al.; An integrated digital microfluidic lab-on-a-chip for clinical diagnostics on human physiological fluids, Lab Chip, 4(4), pp. 310-315, Aug. 2004.

Stanczyk et al.; Standardization of Steroid Hormone Assays Why, How, and When?, Cancer Epidemiol Biomarkers Prev, 16(9), pp. 1713-1719, Sep. 2007.

Steckl et al.; Flexible Electrowetting And Electrowetting On Flexible Substrates; Proc. SPIE 7956; Advances in Display Technologies; and E-papers and Flexible Displays; 795607 (6 pgs.); Feb. 2011.

Stegink et al.; Plasma amino acid concentrations and amino acid ratios in normal adults and adults heterozygous for phenylketonuria ingesting a hamburger and milk shake meal, American Journal of Clinical Nutrition, 53(3), pp. 670-675, Mar. 1991.

Sun et al.; Rapid and direct microRNA quantification by an enzymatic luminescence assay; (author manuscript; 17 pgs.) Analytical Biochemistry; 429(1); pp. 11-17; Oct. 2012.

Svoboda et al.; Cation exchange membrane integrated into a microfluidic device; Microelectronic Engineering; 86; pp. 1371-1374; Apr.-Jun. 2009.

Szarewski et al.; Contraception. Current state of the art. British Medical Journal, 302(6787), pp. 1224-1226, May 1991.

Szymczak et al.; Concentration of Sex Steroids in Adipose Tissue after Menopause. Steroids, 63(5-6), pp. 319-321, May/Jun. 1998.

Tachibana et al.; Application of an enzyme chip to the microquantification of L-phenylalanine, Analytical Biochemistry, 359(1), pp. 72-78, Dec. 2006.

Tan et al.; A lab-on-a-chip for detection of nerve agent sarin in blood; Lab Chip; 8(6); pp. 885-891; Jun. 2008.

Teh et al.; Droplet microfluidics, Lab Chip, 8(2), pp. 198-220, Feb. 2008.

Therrell et al.; Newborn screening in North America, Journal of Inherited Metabolic Disease, 30(4), pp. 447-465, Aug. 2007.

Tian et al., Printed two-dimensional micro-zone plates for chemical analysis and ELISA, Lab on a Chip, 11 (17), pp. 2869-2875, Sep. 2011.

Tobjörk et al., IR-sintering of ink-jet printed metal-nanoparticles on paper, Thin Solid Films, 520(7), pp. 2949-2955, Jan. 2012.

Tomita et al.; Loop-mediated isothermal amplification (LAMP) of gene sequences and simple visual detection of products; Nature Protocols; 3(5); pp. 877-882; (online) Apr. 2008.

Turgeon et al.; Combined Newborn Screening for Succinylacetone, Amino Acids, and Acylcarnitines in Dried Blood Spots, Clinical Chemistry, 54(4), pp. 657-664, Apr. 2008.

(56) References Cited

OTHER PUBLICATIONS

Udenfriend et al.; Fluorescamine: a reagent for assay of amino acids, peptides, proteins, and primary amines in the picomole range, Science, 178(4063), pp. 871-872, Nov. 1972.
Unger et al.; Monolithic microfabricated valves and pumps by multilayer soft lithography, Science, 288(5463), pp. 113-116, Apr. 2000.
Univ. of Maryland—Baltimore Washington Medical Center; Plasma amino acids, 6 pgs., retrieved Feb. 10, 2017 from: http://www.mybwmc.org/library/1/003361, Web address available to applicant(s) at least as of Jan. 2010.
Verkman; Drug Discovery In Academia; Am J Physiol Cell Physiol; 286(3); pp. C465-C474; Feb. 2004.
Walker et al.; A Chemiluminescent DNA Probe Test Based on Strand Displacement Amplification (Chapter 15); Molecular Methods for Virus Detection (1st Ed.), Academic Press, Inc., pp. 329-349; Jan. 1995.
Walker et al.; A passive pumping method for microfluidic devices, Lab Chip, 2(3), pp. 131-134, Aug. 2002.
Wang et al., Paper-based chemiluminescence ELISA: lab-on-paper based on chitosan modified paper device and, Biosens. Bioelectron., 31(1), pp. 212-218, Jan. 2012.
Wang et al., Simple and covalent fabrication of a paper device and its application in sensitive chemiluminescence immunoassay, Analyst, 137(16), pp. 3821-3827, Aug. 2012.
Wang et al.; Highly sensitive detection of microRNAs based on isothermal exponential amplification-assisted generation of catalytic G-quadruplexDNAzyme; Biosensors and Bioelectronics, 42; pp. 131-135; Apr. 2013.
Washburn et al.; Large-scale analysis of the yeast proteome by multidimensional protein identification technology, Nat. Biotechnol., 19(3), pp. 242-247, Mar. 2001.
Watson et al.; Multilayer hybrid microfluidics: a digital-to-channel interface for sample processing and separations; Anal. Chem.; 82(15); pp. 6680-6686; Aug. 2010.
Wheeler et al.; Electrowetting-Based Microfluidics for Analysis of Peptides and Proteins by Matrix-Assisted Laser Desorption/Ionization Mass Spectrometry; Anal Chem; 76(16); pp. 4833-4838; Aug. 2004.
Wheeler; Chemistry. Putting electrowetting to work; Science; 322(5901); pp. 539-540; Oct. 2008.
Wu et al.; Design, Simulation and Fabrication of Electrowetting-Based Actuators for Integrated Digital Microfluidics; Proceedings of the 1st IEEE International Conference on Nano/Micro Engineered and Molecular Systems; Zhuhai, China; pp. 1097-1100; Jan. 18-21, 2006.
Wu et al.; Electrophoretic separations on microfluidic chips, J. Chromatogr. A, 1184(1-2), pp. 542-559, Mar. 2008.
Yan et al., A microfluidic origami electrochemiluminescence aptamer-device based on a porous Au-paper electrode and a phenyleneethynylene derivative, Chem. Commun. (Camb), 49(14), pp. 1383-1385, Feb. 2013.
Yan et al., Paper-based electrochemiluminescent 3D immunodevice for lab-on-paper, specific, and sensitive point-of-care testing, Chem.—Eur. J., 18(16), pp. 4938-4945, Apr. 2012.
Yi et al.; Spangler et al., Eds; Channel-to-droplet extractions for on-chip sample preparation, in Proceedings of Solid-State Sensor, Actuator and Microsystems Workshop, pp. 128-131, Jun. 2006.
Yin et al.; One-step, multiplexed fluorescence detection of microRNAs based on duplex-specific nuclease signal amplification; J. American Chem. Soc.; 134(11); pp. 5064-5067; Mar. 2012.
Yoon et al.; Preventing Biomolecular Adsorption in Electrowetting-Based Biofluidic Chips; Anal Chem; 75; pp. 5097-5102; Aug. 2003.
Yoon; Open-Surface Digital Microfluidics; The Open Biotechnology Journal; 2(1); pp. 94-100; Apr. 2008.
Young et al.; Calculation of DEP and EWOD Forces for Application in Digital Microfluidics, J. Fluids Eng., 130(8), p. 081603-1-081603-9, Jul. 2008.
Yu et al.; Microfabrication of a digital microfluidic platform integrated with an on-chip electrochemical cell; Journal of Micromechanics and Microrngineering; 23(9); pp. 10 pages; doi: 10.1088/0960-1317/23/9/095025; Aug. 2013.
Yu et al., Monolithic porous polymer for on-chip solid-phase extraction and preconcentration prepared by photoinitiated in situ polymerization within a microfluidic device, Analytical Chemistry , 73(21), pp. 5088-5096, Nov. 2001.
Yu et al.; Parallel-plate lab-on-chip electrochemical analysis; Journal of Micromechanics and Microengineering; 24(1); 7 pages; doi: 10.1088/0960-1317/24/1/015020; Dec. 16, 2013.
Yu et al., Preparation of monolithic polymers with controlled porous properties for microfluidic chip applications using photoinitiated free-radical polymerization, Journal of Polymer Science, Part A: Polymer Chemistry, 40(6), pp. 755-769, Mar. 2002.
Yu et al.; A plate reader-compatible microchannel array for cell biology assays; Lab Chip; 7(3); pp. 388-391; Mar. 2007.
Zaffanello et al.; Multiple positive results during a neonatal screening program: a retrospective analysis of incidence, clinical implications and outcomes, Journal of Perinatal Medicine, 33(3), pp. 246-251, May 2005.
Zhang et al.; Multiplexed detection of microRNAs by tuning DNA-scaffolded silver nanoclusters; Analyst; 138(17); pp. 4812-4817; Sep. 2013.
Zhao et al., Lab on Paper, Lab Chip, 8(12), pp. 1988-1991, Dec. 2008.
Znidarsic-Plazl et al.; Steroid extraction in a microchannel system—mathematical modelling and experiments. Lab Chip, 7(7), pp. 883-889, Jul. 2007.
Zuker; Mfold Web Server for Nucleic Acid Folding and Hybridization Prediction; Nucleic Acid Research ; 31(13); pp. 3406-3415; Jul. 2003.
Zytkovicz et al.; Tandem mass spectrometric analysis for amino, organic, and fatty acid disorders in newborn dried blood spots: a two-year summary from the New England Newborn Screening Program, Clinical Chemistry, 47(11), pp. 1945-1955, Nov. 2001.
Fobel et al.; U.S. Appl. No. 15/457,930 entitled "Printed Digital Microfluidic Devices Methods Of Use And Manufacture Thereof", filed Mar. 13, 2017.
Hong et al.; U.S. Appl. No. 16/324,420 entitled "Feedback system for parallel droplet control in a digital microfluidic device," filed Feb. 8, 2019.
Dryden et al.; Integrated digital microfluidic platform for voltammetric analysis; Analytical Chemistry; 85(18); pp. 8809-8816; Sep. 2013.
He et al. (ed); Food microbiological inspection technology; Chapter 5: Modern food microbiological inspection technology; China Quality Inspection press; pp. 111-113; (English Translation included) Nov. 2013.
Analog Devices; Extending the capacitive input range of AD7745/AD7746 Capicitance-to-Digital converter; Analog Devices; Norwood, MA; 5 pages; (year of pub. sufficiently earlier than effective US filing date and any foreign priority date) 2009.
Analog Devices; 24-bit Capicitance-to-Digital converter with temperature sensor, AD7745/AD7746; Analog Devices; Norwood, MA; 28 pages; (year of pub. sufficiently earlier than effective US filing date and any foreign priority date) 2005.
Li et al.; A Low-Cost and High resolution droplet position detector for an intelligent electrowetting on dielectric device; Journal of Lab. Automation 2015; 20(6); pp. 663-669; Dec. 2015.
Yu et al.; Microfabtrication of a digital microfluidic platform integrated with an on-chip electrochemical cell; Journal of Micromechanics and Microengineering; 23(9); doi:10.1088/0960-1317/23/9/095025, 10 pages; Aug. 28, 2013.
Yue; Undergraduate Chemistry experiment (II); Hunan Normal University Press; First Edition; p. 96; (Machine Translation included); Oct. 2008.
Zhang et al.; The permeability characteristics of silicone rubber; In Proceedings of 2006 SAMPE Fall Technical Conference; 10 pages; Nov. 6, 2006.
Jebrail et al.; U.S. Appl. No. 16/455,459 entitled "Digital microfluidic devices and methods," filed Jun. 27, 2019.

(56) References Cited

OTHER PUBLICATIONS

Dambrot; Of microchemistry and molecules: Electronic microfluidic device synthesizes biocompatible probes; 4 pages, retrieved from the internet (https://phys.org/news/2012-01-microchemistry-molecules-electronic-microfluidic-device.html); Jan. 26, 2012.
Jebrail et al.; U.S. Appl. No. 16/499,681 entitled Digital microfluidics apparatuses and methods for manipulating and processing encapsulated droplets,: filed Sep. 30, 2019.
Jebrail et al.; U.S. Appl. No. 16/614,396 entitled "Digital microfluidics systems and methods with integrated plasma collection device," filed Nov. 18, 2019.
Baxendale et al.; Multistep synthesis using modular flow reactors: bestmann-ohira reagent for the formation of alkynes and triazoles; Angewandle Chemie International Edition; 48(22): pp. 4017-4021; May 2009.
Chen et al.; The chemistrode: a droplet-based microfluidic device for stimulation and recording with high temporal, spatial, and chemical resolution; Proceedings of the National Academy of Sciences; 105(44); pp. 16843-16848; Nov. 2004.
Cottam et al.; Accelerated synthesis of titanium oxide nanostructures using microfluidic chips; Lab on a Chip; 7(2); pp. 167-169; Feb. 2007.
Doebler et al.; Continuous-flow, rapid lysis devices for biodefense nucleic acid diagnostic systems; Journal of the Association for Laboratory Automation; 14(3); pp. 119-125; Jun. 2009.
Fan et al.; Integrated barcode chips for rapid, multiplexed analysis of proteins in microliter quanties of blood; Nature Biotechnology; 26(12); pp. 1373-1378; 15 pages (Author Manuscript); Dec. 2008.
Hennequin et al.; Synthesizing microcapsules with controlled geometrical and mechanical properties with microfluidic double emulsion technology; Langmuir; 25(14); pp. 7857-7861; Jul. 2009.
Koster et al.; Drop-based microfluidic devices for encapsulation of single cells; Lab on a Chip; 8(7); pp. 1110-1115; Jul. 2008.
Marre et al.; Synthesis of micro and nanostructures in microfluidic systems; Chemical Society Reviews; 39(3); pp. 1183-1202; Mar. 2010.
Theberge et al.; Microdroplets in microfluidics: an evolving plarform for discoveries in chemistry and biology; Angewandte Chemie International Edition; 49(34); pp. 5846-5868; Aug. 2010.
Torkkeli; Droplet microfluidics on a planar surface; VTT Technical Research Centre of Finland; Publications 504; 214 pages (Dissertation); Oct. 2003.
Wang et al.; An integrated microfluidic device for large-scale in situ click chemistry screening; Lab on a Chip; 9(16); 9(16); pp. 2281-2285; 9 pages (Author Manuscript); Aug. 2009.
Wlodkowic et al.; Tumors on chips: oncology meets microfluidics; Current opinion in Chemical Biology; 14(5); pp. 556-567; Oct. 2010.
Yung et al.; Micromagnetic-microfluidic blood cleansing devices; Lab on a Chip; 9(9); pp. 1171-1177; May 2009.
Hong et al.; U.S. Appl. No. 16/726,740 entitled "Feedback system for parallel droplet control in a digital microfluidic device," filed Dec. 24, 2019.
Soto-Moreno et al.; U.S. Appl. No. 16/843,743 entitled "Multi-cartridge digital microfluidics apparatuses and methods of use," filed Apr. 8, 2020.
Jensen et al.; Free-running enzymatic oligonucleotide synthesis for data storage applications; bioRxiv; 1:355719; 7 pages; Jan. 2018.

\* cited by examiner

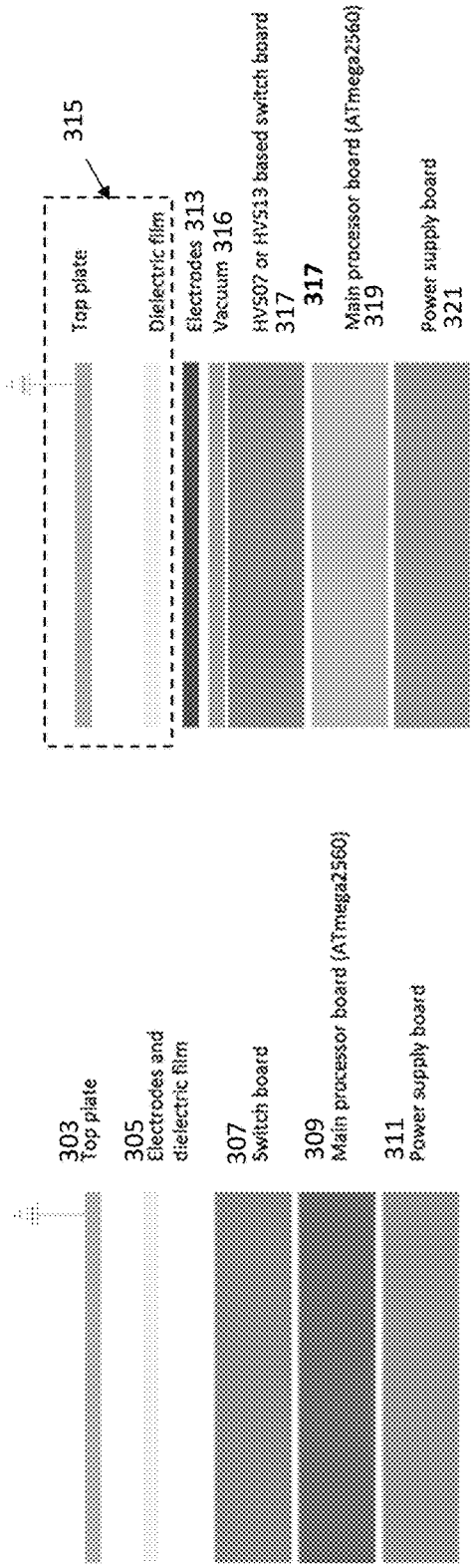
FIG. 3A
FIG. 3B
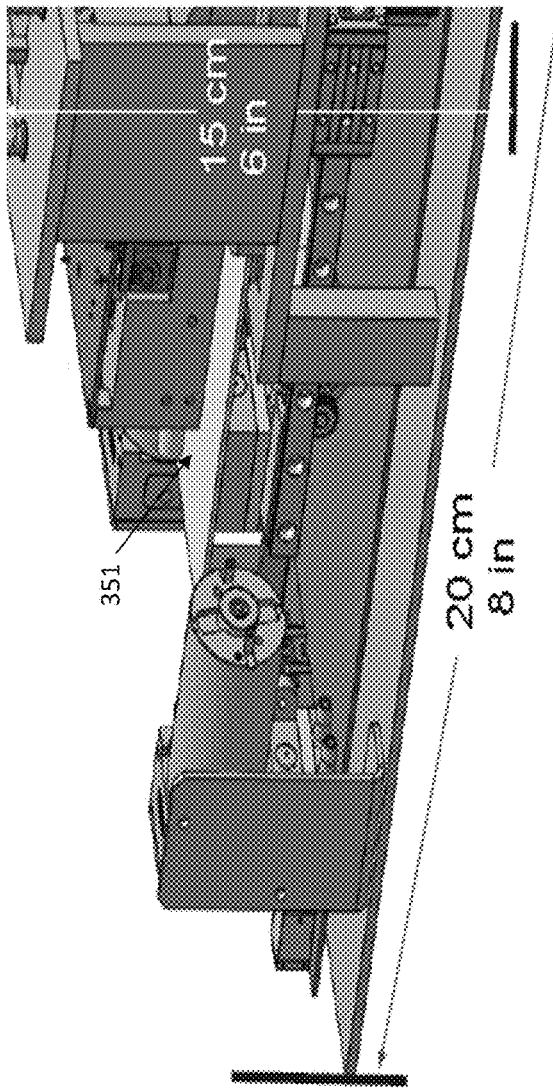
FIG. 3C

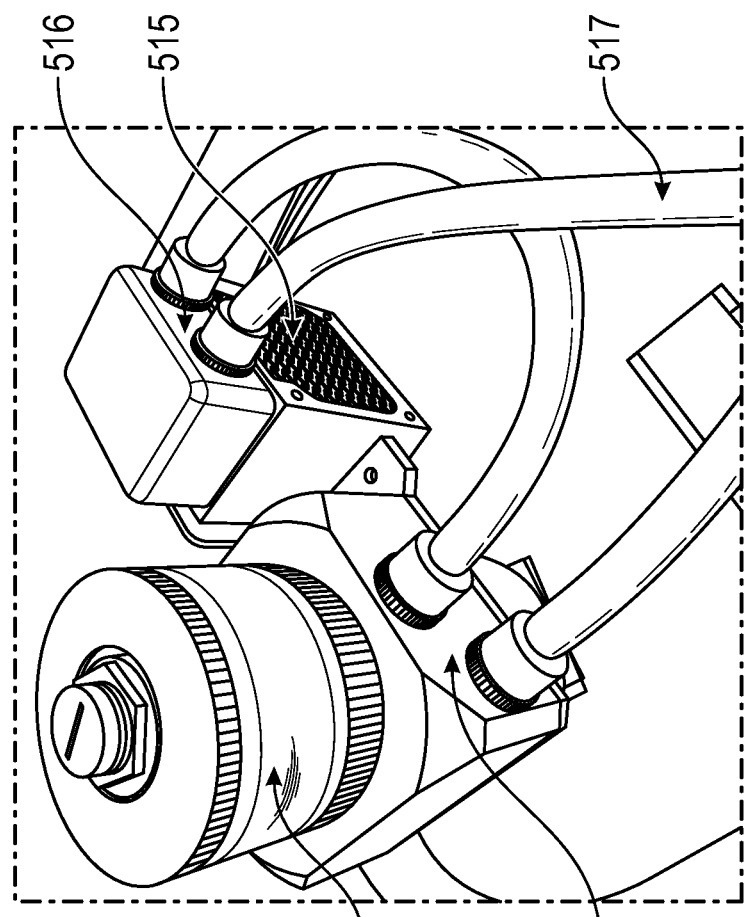
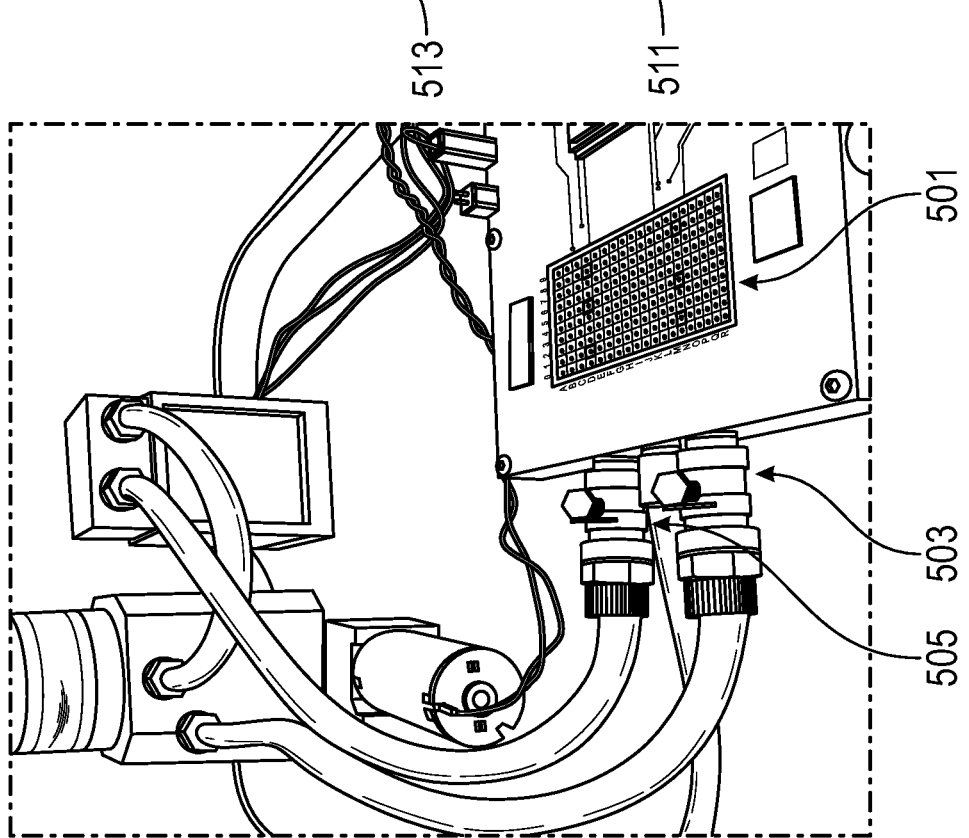
FIG. 5B
FIG. 5A

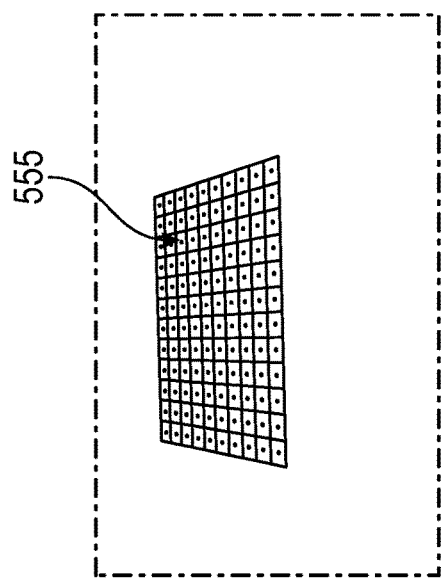
FIG. 5E
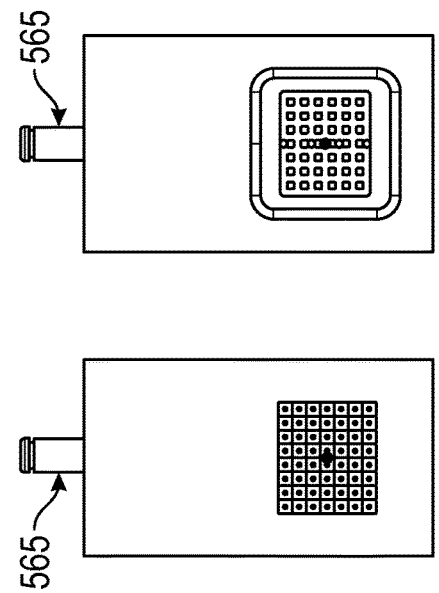
FIG. 5G
FIG. 5F
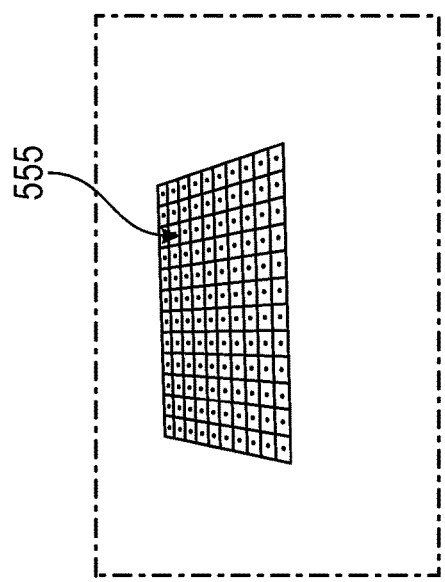
FIG. 5D
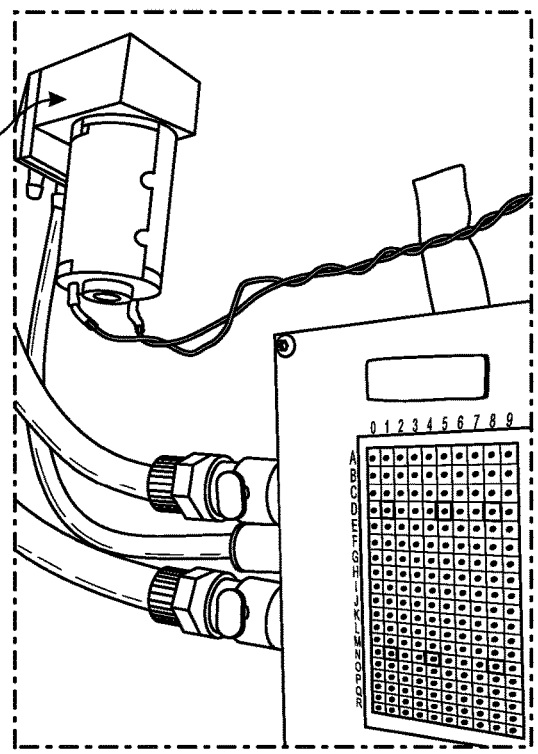
FIG. 5C

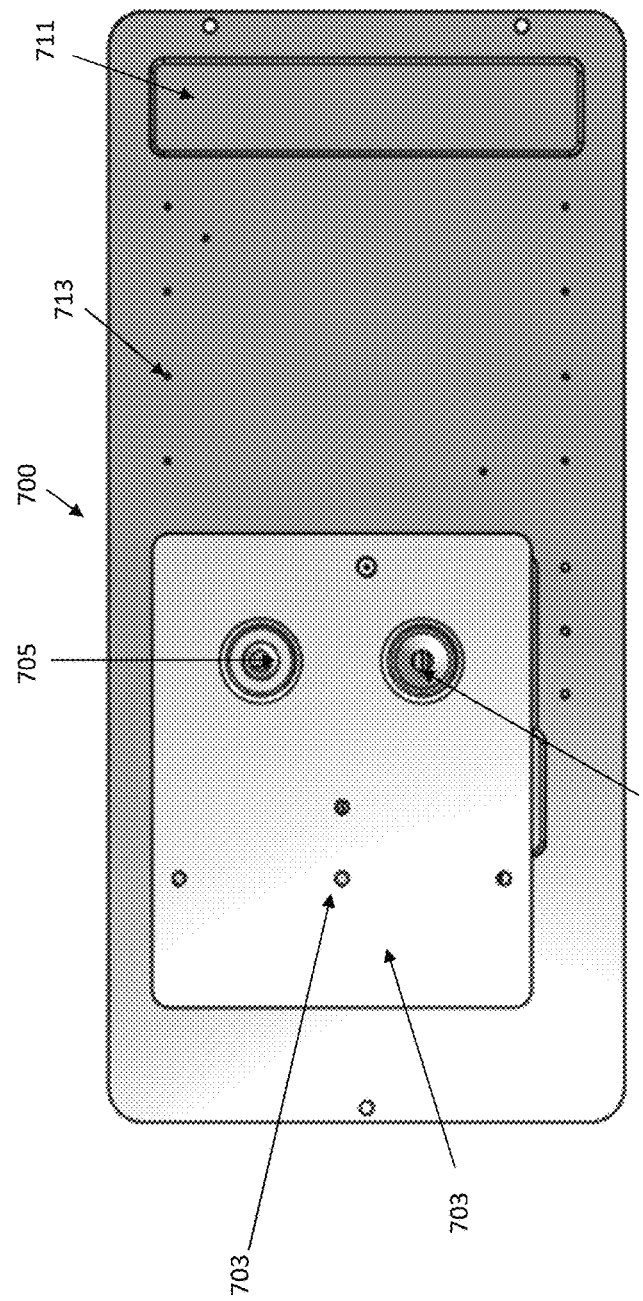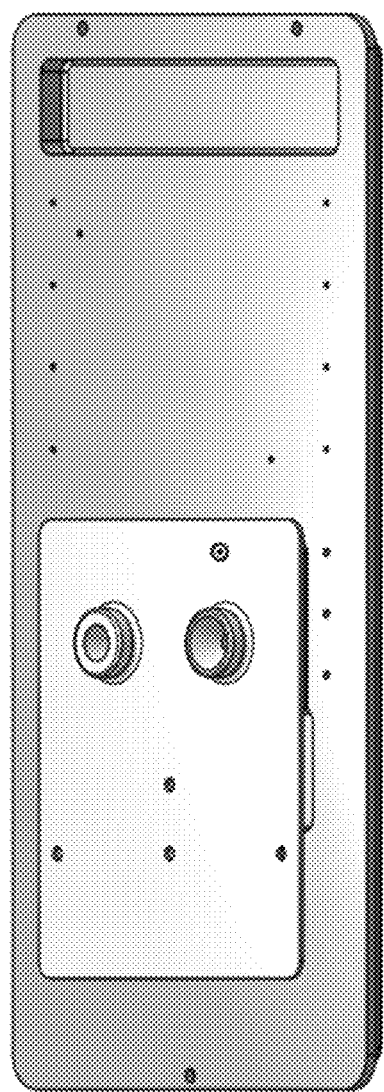
FIG. 7A
FIG. 7B

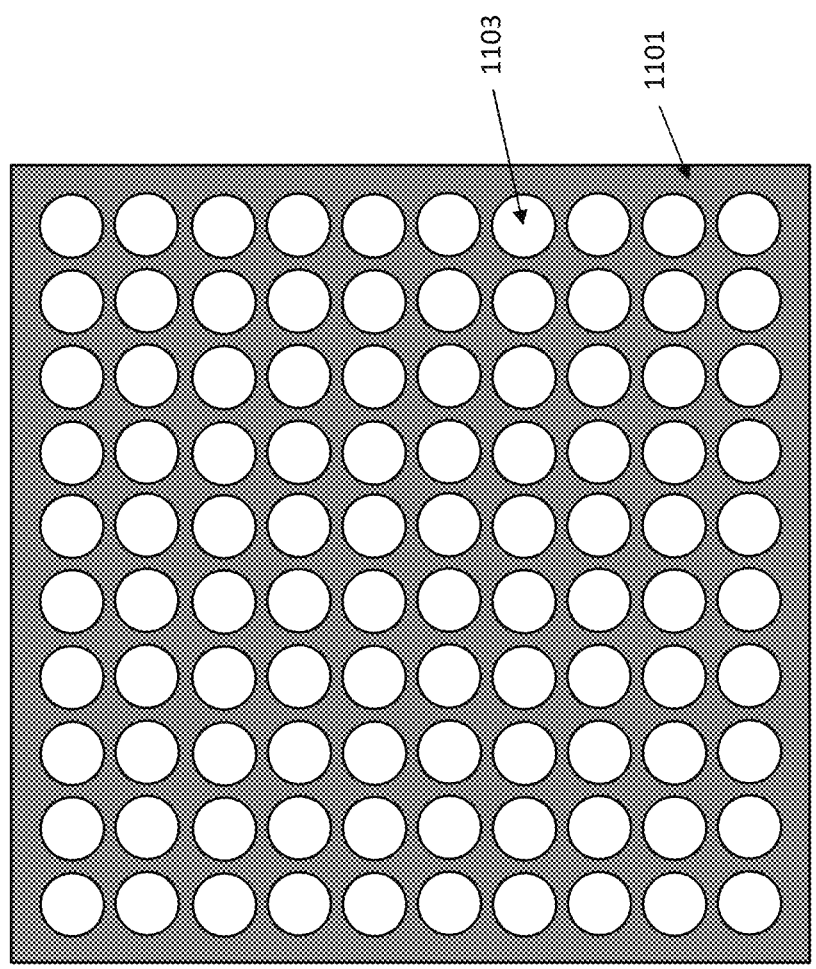
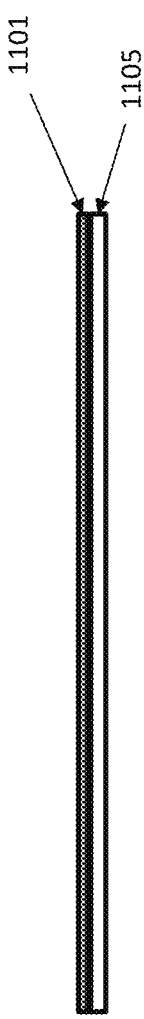
FIG. 11A
FIG. 11B

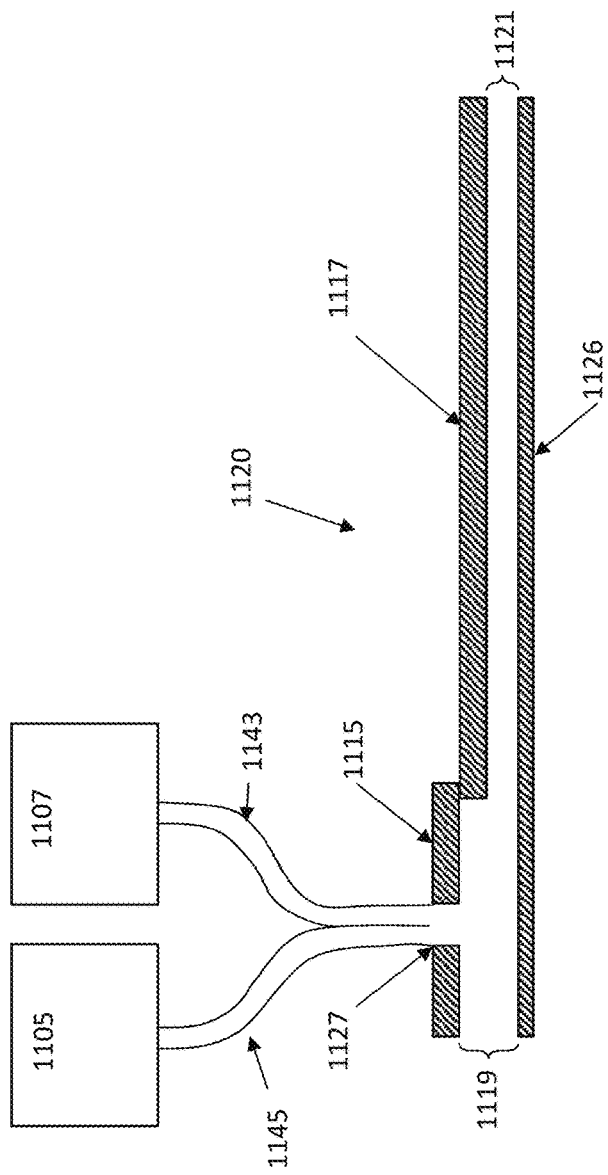
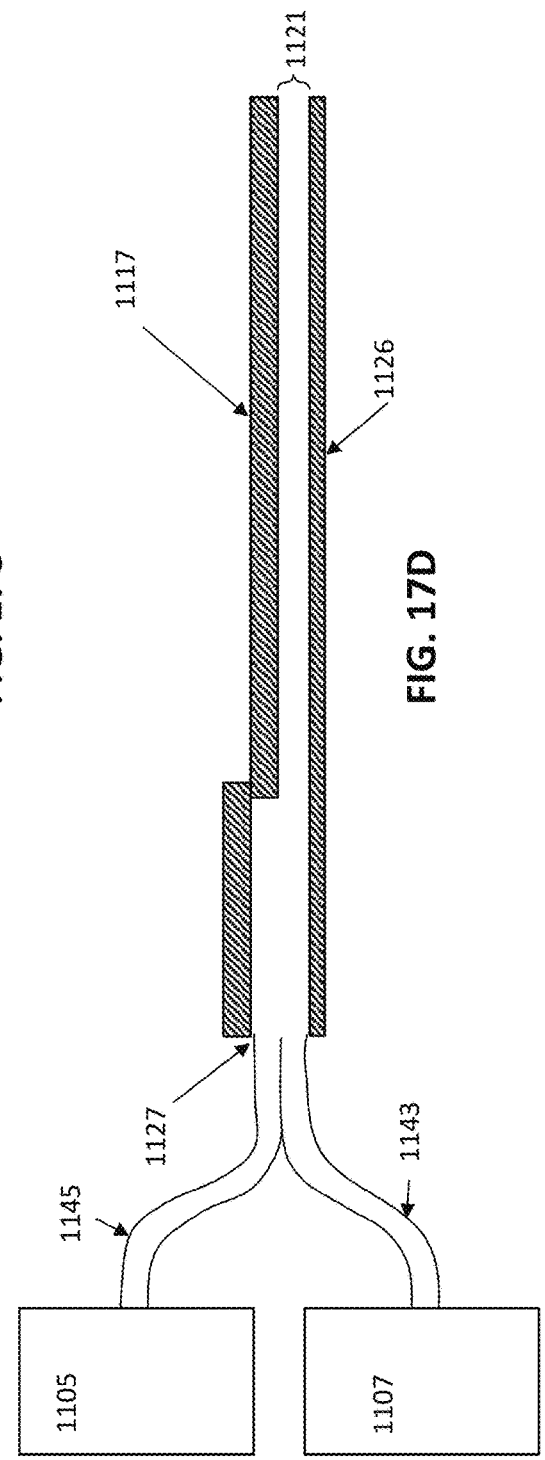
FIG. 17C
FIG. 17D

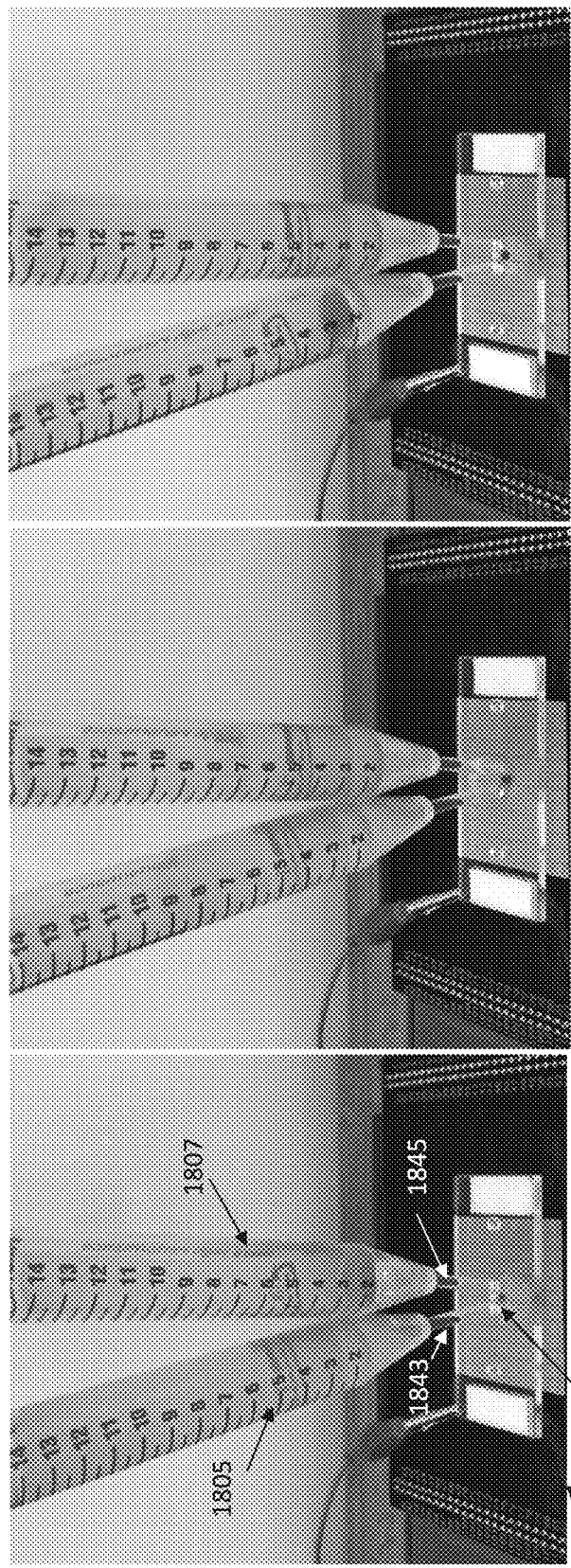

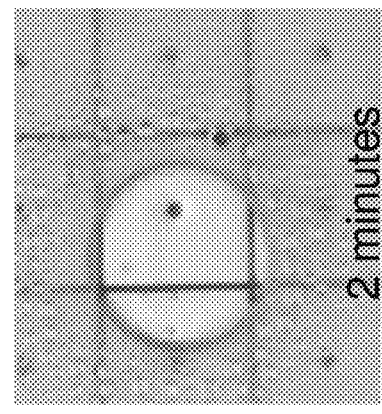
FIG. 19A 0 minutes
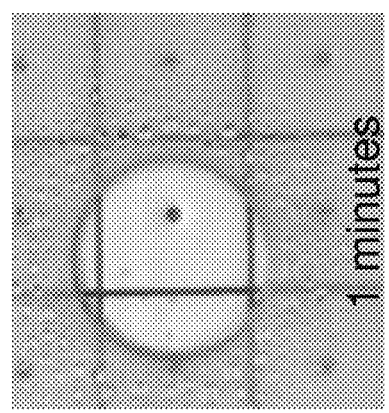
FIG. 19B 1 minutes
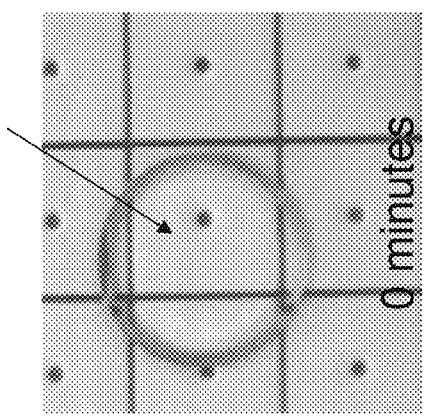
FIG. 19C 2 minutes
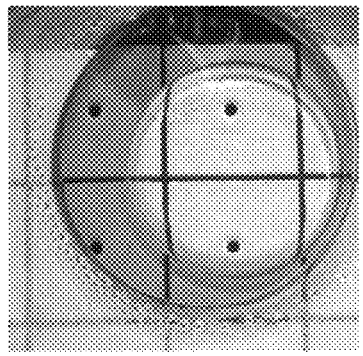
FIG. 20A 0 minutes
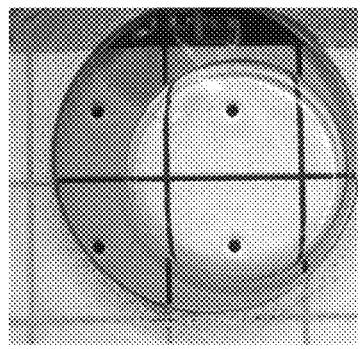
FIG. 20B 60 minutes
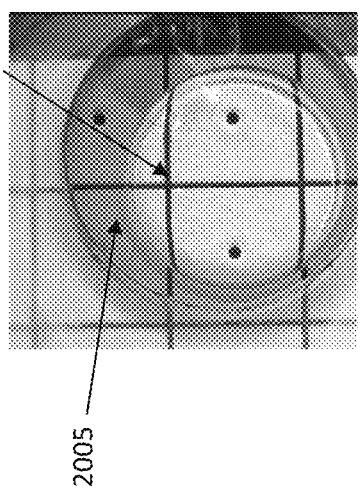
FIG. 20C 120 minutes

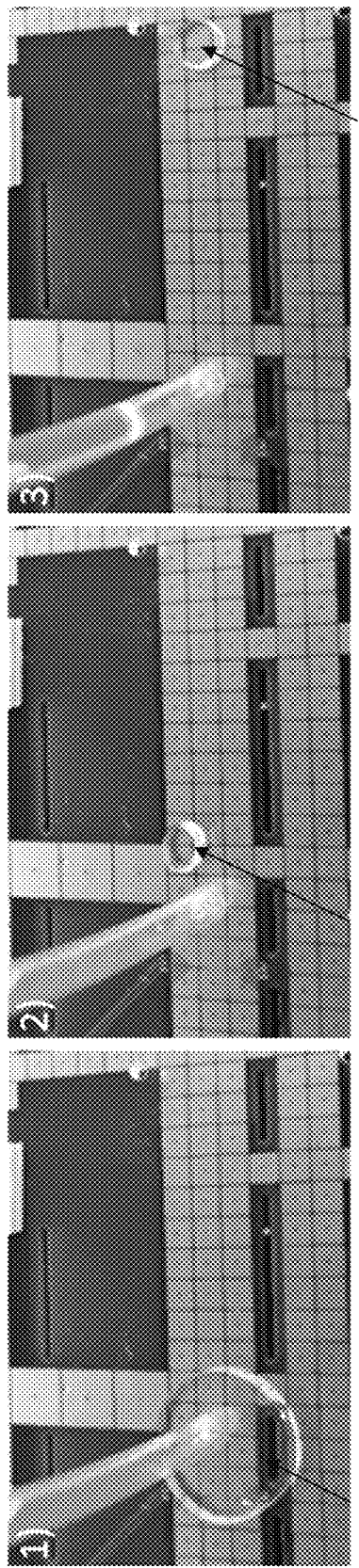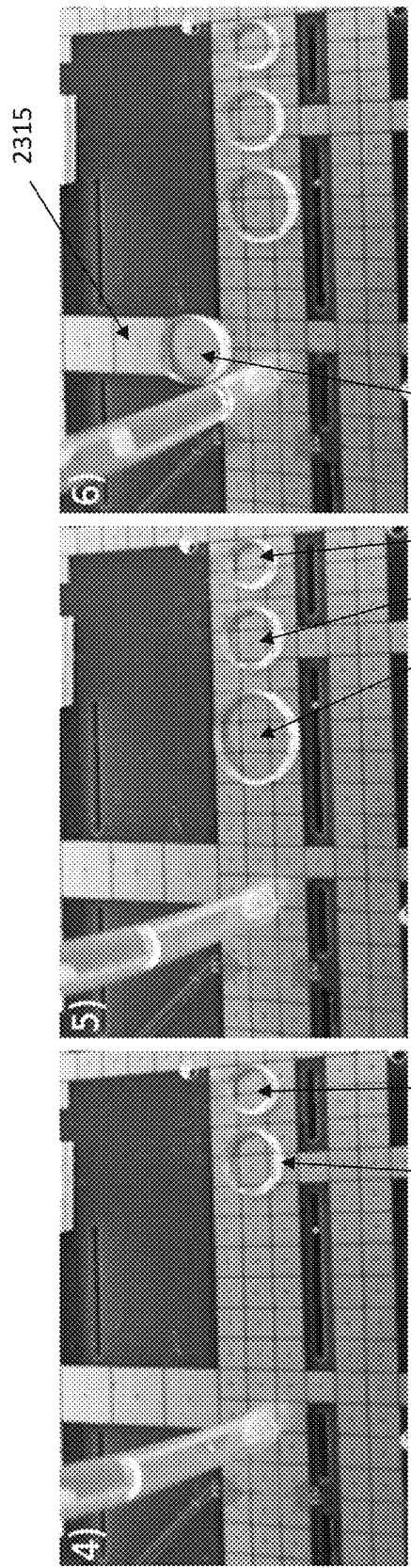
FIG. 23A  FIG. 23B  FIG. 23C
FIG. 23D  FIG. 23E  FIG. 23F

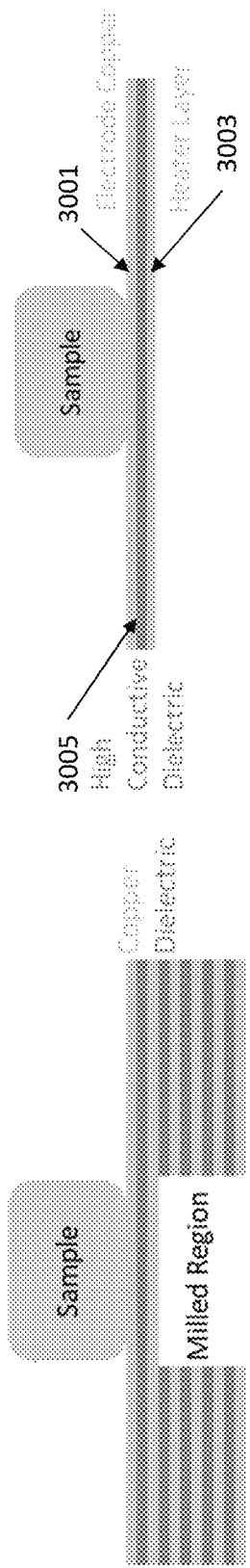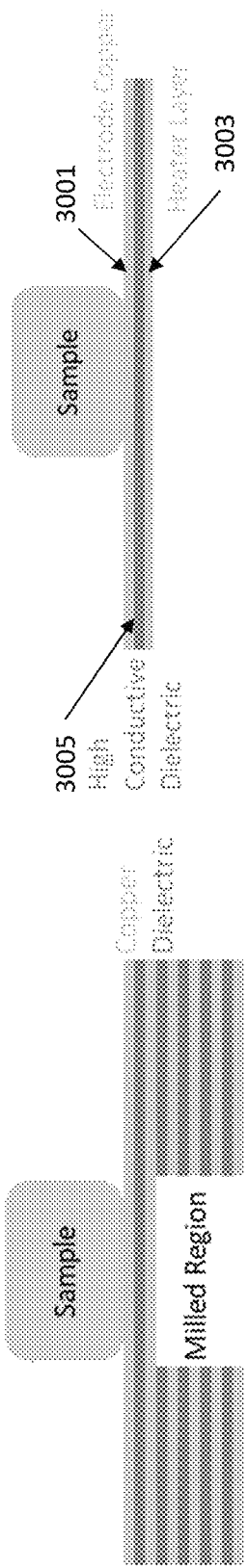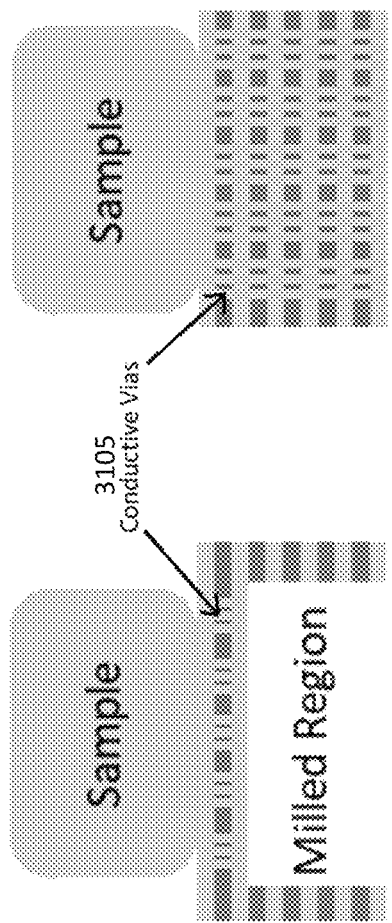
FIG. 30
FIG. 29
FIG. 31B
FIG. 31A

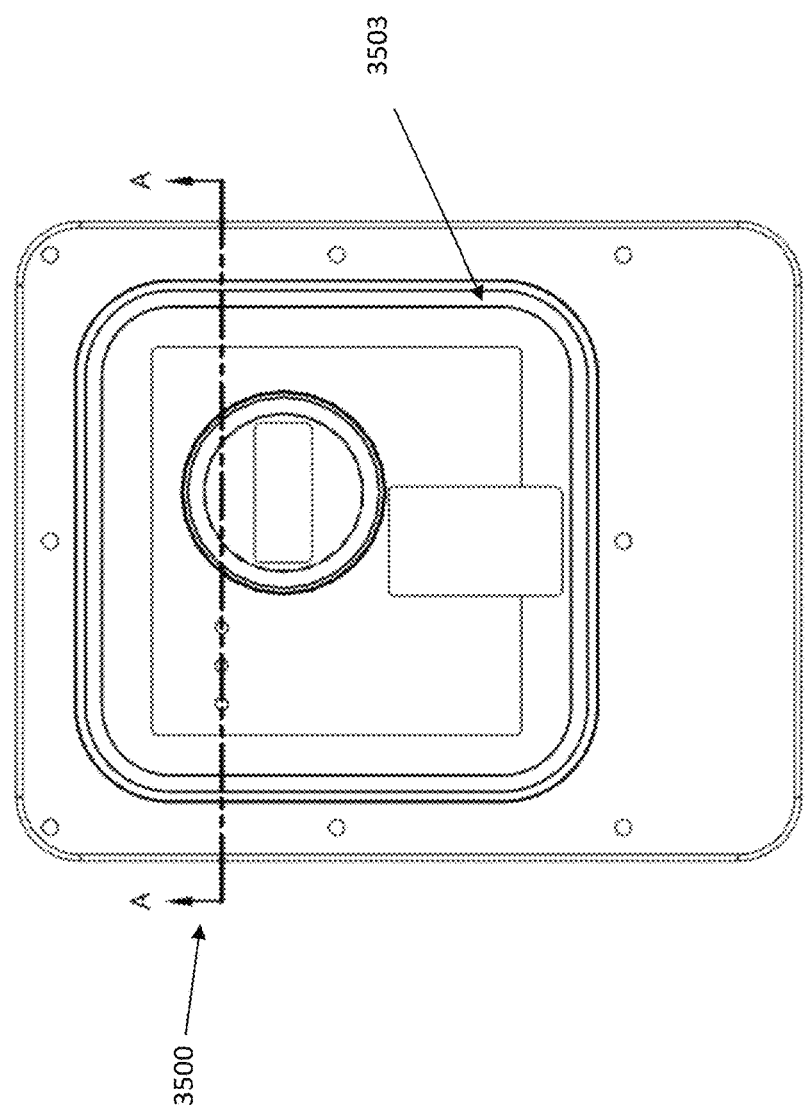
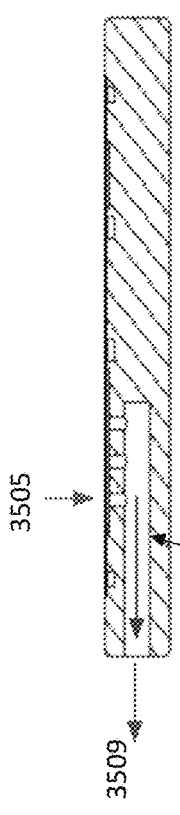
FIG. 35A
FIG. 35B

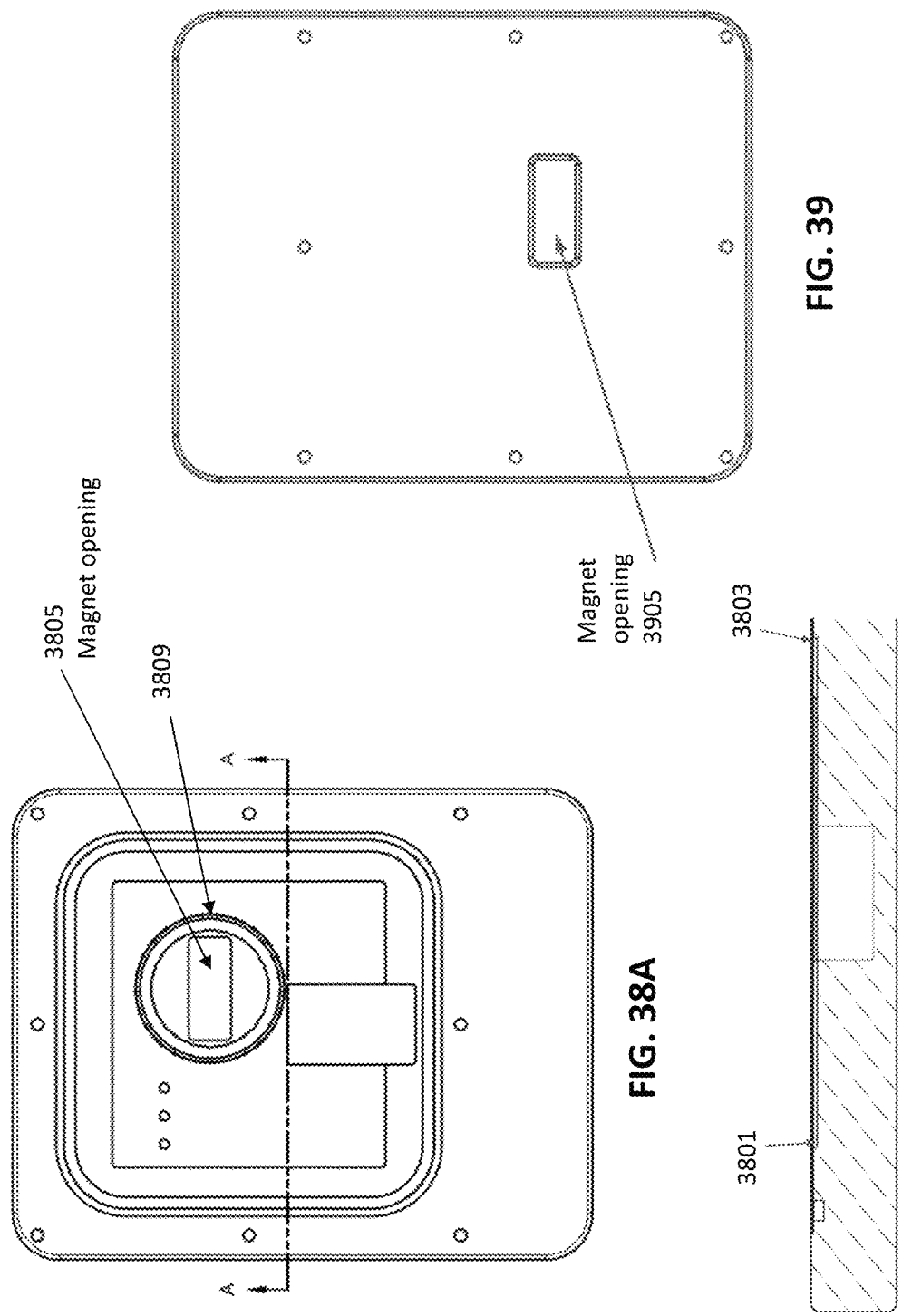

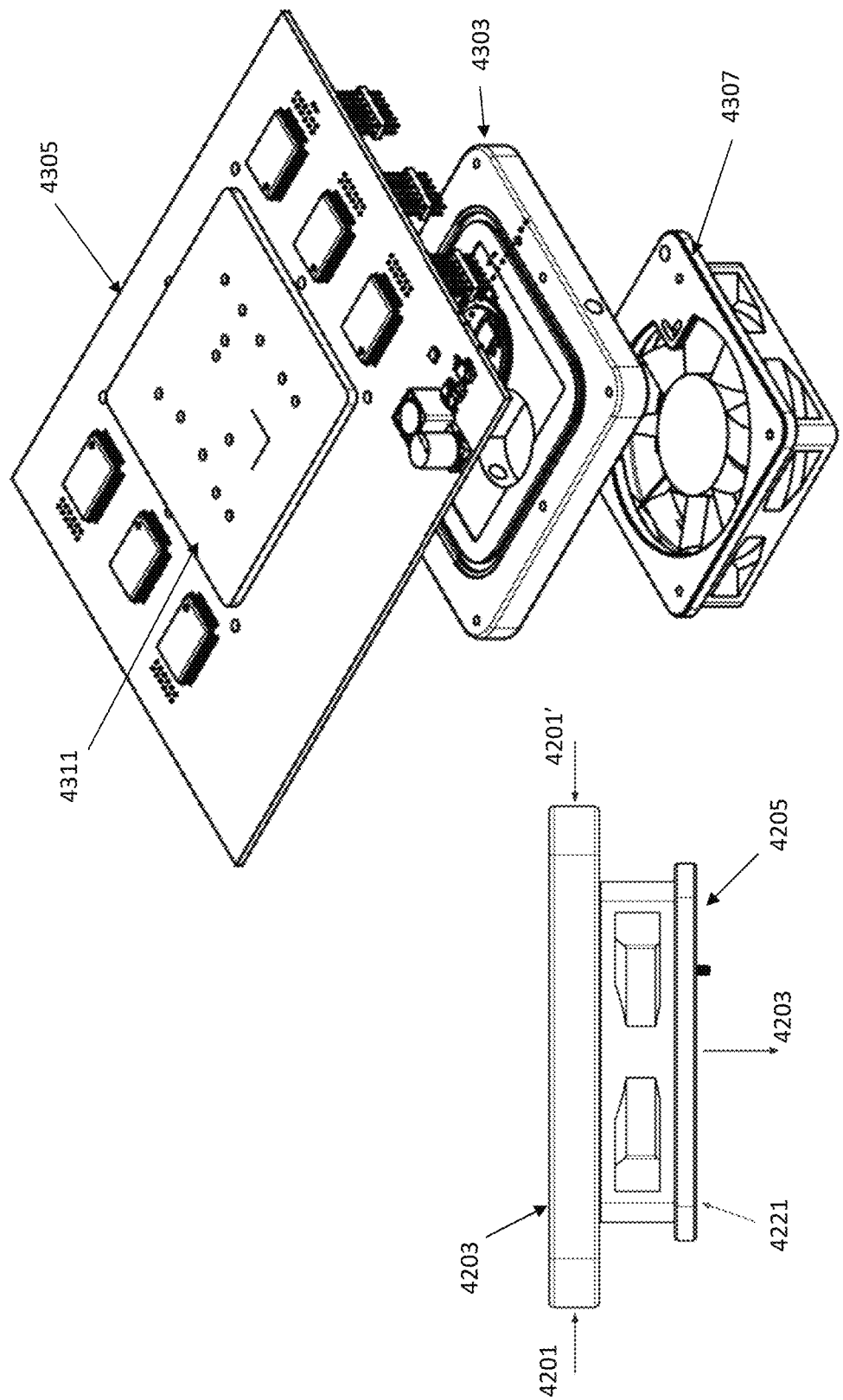

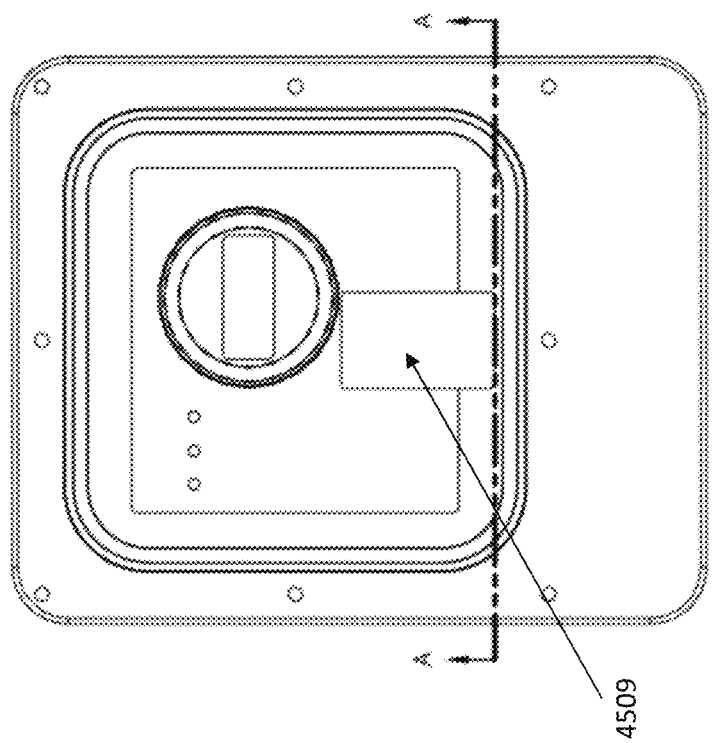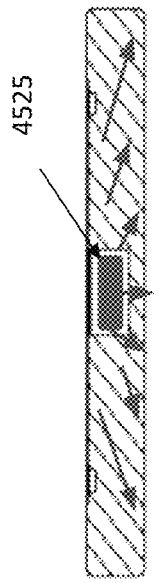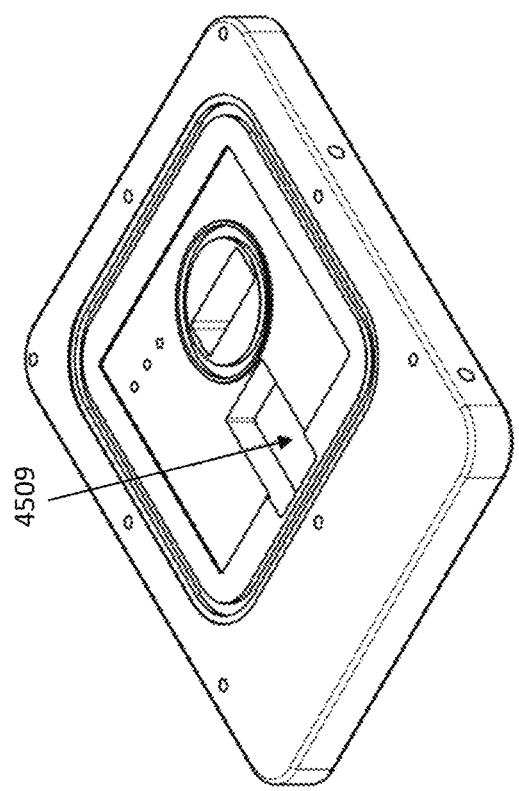

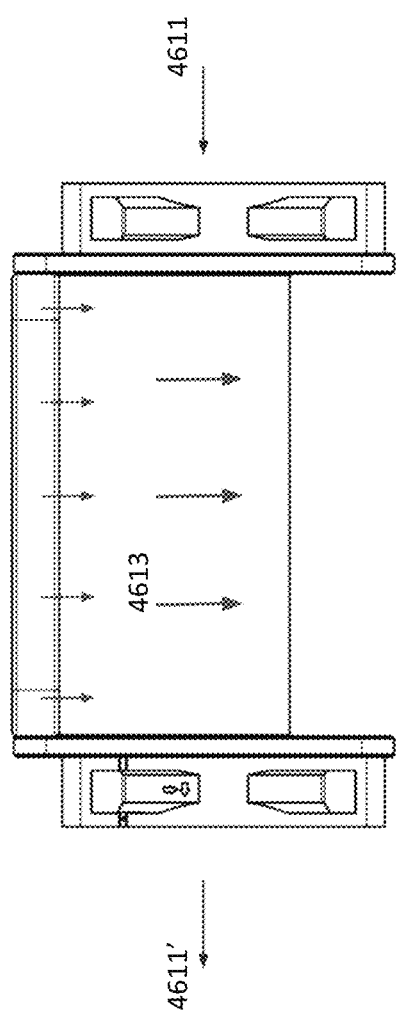
FIG. 46
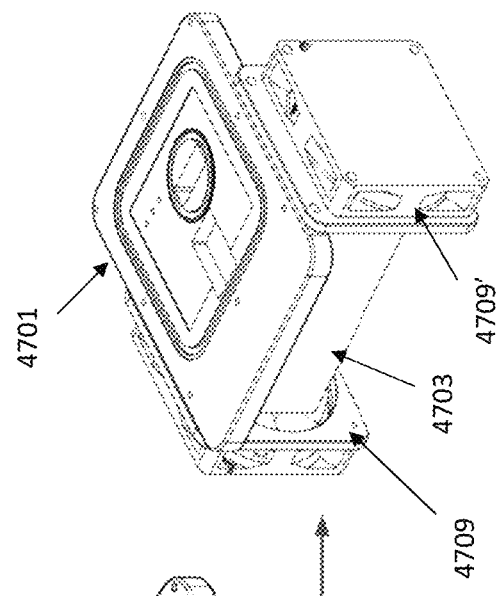
FIG. 47C
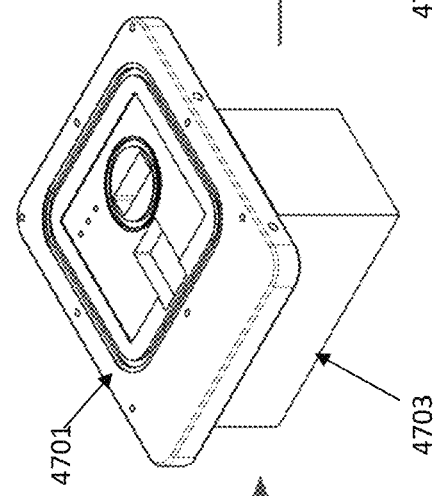
FIG. 47B
FIG. 47A

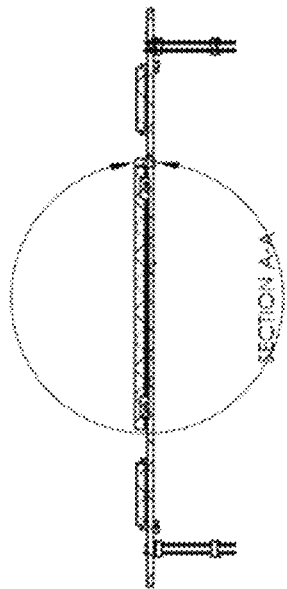
FIG. 52B
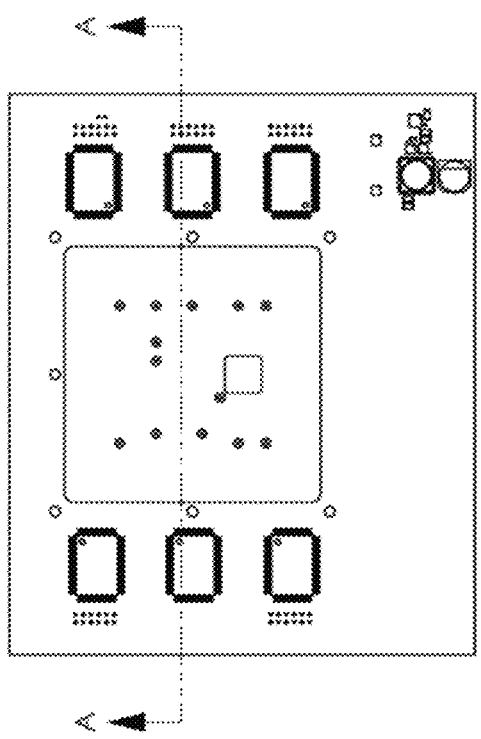
FIG. 52A
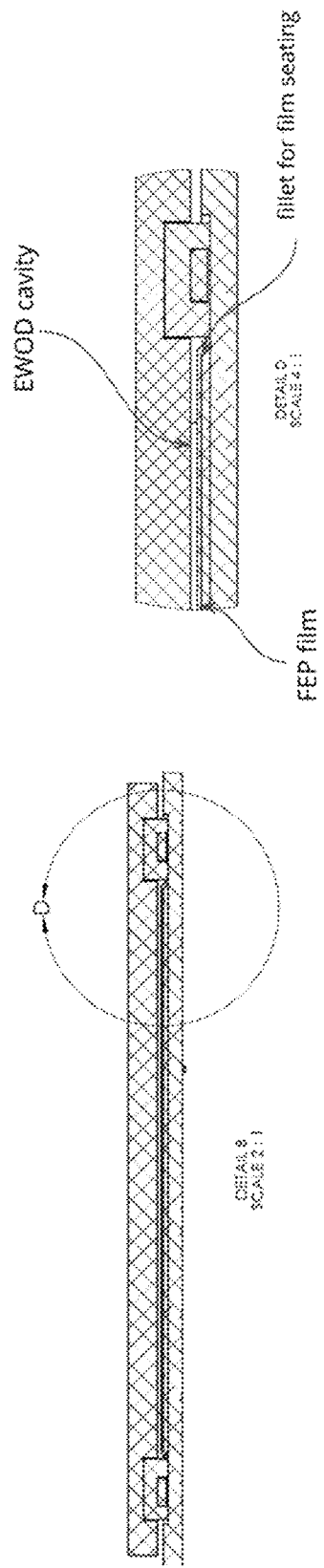
FIG. 52D
FIG. 52C

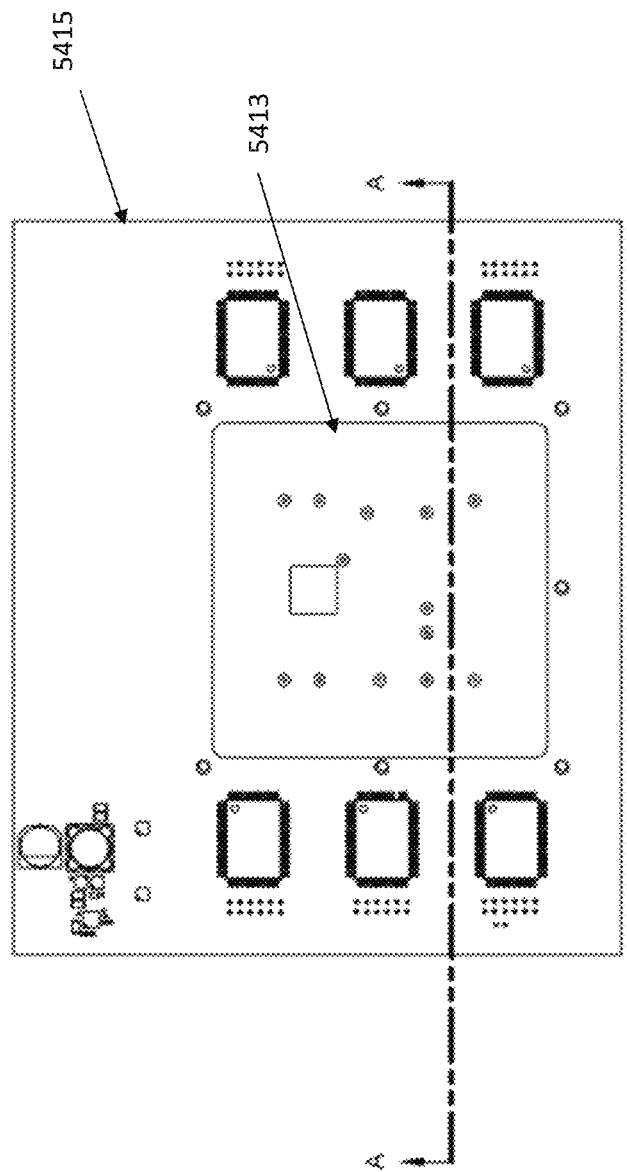
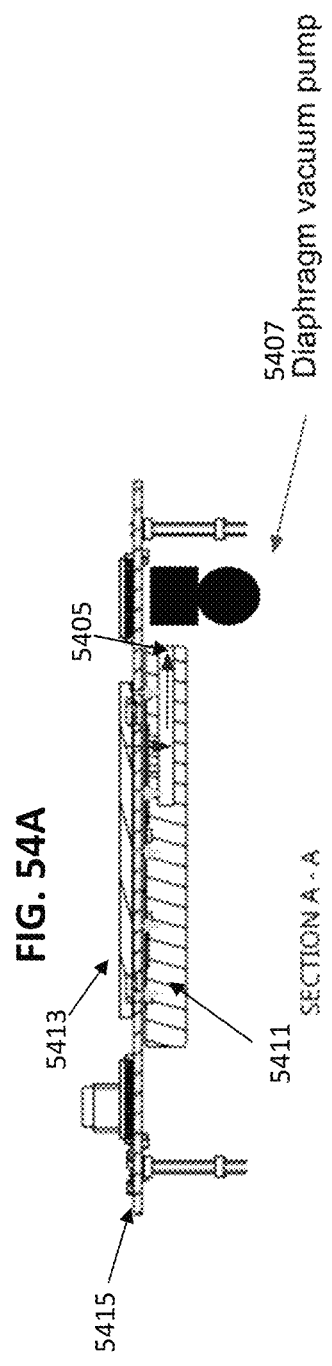
FIG. 54A
FIG. 54B

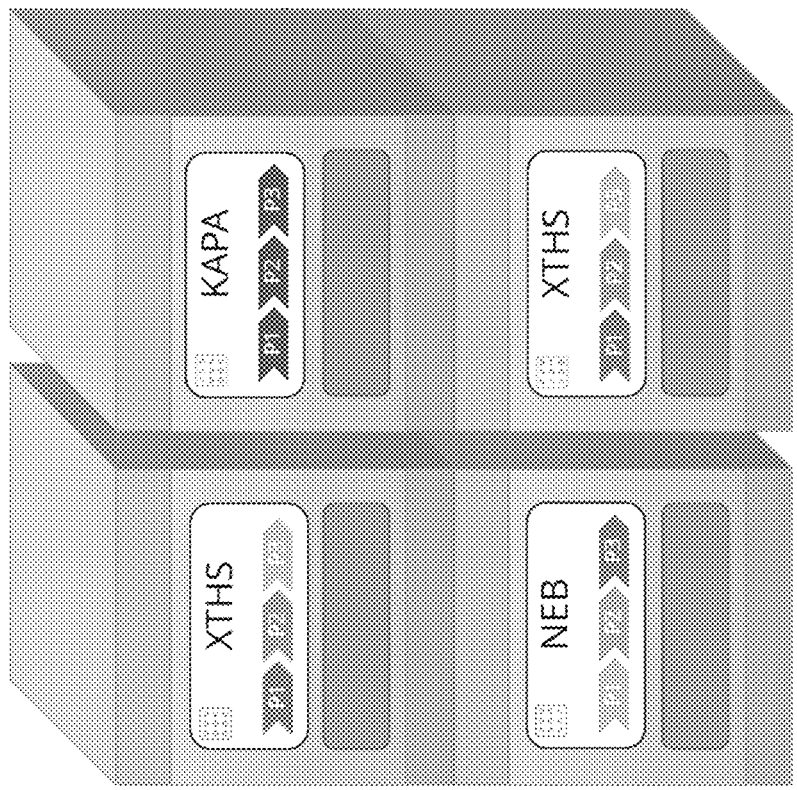
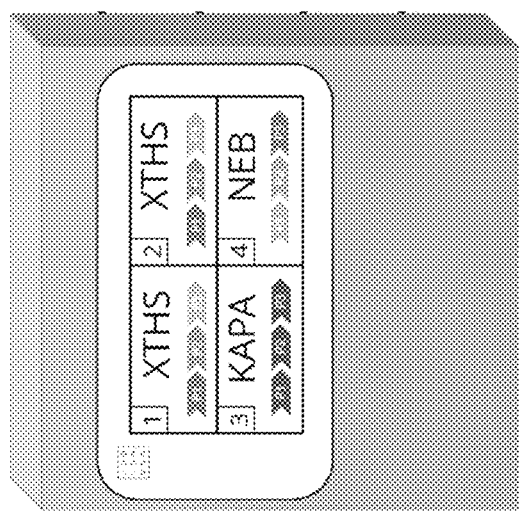
FIG. 56

DIGITAL MICROFLUIDICS DEVICES AND METHODS OF USING THEM

CROSS REFERENCE TO RELATED APPLICATIONS

This application is a continuation of International Patent Application No. PCT/US2018/049415, filed Sep. 4, 2018, titled "DIGITAL MICROFLUIDICS DEVICES AND METHODS OF USING THEM," which claims priority to U.S. Provisional Patent Application No. 62/553,743, filed on Sep. 1, 2017 (titled "DIGITAL MICROFLUIDICS DEVICES AND METHODS OF USING THEM"), and U.S. Provisional Patent Application No. 62/557,714, filed on Sep. 12, 2017 (titled "DIGITAL MICROFLUIDICS DEVICES AND METHODS OF USING THEM"), each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This application generally relates to digital microfluidic (DMF) apparatuses and methods. In particular, the apparatuses and methods described herein are directed to air-gap DMF apparatuses that include a cartridge including the air matrix and ground electrodes and a durable component including the drive electrodes.

BACKGROUND

In recent years, lab-on-a-chip and biochip devices have drawn much interest in both scientific research applications as well as potentially point-of-care applications because they carry out highly repetitive reaction steps with a small reaction volume, saving both materials and time. While traditional biochip type devices utilize micro- or nano-sized channels and corresponding micropumps, microvalves, and microchannels coupled to the biochip to manipulate the reaction steps, these additional components increase cost and complexity of the microfluidic device.

Digital microfluidics (DMF) has emerged as a powerful preparative technique for a broad range of biological and chemical applications. DMF enables real-time, precise, and highly flexible control over multiple samples and reagents, including solids, liquids, and harsh chemicals, without need for pumps, valves, or complex arrays of tubing. In DMF, discrete droplets of nanoliter to microliter volumes are dispensed from reservoirs onto a planar surface coated with a hydrophobic insulator, where they are manipulated (transported, split, merged, mixed) by applying a series of electrical potentials to an array of electrodes. Complex reaction series can be carried out using DMF alone, or using hybrid systems in which DMF is integrated with channel-based microfluidics. Hybrid systems offer tremendous versatility; in concept, each reaction step can be executed in the microfluidics format that best accommodates it.

For many applications it is most convenient to carry out DMF on an open surface, such that the matrix surrounding the droplets is ambient air. FIGS. 1A-1C illustrates one example of an air-matrix DMF apparatus. FIG. 1A shows an example of an air-matrix DMF apparatus 100. In general, the air-matrix DMF apparatus includes a plurality of unit cells 191 that are adjacent to each other and defined by having a single actuation electrode 106 opposite from a ground electrode 102; each unit cell may any appropriate shape, but may generally have the same approximate surface area. In FIG. 1A, the unit cells are rectangular. The droplets (e.g., reaction droplets) fit within the air gap between the first 153 and second 151 plates (shown in FIGS. 1A-1C as top and bottom plates). The overall air-matrix DMF apparatus may have any appropriate shape, and thickness. FIG. 1B is an enlarged view of a section through a thermal zone of the air-matrix DMF shown in FIG. 1A, showing layers of the DMF device (e.g., layers forming the bottom plate). In general, the DMF device (e.g., bottom plate) includes several layers, which may include layers formed on printed circuit board (PCB) material; these layers may include protective covering layers, insulating layers, and/or support layers (e.g., glass layer, ground electrode layer, hydrophobic layer; hydrophobic layer, dielectric layer, actuation electrode layer, PCB, thermal control layer, etc.). Any of these surfaces may be rigid (e.g., glass, PCB, polymeric materials, etc.). The air-matrix DMF apparatuses described herein also include both sample and reagent reservoirs, as well as a mechanism for replenishing reagents.

In the example shown in FIGS. 1A-1C, a top plate 101, in this case a glass material (although plastic/polymeric materials, including PCB, may be used) provides support and protects the layers beneath from outside particulates as well as providing some amount of insulation for the reaction occurring within the DMF device. The top plate may therefore confine/sandwich a droplet between the plates, which may strengthen the electrical field when compared to an open air-matrix DMF apparatus (without a plate). The upper plate (first plate in this example) may include the ground electrode and may be transparent or translucent; for example, the substrate of the first plate may be formed of glass and/or clear plastic. However, although it is transparent, it may be coated with a conductive material and/or may include a ground electrode adjacent to and beneath the substrate for the DMF circuitry (ground electrode layer 102). In some instances, the ground electrode is a continuous coating; alternatively multiple, e.g., adjacent, ground electrodes may be used. Beneath the grounding electrode layer is a hydrophobic layer 103. The hydrophobic layer 103 acts to reduce the wetting of the surfaces and aids with maintaining the reaction droplet in one cohesive unit.

The second plate, shown as a lower or bottom plate 151 in FIGS. 1A-1C, may include the actuation electrodes defining the unit cells. In this example, as with the first plate, the outermost layer facing the air gap 104 between the plates also includes a hydrophobic layer 103. The material forming the hydrophobic layer may be the same on both plates, or it may be a different hydrophobic material. The air gap 104 provides the space in which the reaction droplet is initially contained within a sample reservoir and moved for running the reaction step or steps as well as for maintaining various reagents for the various reaction steps. Adjacent to the hydrophobic layer 103 on the second plate is a dielectric layer 105 that may increase the capacitance between droplets and electrodes. Adjacent to and beneath the dielectric layer 105 is a PCB layer containing actuation electrodes (actuation electrodes layer 106). The actuation electrodes may form each unit cell. The actuation electrodes may be energized to move the droplets within the DMF device to different regions so that various reaction steps may be carried out under different conditions (e.g., temperature, combining with different reagents, magnetic regions, pump inlet regions, etc.). A support substrate 107 (e.g., PCB) may be adjacent to and beneath (in FIGS. 1B and 1C) the actuation electrode layer 106 to provide support and electrical connection for these components, including the actuation electrodes, traces connecting them (which may be insulated), and/or additional control elements, including the thermal regulator 155 (shown as a TEC), temperature sensors, optical sensor(s), magnets, pumps, etc. One or more controllers 195 for controlling operation of the actuation electrodes and/or controlling the application of replenishing droplets to reaction droplets may be connected but separate from the first 153 and second plates 151, or it may be formed on and/or supported by the second plate. In FIGS. 1A-1C the first plate is shown as a top plate and the second plate is a bottom plate; this orientation may be reversed. A source or reservoir 197 of solvent (replenishing fluid) is also shown connected to an aperture in the second plate by tubing 198.

As mentioned, the air gap 104 provides the space where the reaction steps may occur, providing areas where reagents may be held and may be treated, e.g., by mixing, heating/cooling, combining with reagents (enzymes, labels, etc.). In FIG. 1A the air gap 104 includes a sample reservoir 110 and a series of reagent reservoirs 111. The sample reservoir may further include a sample loading feature for introducing the initial reaction droplet into the DMF device. Sample loading may be loaded from above, from below, or from the side and may be unique based on the needs of the reaction being performed. The sample DMF device shown in FIG. 1A includes six sample reagent reservoirs where each includes an opening or port for introducing each reagent into the respective reservoirs. The number of reagent reservoirs may be variable depending on the reaction being performed. The sample reservoir 110 and the reagent reservoirs 111 are in fluid communication through a reaction zone. The reaction zone 112 is in electrical communication with actuation electrode layer 106 where the actuation electrode layer 106 site beneath the reaction zone 112.

The actuation electrodes 106 are depicted in FIG. 1A as a grid or unit cells. In other examples, the actuation electrodes may be in an entirely different pattern or arrangement based on the needs of the reaction. The actuation electrodes are configured to move droplets from one region to another region or regions of the DMF device. The motion and to some degree the shape of the droplets may be controlled by switching the voltage of the actuation electrodes. One or more droplets may be moved along the path of actuation electrodes by sequentially energizing and de-energizing the electrodes in a controlled manner. In the example of the DMF apparatus shown, a hundred actuation electrodes (forming approximately a hundred unit cells) are connected with the seven reservoirs (one sample and six reagent reservoirs). Actuation electrodes may be fabricated from any appropriate conductive material, such as copper, nickel, gold, or a combination thereof.

In the example device shown in FIGS. 1A-1C, the DMF apparatus is typically integrated so that the electrodes (e.g., actuation electrodes and ground electrode(s)) are part of the same structure that may be loaded with sample and/or fluid. The electrode may be part of a cartridge, which may be removable. Although cartridges have been described (see, e.g., US20130134040), such cartridges have proven difficult to use, particularly when imaging through the device and when operating in an air-matrix apparatus.

It would be highly advantageous to have an air-matrix DMF apparatus, including a cartridge that is easy to use, and may be reliably and inexpensively made. Described herein are methods and apparatuses, including systems and devices, that may address these issues.

SUMMARY OF THE DISCLOSURE

Described herein are digital microfluidic (DMF) methods and apparatuses (including devices, systems, cartridges, DMF readers, etc.). Although the methods and apparatuses described herein may be specifically adapted for air matrix DMF apparatuses (also referred to herein as air gap DMF apparatuses), these methods and apparatus may be configured for use in other DMF apparatuses (e.g., oil gap, etc.). The methods and apparatuses described herein may be used to handle relatively larger volumes that have been possible with traditional DMF apparatuses, in part because the separation between the plates forming the air gap of the DMF apparatus may be larger (e.g., greater than 280 micrometers, 300 micrometers or more, 350 micrometers or more, 400 micrometers or more, 500 micrometers or more, 700 micrometers or more, 1 mm or more, etc.). In addition, any of the apparatuses and methods described herein may be configured to include a disposable cartridge that has the dielectric layer forming the bottom of the cartridge; the driving electrodes do not have to be a part of the cartridge; theses apparatuses may be adapted to allow the dielectric to be securely held to the electrodes during operation, which has proven very challenging, particularly when the dielectric layer is slightly flexible.

Any of the methods and apparatuses described herein may include a cartridge in which the ground electrode is included as part of the cartridge. In some variations, the ground electrode may be formed into a grid pattern forming a plurality of cells. The grid pattern may result in clear windows allowing visualization through the ground electrode even when a non-transparent ground electrode (e.g., an opaque or translucent material, such as a metallic coating including, for example, a silver conductive ink) is used to form the ground electrode. The grid pattern may mirror the arrangement of the driving electrodes in the DMF apparatus onto which the cartridge may be placed. For example, the grid pattern cover the spaces between adjacent electrodes when the ground electrode is adjacent to the drive electrodes across the air gap. Alternatively, the ground electrode may be formed of a material that is transparent or sufficiently transparent so that it may be imaged through. In some variations the ground electrode is a conductive coating. The ground electrode may electrically continuous (e.g., electrically contiguous) but may include one or more openings, e.g., through which a droplet within the air gap may be visualized. Thus, in any of these variations the upper plate of the cartridge may be transparent or sufficiently transparent to be visualized through, at least in one or more regions.

For example, a cartridge for a digital microfluidics (DMF) apparatus may have a bottom and a top, and may include: a sheet of dielectric material having a first side and a second side, the first side forming an exposed bottom surface on the bottom of the cartridge, wherein at least the second side of the sheet of dielectric material comprises a first hydrophobic surface; a top plate having first side and a second side; a ground electrode on first side of the top plate. The ground electrode may comprise a grid pattern forming a plurality of open cells. The cartridge may also include a second hydrophobic surface on the first side of the top plate covering the ground electrode; and an air gap separating the first hydrophobic layer and the second hydrophobic layer, wherein the air gap comprises a separation of greater than 280 micrometers.

In any of the cartridges described herein the top plate may include a plurality of cavities within the thickness of the top plate; these cavities may be closed (e.g., sealed) and/or filled with a thermally insulating material having a low thermal mass and low thermal conductivity. In some variations the insulating material comprises air. The cavities may be positioned over the air gap regions that will correspond to heating and/or cooling regions (e.g., thermally controlled regions); the lower thermal mass in these regions may allow for significantly more rapid heating/cooling of a droplet in the air gap under the cavity/cavities. The thickness of the top plate in these regions may therefore include the cavity; the cavity bottom (corresponding to the bottom surface of the top plate) may be less than 1 mm thick (e.g., less than 0.9 mm, 0.8 mm, 0.7 mm, 0.6 mm, 0.5 mm, 0.4 mm, 0.3 mm, 0.2 mm, 0.1 mm, 90 microns, 80 microns, 70 microns, 60 microns, 50 microns, 40 microns, 30 microns, etc.). The cavity bottom may preferably be as thin as possible while providing structural support for the electrode and any dielectric coating on the bottom surface of the top plate. The cavity upper surface may be substantially thicker (e.g., 1.5×, 2×, 3×, 4×, 5×, etc.) than the cavity bottom surface.

The dielectric material forming the bottom surface may be made hydrophobic (e.g., by coating, including dip-coating, etc., impregnating with a hydrophobic material, etc.) and/or it may itself be hydrophobic. For example, the bottom surface (e.g., the bottom surface of a cartridge) may be formed of a film that is both a dielectric and a hydrophobic material. For example, the bottom surface may be a Teflon film (which may include an adhesive or an adhesive portion, such as a Teflon tape) that is both hydrophobic and acts as a dielectric. Other films may include plastic paraffin films (e.g., "Parafilm" such as PARAFILM M). However, in particular, films (such as Teflon films) that are able to withstand a high temperature (e.g., 100 degrees C. and above) are preferred.

A cartridge for a digital microfluidics (DMF) apparatus may generally include a bottom and a top, and may include: a sheet of dielectric material having a first side and a second side, the first side forming an exposed bottom surface on the bottom of the cartridge; a first hydrophobic layer on the second side of the sheet of dielectric material; a top plate having first side and a second side; a ground electrode on first side of the top plate, wherein the ground electrode comprises a grid pattern forming a plurality of open cells; a second hydrophobic layer on the first side of the top plate covering the ground electrode; and an air gap separating the first hydrophobic layer and the second hydrophobic layer, wherein the air gap comprises a separation of greater than 280 micrometers (e.g., greater than 300 micrometers, greater than 400 micrometers, etc.).

The term "cartridge" may refer to a container forming the air gap, and may be inserted into a DMF reading/driving apparatus. The cartridge may be disposable (e.g., single use or limited use). The cartridge may be configured to allow visualization of fluid (droplets) in the air gap. The grid pattern may be particularly useful to allow visualization while still providing the appropriate ground reference to the driving electrode(s). The entire grid may be electrically coupled to form single return (ground) electrode, or multiple ground electrodes may be positioned (via separate and/or adjacent grids) on the top plate.

As mentioned, the grid pattern of the ground electrodes is formed of a non-transparent material.

As used herein the term "grid" may refer to a pattern of repeating open cells ("windows") of any appropriate shape and size, in which the border forming the open cells are formed by an integrated (and electrically continuous) material, such as a conductive ink, metal coating, etc. A grid as used herein is not limited to a network of lines that cross each other to form a series of squares or rectangles; the grid pattern may be formed by forming openings into an otherwise continuous plane of conductive material forming the ground electrode.

Thus, in general, the grid pattern of the ground electrodes may be formed of a conductive ink. For example, the grid pattern of the ground electrodes may be formed of silver nanoparticles. The grid pattern may be printed, screened, sprayed, or otherwise layered onto the top plate.

In general, the borders between the open cells forming the grid pattern may have a minimum width. For example, the minimum width of the grid pattern between the open cells may 50 micrometers or greater (e.g., 0.1 mm or greater, 0.2 mm or greater, 0.3 mm or greater, 0.4 mm or greater, 0.5 mm or greater, 0.6 mm or greater, 0.7 mm or greater, 0.8 mm or greater, 0.9 mm or greater, 1 mm or greater, etc.). As mentioned, the open cells (e.g., "windows") formed by the grid pattern may be any shape, including quadrilateral shapes (e.g., square, rectangular, etc.) or elliptical shapes (e.g., oval, circular, etc.) and/or other shapes (+ shapes, H-shapes, etc.).

In general, the grid pattern of the ground electrode may extend over the majority of the top plate (and/or the majority of the cartridge). For example, the grid pattern of the ground electrode may extend over 50% or more of the first side of the top plate (e.g., 55% or more, 60% or more, 65% or more, 70% or more, 80% or more, 90% or more, etc.).

In any of the cartridges described herein, the sheet of dielectric material may be flexible. This flexibility may be helpful for securing the dielectric to the drive electrodes to ensure complete contact between the dielectric and the drive electrode(s). Typically, the sheet of dielectric material may be sufficiently compliant so that it may bend or flex under a relatively low force (e.g., 50 kPa of pressure or more). The sheet of dielectric may be any appropriate thickness; for example, the sheet may be less than 30 microns thick (e.g., less than 20 microns thick, etc.).

As will be described in greater detail below, any of these apparatuses may include a microfluidics channel formed in the second side of the top plate, wherein the microfluidics channel extends along the second side of the top plate and at least one opening between the microfluidics channel and the air gap.

The top plate may be formed of any appropriate material, including in particular, clear or transparent materials, (e.g., an acrylic, etc.).

For example, a cartridge for a digital microfluidics (DMF) apparatus may include: a flexible sheet of dielectric material having a first side and a second side, the first side forming an exposed bottom surface on the bottom of the cartridge; a first hydrophobic layer on the second side of the sheet of dielectric material; a top plate having first side and a second side; a ground electrode on first side of the top plate, wherein the ground electrode comprises a grid pattern formed of a non-transparent material forming a plurality of open cells along the first side of the top plate; a second hydrophobic layer on the first side of the top plate covering the ground electrode; and an air gap separating the first hydrophobic layer and the second hydrophobic layer, wherein the air gap comprises a separation of greater than 280 micrometers (e.g., 300 micrometers or more, 400 micrometers or more, etc.). Typically, the cartridge has a bottom and a top.

As mentioned, also described herein are cartridges in which microfluidics channels are integrated into the DMF components, including in particular the top plate of the DMF apparatus. Applicants have found that integrating one or more microfluidics channels into the top plate may permit the cartridge to be more compact, as well as allow a higher degree of control and manipulation of processes within the air gap that are otherwise being controlled by the electrowetting of the DMF system.

For example, a cartridge for a digital microfluidics (DMF) apparatus (the cartridge having a bottom and a top) may include: a sheet of dielectric material having a first side and a second side, the first side forming an exposed bottom surface on the bottom of the cartridge; a first hydrophobic layer on the second side of the sheet of dielectric material; a top plate having first side and a second side; a ground electrode on first side of the top plate; a second hydrophobic layer on the first side of the top plate covering the ground electrode; an air gap separating the first hydrophobic layer and the second hydrophobic layer; a microfluidics channel formed in the second side of the top plate, wherein the microfluidics channel extends along the second side of the top plate; an opening between the microfluidics channel and the air gap; and a cover covering the microfluidics channel, wherein the cover includes one or more access ports for accessing the microfluidics channel.

As mentioned, the sheet of dielectric material may be flexible, and may form the bottom-most surface of the cartridge. The sheet may generally be flat (planar) through it may be flexible. The outer surface may be protected with a removable (e.g., peel-off) cover. The dielectric properties may be those generally consistent with a DMF (and particularly an air-matrix DMF) apparatus. The dielectric may be coated on the inner (second) side with the first hydrophobic layer. The hydrophobic layer may be a coating of a hydrophobic material that is relatively inert (e.g., non-reactive with the aqueous droplets that are moved in the air gap).

The top plate may be planar and may be coextensive (or larger) than the bottom dielectric material. The top plate may be any appropriate thickness, and in particular, may be sufficiently thick so that the microfluidic channel may be carved into the second side of the top plate. The ground electrode may be formed on all or some of the first side of the top plate, as mentioned above, and a second hydrophobic layer may be coated over the ground electrode and/or top plate (particularly where open windows through the ground plate expose the top plate). In any of these examples, the thickness of the electrode coating may be minimal, so that the electrodes may be considered flush with the top plate bottom (first) side of the top plate.

In any of the apparatuses and methods described herein, the air gap separating the first hydrophobic layer and the second hydrophobic layer (e.g., between the dielectric and the top plate) may be relatively large, compared to traditional DMF air-gap systems (e.g., >280, 400 micrometers or more, 500 micrometers or more, 1 mm or more, etc.).

The microfluidics channel formed in the second side of the top plate typically extends through the top plate along the second side of the top plate and an access opening between the microfluidics channel and the air gap may be formed between the microfluidics channel and the air gap, into the top plate. Any of the apparatuses described herein may also include a cover covering the microfluidics channel. The cover may be formed of any appropriate material, including acrylic. The cover may include one or more ports or openings into the microfluidics channel and/or into the air gap.

The microfluidics channel may be configured to contain any appropriate amount of fluid, which may be useful for mixing, adding, removing or otherwise interacting with droplets in the air gap. For example, the microfluidics channel may be configured to hold 0.2 milliliters or more of fluid (e.g., 0.3 ml or more, 0.4 ml or more, 0.5 ml or more, 0.6 ml or more, 0.7 ml or more, 0.8 ml or more 0.9 ml or more, 1 ml or more of fluid, 1.5 ml or more, 2 ml or more, 3 ml or more, 4 ml or more, 5 ml or more, 6 ml or more, 7 ml or more, 8 ml or more, 9 ml or more, 10 ml or more, etc.) within the microfluidics channel. The microfluidics channel may connect to one or more reservoirs (e.g., waste reservoir, storage reservoir, etc.) and/or may connect to one or more additional microfluidics channels.

For example, the microfluidics channel may comprise a first microfluidics channel and the opening between the microfluidics channel and the air gap may comprise a first opening; the apparatus may further include a second microfluidics channel formed in the second side of the top plate, wherein the second microfluidics channel extends along the second side of the top plate, and a second opening between the second microfluidics channel and the air gap, wherein the first and second openings are adjacent to each other. The first and second openings may be a minimum distance apart, which may allow the formation of a "bridging droplet" in the air gap having a minimum size. For example, the first and second openings may be within about 2 cm of each other on the surface of the top plate (e.g., within about 1 cm or each other, within about 9 mm or each other, within about 8 mm of each other, within about 7 mm of each other, within about 6 mm of each other, within about 5 mm of each other, within about 4 mm of each other, within about 3 mm or each other, within about 2 mm of each other, within about 1 mm of each other, etc.).

Any of these cartridge may also include a window from the top of the cartridge to the air gap through which the air gap is visible. This may allow imaging into the air gap. This imaging may be used to detect output (e.g., reaction outputs, such as binding, colorimetric assays, RT-PCR, etc.). The window may be any appropriate size; for example, the window may form between 2 and 50% of the top of the cartridge. The window may be on one side of the cartridge and/or at one end of the cartridge. Multiple imaging windows may be used.

As mentioned, the bottom of the cartridge is formed by the first side of the sheet of dielectric material. The top of the cartridge may include a plurality of openings into the air gap.

In general, the cartridge may include one or more reagent reservoirs on the second side of the top plate. For example, the cartridge, in either a reservoir or within the air gap, may include one or more reagents, including in particular lyophilized (e.g., "freeze dried") reagents. For example, the cartridge may include one or more freeze-dried reagent reservoirs on the second side of the top plate.

For example, a cartridge (having a bottom and a top) for a digital microfluidics (DMF) apparatus may include: a sheet of dielectric material having a first side and a second side, the first side forming an exposed bottom surface on the bottom of the cartridge; a first hydrophobic layer on the second side of the sheet of dielectric material; a top plate having first side and a second side; a ground electrode on first side of the top plate; a second hydrophobic layer on the first side of the top plate covering the ground electrode; an air gap separating the first hydrophobic layer and the second hydrophobic layer, wherein the air gap comprises a separation of greater than 500 micrometers; a first microfluidics channel and a second microfluidics channel, wherein the first and second microfluidics channels are formed in the second side of the top plate, wherein the first and second microfluidics channels extend along the second side of the top plate; a first opening between the first microfluidics channel and the air gap and a second opening between the second microfluidics channel and the air gap, wherein the first and second openings are adjacent to each other within about 2 cm; and a cover covering the microfluidics channel, wherein the cover includes one or more access ports for accessing the microfluidics channel.

Also described herein are DMF reader apparatuses for use with any of the cartridges described herein. For example, the DMF reader apparatuses (devices) may be configured to apply a vacuum across the dielectric bottom surface of a cartridge so that the electrodes are in uniformly intimate contact with the dielectric forming each of the unit cells form moving a droplet of fluid within the air gap. The applicant have surprisingly found that simply adhesively securing the dielectric material to the electrodes is not sufficient, as it result in un-equal contact and variations in the power required to move droplets as well as inefficiencies in droplet movement, control and consistency. Further, the use of vacuum, even in combination with an adhesive, has similar problems, particularly when the dielectric is flexible. Described herein are apparatuses and methods of using them in which a vacuum is used to secure the dielectric bottom of a cartridge through a plurality of openings within the drive electrodes themselves, or surrounding/immediately adjacent to the drive electrodes. In variations in which the vacuum is applied through all or the some of the drive electrodes (e.g., spaced in a pattern on the seating surface, e.g., at the corners), the dielectric is consistently held onto the drive electrodes in a uniform manner, even when using a relatively low negative pressure for the vacuum. This configuration may also allow the formation of partitions or barriers within the cartridge by including protrusions on the cartridge-holding surface (onto which the cartridge is held)

For example, described herein are digital microfluidics (DMF) reader device configured to operate with a disposable cartridge having a bottom dielectric surface, a top plate with a ground electrode, and an air gap between the bottom dielectric and the top plate, the device comprising: a seating surface for seating the disposable cartridge; a plurality of drive electrodes on the seating surface, wherein each drive electrode comprises an opening therethrough; a vacuum pump for applying a vacuum to the vacuum ports; and a control for applying energy to sequentially activate and de-activate one or more selected drive electrodes to move a droplet within the air gap of the cartridge along a desired path within the air gap, wherein the DMF reader is configured to apply the vacuum to the vacuum manifold to secure each drive electrode to the bottom dielectric of the disposable cartridge when the disposable cartridge is placed on the seating surface.

In some variations, the apparatus includes a vacuum manifold that couples the vacuum pump to a plurality of vacuum ports for applying a vacuum.

The DMF reader devices described herein may be configured to operate with any of the cartridges described herein, and may be adapted for use with such cartridges. However, it should be understood that the cartridge is not a necessary part of the DMF reader apparatus. In general, these apparatuses may operate with a cartridge (e.g., a reusable or disposable cartridge) that has a bottom dielectric surface, a top plate with a ground electrode, and a gap (e.g., typically but not necessarily an air gap) between the bottom dielectric and the top plate.

The DMF apparatus may also generally include a seating surface for seating the disposable cartridge. The seating surface may include the drive electrodes, which may be flush or substantially flush with the seating surface, and/or any protrusions that may be used to form a partition within the gap region (e.g., air gap) of the cartridge by predictably deforming the dielectric into the gap region. The plurality of drive electrodes on the seating surface may be formed on the seating surface or milled into the seating surface. For example, the seating surface may be a substrate such as a printed circuit board (e.g., an electrically insulating surface), onto which the drive electrodes are attached or formed.

In general, as mentioned above, all or a majority of the drive electrodes in the electrode array, e.g., >50%, >60%, >70%, >80%, >90%, >95%, etc.) may include an opening that passes through the drive electrode and connects to the vacuum source. The vacuum source may be a vacuum manifold that connects these openings through the drive electrodes to a source of vacuum, such as a vacuum pump that is part of the apparatus, or a separate vacuum pump that is connected (e.g., wall vacuum) to the apparatus. The openings through the electrodes may be the same sizes, and they may be located anywhere on/through the drive electrodes. For example, they may pass through the centers of the drive electrodes, and/or through an edge region of the drive electrodes, etc. The openings may be any shape (e.g., round, oval, square, etc.). In some variations the size of the openings may be about 1 mm in diameter (e.g., 1.2 mm diameter, 1.1 mm diameter, 1.0 mm diameter, 0.9 mm diameter, 0.8 mm dieter, etc.).

Typically, the vacuum manifold may be coupled to and/or may include a plurality of vacuum ports that each couple to one (or in some variations, more than one) of the openings in the drive electrodes. The vacuum manifold may be located beneath the seating surface. For example, a vacuum manifold may be tubing or other channels beneath the seating surface that connects to the openings in the drive electrodes.

The DMF apparatuses described herein typically include a controller for coordinating and driving the electrodes. This controller may include one or more processors, memory, and any other circuitry necessary or useful for operating the device, including coordinating the application of energy to activate/inactivate the drive electrodes, the pump(s) for vacuum and/or microfluidic control, one or more valves (e.g., for microfluidic control, vacuum control), temperature control (e.g., resistive heater, Peltier cooling, etc.) the motor (s) (e.g., for driving opening and closing the device door, the optics, etc.), one or more displays, etc.

As mentioned, any of these devices may include one or more projections extending from the seating surface, wherein the one or more projections are configured to form partitions in the air of the cartridge when the vacuum is applied through the openings in the drive electrodes.

Any of these apparatuses may include an optical reader configured to detect an optical signal from a cartridge seated on the seating surface. The optical reader may be movable or fixed. The optical reader may be used to detect (e.g., sense) a feed or change due to one or more interactions (e.g., binding, enzymatic reactions, etc.) in the droplet. The optical reader can be configured to detect an optical signal from a cartridge seated on the seating surface. Thus, the optical sensor(s) may provide a detection of a readout from the apparatus. Any of these device may include one or more motors, e.g., configured to move the optical reader.

The apparatus may also include one or more temperature sensors (e.g., thermistors, etc.). For example, the device may include one or more temperature sensors coupled to the seating surface. In some variations the thermistor may project from the seating surface and form a barrier or chamber within the air gap of the cartridge. Alternatively or additionally, the one or more temperature sensors may be within the substrate of the seating surface and in thermal contact with the seating surface, e.g., via a thermally conductive material, such as copper.

As mentioned, the devices described herein may include one or more heaters, including in particular resistive heaters. For example, the device may include a resistive heater underlying (or overlying) at least some of the drive electrodes; this may allow for temperature-regulated sub-regions of the apparatus. The entire driving electrode surface may also be cooled (e.g., by circulation of a cooling fluid) to slightly below room temperature (e.g., between 15 degrees C. and 25 degrees C., between 15 degrees C. and 22 degrees C., between 15 degrees C. and 20 degrees C., between 15 degrees C. and 18 degrees C., etc.).

The apparatus may also include one or more magnets above or underneath one or more of the drive electrodes configured to be activated to apply a magnetic field. Thus, magnetic beads may be used for binding material or other reactions within the DMF apparatus, and the magnetic beads may be selectively held within one or more regions of the device. For example, one or more neodymium magnets may be used, e.g., by moving the magnet closer or farther from the cartridge to hold magnetic particles in position (e.g., moving it up towards the electrodes by 3 mm, 4 mm, 5 mm, 6 mm, 7 mm, 8 mm, etc.). An electromagnet may be selectively activated or deactivated to hold/release magnetic particles.

Any of the apparatuses described herein may also include one or more Peltier coolers underlying at least some of the drive electrodes configured to cool to 10 degrees C. or less (e.g., 5 degrees C. or less, 7 degrees C. or less, 11 degrees C. or less, 12 degrees C. or less, 15 degrees C. or less, 20 degrees C. or less, etc.).

In addition to the seating surface, any of these DMF reader apparatuses may also include one or more cartridge trays into which the cartridge may be loaded, so that it can automatically be moved into position within the apparatus. For example, any of these apparatuses may include a cartridge tray for holding a cartridge in a predetermined orientation (which may be fixed by the shape of the cartridge and the receiving tray being complementary); the cartridge tray may be configured to move the disposable cartridge onto the seating surface. Once on the seating surface, the vacuum may be applied to lock it into position. In addition, connections may be made from the top of the cartridge to one or more microfluidics ports, e.g., for applying positive and/or negative pressure (e.g., vacuum) to drive fluid within a microfluidic channel on the top of the cartridge and/or into/out of the gap (e.g., air gap) region within the cartridge.

In general, any of these devices may include an outer housing, a front panel display, and one or more inputs (such as a touchscreen display, dial, button, slider, etc.), and/or a power switch. The apparatus may be configured to be stackable, and/or may be configured to operate in conjunction with a one or more other DMF apparatuses. In some variations, a single housing may enclose multiple cartridge seating surfaces, each having a separately addressable/controllable (by a single or multiple controllers) drive electrode arrays, allowing parallel processing of multiple cartridges; in these variations, all of some of the components (pumps, motors, optical sub-systems, controller(s), etc.) may be shared between the different cartridge seating surfaces.

Any of these devices may include an output configured to output signals detected by the device. The output may be on one or more displays/screens, and/or they may be electronic outputs transmitted to a memory or remote processor for storage/processing and/or display. For example, any of these apparatuses may include a wireless output.

As mentioned, any of the DMF apparatuses described herein may also include one or more microfluidic vacuum ports positioned above the seating surface and configured to engage with an access ports for accessing a microfluidics channel of the cartridge when the cartridge is seated on the seating surface.

For example, a digital microfluidics (DMF) reader device configured to operate with a disposable cartridge having a bottom dielectric surface, a top plate with a ground electrode, and an air gap between the bottom dielectric and the top plate, may include: a seating surface for seating the disposable cartridge; a plurality of drive electrodes on the seating surface, wherein each drive electrode comprises an opening therethrough; a plurality of vacuum ports, wherein each vacuum port is coupled to one or more of the openings in the drive electrodes; a vacuum pump for applying a vacuum to the vacuum ports; one or more projections extending from the seating surface; and a control for applying energy to sequentially activate and de-activate one or more selected drive electrodes to move a droplet within the air gap of the cartridge along a desired path within the air gap, wherein the DMF reader is configured to apply the vacuum to the vacuum ports to secure each drive electrode to the bottom dielectric of the disposable cartridge so that the one or more projections partition the air gap when the disposable cartridge is placed on the seating surface.

Also described herein are methods of preventing or reducing evaporation in any of these apparatuses. For example, described herein are methods of preventing droplet evaporation within an air-matrix digital microfluidic (DMF) apparatus, the method comprising: introducing an aqueous reaction droplet into an air gap of the air-matrix DMF apparatus which is formed between a first plate and a second plate of the air-matrix DMF apparatus; sequentially energizing driving electrodes on or in the first plate to move the aqueous reaction droplet within the air gap of the air-matrix DMF apparatus so that it combines with a droplet of nonpolar fluid within the air gap of the air-matrix DMF apparatus, forming a coated reaction droplet in which that the nonpolar fluid coats the aqueous reaction droplet and protects the reaction droplet from evaporation; and sequentially energizing the driving electrodes to move the coated reaction droplet within the air gap of the air-matrix DMF apparatus.

The volume of the nonpolar fluid may be less than the volume of the aqueous reaction droplet. Any of these methods may include combining, within the air gap of the air-matrix DMF apparatus, the coated droplet with one or more additional aqueous droplets. Any of these methods may also include removing the coating of nonpolar fluid by at least partially withdrawing the coated droplet out of the air gap of the air-matrix DMF apparatus into a microfluidic channel. The method may also include adding the droplet of nonpolar fluid into the air gap of the air-matrix DMF apparatus through an opening in the first or second plate. Generally, the droplet of nonpolar fluid may be liquid at between 10 degrees C. and 100 degrees C.

For example, a method of preventing droplet evaporation within an air-matrix digital microfluidic (DMF) apparatus may include: introducing an aqueous reaction droplet into an air gap of the air-matrix DMF apparatus which is formed between a first plate and a second plate of the air-matrix DMF apparatus; sequentially energizing driving electrodes on or in the first plate to move the aqueous reaction droplet within the air gap of the air-matrix DMF apparatus so that it combines with a droplet of nonpolar fluid within the air gap of the air-matrix DMF apparatus (although in some variations the nonpolar fluid may be combined with a sample prior to being loaded into the air gap), forming a coated reaction droplet in which that the nonpolar fluid coats the aqueous reaction droplet and protects the reaction droplet from evaporation, wherein the nonpolar fluid is liquid at between 10 degrees C. and 100 degrees C., further wherein the volume of the nonpolar fluid is less than the volume of the aqueous reaction droplet; and sequentially energizing the driving electrodes to move the coated reaction droplet within the air gap of the air-matrix DMF apparatus. Although the volume of the nonpolar liquid may be less than the droplet volume, the volume of nonpolar liquid jacketing the droplet may be larger than the volume (up to about 3× the volume) of the droplet.

The methods and apparatuses described herein may be particularly well suited for the use with large-volume droplets and processing. Typically most unit droplets of DMF apparatuses, and particularly air-matrix DMF apparatuses, are limited to about 4 microliters or less of aqueous fluid, and the air gap is limited to less than about 250 or 300 micrometers separation between the driving electrodes and the ground electrode (top and bottom plates of the air gap region). Described herein are methods of operating on larger volumes, in which the separation between the drive electrodes (e.g., bottom plate) and the ground electrodes (e.g., top plate) may be much larger (e.g., between about 280 micrometers and 3 mm, between about 300 micrometers and 3 mm, between about 400 micrometers and 1.5 mm, e.g., between 400 micrometers and 1.2 mm, etc., or 400 micrometers or more, 500 micrometers or more, 1 mm or more, etc.). Thus, the unit droplet size (the droplet on a single unit cell driven by a single drive electrode may be much larger, e.g., 5 microliters or more, 6 microliters or more, 7 microliters or more, 8 microliters or more, 9 microliters or more, 10 microliters or more, 11 microliters or more, 12 microliters or more, 13 microliters or more, 14 microliters or more, 15 microliters or more, etc., e.g., between 5-20 microliters, between 5-15 microliters, between 7 and 20 microliters, between 7 and 15 microliters, etc.).

Dispensing large droplets using electrowetting is routinely done with smaller volume (e.g., less than 5 microliters), however, dispensing larger volumes as a single unit has proven difficult, particularly with a high degree of accuracy and precision. Described herein are methods of dispensing a predetermined volume of liquid using electrowetting. For example, described herein are methods of dispensing a predetermined volume of fluid into an air gap of an air-matrix digital microfluidics (DMF) apparatus, wherein the air gap is greater than 280 micrometers (e.g., 300 micrometers or more, 400 micrometers or more, etc.) wide, further wherein the DMF apparatus comprises a plurality of driving electrodes adjacent to the air gap, the method comprising: flooding a portion of the air gap with the fluid from a port in communication with the air gap; applying energy to activate a first driving electrode adjacent to the portion of the air gap that is flooded; and applying suction to withdraw the fluid back into the port while the first electrode is activated, leaving a droplet of the fluid in the air gap adjacent to the activated first electrode.

Applying energy to activate the first driving electrode may include applying energy to activate one or more driving electrodes that are contiguous with the first driving electrode, and further wherein applying suction to withdraw the fluid back into the port while the first driving electrode is activated comprises withdrawing the fluid while the first driving electrode and the one or more driving electrodes that are contiguous with the first driving electrode are active, leaving a droplet of the fluid in the air gap adjacent to the activated first driving electrode and the one or more driving electrodes that are contiguous with the first driving electrode.

The first driving electrode may be separated from the port by a spacing of at least one driving electrode. Any of these methods may further comprise inactivating one or more driving electrodes adjacent a second portion of the air gap that is within the flooded portion of the air gap, and that is between the port and the first driving electrode. The air gap may be greater than 500 micrometers.

Flooding the portion of the air gap may comprises applying positive pressure to expel fluid from the port. The method may further comprising sequentially energizing driving electrodes adjacent to the air gap to move the droplet within the air gap of the air-matrix DMF apparatus.

Applying suction to withdraw the fluid back into the port while the first electrode is activated may comprise leaving a droplet of the fluid having a volume that is 10 microliters or greater in the air gap adjacent to the activated first electrode.

For example, a method of dispensing a predetermined volume of fluid into an air gap of an air-matrix digital microfluidics (DMF) apparatus, wherein the air gap is greater than 280 micrometers wide (e.g., 300 micrometers or more, 400 micrometers or more, etc.) further wherein the DMF apparatus comprises a plurality of driving electrodes adjacent to the air gap, may include: flooding a portion of the air gap with the fluid from a port in communication with the air gap; applying energy to activate a first driving electrode or a first group of contiguous driving electrodes adjacent to the portion of the air gap that is flooded, wherein the first driving electrode or the first group of contiguous driving electrodes are spaced apart from the port by one or more driving electrodes that are not activated; and applying suction to withdraw the fluid back into the port while the first electrode or first group of contiguous electrodes are activated, leaving a droplet of the fluid in the air gap adjacent to the first electrode or first group of contiguous electrodes.

Also described herein are control systems for DMF apparatuses, such as those described herein. In particular, described herein are control systems including graphical user interfaces for operating any of these apparatuses. These control systems (sub-systems) may include software, hardware and/or firmware. Thus, any of these apparatuses may be configured as instructions stored in a non-transient medium (e.g., memory) for performing any of them methods and procedures described herein.

For example, described herein are methods for controlling a digital microfluidics (DMF) apparatus, the method comprising: providing a graphical user interface comprising a menu of fluid handling control commands, including one or more of: move, heat, remove, cycle, wait, breakoff, mix and dispense; receiving a fluid handling protocol comprising user-selected fluid handling control commands; calculating a path for moving fluid within an air gap of the DMF apparatus based on the fluid handling protocol, wherein the path minimizes the amount of overlap in the path to avoid contamination; and executing the fluid handling protocol using the DMF apparatus based on the calculated path.

The fluid handling control commands may include at least one of: move, heat, remove, wait, and mix. For example, the fluid handling commands may include all: move, heat, remove, wait, and mix. A user may select icons corresponding to each of these commands, and may enter them in an order and/or may indicate incubation timing and temperature conditions. The apparatus may automatically determine the optimal path within the air-gap region of the cartridge in order to perform each of these steps (e.g., by moving the droplet(s) to the appropriate region of the cartridge including the heater, magnets, microfluidic ports, etc., so that the droplet(s) may be manipulated as required. For example, receiving the fluid handling protocol may comprise receiving a string of fluid handling control commands. Calculating the path may comprise calculating the path based on the arrangement of heating and cooling zones in the DMF apparatus. Calculating the path may comprise determining the shortest path that does not cross over itself. In general, executing the fluid handling protocol on the DMF apparatus may comprise executing the fluid handling protocol in a disposable cartridge coupled to the DMF apparatus.

Also described herein are digital microfluidics (DMF) reader devices configured to operate with a removable and/or disposable cartridge having a bottom dielectric surface, a top plate with a ground electrode, and an air gap between the bottom dielectric and the top plate, the device comprising: a seating surface for seating the disposable cartridge on an upper surface; a first plurality of drive electrodes on the seating surface, wherein all or some of the drive electrodes comprises an opening therethrough; a thermal control for applying thermal energy to a first region of the seating surface; a plurality of thermal vias, wherein the thermal vias comprise a thermally conductive material and are in thermal communication with the first region of the seating surface but are electrically isolated from the subset of electrodes and further wherein the thermal vias are in thermal communication with the thermal control; a plurality of vacuum ports, wherein each vacuum port is coupled to one or more of the openings through the drive electrodes; a vacuum pump for applying a vacuum to the vacuum ports; and a control for applying energy to sequentially activate and de-activate one or more selected drive electrodes to move a droplet within the air gap of the cartridge along a desired path within the air gap.

The thermal vias may have any appropriate dimensions. For example, each thermal via may have a diameter of between about 0.5 and about 2 mm (e.g., between about 0.5 mm and about 1.8 mm, between about 0.5 mm and about 1.5 mm, between about 0.5 mm and 1.2 mm, between about 0.8 mm and 1.2 mm, etc.). Any number of thermal vias may be used per cell (e.g., there may be between about 5-15 thermal vias associated with a region corresponding to a single electrode in the first region).

The thermal vias may each be filled with a thermally conductive material; the material may be electrically conductive or electrically insulative. In some variations the thermally conductive material is a metal. The reader may further include one or more resistive heaters underlying at least some of the drive electrodes.

The seating surface may be formed or at least partially formed on a printed circuit board (PCB), including on an array of electrodes formed on the PCB. As mentioned above, any of the readers described herein may include one or more magnets; in some variations the magnet(s) may be underneath one or more of the drive electrodes configured to be activated to apply a magnetic field. For example, the magnetic field may pass through an opening in the drive electrode. The reader may include one or Peltier coolers underlying at least some of the drive electrodes configured to cool to less than 10 degrees C.

Also described herein are methods of detecting the location and/or identity of a material in an air gap of a digital microfluidics (DMF) cartridge. The material may include a droplet (e.g., aqueous droplet) a wax, a droplet coated/ensheathed in a wax (e.g., liquid wax), an oil droplet, a droplet with magnetic particles, etc. The identity may be determined for a material at a specific location in the air gap, e.g., between the upper and lower surfaces forming the air gap in the cartridge. The cartridge may be divided up into cells (e.g., regions above individual drive electrodes.

For example a method of detecting the location and/or identity may include: disconnecting a reference electrode on a first side of the air gap of the DMF cartridge from a driving circuit; setting the voltage of one or more drive electrodes of an array of drive electrodes on a second side of the air gap to a high voltage while setting all other drive electrode of the array of drive electrodes to ground; sensing the voltage at the reference electrode; determining a capacitance between the first side of the air gap and the second side of the air gap based on the voltage sensed at the reference electrode; and identifying the material in the air gap adjacent to the one or more drive electrodes based on the determined capacitance.

The method may also include reconnecting the reference electrode to the driving circuit, and driving a droplet within the air gap by applying a voltage between the reference electrode and one the drive electrodes. These steps may be repeated iteratively, to track movement of material in the air gap.

Disconnecting the reference electrode may comprise allowing the reference electrode to float (e.g., not ground). The reference electrode may be the entire upper electrode (on the first side of the air gap, opposite from the array of drive electrodes). Disconnecting the reference electrode from the drive circuitry (e.g., from the controller driving movement of a droplet in the air gap by digital microfluidics) may include connecting the reference electrode to sensing circuitry for detecting the voltage at the reference electrode and therefore the capacitance of the air gap. The reference circuitry may include on or more reference capacitors arranged to allow measurement of the air gap capacitance.

Setting the voltage of the one or more of drive electrodes to a high voltage may comprises setting the one or more of the drive electrodes to between 10 and 400V (e.g., between 100V and 500V, e.g., about 300V, etc.).

Any of these methods may include determining a total capacitance for the air gap by setting the voltage of all of the drive electrodes of the array of drive electrodes to the high voltage while the reference electrode is disconnected from the driving circuit and sensing the voltage a the reference electrode to determine the total capacitance. The method may further include determining the total capacitance using one or more reference capacitors connected to the reference electrode when the reference electrode is disconnected from the driving circuit. For example, determining the capacitance between the first side of the air gap and the second side of the air gap based on the voltage sensed at the reference electrode may further comprise using the total capacitance.

Identifying the material in the air gap may comprise using a reference database comprising a plurality of ranges of capacitance to identify the material in the air gap based on the determined capacitance.

Also described herein are cartridges (e.g., disposable and/or removable cartridges) for a digital microfluidics (DMF) apparatus that include a tensioning frame to keep the bottom dielectric material in tension and therefore flat. For example, any of the cartridge described herein may include: a sheet of dielectric material having a first side and a second side, the first side forming an exposed bottom surface on the bottom of the cartridge, wherein at least the second side of the sheet of dielectric material comprises a first hydrophobic surface; a tensioning frame holding the sheet of dielectric material in tension so that it is substantially flat; a top plate having a first side and a second side and a thickness therebetween; a ground electrode on the first side of the top plate; a second hydrophobic surface on the first side of the top plate covering the ground electrode; and an air gap separating the first hydrophobic layer and the second hydrophobic layer, wherein the air gap comprises a separation of greater than 280 micrometers. Any of the other cartridge features described herein may be included with these cartridges.

Any of these cartridges may also include a lip extending at least partially (including completely) around, and proud of, the sheet of dielectric material. This lip may engage with a channel or trough on the seating surface. Alternatively or additionally, the cartridge may include a peripheral channel or trough into which a projection on the seating surface of the reader engages.

The tensioning frame may include an outer frame and an inner frame. The sheet may be held between the outer and inner frames. These cartridges may include any of the other cartridge features mentioned herein.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 3A shows an example of a typical DMF arrangement, e.g., using a rigid cartridge; FIG. 3B shows an example of a DMF configuration in which the cartridge 315 is a disposable portion that does not include the electrodes but that is held onto the reusable electrodes by a plurality of localized vacuum ports (adjacent to or passing through the electrodes).

FIG. 3C is an example of a DMF apparatus configured as a compact driver/reader that is configured to work with a removable/disposable cartridge. The DMF apparatus includes an array of electrodes (e.g., greater than 500 different electrodes), and multiple independent regions for heating/cooling (thermal cycling, etc.) controlling magnetic beads, pumping microfluidic channels, automatic seating and sealing of the cartridge, as well as optical viewing/management.

In FIG. 3F the tray is shown extended. The dimensions show are for illustrative purposes only, and may be larger or smaller by, e.g., +/−5% (e.g., 10%, 15%, 20%, 25%, 30%, 35%, 40%, 50%, 75%, 100%, etc.).

FIG. 3I is a front view of an apparatus is configured to process six cartridges, and includes six access controls and display panels, which may be color coded. Within the outer housing shown, components such as the pumps, motor(s), optics, controllers, etc. may be shared, and/or multiple separate components (e.g., electrode arrays, sub-controllers, etc.) may be used. The housing may be configured to allow stacking of a plurality of apparatuses.

In FIG. 4A, 18 rows and 10 columns are shown; larger or smaller arrays may be used.

In FIG. 4B, a temperature sensor (e.g., thermistor) is shown.

FIG. 5A shows a partially dis-assembled view of the apparatus, showing connections that may be made between the electrode-containing PCB, a liquid coolant, and the vacuum for securing the cartridge dielectric onto the electrodes.

FIG. 5B shows an example of a fan and heatsink, reservoir and pump that may be used for the liquid coolant of the cartridge-contacting surface(s), including the electrodes. The pump, tubing, fan, heatsink and reservoir may be used to move water or liquid coolant below the electrodes so that the coolant can absorb the heat while passing below the electrodes, where it may then be re-circulated after being cooled again while passing through the fan and heatsink.

FIG. 5C shows another view of a PCB with the electrodes similar to that shown in FIGS. 4A-4C, connected to a vacuum pump as well as the liquid coolant (input and output).

FIGS. 5D and 5E illustrate the application of vacuum to secure a cartridge (shown here as a proof of concept by just the dielectric material. In FIG. 5D the vacuum is off, and the dielectric is not secured against the electrodes. The dielectric may wrinkle, and may include regions of poor contact, including poor electrical contact. By comparison, FIG. 5E shows the dielectric held against the electrodes by a plurality of openings through the electrodes, which holds the dielectric uniformly against the electrodes, and results in surprisingly uniform electrical properties between the removable cartridge and the electrodes.

FIG. 5F shows an example of a top view of a PCB showing a small electrode array with holes formed through the central region of each electrode.

FIG. 5G shows a portion of the PCB of FIG. 5F below the electrodes (over which the other layers may be formed), showing the holes through the PCB forming that may be connected to the vacuum pump.

In FIG. 6, the removable cartridge has been made transparent (a microfluidics region above the top plate, air-gap and dielectric forming the DMF portion of the cartridge has been made transparent). The different regions are indicated by different boxes, and may be distributed in a particular arrangement over the array. For example, in FIG. 6, seven of the electrodes are configured as magnetic regions 605, which can apply a local (to that electrode) magnetic force to retain a magnetic bead or particle within a droplet on the electrode. Eight of the peripheral regions (each spanning six electrodes) are configured as cooling zones, which may be in thermal contact with a Peltier device or other thermal cooling region. In addition, in FIG. 6, six 16-electrode regions on the left side are configured as cooling zones which may also be in thermal contact with the same or different Peltier device (e.g., holding them below 10 deg. C.). Two central heating zones (one spanning five electrodes, the other spanning 32 electrodes) are also included, and may be thermally cycled over the entire zone or over regions of the zone(s). Four optically read zones (each spanning four electrodes) are spaced apart from each other on the right side perimeter of the device. In general, the heating and/or thermally cycling regions are centrally located, apart from the peripheral cooling/storage regions. There may be overlap between the zones, such as the magnetic zones and the heating/cooling zones.

FIG. 6 also shows, in a transparent view, a microfluidics portion that may be formed above (and in the top plate, as described) the air gap. For example, in FIG. 6, the microfluidics portion 611 includes a pair of serpentine microfluidics channels 615, 616 that each connect to an opening (which may be regulated by a valve) into the air gap. The microfluidics portion may also include valves. In FIG. 6, the microfluidics channel also includes a pair of ports 617, 618 through which positive and/or negative pressure may be applied to modulate (along with any valves) the movement of fluid in the microfluidics region and (in some variations) into or out of the air gap. The microfluidics portion may also include one or more waste chambers 621, FIG. 7A is a top view of an exemplary cartridge as described herein. In this example the cartridge includes a DMF portion, including a top plate and dielectric, separated by an air gap, and a microfluidics portion that connects into the air gap, and may externally connect to a channel input and/or output. Fluid may be applied into the cartridge through one or more openings into the air gap (shown as small openings) and/or through the channel input/outputs. The right side of the cartridge includes a window region, allowing optical viewing through the cartridge.

FIG. 7B shows a top perspective view of the cartridge of FIG. 7A.

FIGS. 11A and 11B show front and side views, respectively, of another variation of a top plate including a ground electrode formed of a non-transparent conductive ink (e.g., silver conductive ink, carbon conductive ink, etc.), formed in a grid pattern including a plurality of window openings forming the grid.

In FIG. 15A, the microfluidics portion of a cartridge is shown as a pair of channels each connected to an inlet/outlet, and each ending in a bridging region forming an opening into the air gap of the DMF portion of the cartridge (in this example, below the microfluidics portion). Fluid may be removed, added, washed, etc. into/out of the air gap of the DMF portion. In FIGS. 15B and 15C, fluid washed through the bridging droplet and into the air gap by alternating and applying suction between the inlet/outlet, as shown. In this example, external fluidic components (e.g., tubing and reservoirs) are integrated into the top plate of the DMF portion, allowing a compact form factor. The microfluidics channels may be used for adding/removing reagent (e.g., removing waste, washing, etc.). The bridging droplet may be an electrode or group of electrodes and the size of the droplet may be regulated by DMF.

In FIG. 17A, the fluid application and extraction device is connected through the top plate. In FIG. 17B, the fluid application and extraction device is connected from the side plate.

FIG. 17C is another example of a DMF cartridge configured for mixing, extraction, adding, etc. fluid with one or more droplets in the air gap of the DMF cartridge. In FIG. 17C, the interface 1127 for the fluid lines, which may be microfluidic channels, including microfluidic channels formed in part by the top plate 1117, interfaces through the top plate, and (unlike FIG. 17A) the air gap in this interface region may be larger than the air gap in other portions of the DMF cartridge. In FIG. 17D, the interface 1127 for the fluid line(s) is at the edge of the air gap, similar to FIG. 17B; in FIG. 17D, the air gap region is larger than in other regions of the cartridge. In any of the FIGS. 17A-17D, the fluid lines (e.g., 1143, 1145) and reservoirs (1105, 1107) may form part of the DMF apparatus, and may interface with a port on the cartridge, e.g., the top surface of the cartridge, and/or one or more valves.

FIGS. 18A-18C illustrate operation of a fluid application and extraction device similar to the one shown in FIG. 17A.

FIGS. 19A-19C illustrates the effect of evaporation on a droplet over 2 minutes in an air-gap DMF apparatus held at 95 degrees C., showing substantial evaporation.

FIGS. 20A-20C show the resistance to evaporation when using a jacketing of nonpolar material (e.g., liquid paraffin) after one hour (FIG. 20B) and two hours (FIG. 20C), showing little or no evaporation.

FIGS. 21A-21B show the movement of the aqueous (polar) droplet while coated with a non-polar jacketing material that is moved along with the droplet. FIGS. 21C-21D illustrate adding additional polar material to the droplet, which expands to include the additional polar material.

As shown in FIGS. 22A-22D, droplet break off from a large volume may be used to dispense a predetermined volume. In FIG. 22A, a dispensing electrode is activated, spaced from the dispensing port (tube). In FIG. 22B, the reagent to be dispensed is applied into the air gap, flooding the region including the dispensing electrode that is separated from the dispensing port by at least one electrode. In FIG. 22C the reagent is then sucked back into the dispensing port, while the dispensing electrode(s) is/are active, but the electrode(s) between the dispensing port and the dispensing electrode(s) is/are not active, forming a neck, which (as shown in FIG. 22D) eventually breaks off, leaving the droplet of a predetermined volume on the dispensing electrode(s).

FIGS. 23A-23F illustrate example of dispensing droplets of predefined volumes using the technique described in FIGS. 22A-22D, above.

FIG. 29 is an example of a portion of a reader (e.g., cartridge seat portion) having a reduced thermal mass to enhance the rate of temperature regulation of cartridge held on the seat portion.

FIG. 30 is another example of a portion of a reader (e.g., cartridge seat portion) having a reduced thermal mass to enhance the rate of temperature regulation of cartridge held on the seat portion.

FIGS. 31A and 31B illustrate examples of readers include thermal vias for helping control the temperature of a cartridge (e.g., of one or more cells of an air gap of a cartridge).

FIG. 34A shows one example of a range of capacitances corresponding to the peresences or absence of various materials (e.g., aqueous droplet, wax, etc.) in the air gap at a particular cell. FIG. 34B is a graph showing exemplary voltge measurments from the sensing electrode (top electrode). FIG. 34C is is a graph showing an example of the change in electrical permittivity of water as a function of temperature.

FIG. 35A is a top view of one example of a vacuum chuck.

FIG. 35B is a cross sectional view of the vacuum chuck of FIG. 35A.

FIG. 38A shows another example of a vacuum chuck.

FIG. 38B shows a cross sectional and zoomed-in view of this chuck.

FIG. 39 shows a bottom view of a chuck similar to that shown in FIGS. 35A-35B.

FIG. 42 shows a front view of a chuck and a fan.

FIG. 43 shows an example of an arrangement of a chuck, a fan and a PCB (part of a seating surface).

FIG. 44 is a perspective view of a chuck that may include a thermal (e.g., heat) dissipation system for regulating temperature of a cartridge.

FIG. 45A is a top view of the chuck of FIG. 44.

FIG. 45B is a sectional view through the chuck of FIG. 45A.

FIG. 46 shows a side view of an assembly of a chuck, a heat sink and a pair of cooling fans, with arrows indicating the flow of temperature (cooling the chuck and therefore the cartridge when loaded onto the apparatus).

FIGS. 47A-47C illustrate the assembly of a vacuum chuck and cooling sub-system (e.g., heat sink block and cooling fans).

FIG. 52A is a top view of a PCB of a reader to which a cartridge may be seated on.

FIG. 52B is a side view of the PCB portion shown in FIG. 52A

FIG. 52C is an example of a side view of a cartridge shown on a seating surface of a reader.

FIG. 52D is an enlarged view from FIG. 52C.

FIG. 54A is a top view of a PCB (that may form the seating surface) of a reader.

FIG. 54B is a side sectional view through the portion of the reader shown in FIG. 54A.

FIG. 56 schematically shows four independently controlled 1-plex modules with a console unit that may operate all of them.

DETAILED DESCRIPTION

In general, described herein are digital microfluidics apparatuses and methods. In particular, described herein are air-matrix digital microfluidics apparatuses, including systems and devices, and methods of operating them to process fluid samples. For example, a DMF apparatus may include a compact DMF driver/reader that is configured to work with a removable/disposable cartridge. The DMF driver/reader may include an array of drive electrodes that are adapted to align and secure a cartridge in position by applying negative and/or positive pressure at multiple points, and specifically at the electrode-contact points, on the cartridge. The cartridge may include an air gap that is open to the environment (e.g., to the air) via openings such as side (lateral) openings and/or top openings. The air gap may be formed between two dielectric layers. An upper, top, region may include one or more ground electrodes. The ground electrode may be advantageously formed of a non-transparent material that is patterned to include one or more windows that allow imaging through the top. These windows may be arranged over the electrode, so that the ground region extends opposite the drive electrodes and around and/or between the drive electrodes.

Any of the apparatuses described herein may also include a fluid application and extraction component (e.g., a fluid application and/or extraction device) that is connected through the top, or through the side of the cartridge, into the air gap. Any of the apparatuses described herein may include or use a non-polar jacketing material (e.g., a non-polar liquid such as a room temperature wax) that forms a protective jacket around the aqueous droplet(s) in the apparatus, and may be moved with the droplet. Also described herein are user interfaces for interacting with the apparatus, including user interfaces for controlling the apparatus to move, mix, combine, wash, magnetically concentrate, heat, cool, etc. These user interfaces may allow manual, automatic or semi-automatic entering, control and/or execution of a protocol.

Figure 1:
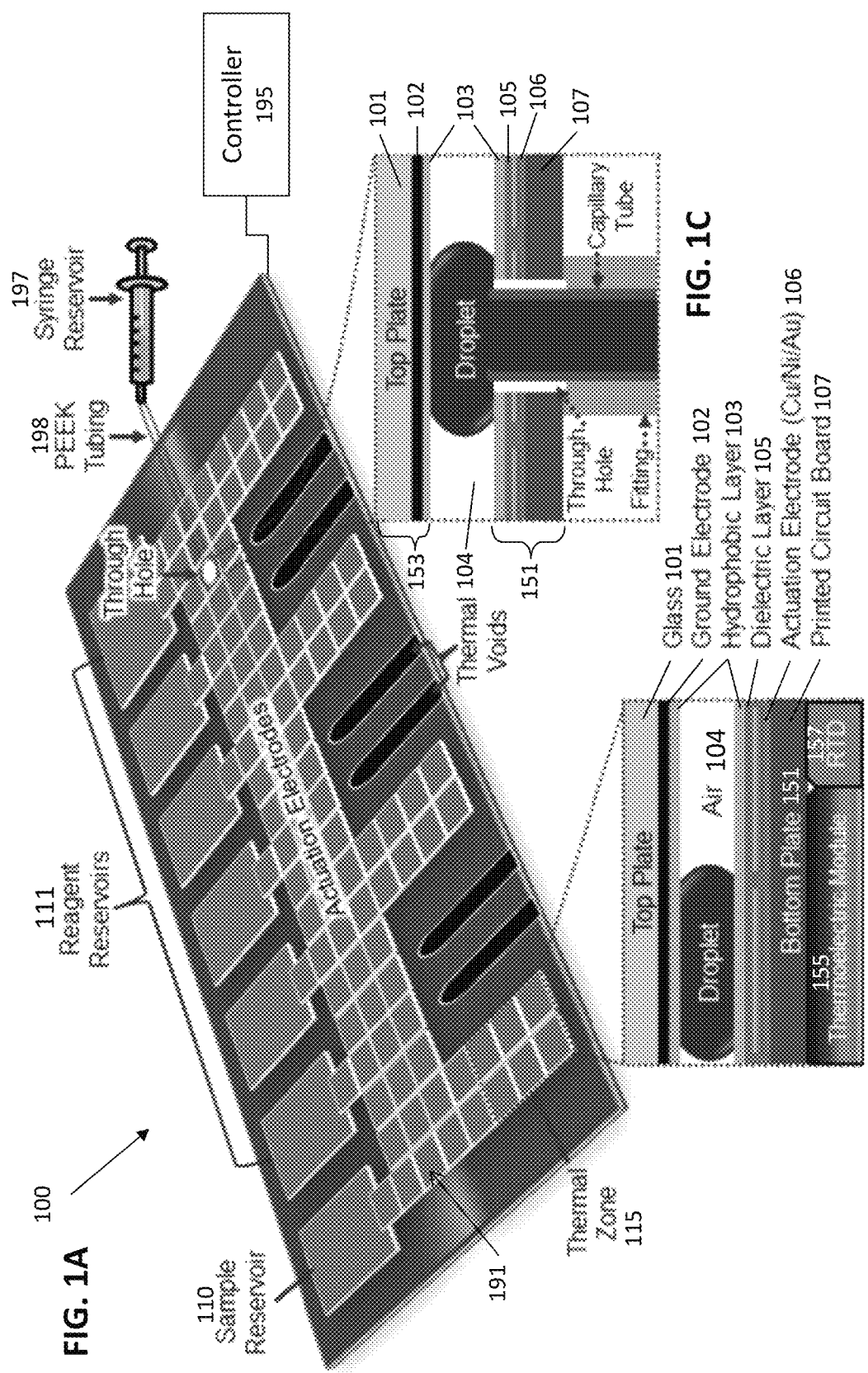
FIG. 1A is a schematic of one example of an air-matrix digital microfluidic (DMF) apparatus, from a top perspective view.
FIG. 1B shows an enlarged view through a section through a portion of the air-matrix DMF apparatus shown in FIG. 1A, taken through a thermally regulated region (thermal zone).
FIG. 1C shows an enlarged view through a second section of a region of the air-matrix DMF apparatus of FIG. 1A; this region includes an aperture through the bottom plate and an actuation electrode, and is configured so that a replenishing droplet may be delivered into the air gap of the air-matrix DMF apparatus from the aperture (which connects to the reservoir of solvent, in this example shown as an attached syringe).
Figure 2:
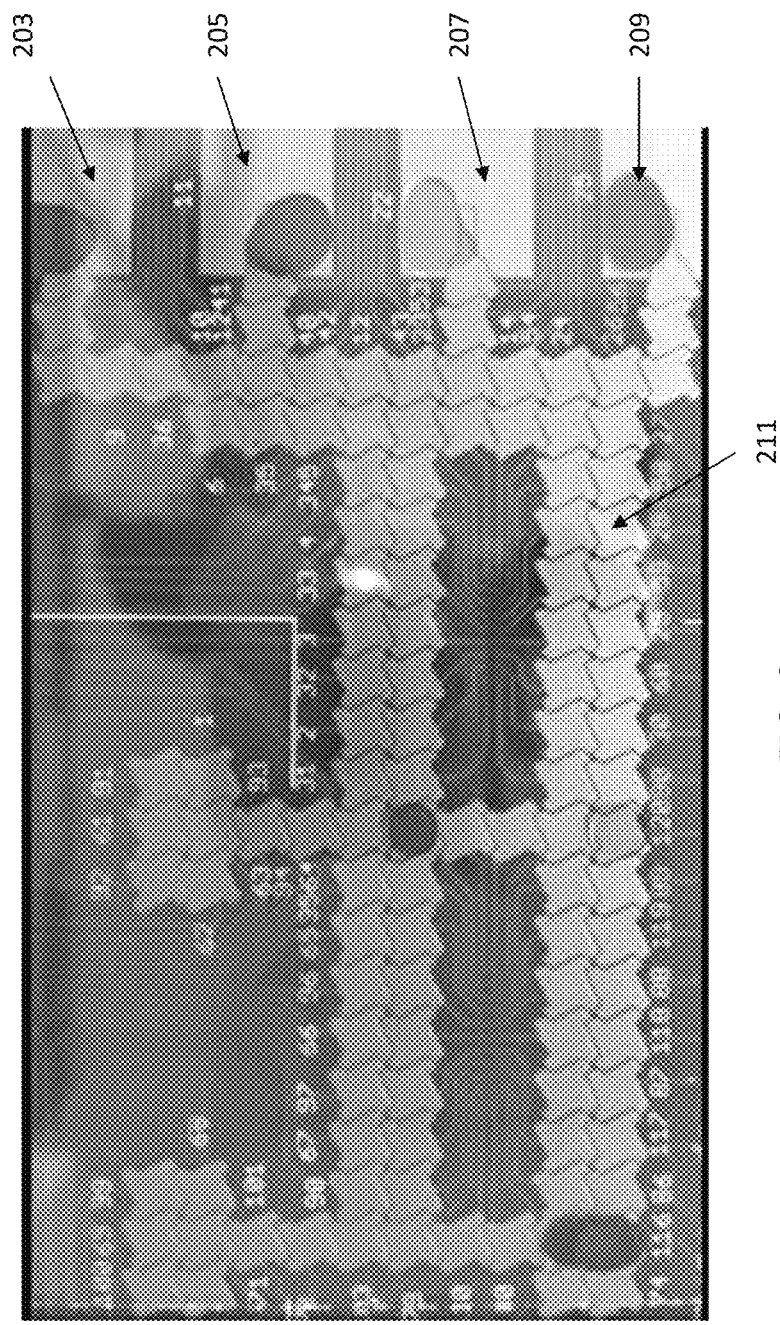
FIG. 2 is an example of a DMF surface using a rigid cartridge including the electrodes and an air-gap region, similar to that shown in FIGS. 1A-1C.

FIG. 2 illustrates an example of a DMF apparatus that is similar to the one shown in FIGS. 1A-1C. In FIG. 2, the DMF apparatus includes a plurality of drive electrodes 201 (which are shaped into non-square/non-rectangular shapes and positioned adjacent to each other in rows or lines. In FIG. 2, four reservoir regions 203, 205, 207, 209 are positioned on the right side, and may be preloaded or otherwise hold droplets of materials to be added during operation of the DMF apparatus. Some or all of the electrodes may be heated or cooled.

In the apparatus of FIG. 2, the DMF driving electrodes 211 are solid, planar electrodes. The application of energy between the driving electrodes and the ground or reference electrode result in movement of an aqueous (e.g. polar) droplet. In FIG. 2, the ground or reference electrode is formed as a conductive, transparent coating (e.g., ITO) on the upper plate, which is also clear (transparent). This allows the device to be monitored, including monitoring any of the cells, e.g., unit cells, from above the air matrix/air gap.

However, it would be beneficial to provide DMF reader apparatuses (e.g., devices, systems, etc.) that may be used with disposable cartridges that do not include the drive electrodes. FIGS. 3A and 3B show the different configurations of a DMF system that includes integrated drive electrodes (FIG. 3A) and a system in which the drive electrodes are part of the reader, but the cartridge includes only the ground electrodes (e.g., top plate), air gap and the dielectric bottom. For example, in FIG. 3A, the air gap is formed between the grounded top plate 303, and the drive electrodes and dielectric film 305 (e.g., a Teflon film). The drive electrodes and dielectric film may be part of a cartridge that includes the top plate, and may be separately attached onto the substrate (switch board 307) that connects to a main processor 309 and a power supply board 311.

In contrast, in FIG. 3B, the cartridge does not include the drive electrodes 313, but instead includes the top plate/ground electrode, dielectric and an air gap between them 315. As will be described in greater detail herein, a vacuum (e.g., vacuum manifold) may be positioned beneath the electrodes 313 to apply pressure (e.g., between 50 kPa and 250 kPa, 50 kPa or greater, 60 kPa or greater, 70 kPa or greater, 80 kPa or greater, 90 kPa or greater, 100 kPa or greater, 110 kPa or greater, etc.) to fully secure the dielectric, and therefore the rest of the cartridge, to the reader apparatus. The electrodes may be supported on a substrate, such as a printed circuit board or switch board 317, which may also be connected to the main processor 319 and power supply 321. As shown in FIG. 3B, the dielectric film may also be hydrophobic (e.g., a Teflon film may be used) or may be treated, coated, sprayed, dipped into, etc., a hydrophobic material to make at least the side facing the air-gap hydrophobic.

FIG. 3C is an example of a compact DMF driver/reader that may be used with any of the cartridges described herein. In the side perspective view shown in FIG. 3C, dimensions (height of 15 cm or 6 inches, width of 20 cm or 8 inches) are exemplary only, but show the compact nature of the reader. The reader may include a cartridge seating surface 351, beneath which the vacuum, heating, cooling, magnetic and other components, including control circuitry may be positioned. In this example, microfluidics control components (e.g., valves, pumps, etc.) may be positioned above the cartridge seating surface, for control of these elements.

Figure 3D:
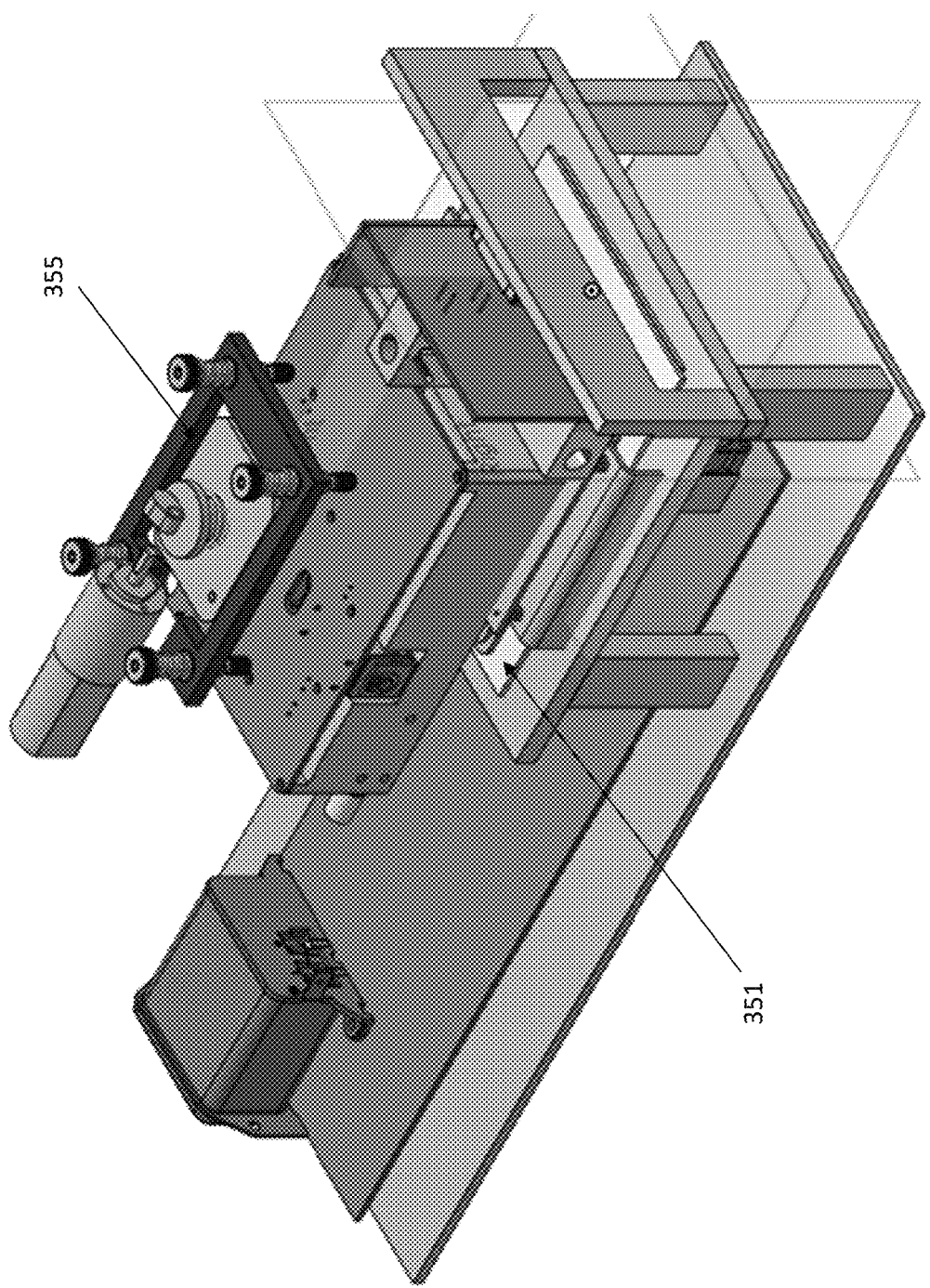
FIG. 3D is another example of a DMF apparatus as described herein configured as compact driver/reader that may include greater than 900 (e.g., greater than 920 different electrodes), independent heaters for isothermal regions and thermal cyclers, magnetic zones that can be independently engaged/disengaged, pumps and valves for operating microfluidics in the disposable cartridge (in addition to the DMF control via the plurality of electrodes), a vacuum manifold coordinated with the plurality of electrodes (e.g., having ports that pass through the electrodes to seal and secure the dielectric to the electrodes for accurate and reliable DMF control, multiple independent qPCR zones, multiple optical channels, and a draw-mechanism for inserting/removing the cartridge allowing access from both above and below the apparatus. The apparatus show in FIGS. 3C and 3D may provide liquid cooling of ambient and heating zones.
Figure 3E:
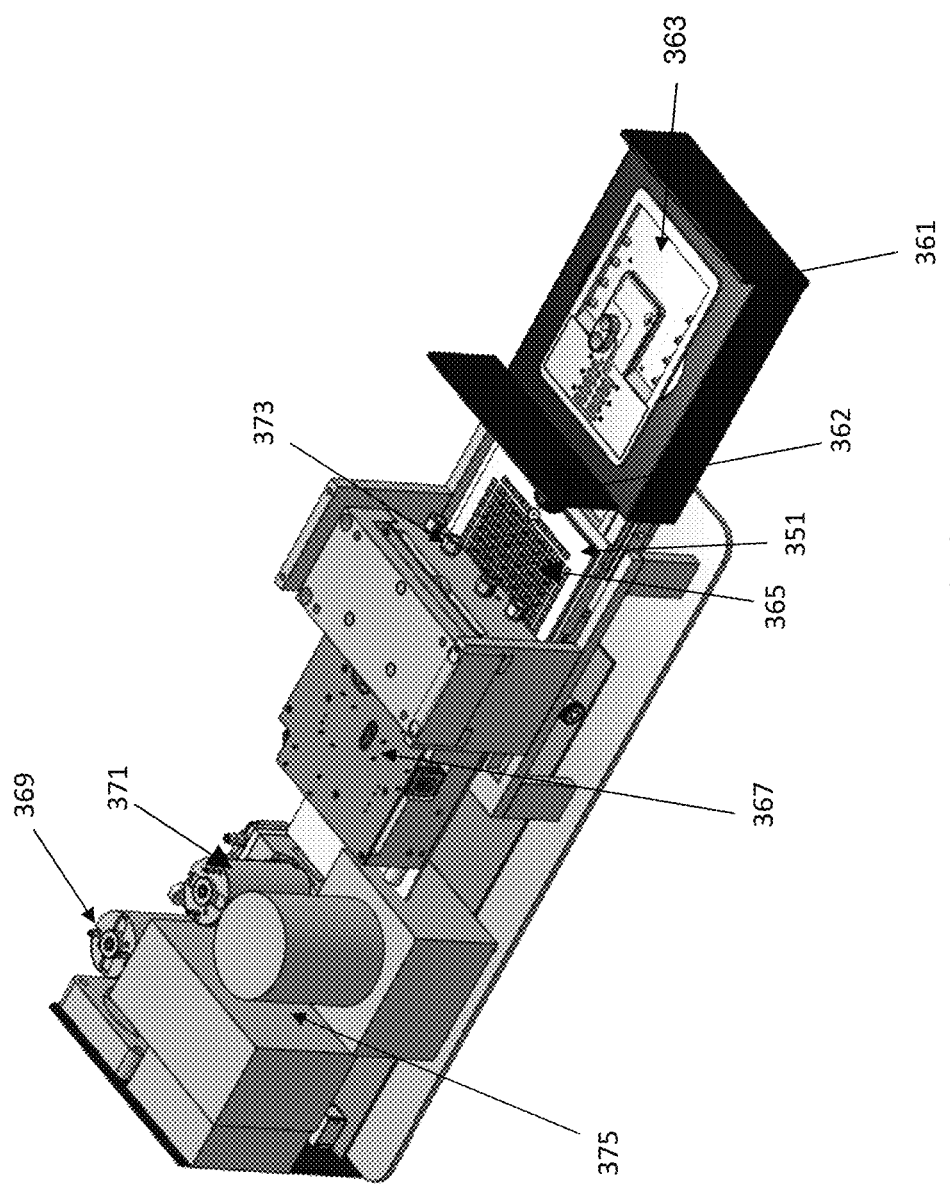
FIG. 3E is another example of the apparatus shown in FIGS. 3C-3D, showing an exemplary arrangement of the pumps (e.g., vacuum pumps to secure the cartridge, a liquid cooler and compressor, one or more motors for actuating the drawer that receives the cartridge and for actuating the optics, a control for opening/closing the drawer, a manifold for operating any microfluidics on the cartridge (in addition to or instead of the DMF), and an electrode array for driving DMF in the cartridge. In this example, a disposable cartridge is shown inserted into the apparatus.

FIG. 3D illustrate another example of a DMF reader apparatus including integrated drive electrodes on part of the seating surface. A drawer (not shown) may be used to insert/remove the cartridge and seat it onto the seating surface, where a vacuum may be used to secure the cartridge in position and make complete electrical contact between the drive electrodes and the dielectric of the cartridge. Both the microfluidics handing portion 355 and the optics (e.g., optical reader) may be positioned above the seating surface. FIG. 3E shows another perspective view of the apparatus of FIGS. 3C and 3D, showing the drawer 361 holding an exemplary disposable cartridge 363. The drawer may open/close (e.g., by pushing a control, such as a button 362) to pull the cartridge into and out of the apparatus, as shown, and position the cartridge on the seating surface which includes a driving electrode array 365, in which each of the driving electrodes (in this example, and shown in greater detail below) includes an opening for the application of a vacuum to hold the dielectric onto the driving electrodes. Above the seating surface, and therefore the cartridge, the microfluidics portion may engage with the cartridge when held on the seating surface. For example, a microfluidics valve manifold 367 may be included, and may connect to a pump or pump 369. The same, or a separate pump 371 may be used to provide the pressure for holding the dielectric onto the seating surface through the electrodes. The system may also include an optics sub-system 373 for imaging through at least a portion of the cartridge, in order to report-out data about the reaction being performed on the apparatus. A motor for driving the optics and/or the drawer opening/closing may also be included. A liquid cooler and compressor 375 may be included as well, for circulating a cooling liquid, e.g., under the cartridge.

Figures 3F, 3G, 3H:
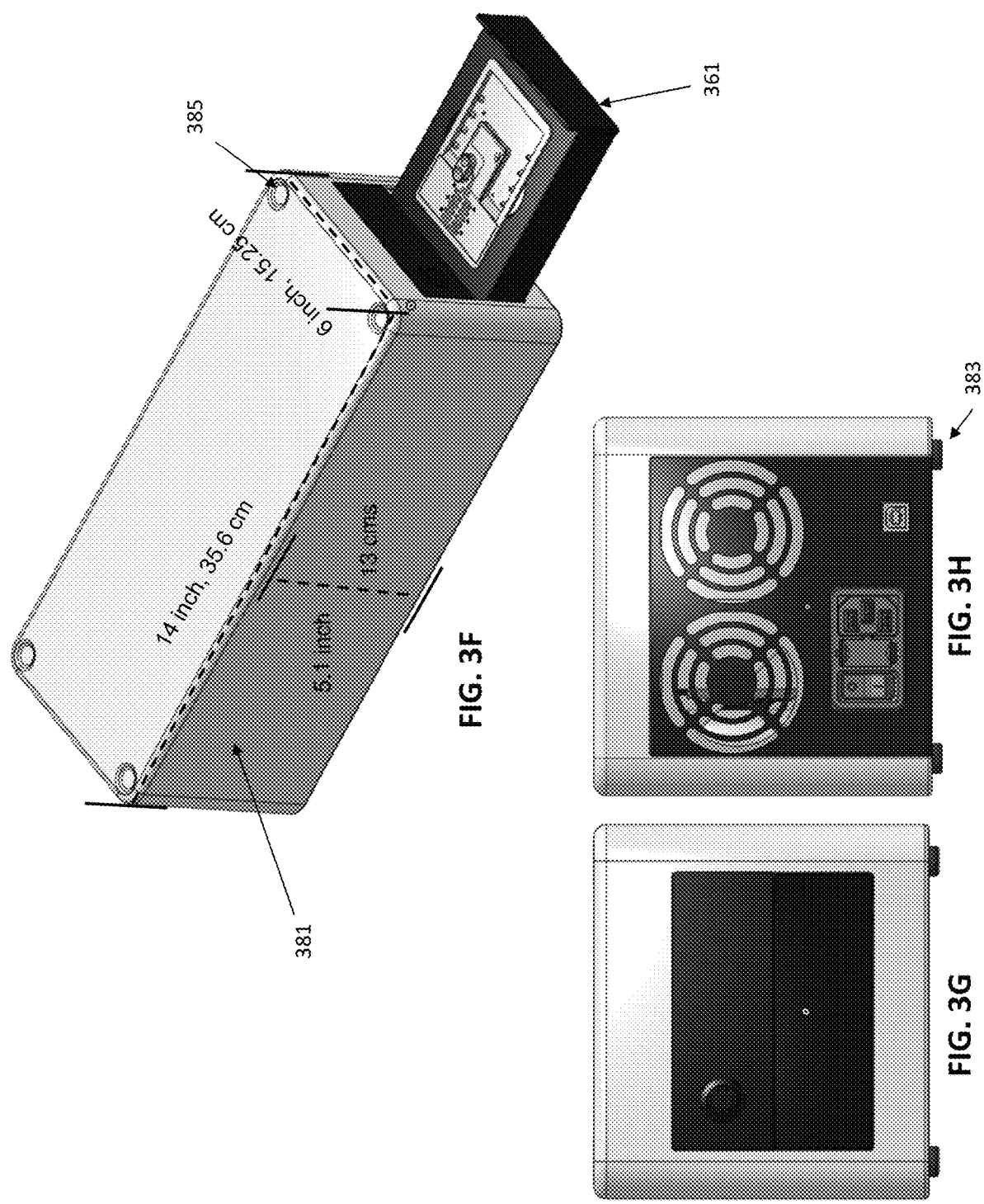
FIG. 3F is an example of the outer housing of an exemplary DMF apparatus such as the one shown in FIGS. 3C-3E, configured as a single tray (cartridge) apparatus.
FIGS. 3G and 3H show an example of the front (FIG. 3G) and back (FIG. 3H) sides of the exemplary DMF apparatus of FIG. 3F. The tray for loading/unloading the cartridge is shown closed.

FIG. 3F shows a side perspective view of the apparatus of FIG. 3E with the drawer 361 open and the cover 381 on. The housing may include feet 383 that may engage with receiving sites 385 on the top surface, so that these device may be easily and securely stacked. FIGS. 3G and 3H show front and rear views, respectively.

Figure 3I:
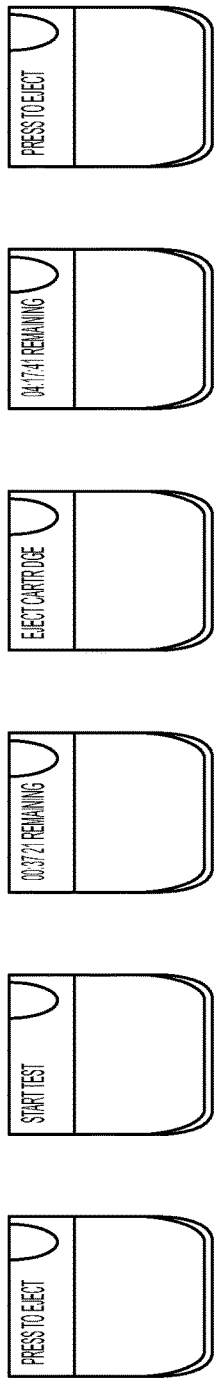
FIG. 3I illustrates another example of an exemplary DMF apparatus configured to process a plurality of cartridges.
Figure 3J:
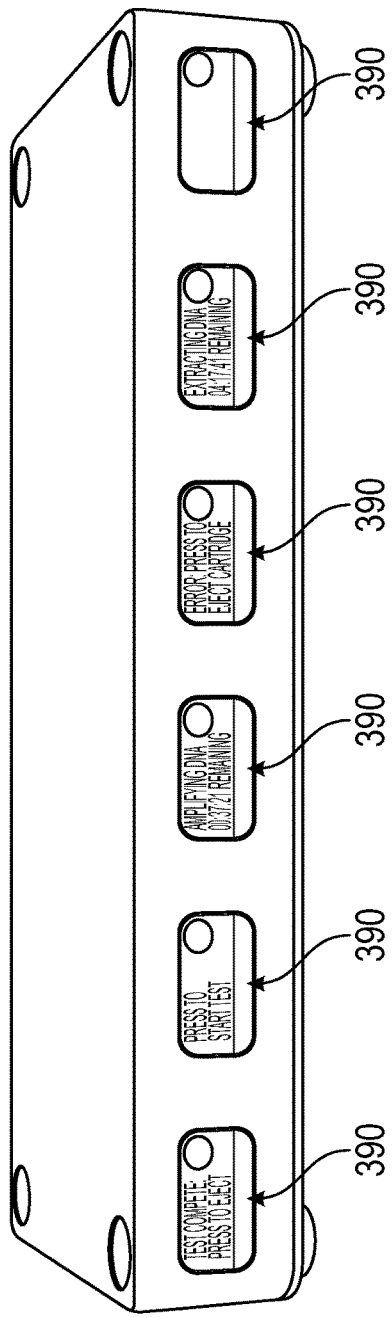
FIG. 3J is a front perspective view of the apparatus of FIG. 3I.
Figure 3K:
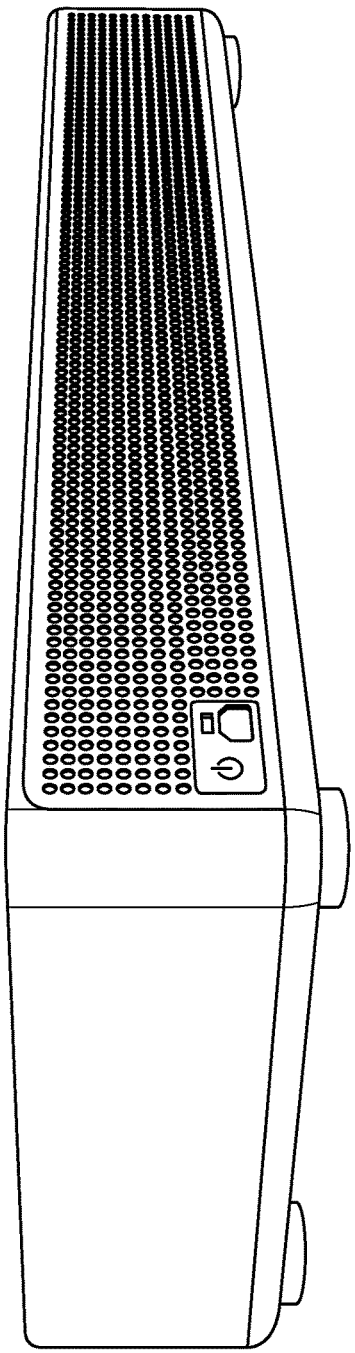
FIG. 3K illustrates an example of a back view of the multiplexed apparatus of FIGS. 3I-3J.
Figure 3L:
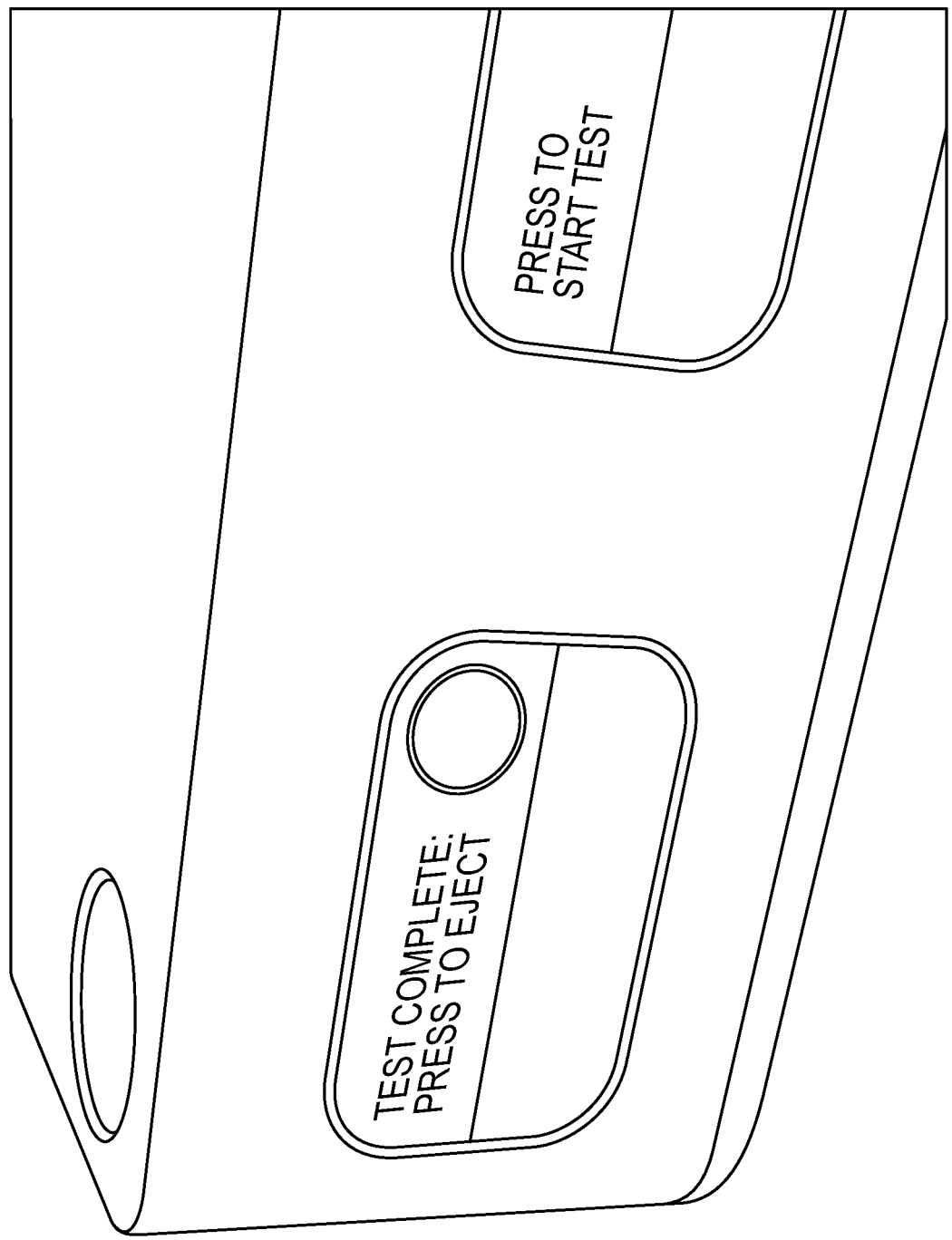
FIG. 3L is an enlarged view of the far left cartridge drawer, including a cartridge-specific display, input (e.g., button, touchscreen, etc.), and the cartridge drawer.

In some variations, the apparatus may include a plurality of cartridge-receiving sites (e.g., seating surfaces) for operating in parallel on multiple cartridges. For example, FIGS. 3I-3K illustrate an example of an apparatus in which six cartridge receiving drawers can be used to operate on up to six separate cartridges simultaneously. In this example, each receiving drawer may include a button for opening/closing the drawer, and a separate readout screen 390 may be included. FIGS. 3I and 3J show front, and front perspective views, respectively, and FIG. 3K is a rear view. In this variation, internal components, such as the processor(s) and optical sensor(s) may be shared between the different seating surfaces within each sub-region of the apparatus. FIG. 3L shows a detailed view of one example of a front of the apparatus.

Figure 4A:
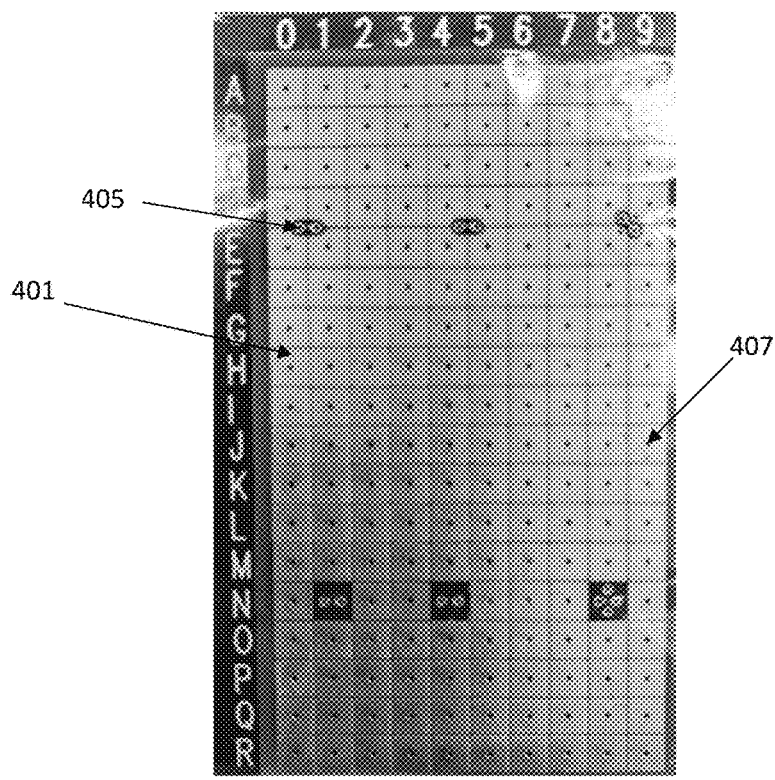
FIG. 4A shows a top view of the electrodes (e.g., electrode array) formed as part of the apparatus. The electrodes may include a plurality of vacuum openings through them, as shown. The electrodes may define different regions, including thermally controlled regions (e.g., regions having a thermistor and/or cooling and/or heating.
Figure 4B:
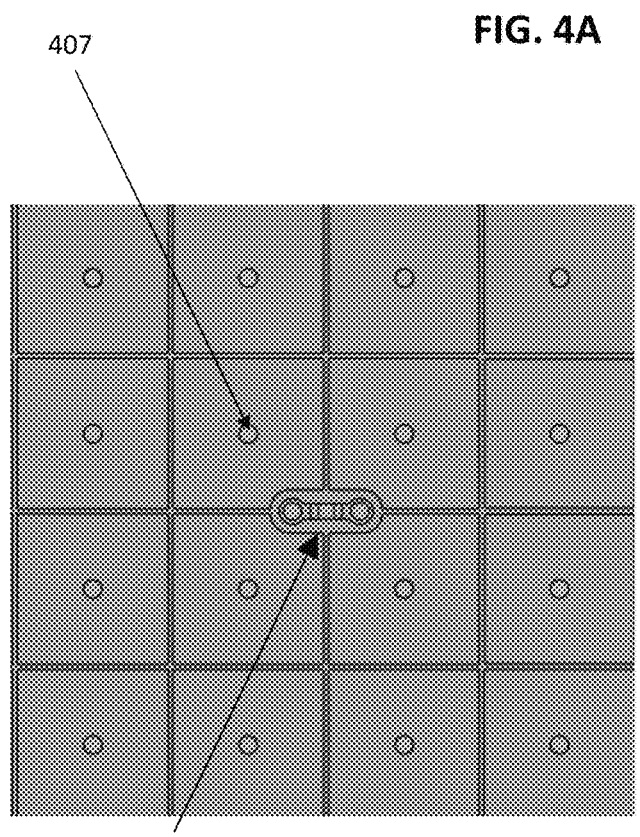
FIG. 4B shows an enlarged region of the electrodes, forming the upper electrode layer, showing the vacuum openings through most (e.g., >50%, 55%, 60%, 65%, 70%, 75%, 80%, 85%, 90%, 95%, etc.) or all of the electrodes. Although square electrodes are shown (with centered vacuum openings), other electrode shapes, e.g., interlocking, rectangular, circular, etc., or vacuum opening locations (off-centered, etc.) through the electrodes may be used.

The seating surface of an exemplary DMF reader device is shown in greater detail in FIGS. 4A-4C and FIGS. 9A-9C. In FIG. 4A, the seating surface includes an array of driving electrodes 401 (labeled in rows 0-9 and columns A-R). Each of these driving electrodes includes a central hole or opening through the electrode, through which a vacuum can be applied to hold the dielectric of the cartridge against the drive electrodes. In FIG. 4A, the seating surface also includes temperature sensors (thermistors 405) positioned between the electrodes in different orientations. FIG. 4B shows a slightly enlarged view of the seating surface, including the driving electrodes, showing a thermistor 405 between the driving electrodes. The vacuum openings 407 are more clearly visible in FIG. 4B. Any shape and size of driving electrodes may be used, including interlocking driving electrodes. In addition, the pattern of driving electrodes may be formed that is not monolithic; for example the electrode pattern may include open regions that do not include driving electrodes (e.g., regions surrounding driving electrodes, etc.) as shown in FIGS. 1A and 2.

Figure 4C:
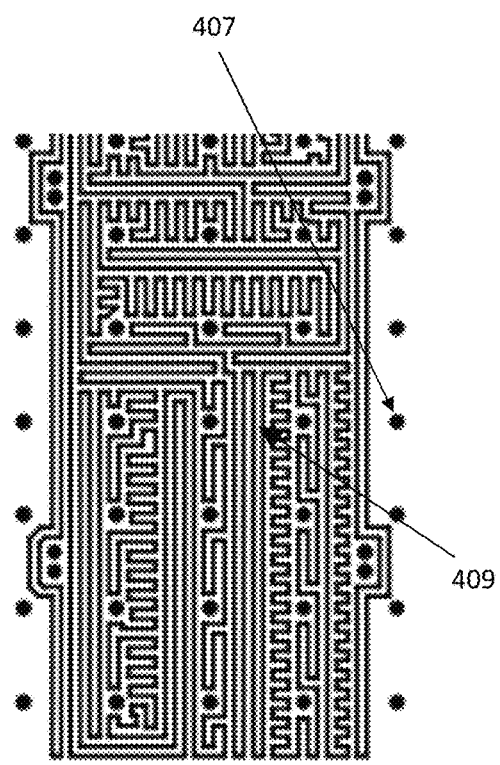
FIG. 4C illustrates a resistive heating layer that may be present beneath the electrode layer (such as is shown in FIG. 4B). One continuous, or multiple separate, trace(s) of resistive material may be used beneath the array. The black dots indicate the vacuum manifold (forming the plurality of vacuum openings through the electrodes. The resistive heating layer may be electrically isolated from the electrodes above them; the current applied through the resistive heating layer may be regionally controlled, by a controller. The controller may include PID control.

FIG. 4C shows an example of a heater that may be positioned underneath some of the drive electrodes, such as the sub-set of drive electrodes shown in FIG. 4B. In this example, resistive heating circuitry 409 may underlie the drive electrodes (e.g., embedded at any layer of the PCB forming the seating surface). In general, resistive heating and thermistors may be embedded at any layer of the electrode PCB board. The heater may be part of the PCB with the electrodes and thermistor, as shown in FIGS. 4A-4C. The current, and therefore the temperature of the driving electrodes and/or the adjacent dielectric (and therefore any droplet on the cell under the dielectric/driving electrode) may be regulated, e.g., by a PID control loop, in combination with the thermistor. To cool it down the dielectric (and the entire seating surface), a liquid cooler may be circulated through the substrate, e.g., on the bottom of the seating surface. In the example of FIG. 4C, the resistive heater is shown as a continuous trace of low-resistive material (e.g., having a resistance between about 10-15 ohms).

Any appropriate temperature regulating technique may be employed. For example, stirring (e.g., magnetic stirring) may be used. Even a small-volume droplet may contain a range of local temperatures, so the temperature distribution may have a standard deviation. This can be reduced by stirring, e.g., via magnetic beads. With enough stirring, the droplet may be brought close to isothermal. In any of these variations, the top plate may be used to help regulate the temperature. For example, the top plate may be used for heatsinking. A thermal conductor (e.g., a steel block) on top of the top plate may greatly speed up the time it takes for the top plate to cool down. If the top plate has a large thermal mass, or a mass is added to it, this may reduce the time needed for a set number of thermal cycles.

Differences in temperature between the top plate and a bottom heater (e.g., a buried heater) may help determine the temperature standard deviation. Heating the top plate in tandem with the electrode may reduce the time necessary to raise the temperature. For example, the top plate may include a local resistive heater, similar to that shown in FIG. 4C. The heated/cooled top plate may be achieved separately from the cartridge by including a top thermal mass that engages with the top of the cartridge when it is on the seating surface. For example, a heated and/or cooled top thermal mass may be a manifold that is pressed down onto the cartridge.

As mentioned, a liquid coolant may be applied to the bottom and/or the top of the cartridge. In particular, a circulating liquid coolant may be used. In some variations, the entire bottom of the cartridge may be cooled (e.g., to within 3-5 degrees of room temperature, e.g., between 15-35 degrees C.). In FIG. 5A, an example of a seating surface 501 is shown removed from the device to illustrate a liquid coolant coupled to the substrate of the seating surface so that coolant may be pumped into 503 and out of 505 through the seating surface 501.

FIG. 5B illustrates a pump 511, tubing 517, fan 515, heatsink 516 and a reservoir 513 are used to move water or liquid coolant below the electrodes. The coolant absorbs the heat while passing below the electrodes and is cooled again while passing through the fan and heatsink.

As mentioned above, the vacuum applied by the device through the openings in the electrodes permits the dielectric of the cartridge to be securely and releasably held. Openings that do not pass through the electrodes do not hold the dielectric smoothly on the seating surface. However, when the vacuum is applied through all of the driving electrodes that may be activated, the dielectric is held flat against the driving electrodes and a consistently lower energy may be applied. For example, FIGS. 5D and 5E illustrate securing a dielectric (shown unattached to a cartridge, for illustration purposes) onto a seating surface having electrodes with openings through which a vacuum is applied. In FIG. 5D the vacuum is off, and the dielectric 555 is loosely resting on the seating surface, with numerous wrinkles. In FIG. 5E, the vacuum is applied through the electrodes.

The use of a vacuum in this way allows for a reduced dielectric thickness, and thus lower power (e.g., voltage) requirements. Compared to the use of adhesive, or the use of a vacuum applied external to the electrodes, the configuration shown in FIGS. 5A-5E resulted in a reduction of the power requirements for DMF being halved. In the examples shown, the thickness of the dielectric may be between 7-13 microns. When an adhesive is used, the dielectric is almost twice as thick (e.g., 25 microns).

In FIG. 5C, a pump 560 is shown connected via tubing to a vacuum manifold that is configured to pull air through the holes in the electrodes. The dielectric film sits on top and stays rigid as long as the pump is pulling air. In addition, any projection in the surface of the dielectric (particularly those that are around or slightly smaller than the width of the air gap of the cartridge) will not interfere with the seal, but will form enclosures, channels, barriers, or other structures within the air gap, which may help partition the air gap.

FIGS. 5F and 5G illustrate the upper and an intermediate layer of the seating surface, showing the connection between the vacuum source (via connector 565), though a mechanical and/or tubing manifold (FIG. 5G) and out of the openings through the electrodes (FIG. 5F).

Figure 9B:
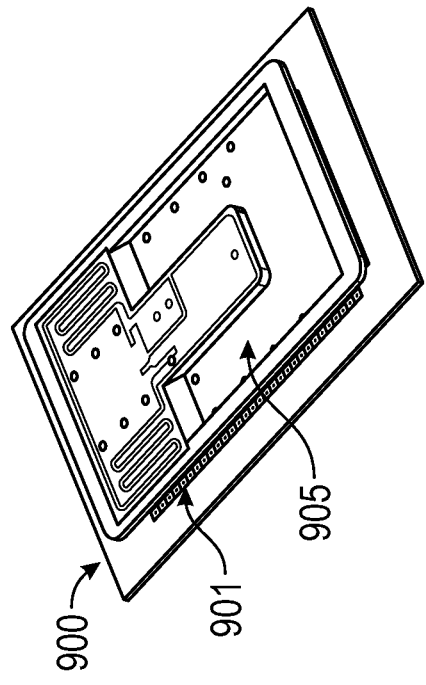
FIG. 9B shows a cartridge over the open array, held in place by a vacuum to keep it rigidly attached over the electrodes.
Figure 9A:
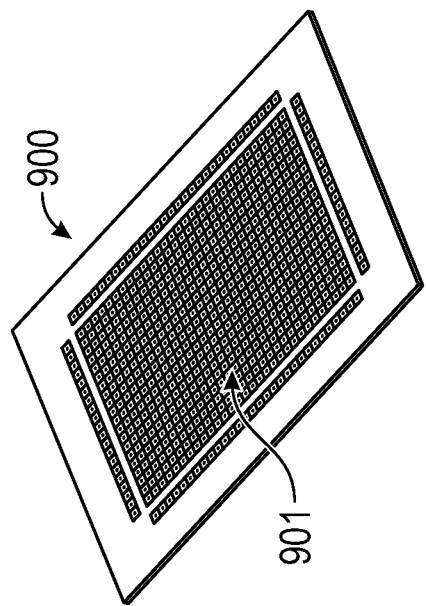
FIG. 9A shows an example of an open array of electrodes under a disposable plastic top plate and a dielectric.
Figure 9C:
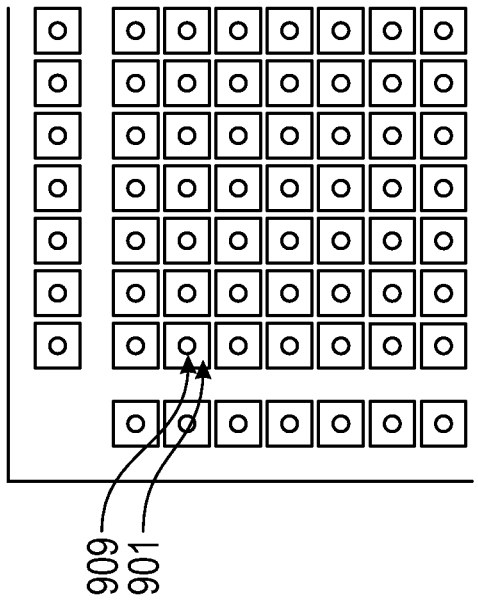
FIG. 9C illustrates the use of openings through the electrode array; these openings may be used to apply suction (e.g., vacuum) sufficient to hold the cartridge (e.g., the bottom, dielectric layer) aligned and secured to the apparatus. Positive pressure may be applied to release the cartridge.

FIGS. 9A to 9C illustrate an example of a seating surface 900 onto which the cartridge may be held by the vacuum ports through the electrodes. In FIG. 9A, the seating surface is formed on a substrate (e.g., a PCB or other electrically insulated surface), and includes an array of electrode 901, shown in this example as quadrilateral (e.g., square) shapes. Any other appropriate shape may be used. The drive electrodes 901 are thin conductive surfaces that may be flush or substantially flush with the seating surface, or may project slightly above the seating surface. In FIG. 9B, a cartridge 905 is shown placed atop the array of drive electrodes 901 on the seating surface 900. This cartridge may be placed on the seating surface by a drawer (as shown in FIGS. 3E and 3F, above. Once on the seating surface, a vacuum may be applied through all or a subset of the drive electrodes (e.g., those over which a fluid will be transported in the air gap) to hold the dielectric (and therefore the cartridge) in position. As mentioned above, without the vacuum being applied through the electrodes themselves, more energy may be required to drive fluid within the air gap reliably, and the dielectric must be thicker. FIG. 9C shows an enlarged view of a portion of the seating surface 900, showing electrodes 901 having a central opening 909 into the vacuum manifold.

The seating surface of the apparatus may be divided up into functional regions, controlling the location and operation of different portions, including heating, magnetic bead control, washing, adding solution(s), cooling, imaging/detecting, etc. These regions may be defined in the DMF reader apparatus. For example, returning now to FIG. 6, FIG. 6 illustrates different functional regions that are defined based on the connections within and/or beneath (or in some variations, above) the seating surface. For example, in FIG. 6, solution may be dispensed through the top of the cartridge (e.g., the top plate), via one or more holes. The drive electrodes under the secured dielectric may therefore form a plurality of unit cells (one drive electrode per unit cell), and each cell or region of cells (multiple cells) may be controlled to perform a specified function. For example, in FIG. 6, the DMF apparatus includes an arrangement of zones or unit cells such as cooling zones (e.g., cooling via underlying Peltier zone) 605 that are arranged around the periphery of the cartridge. These regions may also be used to store solution, and may be held at between 3 degrees C. and 20 degrees C. (e.g., below 10 degrees C., between about 2 degrees C. and 25 degrees). The central heating zone(s) 609 may be used for heating a droplet. One or more magnetic zones 603 may be used for turning on/off magnetic fields that may be useful to immobilize a magnetic particle (e.g., for removing a material, etc.). Any of the zones may overlap. For example, at least one unit cell in the heating zone may also be a magnetic zone. Other functional zones include imaging/optical zones. In this case, the dual functions may be possible because the magnet may be positioned right under the heating zone when using resistive heating.

Figure 6:
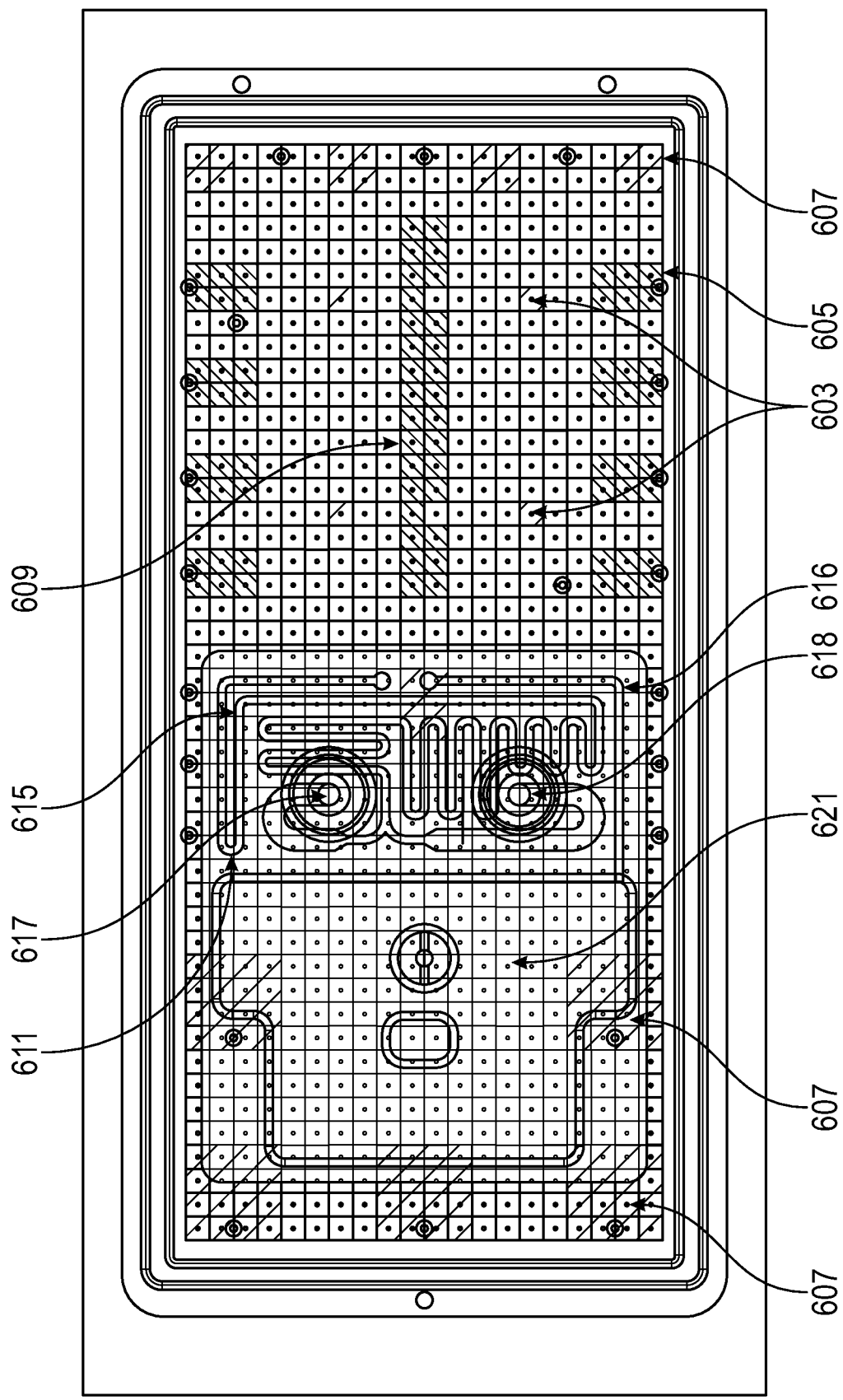
FIG. 6 illustrates the different functional regions that maybe formed by the electrode array and/or removable cartridge.

In addition to the zones formed by the configuration of the seating surface of the DMF apparatus, functional zones for providing an aliquot of solution, mixing a solution, and/or removing solutions may be formed into the cartridge, e.g., but cutting into the top plate to provide intimate access the air gap. In FIG. 6, the upper (top plate) microfluidics region has been made transparent. In general, a micro channel may be used for mixing, dispensing and taking to waste on top plate from the air gap region. In addition, any of these cartridges may also include a reagent reservoir in the top plate. The microfluidics may be controlled by one or more valves (e.g., valve control) for dispensing and mixing and taking to waste.

Cartridges

In general a cartridge as described herein may include a dielectric, a first hydrophobic coating on the dielectric, a second hydrophobic coating on a ground electrode (and/or top pate) and the top plate onto which the ground electrode is coupled. The hydrophobic coating may be a Teflon coating, for example. The cartridge may also include one or more microfluidic channels, particularly those formed directly into the top plate with controlled access into the air gap.

For example, FIGS. 7A-7D illustrate one example of a cartridge 700 including a microfluidics region 703 on the upper surface, covered by a cover 703 having one or more access ports 705, 707 for accessing the microfluidics portion of the device. The cover 703 may also include one or more valves and/or one or more openings 709 that may be used for delivering removing fluid and/or gas (e.g., air). The cartridge may also include openings through the top plate 713, including openings that connect the microfluidics channel to the air gap region within the channel.

Figure 7C:
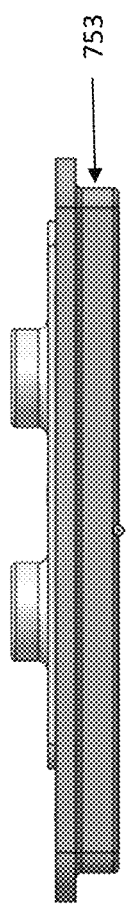
FIG. 7C is an end or side view from the left side of the cartridge of FIGS. 7A and 7B, showing the upper microfluidics channels and the lower DMF portion (showing the spacing between the top, ground, plate and the dielectric, forming the air gap.
Figure 7D:
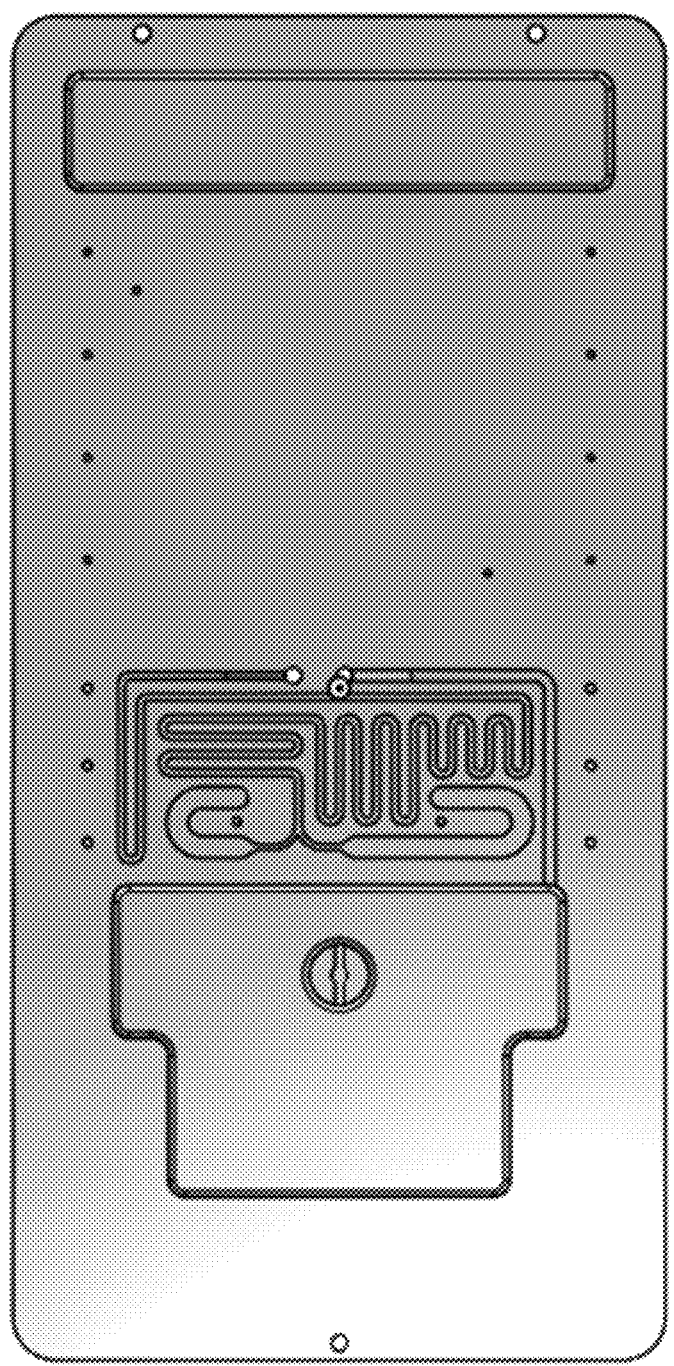
FIG. 7D is a top view of the cartridge of FIGS. 7A-7C, with the cover for the microfluidics channels removed, showing the channels.

Any of the cartridges described herein may also include one or more transparent window regions 711 for optically imaging one or more regions (readout regions) within the air gap. FIG. 7B is a top perspective view of the cartridge of FIG. 7A. FIG. 7B shows a side view of the cartridge, showing the lowest bottom dielectric film 751 material. The air gap is not visible in FIG. 7C, but may refer to the spacing 753 between the dielectric and the ground electrodes. FIG. 7D shows the top plate with the cover removed. Comparing FIG. 7A to FIG. 7D, with the top removed, both the first and the second microfluidics channels are shown, each with an opening from the microfluidics channel into the air gap. In FIG. 7D, the two channels may be simultaneously used by pushing/pulling fluid through one channel into the cell underlying them for rinsing, mixing, removing waste, etc. In FIGS. 7A-7D, there are via holes through the top plate in to air. Although the top plate may be thicker, in some variations it may be beneficial to include more reagents, including freeze-dried reagents that may be rehydrated.

Figure 8B:
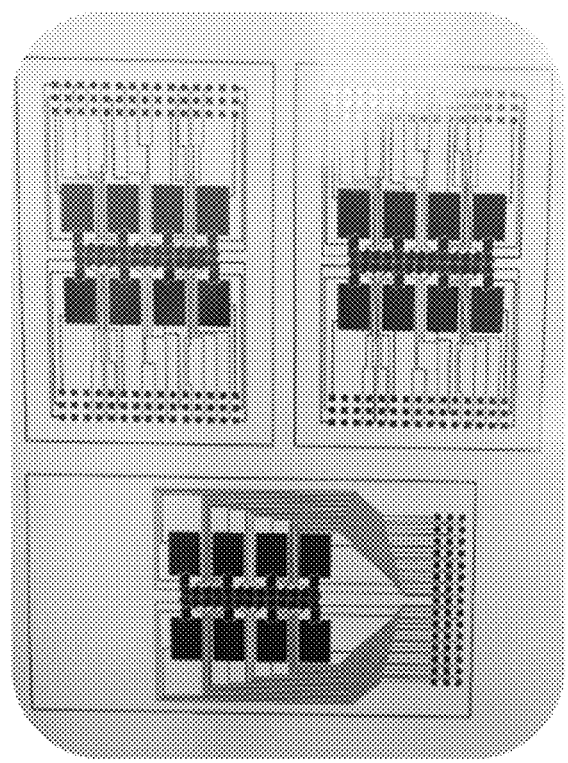
FIG. 8B shows paper digital microfluidics that may be used as part of a cartridge.
Figure 8A:
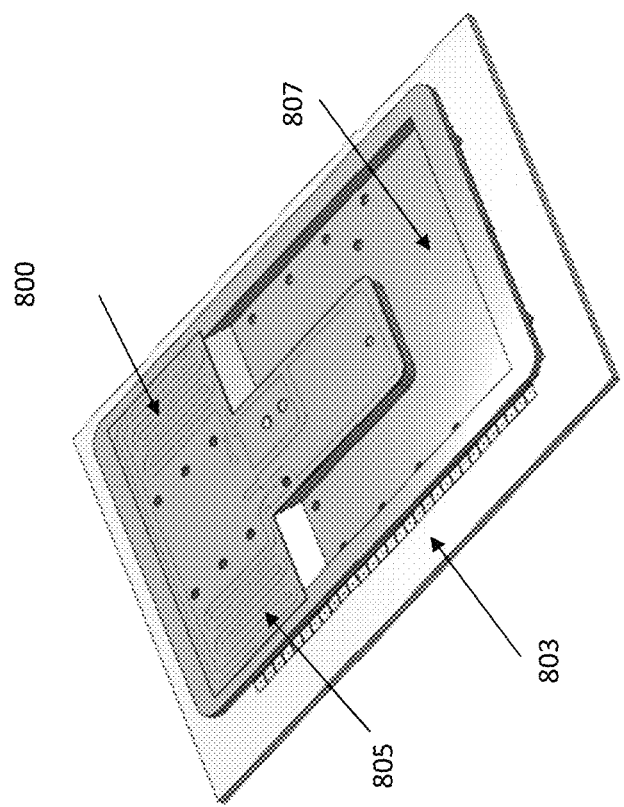
FIG. 8A is an example of a disposable cartridge, including a plastic top plate and a dielectric.

FIGS. 8A-8B illustrate different example of cartridges that may be used. In FIG. 8A, an exemplary cartridge 800 (similar to that shown in FIGS. 7A-7D) is shown over a seating surface 803 including electrodes. The cartridge 800 includes a microfluidics portion 805 formed above the air gap (not visible in FIG. 8A), on one end of the cartridge. The other end of the cartridge includes a window region 807 through which a portion of the air gap may be imaged. The both the front (window) region and the back (microfluidics) regions of the cartridge may include access regions for accessing the air gap and/or microfluidics portions. In FIG. 8B, three different DMF design configurations on paper are shown. Paper DMF devices were formed by inkjet printing arrays of silver driving electrodes and reservoirs connected to contact pads onto paper substrates.

Figure 10A:
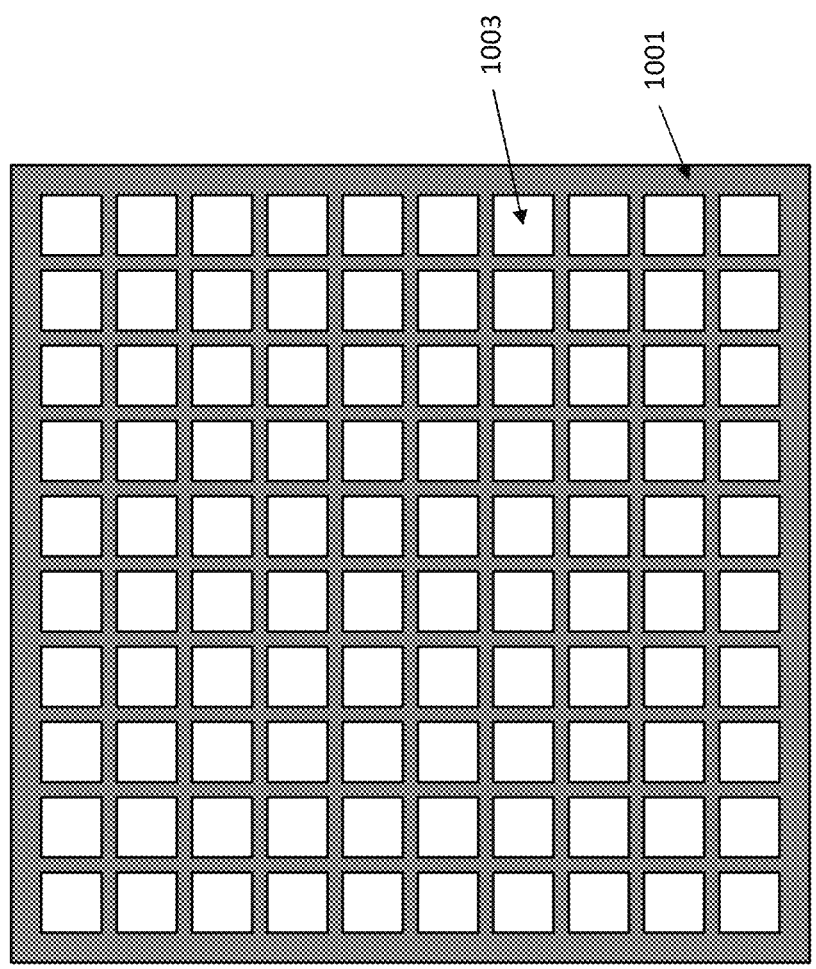
FIG. 10A schematically illustrates an example of a patterned ground electrode on a top plate as described herein.
Figure 10B:
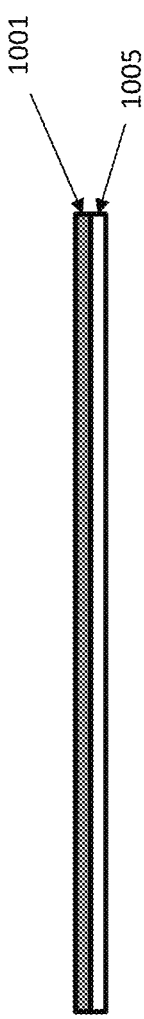
FIG. 10B shows a side view of the patterned top plate shown in FIG. 8A.

Within the cartridge, the top plate may be any appropriate material, including transparent materials, such as acrylics. The top plate may be formed of (or may contain) one or more conductive polymers. The ground electrode(s) may be formed on the top plate. In particular, the ground electrode may be formed of a conductive material, including in particular, printed conductive materials, such as conductive inks. The return electrode may be, in particular, a pattern (e.g., a grid pattern) having a plurality of window openings forming the grid. The pattern may be selected so that when the cartridge is secured to the seating surface of the reader the window openings align with the drive electrodes. In FIG. 10A, the ground electrode 1001 is shown, having a grid pattern including a plurality of open, square-shaped windows 1003. As already mentioned, the window openings forming the grid pattern may be any appropriate shape, including other quadrilateral shapes (e.g., rectangular, etc.), other polygonal shapes, elliptical (e.g., circular, oval, etc.) shapes, regular and non-regular shapes. An additional layer, such as a hydrophobic layer, may overlay both the conductive material pattern and the plate. FIG. 10B shows an exemplary side view (thickness not to scale) showing the plate 1005 and the conductive, patterned electrode 1001. In general, none of the figures described herein are necessarily show to scale, unless indicated otherwise.

FIGS. 11A and 11B show another example of a ground electrode 1101 formed into a grid pattern, having elliptical 1103 (in this example, circular) window openings, formed onto a first plate 1105.

For example, the electrode may be formed of a conductive ink such as a silver ink, as shown in FIG. 8B. Such printable inks may have advantages over other conductive materials previously described, such as ITO, despite not being clear. The use of silver nanoparticles formed into a grid may result in lower, more repeatable and more accurate energy requirements. In FIG. 10A-10B, the pattern of the electrode has a minimum thickness of between about 50 and 200 microns (e.g., 100 microns). The outline around the open windows may be configured to be positioned over the spaces between adjacent electrodes in the drive electrode array. When the cartridge is aligned and secured in position over the drive electrodes, the overlap spacing between the drive electrodes on the bottom plate are covered, but the central regions (which in particular, may include openings for applying the vacuum as described above) may be centered in the window. Since many conductive inks (e.g., including silver ink) are not transparent, the open windows may allow visualization of the air gap beneath the ground electrode. Although the minimum thickness may be between 50 and 150 microns, in practice, the minimum thickness of the grid pattern may be greater than 100 microns width; for example, the minimum thickness may be between 100 and 200 microns.

Figure 12B:
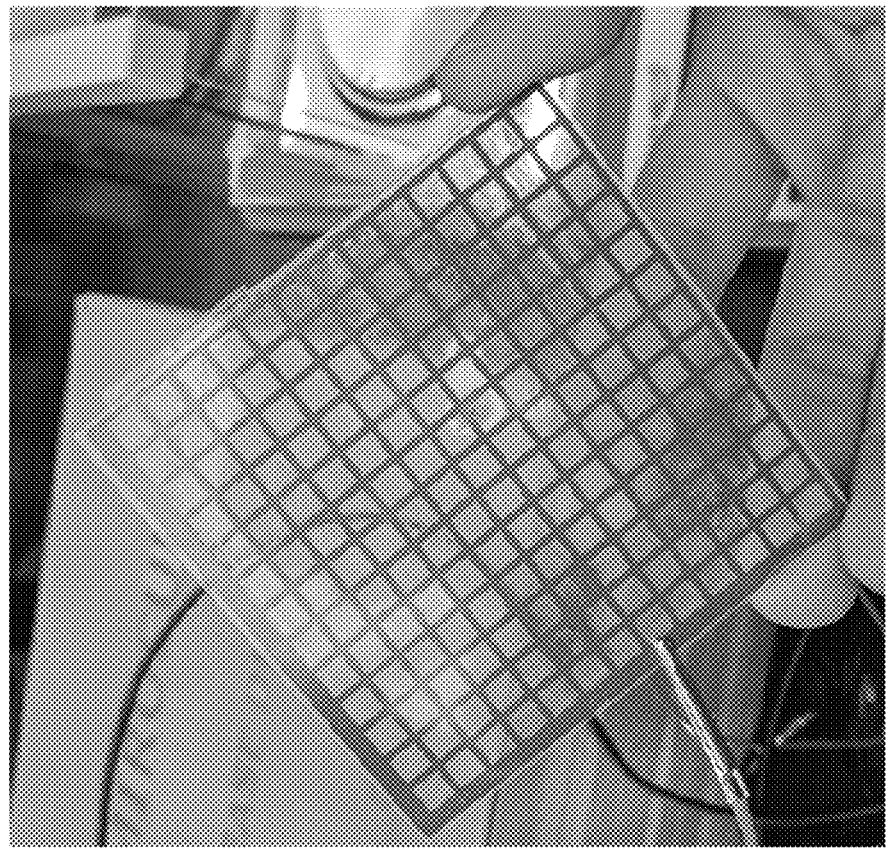
FIG. 12B shows an example of a patterned top plate ground electrode (including a plurality of openings there through).
Figure 12A:
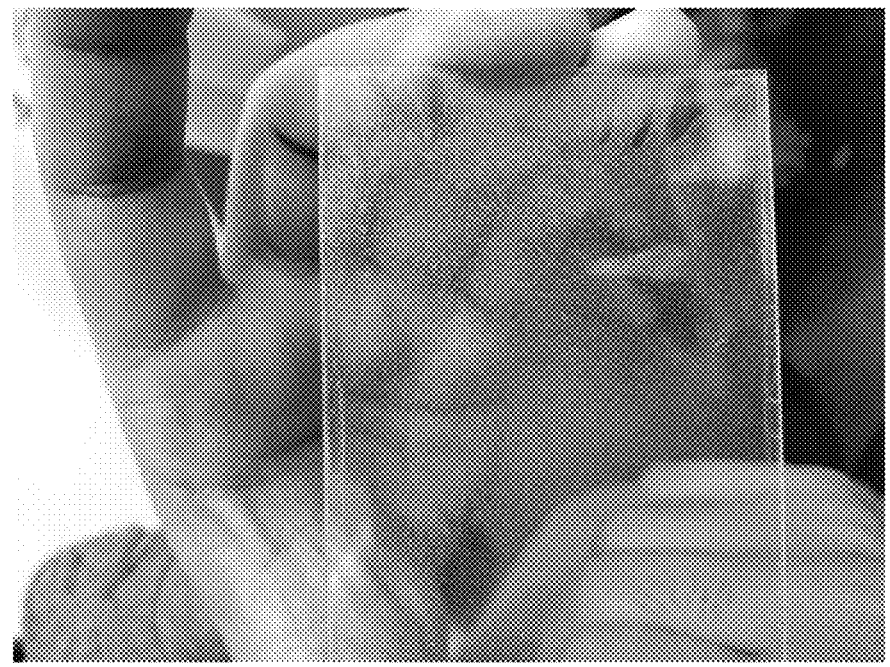
FIG. 12A is an example of conductive ink applied to form the ground electrode on a top plate.

The ground electrode may be formed onto a substrate (e.g., top plate) in any appropriate manner. For example, FIGS. 12A and 12B illustrate two methods of forming the ground electrode. In FIG. 12A, the top electrode is formed by coating the clear substrate with a conductive ink, and allowing the resulting layer to dry. In FIG. 12B, a pattern such as those described above, is formed by a printing technique (e.g., screening, printing, etc.). In FIG. 12B, the pattern is formed by printing a conductive silver nanoparticle ink in a pattern similar to that shown in FIG. 10A.

Figure 13A:
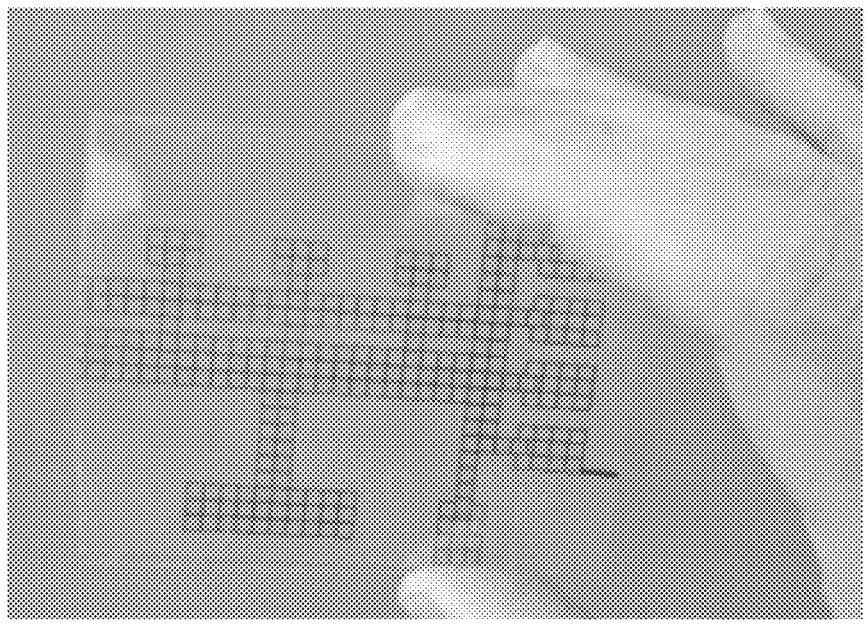
FIGS. 13A and 13B illustrate example of patterned ground electrodes (top plates) on a flexible, transparent substrate.
Figure 13B:
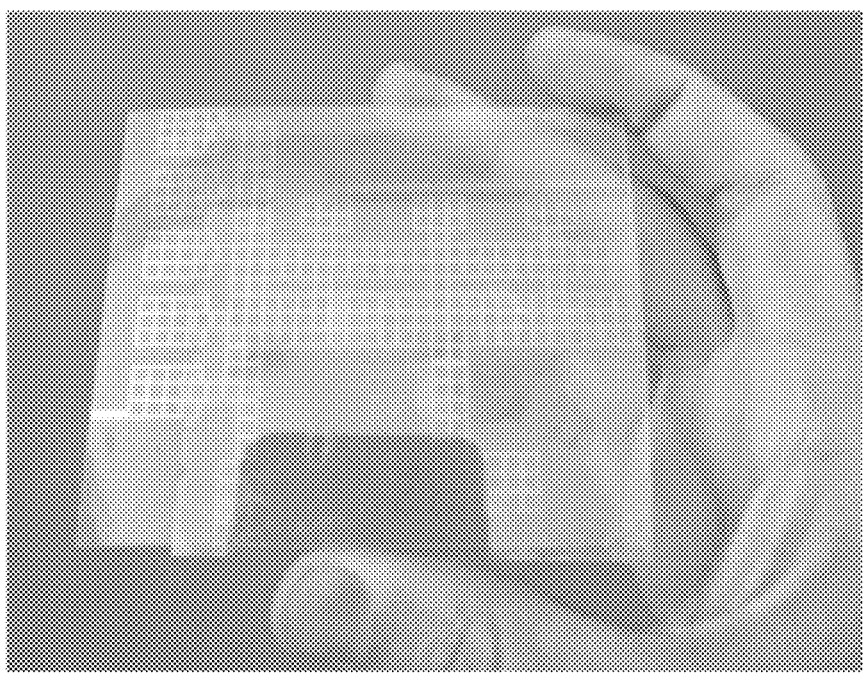
Figure 14C:
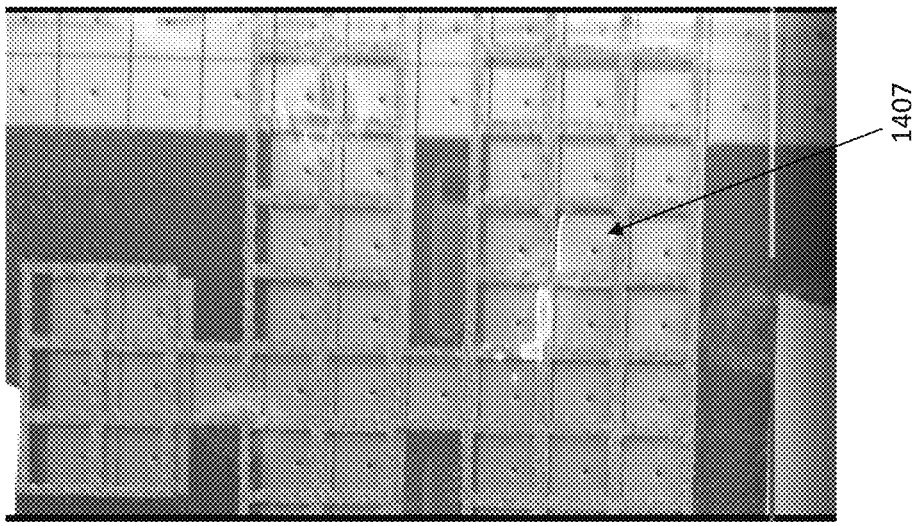
FIGS. 14A-14C illustrate operation of a DMF apparatus using a patterned ground electrode.
Figure 14B:
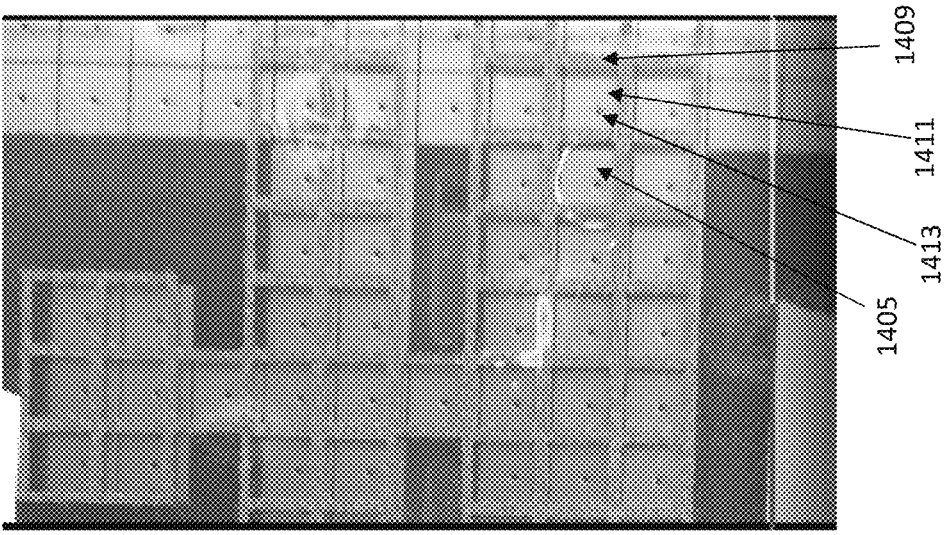
Figure 14A:
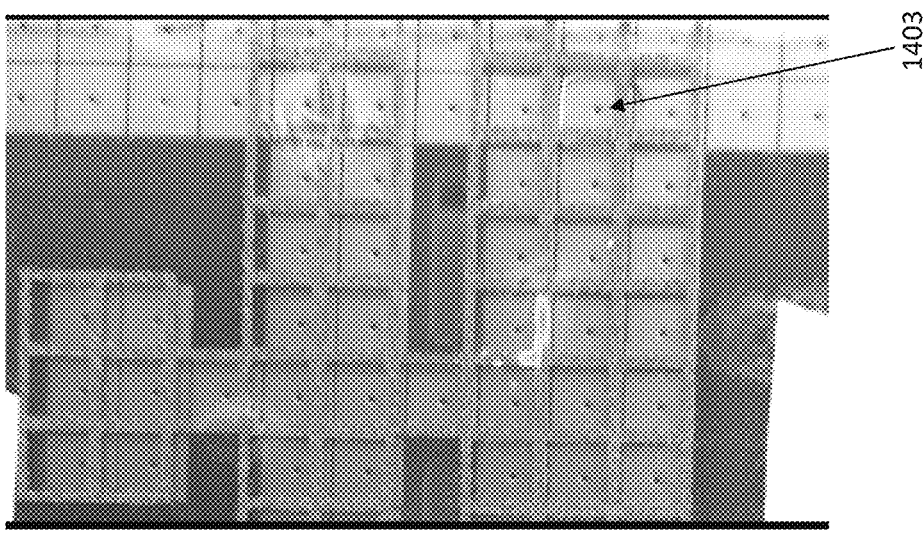

FIGS. 13A and 13B show an example of a top plate having a grid patterned ground electrode. In FIGS. 13A and 13B the grid pattern is formed into a second order pattern having regions including reservoirs for storing fluids in the air gap, as well as passages and chambers where different reactions (heating, mixing, cooling, etc.) may be performed. FIGS. 14A-14C illustrate operation of the ground plate of FIG. 13A-13B, showing the drive electrodes driving movement of a droplet using this ground plate configuration in the cartridge. In FIG. 14A a droplet 1403 is held in the air gap on a first unit cell. In FIG. 14A, the air gap is between a dielectric that is pulled down onto the seating surface and the driving electrodes by a vacuum pulled though the driving electrodes. The pattern of the grid forming the ground electrode matches the arrangement of the driving electrodes in the seating surface. The drive electrodes 1411 each include an opening 1413 connected to a vacuum manifold through which vacuum is applied to hold the dielectric, and therefore the cartridge, in position.

Between FIG. 14A and FIG. 14B, power is applied to the electrode underlying the droplet and to one or more adjacent electrodes in a sequence allowing a change in the electrowetting of the droplet, driving the droplet 1405 to the left, as shown in FIG. 14B; this process may be repeated, as shown in FIG. 14C, moving the droplet to another unit cell 1407 in the air gap. The movement using the grid-patterned ground electrode is equivalent or better than the movement of a monolithic ground electrode.

In any of these variations the return electrode(s) on the top plate of the cartridge may be formed of a material that is layered onto the top plate. For example, the electrically conductive layer forming the return electrode eon the top plate may be formed of aluminum and a film of dielectric and/or hydrophobic material. In some variations, the electrode(s) may be formed of ITO, an adhesive and a dielectric and/or hydrophobic film. In some variations the conductor may be formed of an ITO film (including a primer and Teflon coating).

Figure 15A:
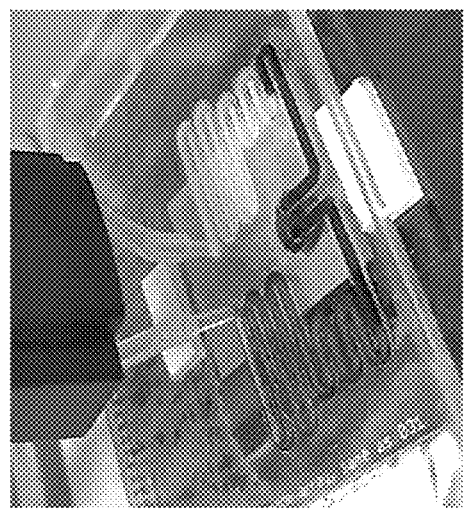
FIGS. 15A-15C illustrate one example of a microfluidics channel interfacing with a DMF air gap region as described herein.
Figure 15B:
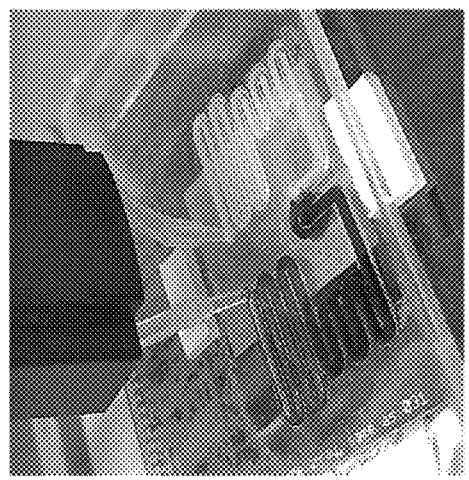
Figure 15C:
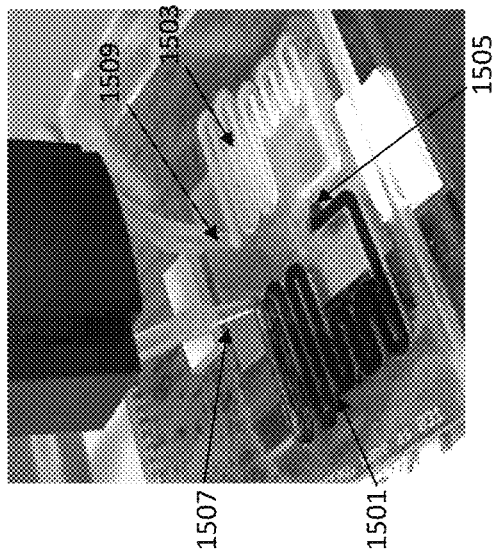

As already discussed above, any of these apparatuses and methods may include one or more microfluidics channel(s) integrated into the cartridge. In particular, the apparatus may include a microfluidics mixing and extraction region. This is illustrated in FIGS. 15A-15C. For example two microfluidics channels 1501, 1503 may be formed into the top plate of the air gap, and an opening in to the air gap may be positioned within a fixed distance from each other. Fluid may be passed from one microfluidics channel to another microfluidics channel, through the air gap. The region of the air gap between these openings may bridge these two regions 1505. This configuration may be used to mix a larger droplet (e.g., greater than 5 microliters, greater than 7 microliters, greater than 10 microliters, greater than 15 microliters, greater than 20 microliters, greater than 25 microliters, greater than 30 microliters, greater than 1 ml, etc.) than could be easily done within the air gap.

For example, in FIG. 15A, a first pressure source 1507 (negative pressure and/or positive pressure) is shown attached to one end of the microfluidics channel, and a second pressure source 1509 (positive and/or negative pressure) is shown attached to another microfluidics channel. Fluid may be withdrawn from the air gap through the opening 1505 into the first channel 1501; alternatively or additionally, by applying positive pressure 1507, fluid may be moved from the first channel 1501 into the air gap through the opening 1505; concurrently, fluid may be drawn from the air gap at or near the same opening 1505 into the second channel by applying negative pressure 1509 within the second channel. Alternating positive and negative pressure may pass relatively larger volumes of solution between the two microfluidics channels, in and out of the air gap, as shown in FIGS. 15B and 15C.

In the example shown in FIGS. 15A-15C, the top plate integrates microfluidic channels, as well as reservoirs and tubing; alternatively or additionally, one or more ports (e.g., for connecting to the pressure source(s), valves, and the like may be included. For example, a cover over the microfluidics channels may be included with port(s) and/or valves and the like. Positive and negative pressure may be applied within the microfluidics channel(s), for example, by reversing the polarity of a peristaltic pump.

Figure 16B:
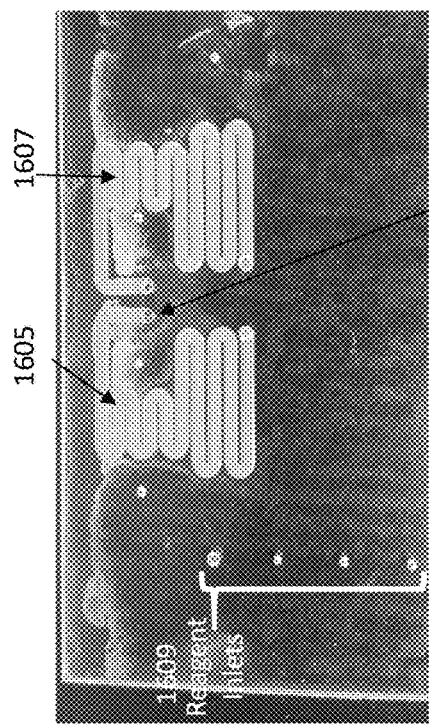
FIG. 16B shows an example of a top plate into which microfluidic channels have been formed.
Figure 16A:
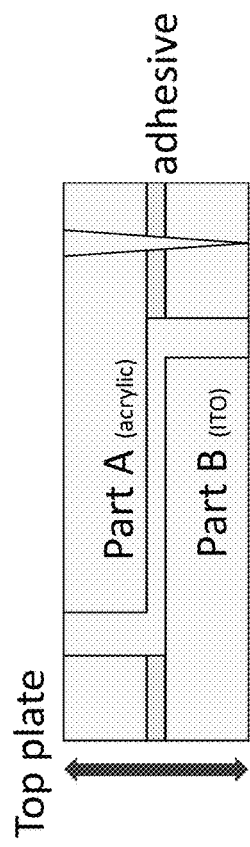
FIG. 16A shows one example of a section through a top plate to form a microfluidics channel immediately adjacent to the DMF portion (e.g., above or below the DMF portion, as part of the top plate).

FIGS. 16A-16D illustrate examples of microfluidics channels that may be included. For example, FIG. 16A illustrates the formation of a microfluidics channel formed in part by the top plate. In FIG. 16A, a portion of the channel may be formed in the plate (e.g., the acrylic plate) itself, where a second portion of the channel may be formed from another material that has its other side coated with a conductive material (i.e., indium tin oxide, copper, nickel, chromium and gold). The layers may be held together by an adhesive, and/or may be bonded together.

For example, microfluidic channels in any of the cartridges and apparatuses described herein may be formed by laser cutting. For example, in FIG. 16A, a raster channel may be cut into part B (the acrylic forming the top plate), and a hole may be cut in part B. In addition, one or more pump holes may be cut into part A. a double-sided adhesive (e.g., tape) may be used to secure part A to part B, and a roller may be used to place part A on part B, avoiding air bubbles. Thereafter, pipette holes may be cut out for dispensing reagents, and the bottom may be Teflon (e.g., hydrophobic) coated and the entire assembly baked at between 80-200 degrees (e.g., between 90-18 degrees, etc.). The ground electrode may already be formed onto the plate.

Figure 16D:
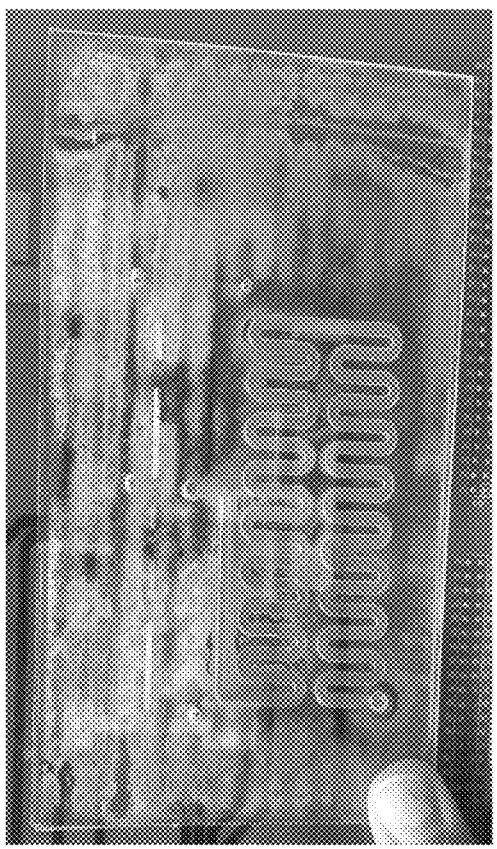
FIG. 16D shows another example of a microfluidics channel formed into a top plate of a DMF portion of a cartridge.
Figure 16C:
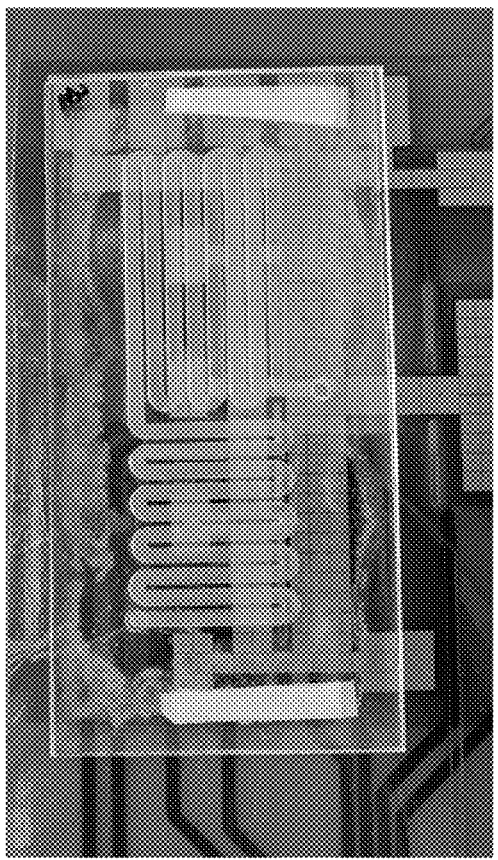
FIG. 16C is another example of a top plate of a DMF apparatus configured as a microfluidics channel. The top plate is shown as an acrylic material into which channels and holes have been formed (e.g., by milling, cutting, rastering, etc.).

FIG. 16B illustrates another example of a set of microfluidic channels 1605, 1607 formed into the top plate. A set of reagent inlets 1609 are shown as well, providing openings into the air gap region for loading regents. Alternatively or additionally, reagents may be pre-loaded (wet or dry/lyophilized) into the cartridge, including in one or more reservoirs above the top plate or in the top plate, e.g., in a microfluidics channel, and/or directly into the air gap region. FIGS. 16C and 16D illustrate additional examples of microfluidics channels that may be formed into a top plate of a cartridge.

Figure 17A:
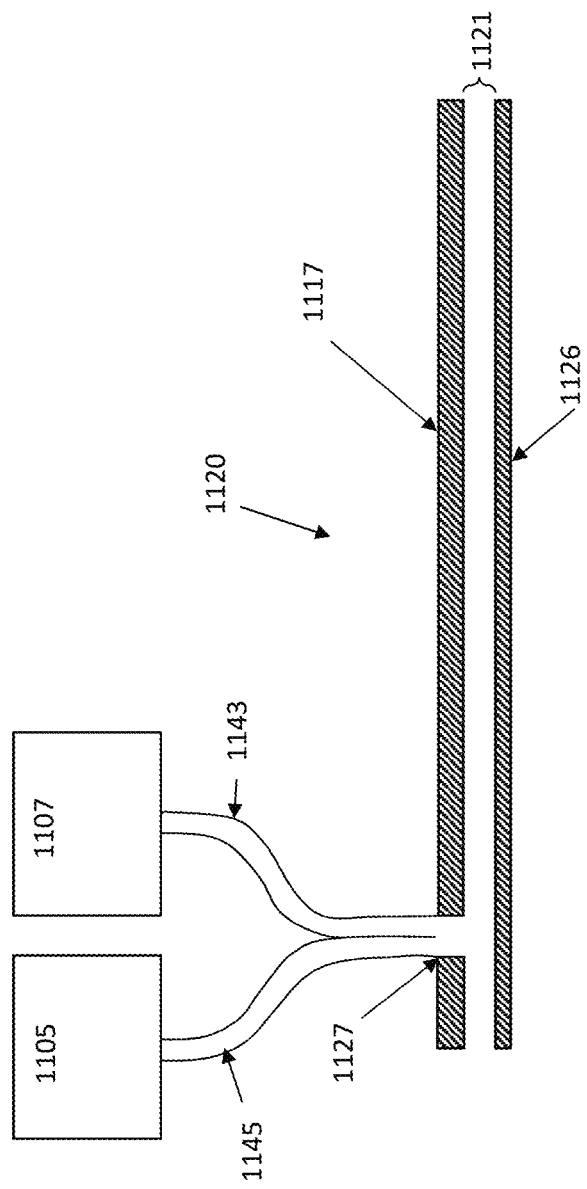
FIGS. 17A and 17B illustrate extraction and mixing of fluid in a DMF apparatus (e.g., cartridge) as described herein, using a fluid application and extraction technique that includes a bifurcated channel, allowing a large volume of fluid to be exchanged between two reservoirs.
Figure 17B:
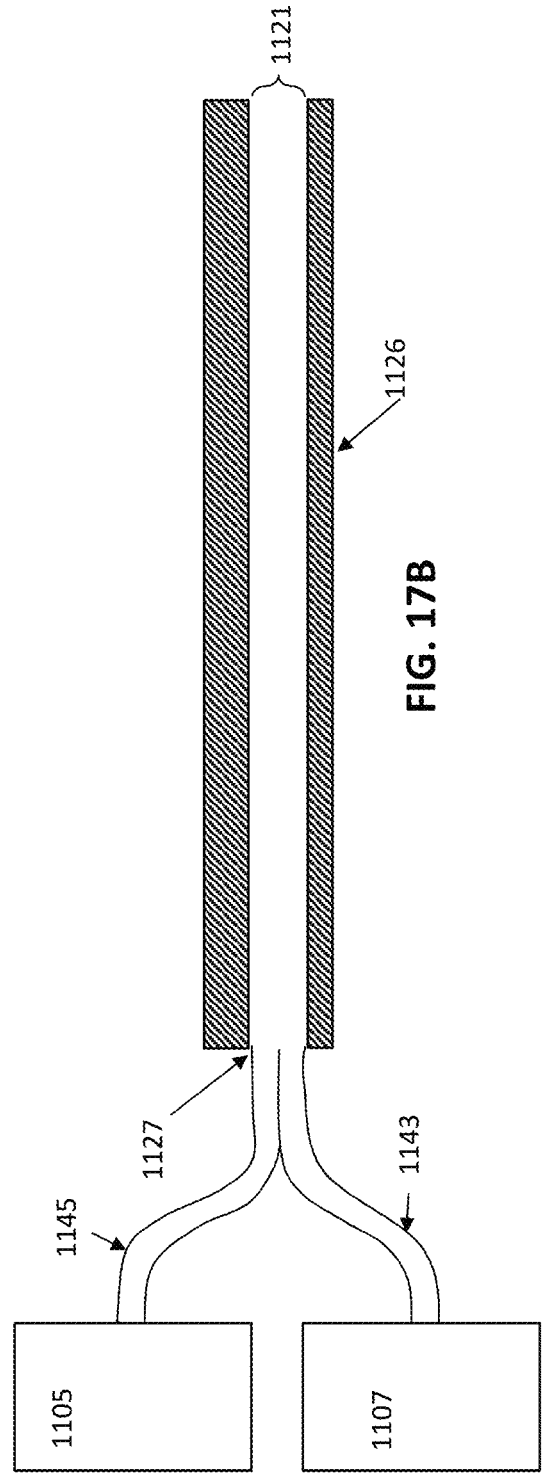

FIGS. 17A and 17B illustrate schematically examples of a method for applying and removing (including washing) fluid to/from the air gap of a DMF apparatus 1120. In FIG. 17A, for example, the air gap 1121 of the cartridge is formed between the top plate 1117 and the bottom dielectric 1126. A connector interface 1127 connects a combined inlet/outlet port for a first fluid channel 1143 and a second fluid channel 1145. These fluid channels may be connected one or more reservoirs 1105, 1107. As already described above, in some variations, two separate connector interfaces (ports) may be used, one connected to each fluid line (e.g., which may be a microfluidics channel, as described above). A bridging droplet in the air gap region 1121 may connect to both inlet and outlet lines, and fluid may be drawn into and out of the fluid lines 1143, 1145 to mix the droplet, add fluid to the droplet, remove fluid from the droplet, expose a solid phase capture element (e.g., magnetic bead, non-magnetic bead, etc.) to the same fluid repetitively to deplete the fluid from the analyte of interest, e.g., to concentrate the analyte on the solid phase or other surfaces), etc.

Alternatively, as shown in FIGS. 17C and 17D, the cartridge may include air gaps of different heights. For example, in FIG. 17D, the air gap for the region around the connector interface 1127 may be greater (e.g., between 0.5 and 2 mm) larger than the air gap between other regions of the top plate and the dielectric 1121, as a portion of the top plate 1115 (or a separate top plate 1115 connected to another top plate 1117) may be spaced further from the dielectric 1126. Similarly, in FIG. 17D, the air gap 1119 near the connector interface at the edge of the apparatus may be larger than the air gap 1121 in other regions, e.g., by spacing a portion of the top plate 1117 further from the dielectric 1126 bottom layer.

A prototype DMF apparatus and cartridge illustrating the principle shown in FIG. 17C is illustrated in FIGS. 18A-18C, and was used to demonstrate the proof of principle for mixing larger volumes of solution in an air gap of a DMF cartridge. In FIG. 18A, the upper plate of the DMF cartridge included an opening through the top plate 1801 connected to a first fluid line 1843 and a second fluid line 1845. By alternating negative pressure (suction) between the first and second fluid line, fluid was moved back and forth between the first reservoir 1805 and the second reservoir 1807, as shown in the sequence of FIGS. 18A, 18B and 18C. In this example, magnetic particles holding an analyte of interest are magnetically held within the air gap (e.g., against the bottom, e.g., hydrophobic coated dielectric) by the DMF apparatus 1809 while the fluid is exchanged between the reservoirs, enhancing binding and/or rinsing.

In any of the air-gap apparatuses described herein, evaporation may be controlled or reduced, particularly when heating the droplets within the air gap. FIGS. 19A-19C illustrate the effects of evaporation on a droplet 1903 after only a few minutes. The intact droplet is shown in FIG. 19A. After one minute at 95 degrees C., the droplet volume has noticeably decreased (e.g., losing between 5-15% of the volume of the droplet, as shown in FIG. 19B. After two minutes (FIG. 19C), the droplet is between 20-34% smaller. To prevent this loss due to evaporation, the droplet within the air gap may be sheathed or covered in a nonpolar jacket, as illustrated in FIGS. 20A-20C. For example, a liquid paraffin material (e.g., a nonpolar material that is liquid at the working range described herein, e.g., between 10 degrees C. and 99 degrees C., may be used. In FIG. 20A, a droplet 2003 jacketed in liquid paraffin 2005 is heated (e.g., to 65 degrees C. or above). After one hour (FIG. 20B), the droplet has not appreciably evaporated. Similarly after 2 hours (FIG. 20C), the droplet has remained approximately the same volume.

In use, the nonpolar jacketing material may be added and removed at any point during a DMF procedure, as illustrated in FIGS. 21A-21I. Surprisingly, removal may be accomplished, for example, by drawing the jacketed droplet up out of the air gap, e.g., out of a port entering into a microfluidics channel as described above. The liquid paraffin, for example, may be removed into a waste reservoir by applying a negative pressure to a droplet from a port through the top or side of the air gap. The lower-density liquid paraffin may be the first layer that gets drawn up, leaving the aqueous droplet behind. Previously it was believed to be difficult or impossible to remove the jacket of nonpolar liquid.

Figure 21A:
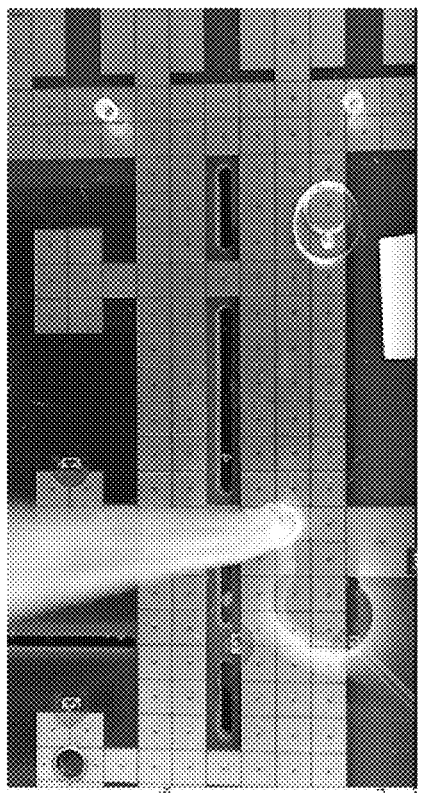
FIGS. 21A-21D illustrate the use of a non-polar jacketing material in an air-matrix DMF apparatus.
Figure 21B:
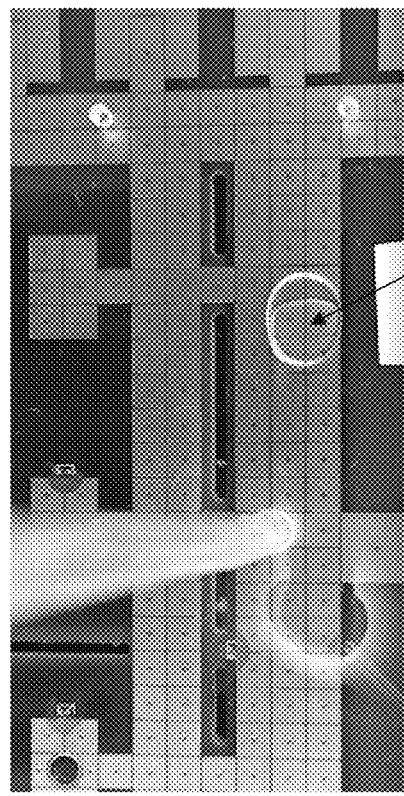
Figure 21C:
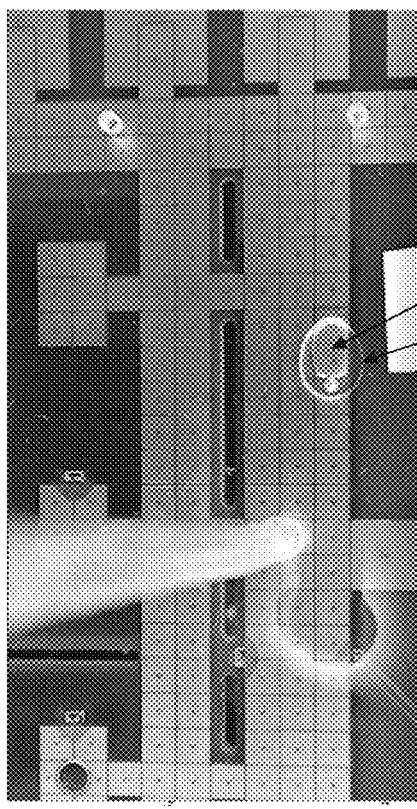
Figure 21D:
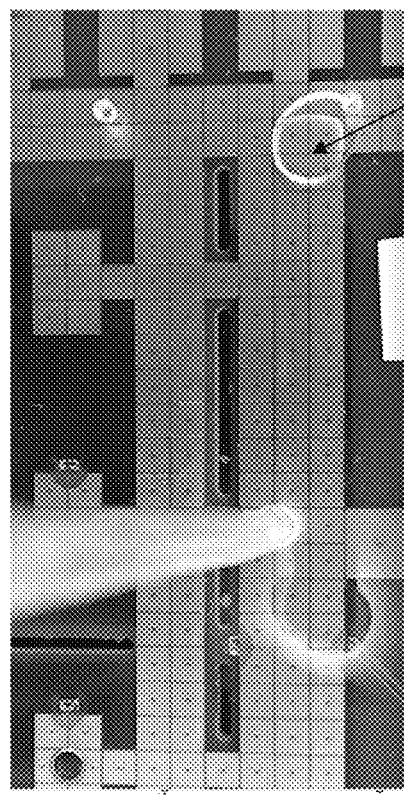

For example, FIG. 21A shows a jacketed droplet in which the aqueous droplet 2101 is surrounded by a nonpolar liquid 2103 (e.g., liquid paraffin). In this example, a small bubble has also been formed in the liquid paraffin. The droplet may be easily moved, as shown in FIG. 21B, showing the droplet moving by the coordinated application of energy to the driving electrodes to alter the electrowetting of the aqueous droplet. In FIG. 21B, the jacketed droplet has been moved to the right. Initially, the aqueous droplet may be combined with the nonpolar liquid by applying the nonpolar liquid into the air gap either directly on the droplet, or in a region of the air gap that the droplet may be moved into. The jacketed droplet may also be combined with one or more additional droplets that may include a nonpolar liquid droplet of their own, or may be unjacketed. In some variations, a jacketing droplet (including a small aqueous droplet and a relatively large volume of nonpolar solution may be combined with the target droplet in order to jacket the target droplet. The small amount of aqueous liquid in the jacketing droplet may be a buffer, diluent, or other solution that allows the jacketing droplet to be moved in the air gap. This technique is particularly helpful when used with DMF cartridges having larger (e.g., 0.5 mm or greater) gap widths. A larger gap width may otherwise make it difficult for the larger droplets to maintain a jacket of typically less dense nonpolar jacketing material. FIGS. 21C and 21D illustrate a droplet 2101 that has been combined with another droplet, forming a larger jacketed droplet 2101'. The larger droplet may also be moved by controlled actuation of the driving electrodes, as shown in FIGS. 21C and 21D.

Figure 21E:
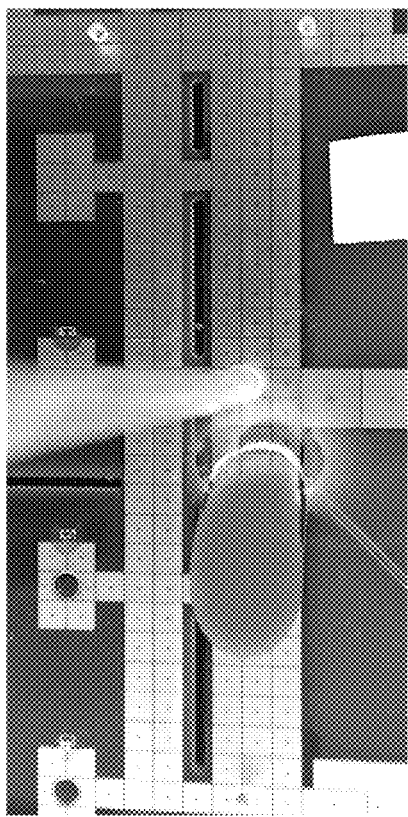
FIG. 21E-21I illustrate adding a large sample to a jacketing material, and mixing the sample.
Figure 21F:
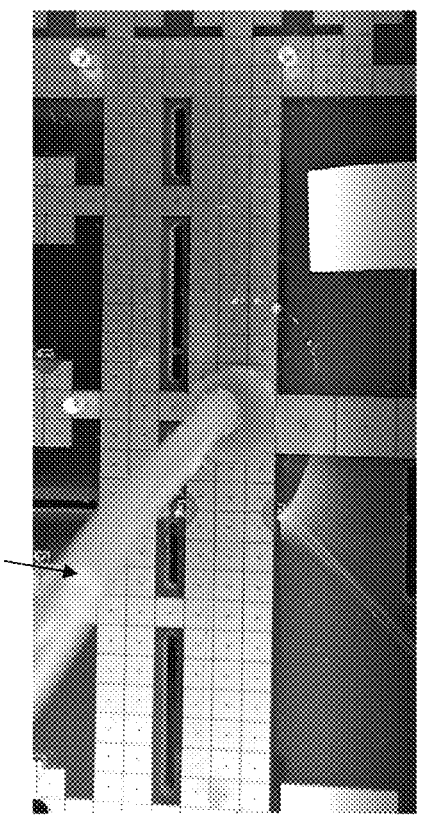
Figure 21G:
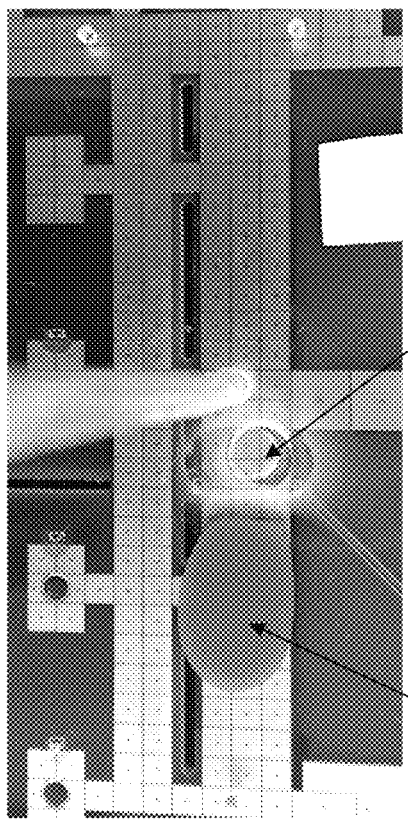

FIGS. 21E to 21I illustrate the use of a nonpolar liquid jacket in a sample including a magnetic bead material. In FIG. 21E, a jacketing droplet includes a small amount of aqueous liquid 2121 and a relatively large amount of nonpolar jacketing material 2123, the two may be combined, for example, by moving the jacketing droplet 2123 into the sample droplet 2121, as shown in FIG. 21F, allowing them to combine so that the jacketing material is now jacketing the sample droplet. In in his case, the sample droplet is quite large, and includes a concentration of sample absorption magnetic beads.

Figure 21H:
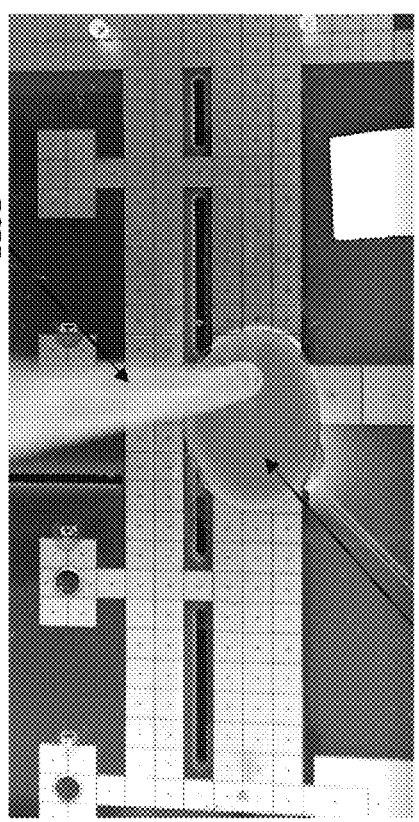
Figure 21I:
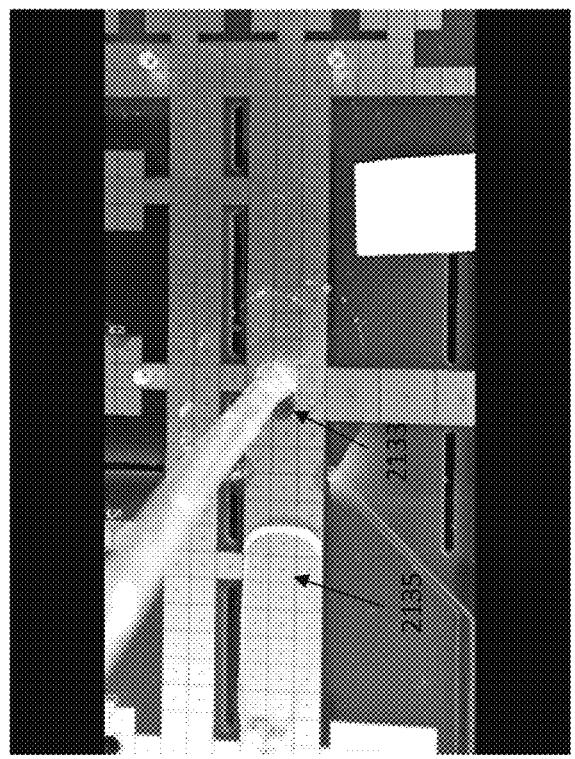

Once combined, the jacketed droplet 2121' may be moved (by DMF) to a port into the air gap from which solution may be extracted, as shown in FIG. 21H. In this example, the solution may be mixed by applying positive and negative pressure to move the solution into and out of the fluid channel 2131. The nonpolar solution jacketing the droplet may be removed by applying negative pressure to pull the solution out of the air gap though the top port; the first solution removed is the jacketing material. Thereafter, as shown in FIG. 21I, the magnetic particles to which a desired analyte has been bound may be held onto the bottom side of the air gap, e.g., by applying a magnetic field, and the droplet solution may be removed, and/or washed, in the absence of nonpolar jacketing solution, which may otherwise interfere with the binding or release of the analyte from the magnetic particles. In FIG. 21I, the magnetic particles 2133 are left in the air gap, and a separate washing buffer may be applied by moving a washing and/or elution droplet 2135 over the magnetic particles.

In addition to the techniques for controlling evaporation discussed above (e.g., using a jacket of nonpolar liquid), any of the methods and apparatuses described herein may also include controlling the partial pressure of water vapor inside the cartridge to create "zero evaporation" conditions, e.g., by balancing the rates of water molecules leaving and entering the water surfaces. The balance does not need to be perfect, but may be adjusted by adjusting the temperature and pressure so as to stay as close as possible to the zero evaporation condition. This may vary with temperature; for example, once relative humidity is controlled, it may be best to adjust the humidity up and down with the temperature, e.g., during hybridization or PCR cycling using the apparatus. Alternatively or additionally, any of these apparatuses may use local replenishment to adjust for evaporation by moving droplets slightly to recapture nearby condensation (see, e.g., FIGS. 19B-19C, showing evaporative droplets surrounding the main droplet). Any of these methods and apparatuses may also or alternatively use walled-in heating zones to reduce the surface area from which evaporation may occur. For example, as mentioned above, in some variations the seating surface of the DMF apparatus may include projections forming local regions within the cartridge, since the vacuum may be precisely applied to control the contact between the flexible dielectric and the electrodes, projection on the seating surface may create chambers or channels within the air gap, including forming partially wall-in heating zones that may reduce evaporative surface area. In some variations, the top plate may be spaced differently across the cartridge; the evaporation rate may be lower for thinner droplets compared to thicker droplets. Thus, any of the heating regions may have a narrower width of the air gap to reduce evaporation.

In any of the large-volume droplet DMF cartridges, e.g., DMF cartridges having a gap separation of 0.5 mm or greater (e.g., 0.6 mm or greater, 0.7 mm or greater, 0.8 mm or greater, 0.9 mm or greater 1 mm or greater, e.g., between 0.4 mm and 2 mm, between 0.5 mm and 2 mm, between 0.5 mm and 1.8 mm, between 0.5 mm and 1.7 mm, etc.), it has proven particularly difficult to dispense droplets having a predictable volume, as the surface tension of the relatively large droplets may require a greater amount of energy to release a smaller droplet from the larger droplet. In general, in digital DMF systems, the ratio between spacer (air gap) thickness and electrode size dictates the volume of droplet dispensing. In the conventional digital microfluidic approach, spacer thickness of less than about 500 micrometers (0.5 mm) allows for electrowetting forces to split a unit liquid droplet from a larger amount of liquid volume; this has not been possible with higher spacer thicknesses (e.g., greater than 500 micrometers). Described herein are methods for splitting unit droplets from larger volumes in air gaps having a width (e.g., spacer thicknesses) of 500 µm or greater. In some variations this may be performed by, e.g., flooding a region of the air gap with a solution to be dispensed from a port (which may be a side port, top port or bottom port), and then selectively activating a cell (corresponding to a driving electrode) in the flooded region, then withdrawing the solution back into the port (or another port) that is offset from the activated electrode so that a droplet remains on the activated electrode as the solution is withdrawn into the port; the droplet on the activated electrode breaks off from the larger flood volume (e.g., by necking off), leaving the dispensed droplet behind, where it may then be driven by the drive electrodes, combined with one or more other droplets, etc.

For example, an integrated companion pump may be used to drive a large volume of aqueous solution into a DMF device (e.g., into an air gap of the DMF cartridge) and over an activated electrode. The aqueous solution may then be withdrawn away from DMF device, dispensing behind a unit droplet over the activated electrode. FIGS. 22A-22D illustrate an example of this method. In FIG. 22A, a port 2201 into the air gap 2205 of the DMF cartridge connects to a fluid channel (e.g., a microfluidics channel as described above), shown in FIG. 22A as a tube 2209, holding an aqueous solution (reagent 2203). In this example, a single drive electrode 2207 has been actuated; alternatively in some variations, the electrode is not activated until after flooding the region of the DMF apparatus. Pre-activating it may help distribute a predefined amount onto the unit cell defined by the drive electrode. In any of these examples more than one contiguous drive electrodes may be activated to dispense larger-volume droplets.

Figure 22A:
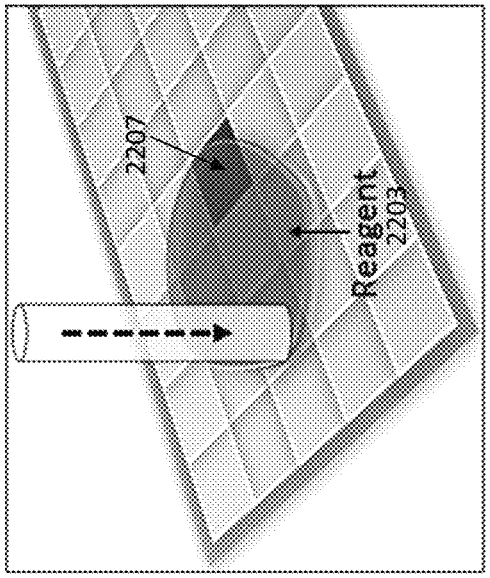
FIGS. 22A-22D illustrate the control of droplet volume when dispensing droplets (e.g., reagents) into an air-gap of a DMF apparatus. In particular, the air-gaps described herein may be large air-gaps (e.g., greater than 280 micrometers, greater than 300 micrometers, >400 micrometers, >500 micrometers, >600 micrometers, etc. separation between the top and bottom dielectrics). In such cases, the electrowetting forces alone may not be sufficient to dispense droplets of a predetermined volume.
Figure 22B:
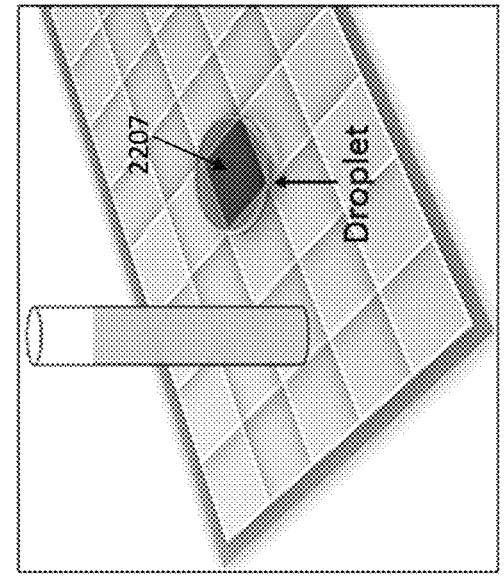

Next, as shown in FIG. 22B, the region of the air gap including the activated drive electrode is flooded with the aqueous solution 2203. FIG. 22A shows the release of a large volume (e.g., 250 µL) from the channel (tube 2209). In some variations, as the reagent nears the distal end channel 2209, a drive electrode 2207 is activated (e.g., AC potential of 390 Vrms, or by otherwise creating an alternating field effect using a DC potential), which may generate an electrowetting force that further encourages transfer of the reagent from tube 2209 to the activated drive electrode 2207; further flow from the channel occurs so that the droplet grows to fully cover the activated drive electrode(s).

Figure 22C:
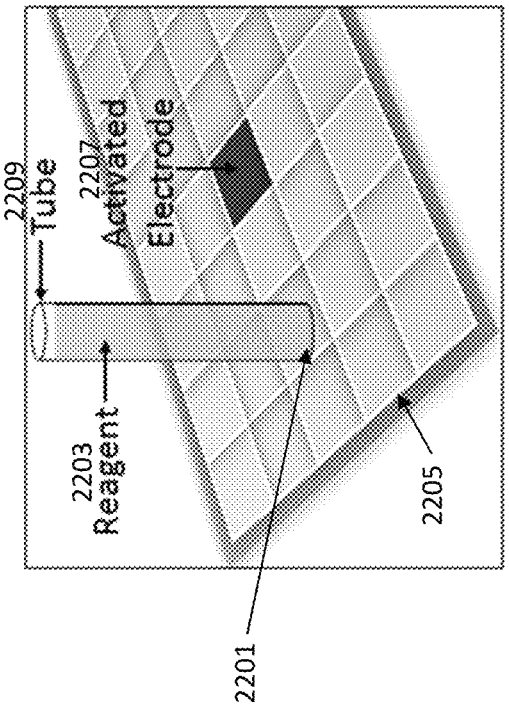
Figure 22D:
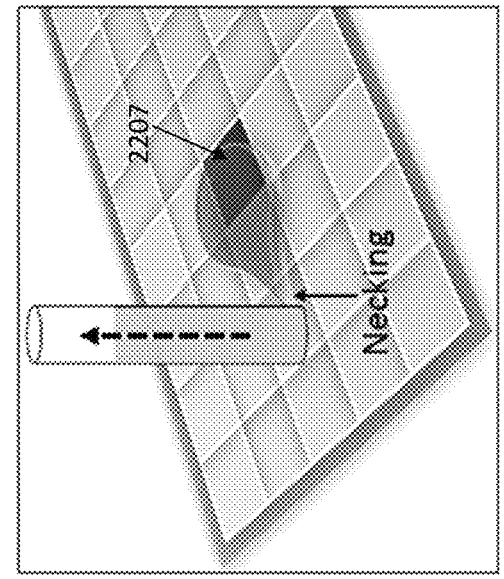

In FIG. 22C, the aqueous solution (reagent 2203) is then withdrawn from the air gap through the same port 2201 or a separate port, where the activated drive electrode(s) is/are separated from the port into which the solution is being drawn by a distance (e.g., the distance may be approximately equivalent to the width of the activated electrode); this distance is sufficient so that the droplet on the activated drive electrode(s) necks off of the liquid being withdrawn back into the channel 2209. For example, aspirating the reagent back into the tube as shown in FIG. 22C may result in necking of the droplet from the rest of the solution; the neck region continuously shrinks until a unit droplet (e.g., 10 µL) is left behind on activated drive electrode, as shown in FIG. 22D. The same process can be repeated with activating two, three and five electrodes to dispense approximate multiples of the unit droplet (e.g., 20, 30 and 50 µL), respectively as shown in FIG. 23A-23E. Multiple droplets may be separately dispensed and combined, or alternatively multiple electrodes may be used to dispense larger volumes at once, as mentioned. The size of the droplet (droplet volume) may be based in part by the size of the driving electrodes and the spacing of the air gap.

FIGS. 23A-23F illustrate the dispensing of various predefined volumes of solution from a reservoir above the cartridge using the method described above. In FIG. 23A, for example, the region of the air gap including the port connecting to a channel holding solution above the larger air gap (e.g., 0.5 mm width) is flooded with solution 2301, as shown, and a single activated electrode is used to break off a predetermined volume of solution (e.g., 10 microliters), shown in FIG. 23B. This droplet may be moved away from the flooding region, and the process repeated multiple times to produce multiple droplets of approximately uniform volume (e.g., 10 microliters +/−5%, 10%, 15%, 20%, 25%, etc.). In FIG. 23D, a first unit droplet 2303 (e.g., having a 10 microliter volume) is shown adjacent to two combined unit droplets 2305, which form a second droplet having 2× the volume, e.g., 20 microliters. Similarly, FIG. 23E shows a large droplet 2307 (e.g., 50 microliters) formed by combining five unit droplets. FIG. 23F illustrates the use of a larger driving electrode 2315 (e.g., having approximately 4× the surface area) that may be activated when flooding the air gap region to form a larger unit droplet 2311 (e.g., a 40 µL unit droplet).

Thus, by flooding or flushing a dispensing region of the air gap with a large volume of aqueous solution, and activating a drive electrode (or over an already-active drive electrode), then removing the solution (e.g. pumping it out) a relatively precise volume droplet may be left behind. As mentioned, when using large-volume DMF apparatuses (cartridges), e.g. having a spacing of between 0.4 or 0.5 and up to 3 mm, this technique may be used to dispense smaller-volume droplets from larger-volume reservoirs with a reasonable amount of force; unlike air gap DMF apparatuses having smaller air gaps, which may directly dispense smaller volume droplets form a larger volume by applying electrowetting energy, the larger force effectively prevents directly dispensing by DMF in larger air-gap devices. In many of the examples provided herein, the gap spacing of the air gap is between 1 mm and 1.3 mm (e.g., approximately 1.14 mm), though at least up to a 3 mm spacing has been successfully used.

Dispensing of solution as described herein may be particularly important in processing samples (e.g., mixing, etc.) as well as replenishing solution lost due to evaporation in such systems.

User Control Interface

In any of the apparatuses and methods described herein, a DMF apparatus may be controlled by a user so that the DMF apparatus can execute one or more protocols (e.g., laboratory procedures) on a sample that is inserted into the DMF apparatus (e.g., cartridge). For example, a DMF apparatus may include a user interface that dynamically and flexibly allows the user to control operation of the DMF apparatus to perform a user-selected or user-entered protocol. In general, there are numerous considerations when translating a processing protocol for operation by a DMF apparatus, including preventing contamination during the procedure. Contamination may occur when moving a sample droplet, in which the protocol is being performed, over a path taken by earlier steps in the procedure (or parallel steps). Typically, the one or more reaction droplets that are being processed may need to be moved to different locations within the air gap of the DMF cartridge, and/or temporarily out of the air gap region. It would otherwise be difficult for the user to coordinate these movements both to avoid earlier or future paths (e.g., contamination) and to remember which locations are appropriate for heating, cooling, mixing, adding, removing, thermal cycling, etc.

Described herein are user interfaces for controlling the operation of the DMF apparatus that allow the user to more easily enter protocol information/steps into the DMF. This may be accomplished in part by providing a set of graphical step representations (e.g., showing mixing, adding, heating, cooling, cycling, washing, etc.) of steps that may be performed, and allowing the user to select/enter these steps in a manner that also intuitively provides the duration of the steps, or the degree (e.g., temperature, etc.) to be applied. Once entered, the apparatus may then determine an efficient pathway to perform the entered protocol within the predefined layout constraints of the DMF apparatus and/or cartridge to avoid contamination. For example, any of these apparatuses may determine a pathway (pathfinding) that prevents or reduces path crossing within the air gap where such crossovers may result in contamination.

Figure 24:
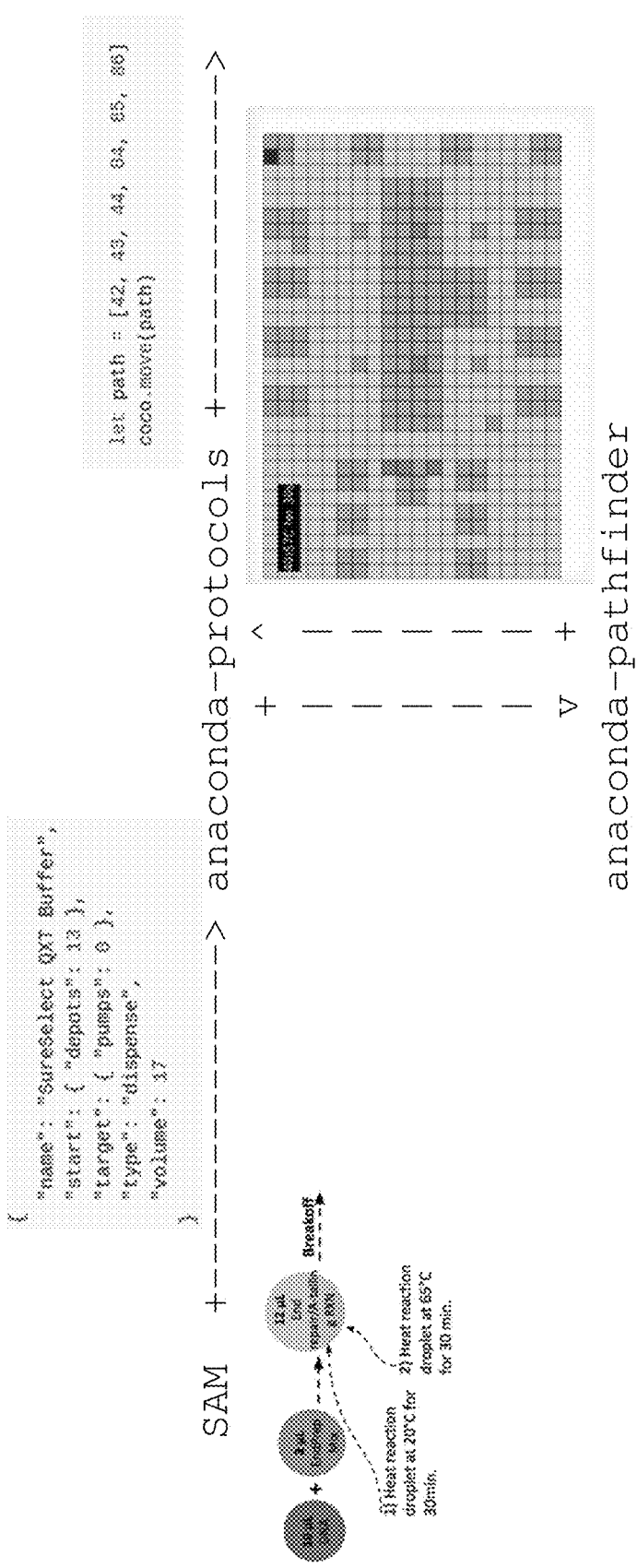
FIG. 24 shows an example of a method of controlling a DMF apparatus as described herein, including programming the apparatus using a graphical user interface.

FIG. 24 is an exemplary schematic, illustrating the steps involved in controlling any of the DMF apparatuses described herein. For example, in FIG. 24, the user may enter the protocol using a graphical/visual user interface (referred to herein as "SAM"). This may be described in greater detail in reference to FIGS. 25A-26B). The graphical protocol may then be translated into a series of target goals and this target protocol may then be used by the apparatus to tailor this protocol to the DMF apparatus. In FIG. 24, the system may determine a path, and derive the control of the drive electrodes, heater, cooling (e.g. Peltier), magnetic(s), microfluidics (pump(s), etc.), etc. in order to accomplish the protocol. The path may be optimized to require the shortest pathways, but constrained by limiting or reducing overlap in the path(s), to prevent contamination, loss of materials (including reagents and/or Teflon), heat dissipation, etc.

Figure 25A:
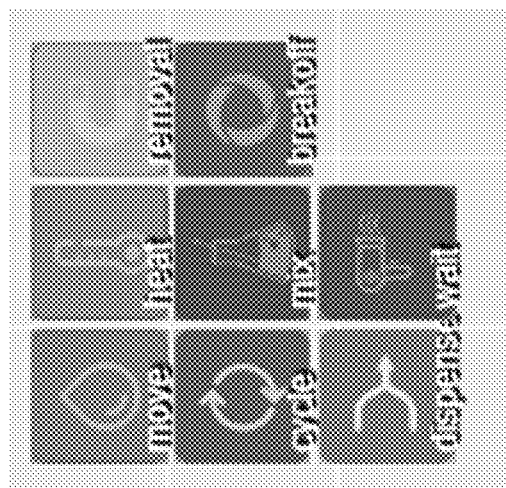
FIG. 25A illustrates an example of visual controls or commands (FIG. 25A) and a protocol describes using these visual controls/commands (FIG. 25B).
Figure 25B:
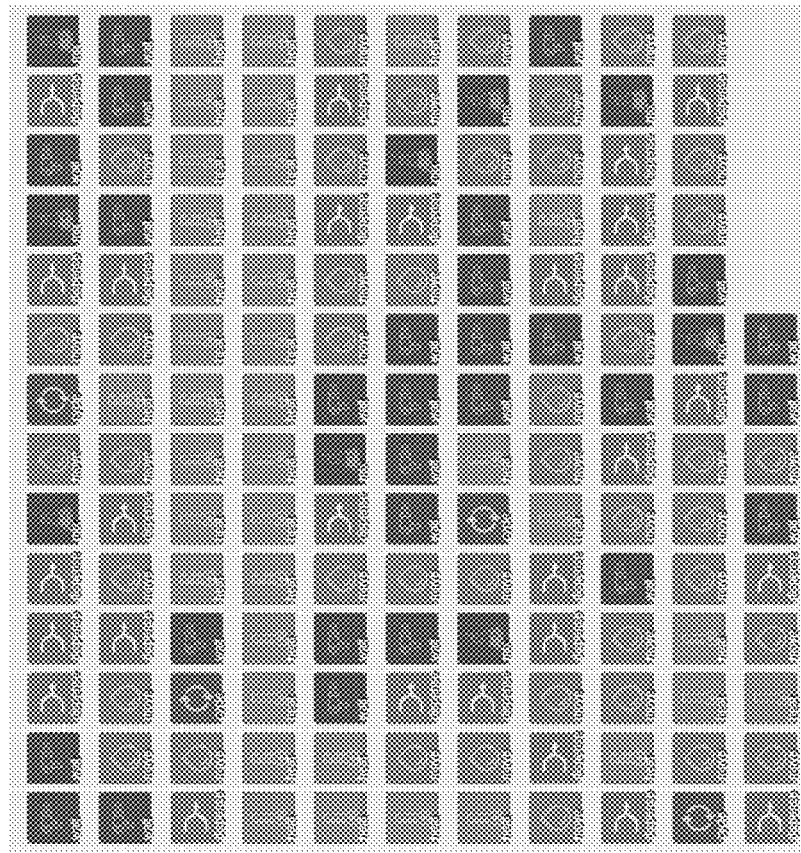

As mentioned, FIGS. 25A and 25B illustrate one example of a visual interface (e.g., graphical user interface) for entering a desired protocol. In FIG. 25A, a set of control icons ("move", "heat", "removal", "cycle", "mix", "breakoff", "dispense", and "wait") are shown. The user may select or arrange these icons in order to provide a graphical representation of a processing protocol, as shown in FIG. 25B. Each of the icons may have an associated duration, and thus, these icons may be used to select processing instructions, or steps, for a sample. In this example, the icons are uniquely identified by one or more of: color, image, and text.

The user may input the protocol directly into the apparatus, or into a computer or other processor in communication with the DMF apparatus.

Once entered, the protocol may be translated into a data structure format (e.g., a JSON format that indicates the name of the protocol and sample, where the sample goes, what volume to use, etc.). This data structure may then be directly used or converted into a format (e.g., java script) so that the apparatus may determine the paths to take in the cartridge in order to achieve the desired protocol. The path finding may be done locally (e.g., in the DMF apparatus) or remotely and communicated to the DMF apparatus. The path finding may be configured to maximize based on the shortest path length that also avoids cross over, or some cross-overs, to prevent contamination. Thus, the apparatus may determine the shortest route that avoids contamination. In general, the user interface can allow the user to easily select the desired actions and elements (e.g., mixing, etc.); the apparatus may already be familiar with the reagents (e.g., elements of the device). The user can then select the actions, durations, temperatures, etc.

Figure 26A:
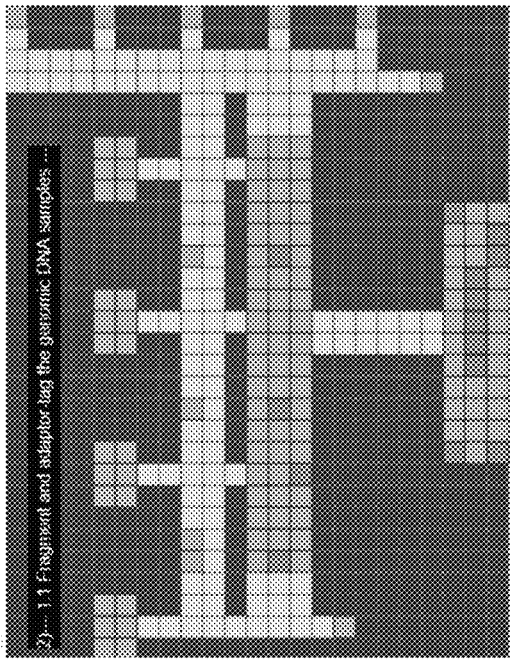
FIGS. 26A-26H illustrate an example of a user interface for controlling a DMF apparatus as described herein.
Figure 26B:
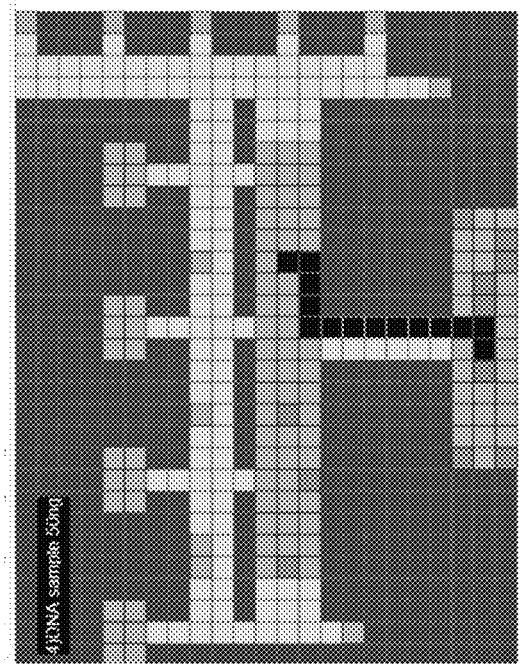
Figure 26C:
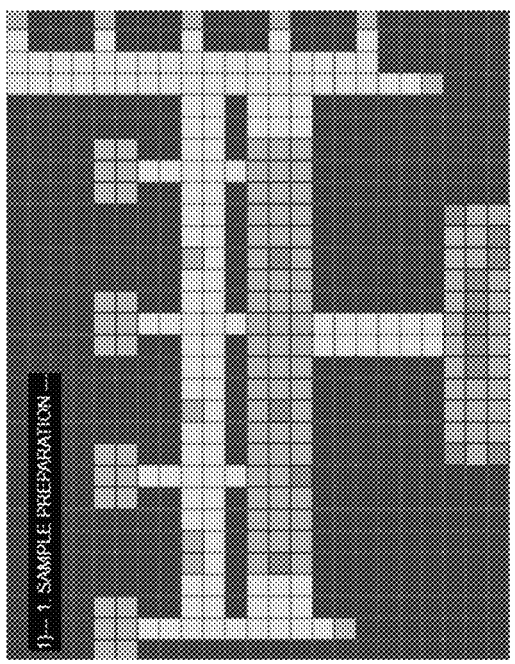
Figure 26D:
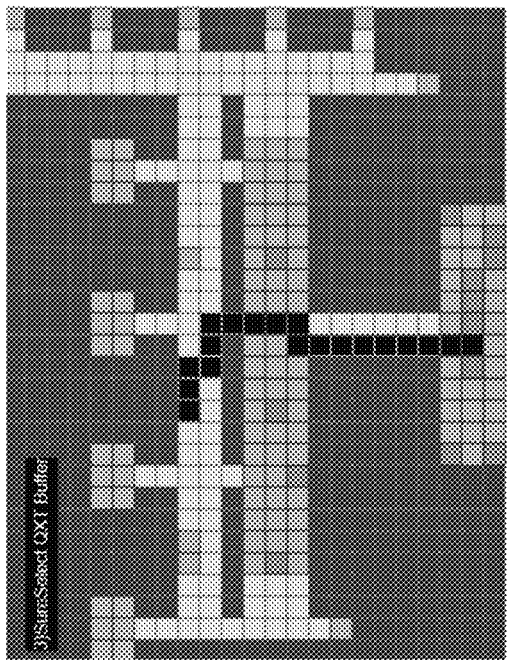
Figure 26E:
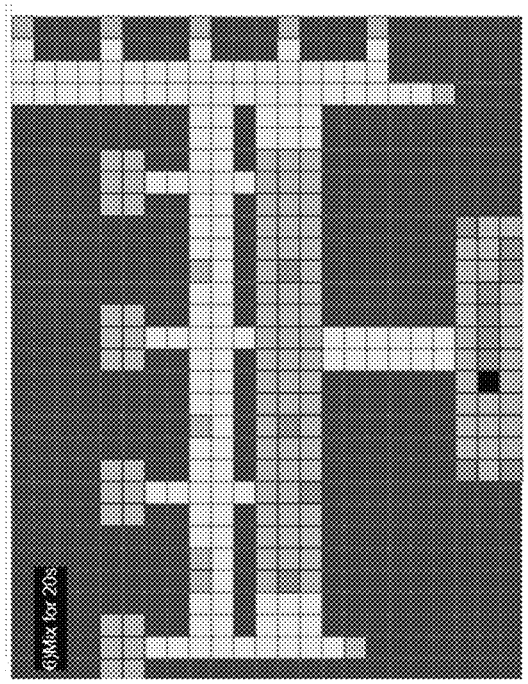
Figure 26F:
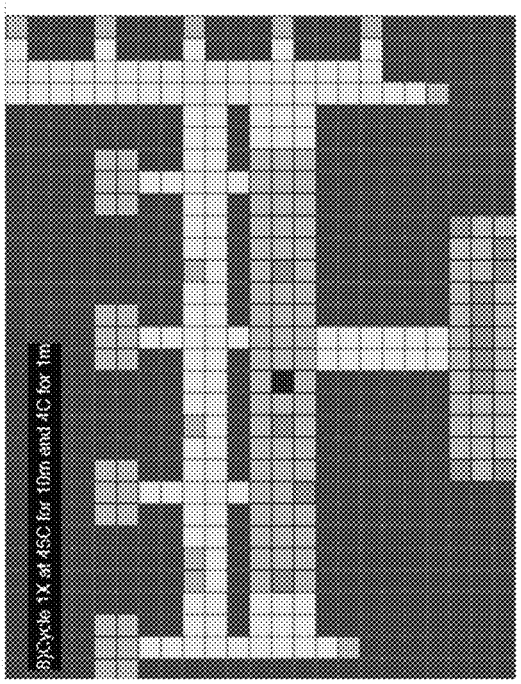
Figure 26G:
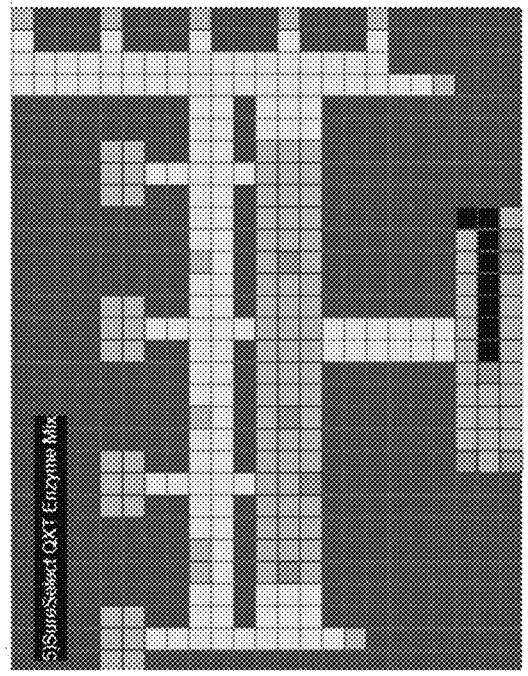
Figure 26H:
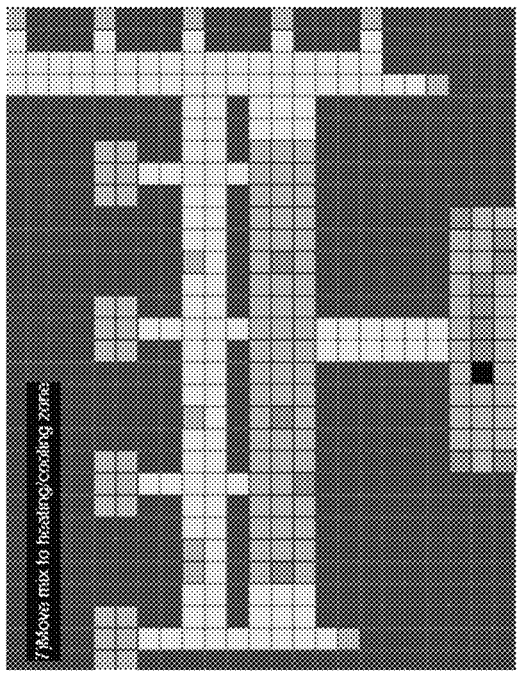

FIGS. 26A-26H illustrate one example of an apparatus determining a pathway from an input protocol. For example, FIG. 26A shows a graphical illustration of a particular configuration of DMF cartridge air-gap planning a first set of steps, e.g., sample preparation. The apparatus may know the distribution of the cells within the air gap, as well as the configuration of the functional zones (heaters, coolers, mixing/microfluidics, waste removal, dispensing, etc.) in the DMF cartridge. FIG. 26B is a graphical illustration of the apparatus determining the path for tagging a sample having genomic DNA (or fragments of DNA) with an adapter tag. In FIG. 26C, a step of moving a first buffer (e.g., SureSelect QXT buffer) to an appropriate location for future processing is performed. The path may be chosen in light of both past movements and future movements and may be recursively modified as the future protocol steps are defined. In FIG. 26D, the path for moving the DNA sample is shown (in black). FIG. 26E shows the movement of an enzyme mix from a cooled region where it is beings stored to combine with the sample; FIG. 26F shows the user of mixing of the sample with the buffer and enzyme mix. The mixed sample may then be moved (FIG. 26G) along a calculated pathway to a heating/cooling zone for cycling (FIG. 26H). Additional steps may then be performed as indicated.

Thermal Control

Any of the apparatuses described herein may include features for thermal control (e.g., heating and/or cooling), and/or droplet detection (e.g., tracking and/or identification). For example, the apparatus, including the cartridge and reader, may be configured to quickly and accurately cycle droplet temperatures. Alternatively or additionally, droplet detection may quickly and accurately scan the electrode grid for droplets (including, but not limited to reagents, wax, water, etc.).

As described above, the reader may be configured to include one or more thermal control elements, including cooling and/or heating. For example, the reader may include resistive heating in some of the cells, to heat a droplet within the air gap. For example, in some variations a resistive heater may be included in layer 2 of the printed circuit board (PCB), such as part of a first copper layer under the surface of the PCB. The apparatus may also include a heat sink or cooling element, such as a liquid cooler (chiller) that is in constant thermal connection with the PCB. Any of these variations may also include one or more of thermal mass reduction, which may enhance the rate of temperature change in a cell, and/or thermal conduction through the PCB (e.g., through the electrodes that form part of the PCB in the reader).

Figure 28:
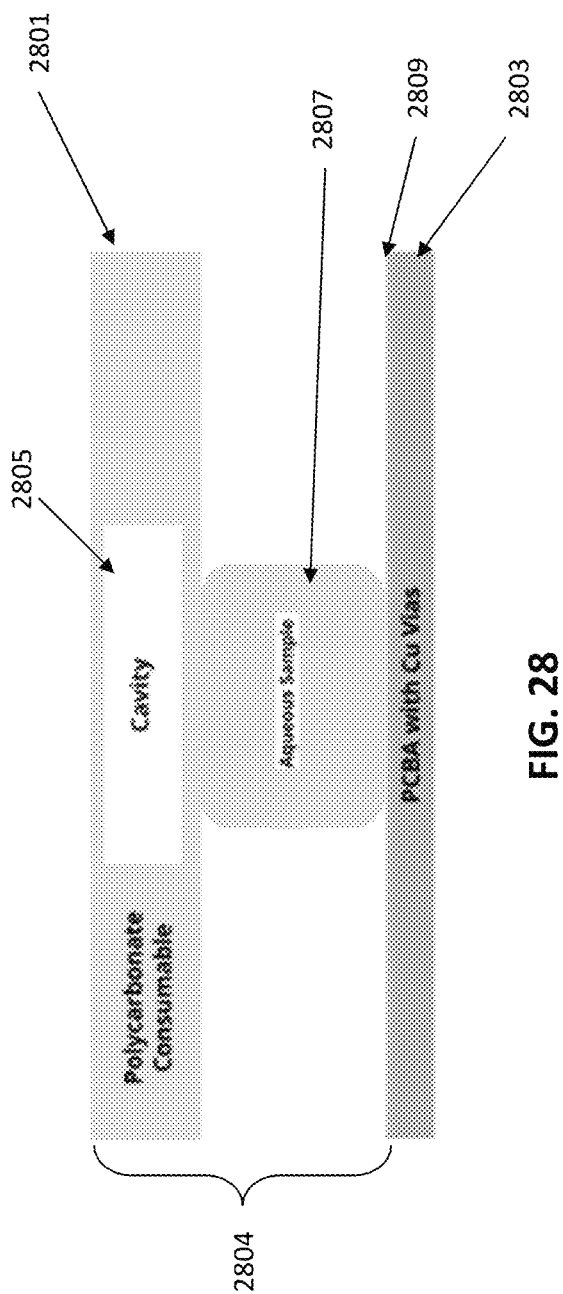
FIG. 28 illustrates an example of a portion of a cartridge showing a thermally controlled region.

Thermal Mass Reduction may refer to the reduction or removal of thermal mass from the apparatus (e.g., system, device, etc.) to reduce the total required amount of energy to reach a temperature or temperature range. Ideally, when there is less thermal mass, less energy needs to be taken out of the system to decrease the sample temperature during thermal cycling, thus enabling faster cycle rates without the need for a very large heating and cooling system (i.e. no more liquid cooling to the stack up). The apparatuses and methods described herein may reduce thermal mass by reducing/removing thermal mass from above a droplet or region holding one or more droplets in the upper (top) plate of the cartridge. For example, when the upper/top plate is formed of an acrylic or polycarbonate material, the thermal mass above the air gap region may be reduced by including one or more cavities in the top plate (e.g., the polycarbonate and/or acrylic structure) and filling the cavity with a thermally insulating material, or a material that has a low thermal conductivity (such as air). The cavities may be positioned in the top plate of the cartridge over a thermally controller region, so that when a droplet of material is below the cavity, the heating/cooling applied by the reader, e.g., from the PCB, may more rapidly change the temperature of the droplet in the air gap region. Removing the thermal mass above the droplet may be incorporated in the design of any of the cartridges described herein. The cavity may be formed near the bottom surface of the top plate (e.g., immediately on one side of the air gap); the cavity may be partially through the thickness between the top and bottom surfaces of the top plate. FIG. 28 illustrates an example of a portion of a cartridge showing a thermally controlled region in the top plate 2801 of the cartridge 2804. The cartridge may be positioned onto the reader 2803. A droplet 2807 within the air gap region of the cartridge (e.g., the region bounded by the bottom surface of the upper plate 2801 and the top surface of the lower sheet of dielectric material 2809. Thus, in variations in which the cartridge body, including the top plate is formed of a solid piece of polycarbonate on the top plate, one or more cavities may be created (e.g., FIG. 29) and may be enclosed or filled with an insulating material that has a low thermal mass. This may prevent heat from the sample transferring to storage region above it. The void replacement material can be air or a similar material that has low thermal conductivity and low thermal mass.

Alternatively or additionally, thermal mass may be removed from the PCB by removing material (e.g., with precision milling) and/or using materials having a very low thermal mass. For example, one or more layers of the PCB may be removed in the heater zone (e.g., heating or thermally controlled region) to reduce thermal mass. This may be done from the bottom side of the board as to not disrupt the surface finish of the electrodes.

FIG. 29 is an example of a milled region in a PCB of a reader apparatus that has a lower thermal mass in order to increase the response time for temperature change of a droplet in the air gap of the cartridge. In This schematic example, showing sectional view, the layers of the bottom (e.g., PCB) may include one or more layers, e.g., of copper and dielectric beneath the droplet (in the PCB of the reader) has been milled to create a cavity or void which may be filled with a thermally insulating material, including air. Thus, thermal conduction through the PCB may be reduced. In general, the cavities in the top and/or bottom plate may help thermally isolate the droplet in the air gap between the top and bottom plates.

In addition to speeding temperature changes in the droplet by reducing thermal mass, any of the methods and apparatuses described herein may increase the thermal conductivity between a heater source and an electrode to improve performance. For example, if the heater layer on the PCB is in layer 2, then using a high thermally conductive dielectric layer will increase heat transfer from the heater layer to the electrodes, as illustrated in FIG. 30. FIG. 30 shows a high conductive dielectric 3005 between the heater 3003 and electrode 3001 copper regions.

In some variations, the reader (and in particular the PCB portion of the reader) may alternatively or additionally be configured to increase thermal conductivity by including one or more thermal vias near each active (e.g., driving) electrode/cell. The thermal via may be a channel or passage in thermal contact with the region near the electrode(s), including the region underlying the electrode(s), such as the PCB material, of the thermal control region, and may be filled with any thermally conductive material. For example filling the vias with a thermally conductive material (such as, but not limited to: copper, epoxy, resin, etc.) may further increase the thermal conductivity and may dramatically increase the thermal response time of the droplet or other material in the air gap. Thus heating and/or cooling may be much faster than without the vias. The thermally conductive vias can be implemented with or without a milled region in the PCB (shown in FIG. 31A, showing a milled region with thermally conductive vias, and 31B, showing thermally conductive vias without a milled region). For example, FIG. 31A illustrates a plurality of thermal conductive vias 3105 in an example of a bottom plate (e.g., PCB) with that has been milled to provide a region of thermal isolation around the thermally controlled active region.

The vias may be filled with any appropriate thermally conducive material. In some variations the vias are filled with a thermally conductive material that is not electrically conductive (e.g., epoxy, resin, etc.).

One end of the vias may be in thermal contact (e.g., may touch) with a region adjacent to the ultimate upper surface (e.g., the cartridge-contacting surface) and/or the electrodes of the reader device. In particular, when the thermal vias are filled with an electrically conductive material (e.g., copper) the thermally conductive vias may contact a region immediately adjacent to the electrodes, but not in electrical contact with the electrodes. Another portion of the thermal via may be in thermal contact with a heat sink beneath the upper surface (e.g., on a side and/or bottom surface). In some variations the opposite end of the vias may be in contact with a temperature controlled surface (e.g., cooled surface, heated surface, etc.). In some variations the vias may be in thermal communication at one end region with a thermal controller (e.g., heater, cooler, heat sink, etc.); the vias may pass through the vacuum chuck on which the PCB sits.

The vias may be any appropriate dimensions. For example, the thermally conductive vias (referred to herein as thermal vias or simply vias) may have a dimeter of between 0.1 mm and 3 mm, 0.1 mm and 2 mm, 0.5 mm and 1.5 mm, about 0.8 mm, about 1 mm, about 1.2 mm, about 1.4 mm, etc. The thermal vias may have a round, oval, rectangular, square, triangular, or any other cross-section and may be cylindrical, extending through the printed circuit board from the thermal control (e.g., one or more of a heater, cooler, heat sink, etc.) to the region immediately beneath the electrode or immediately adjacent to the electrode (in some variations, without contacting the electrode, so that they remain electrically, but not thermally, isolated from the electrodes).

As mentioned, any appropriate number of vias may be formed per each cell (e.g., associated with each electrode driving movement of fluid in the air gap of a cartridge). For example, each cell in the thermally controlled region (which may include multiple thermally controlled cells) may be in contact with 2, 3, 4, 5, 6, 7, 8, 9, 10, 11, 12, etc., or more vias. For example, each thermally controlled cell may be in contact with more than 8 vias.

The use of thermal vias may provide a dramatic improvement over variations in the rate of heating and/or cooling of the thermally controlled regions, compared to systems that do not include thermal vias.

Cartridge Features

Figure 32:
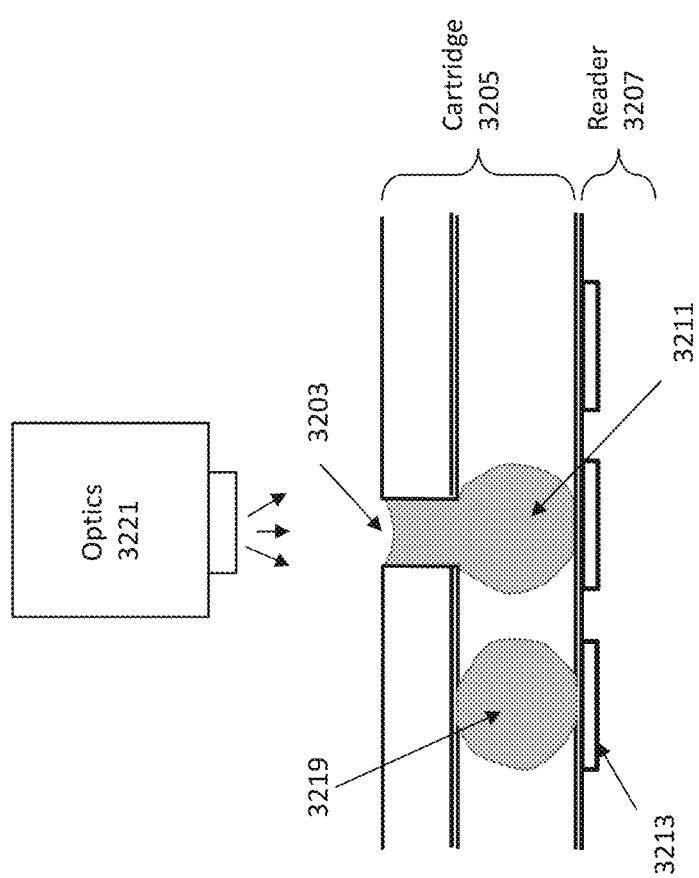
FIG. 32 is an example of a cartridge including an opening in the top plate for sampling or adding fluid to a droplet in the cartridge.

In addition to the features described above, any of the cartridges may alternatively or additionally include one or more openings into or through the top plate over some of the cells (e.g., regions that will correspond to one or more drive electrodes). These openings may be open and may allow direct imaging 3221, as illustrated in FIG. 32. Alternatively or additionally, an opening may be used for passive dispensing of fluid from the air gap. For example, in FIG. 32, an opening 3203 in the top plate of the cartridge 3205 may be used to passively dispense fluid from a droplet 3211 positioned beneath the opening; the drop let may be moved under the opening via DMF as described above. Once positioned a predetermined amount of fluid may be passively dispensed from the droplet into the opening, e.g., via capillary action, and the droplet may be moved away from the opening. The sampled material may then be analyzed or processed using the microfluidics in top of the cartridge and/or may be analyzed in place. Alternatively, the material sampled may be added to another droplet 3219 after the first droplet 3211 has been moved away; positioning the second droplet under the opening through the top plate that includes the sampled material 3203. This sampled material (fluid) from the first droplet may be a metered amount, based on the dimensions of the opening 3203. The top plate may include a hydrophilic surface or surface coating. In some variations, an opening in the top plate may be pre-loaded with a material, such as a liquid wax or other coating material that maybe combined with a droplet when the droplet is moved under the opening (e.g., to dispense a coating material, such as an anit-evaporation coating of liquid paraffin, oil, etc.). An opening in the top plate may also act as a thermal insulator. The opening may extend over a portion of the cell so that the return electrode may be on the edges of the opening. The opening may be any size and dimension (e.g., round, square, etc.). Although the variation shown in FIG. 32A illustrates imaging through the top plate (using optic 3221), in some variations the imaging may be done from the bottom, through the bottom of the cartridge. For example a region of the bottom of the cartridge (e.g., the dielectric film) may be transparent or optically permeable for imaging (e.g., fluorescence).

Figure 27A:
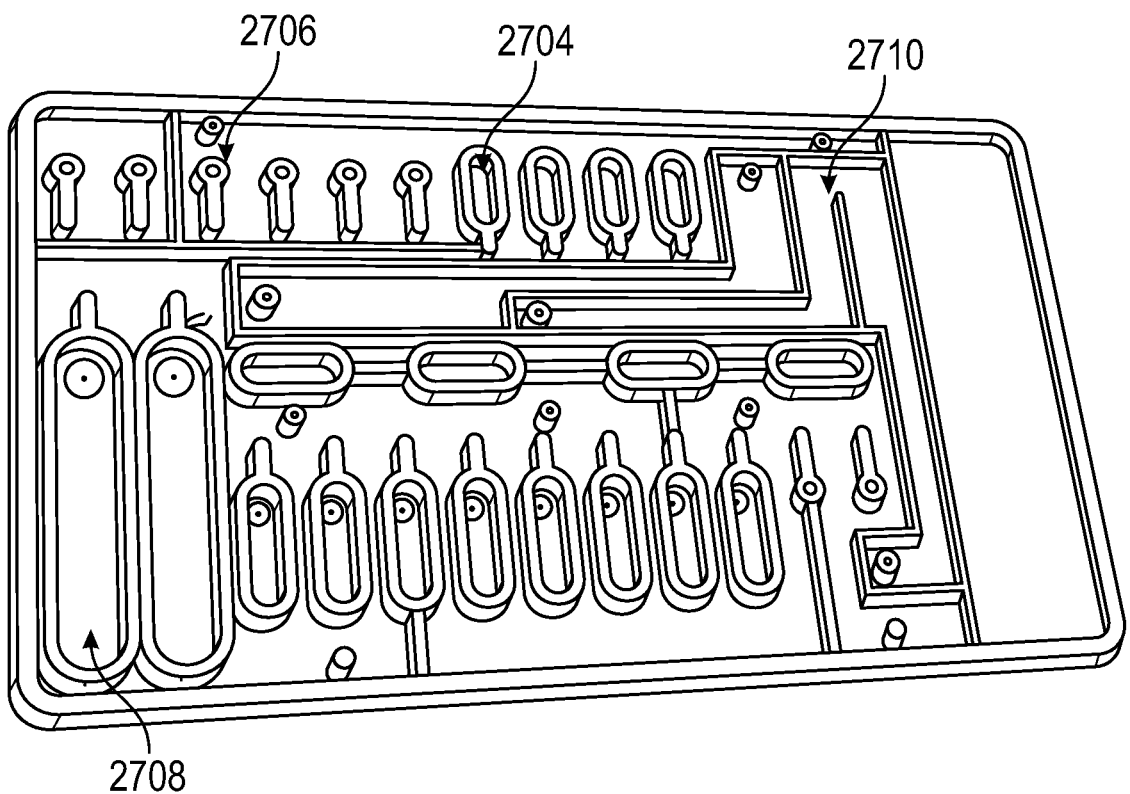
FIGS. 27A and 27B illustrate top and bottom perspective views, respectively of one example of a top portion of digital microfluidics cartridge as described herein.
Figure 27B:
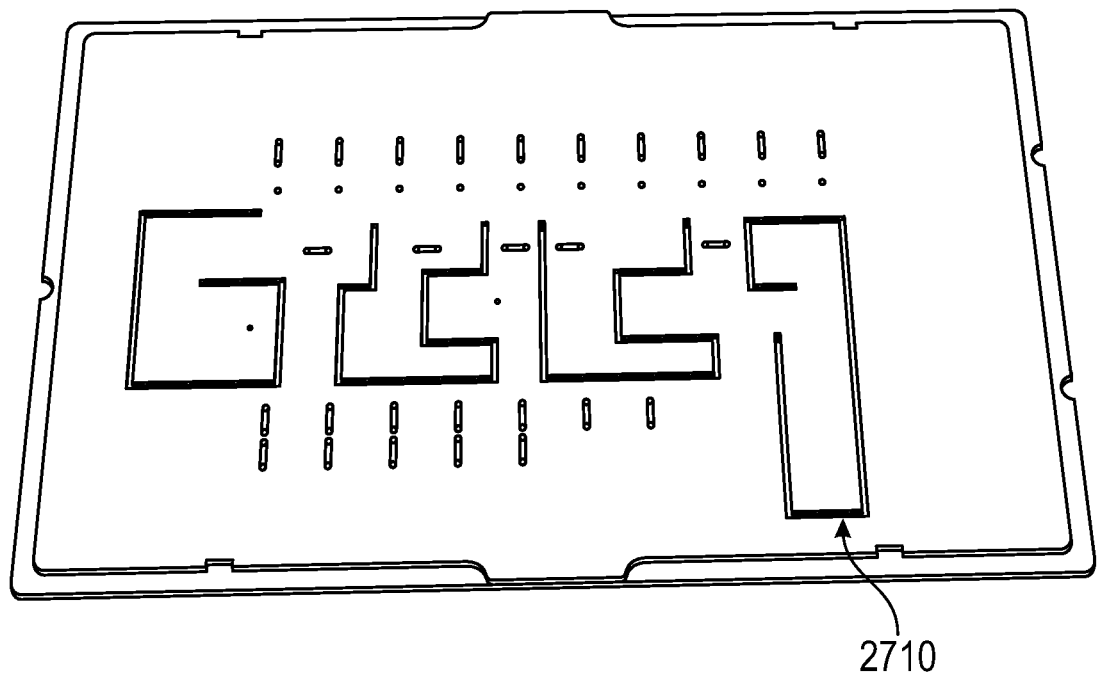

In any of the cartridges described herein, the top plate may include a plurality of manifold for delivery of one or more materials into the air gap. FIGS. 27A and 27B illustrate one example of a top plate, formed of a polymeric material (e.g., acrylic and/or polycarbonate). FIG. 27A shows the upper region of the top plate (which may be covered by one or more covers, not shown. In FIG. 27A, a plurality of dispensing regions 2704, 2706, 2708 of different sizes are included. For example a smaller 2706 (e.g., 2-20 microliter size), medium 2704 (e.g., 100 microliter to 1 mL) and large 2708 (e.g., 1 mL to 5 mL) are shown, as are waste and/or mixing regions 2710. These chambers may be preloaded with fluid, and each may include an opening into air gap region. A pressure control may be used to apply pressure to drive the fluid out of the opening of the dispensing region and into the air gap, which may be controlled by the reader or other device holding the cartridge. Thus, the reader may include one or more pressure interface(s) that may be used to control the release of fluid from and fluid handling in the top pate. FIG. 27B illustrates a bottom side of the top plate portion shown in FIG. 27A. The bottom side may be coated or covered with the electrode and/or a dielectric and/or a hydrophobic coating, a described above. In FIG. 27B, the top plate may also or alternatively include one or more channels 2712 in the surface of the plate that may allow for mixing as described above. The bottom surface of these channels may be formed by the upper dielectric and/or return electrode (which, in some variations, may include a dielectric, hydrophobic film and/or electrode layer).

In any of the cartridges described herein, the bottom surface, which may be configured to contact the seating surface of the reader and in particular the drive electrodes in the reader, is formed of a dielectric material, as described above. The bottom surface may be a sheet of dielectric material having a first side and a second side (the first side forming an exposed bottom surface on the bottom of the cartridge). The second side of the sheet of dielectric material may comprise a hydrophobic surface and may form one side of the air gap. The bottom surface may be, for example, a film that is either itself dielectric, and/or that is coated with a dielectric material. For example, in some variations the film is a dielectric and/or hydrophobic film. It may be beneficial to have this bottom surface be substantially flat. Any of the cartridges described herein may be configured apply tension to the sheet of dielectric material. For example, any of these cartridges may include a frame to hold the dielectric material in tension. Thus the cartridge may include a tensioning frame holding the bottom sheet of the cartridge.

The dielectric and/or hydrophobic film tensioning design may pretension a sheet (e.g., a dielectric and/or hydrophobic film) such that the surface of the sheet is planar throughout, and remains planar during its interface with the reader seating surface (e.g., the PCB) and during use of the DMF apparatus. The goal of the tensioning frame holding the film (e.g., A dielectric and/or hydrophobic) in the cartridge is to interface with the seating surface (e.g., of the PCB interface) to ensure that the film remains in complete contact with the electrode grid (e.g., driving electrodes) throughout use of the apparatus.

In any of the cartridges described herein the bottom of the cartridge may include a sheet of dielectric material having a first side and a second side, the first side forming an exposed bottom surface on the bottom of the cartridge, as described above. Any of the cartridges described herein may include a tensioning frame to hold the sheet flat by applying tension. The sheet, while exposed as the bottom of the cartridge, may be slightly recessed compared to the outer perimeter of the cartridge bottom, which may fit into a lip or recess on the reader device, as will be described in further detail below. Thus the sheet of dielectric material at the bottom of the cartridge need not be the bottommost surface.

For example, FIGS. 49A-51 illustrate one example of a cartridge assembly that includes a frame to stretch/smooth the bottom (e.g., dielectric sheet) of the cartridge. FIGS. 49A-49D illustrate one example of a tensioning frame. In this example, the cartridge body features a two-part film tensioning mechanism. The two parts, shown in FIGS. 49A-49B (and assembled views in 49C-49D), may include a tensioning frame 4901 and a dielectric and/or hydrophobic film frame 4903. When assembled, the film forming the bottom of the cartridge may be adhered to the dielectric and/or hydrophobic film frame 4903. The film and film frame 4903 assembly may be inserted into a groove in the tensioning frame 4911 employing a connector (e.g., a snap-fit mechanism). Upon snapping into the tensioning frame, the film may be pulled taught in all directions in an X-Y plane. This frame assembly may then be fastened into the cartridge body. The assembled frame may include lower profile (e.g., cut-out) region 4909 that may provide access to electrically connect the return electrode on the upper plate, bypassing the film on the cartridge bottom surface.

Figure 50A:
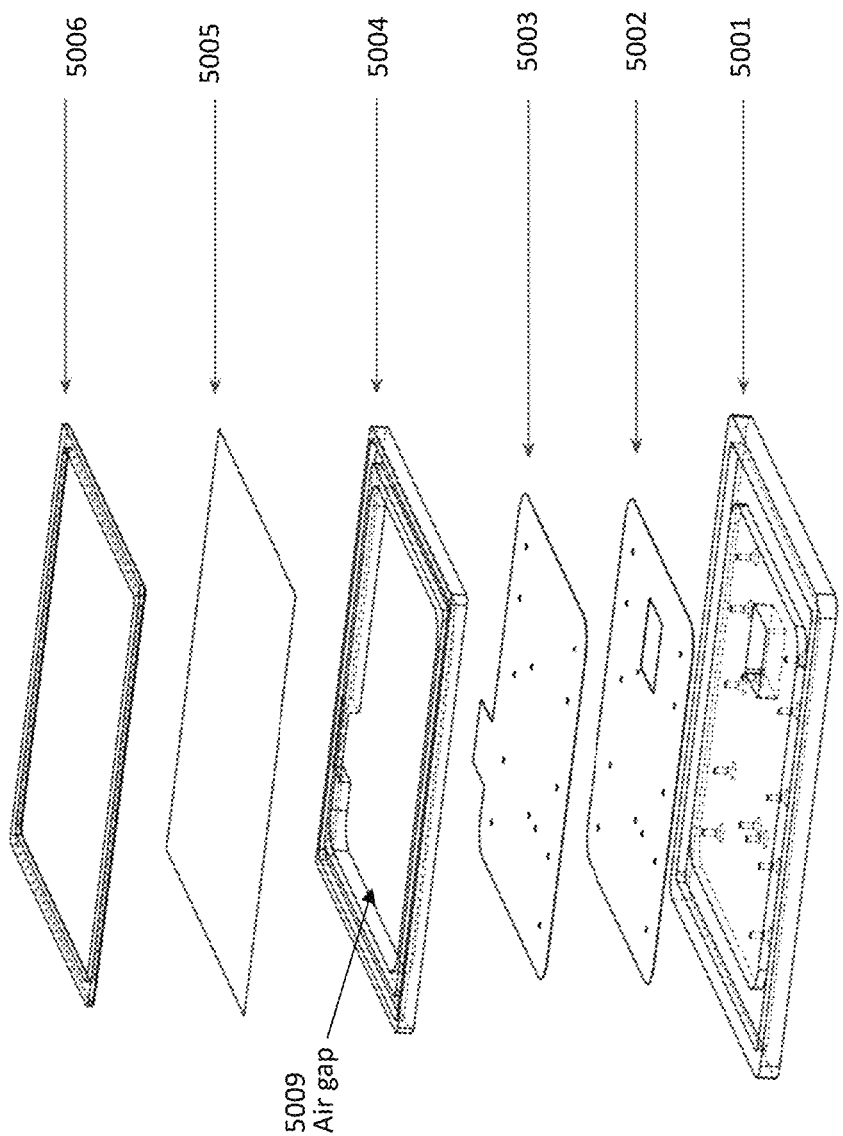
FIG. 50A is an example of an exploded view of a cartridge.

One example of a cartridge including a frame for holding the bottom membrane flat is shown in the exploded view of FIG. 50A. In FIG. 15A, the individual components in the cartridge and film tensioning assembly are shown. This figure also outlines their arrangement during assembly. The first two components to assemble may include, e.g., an optically clear double-sided adhesive 5002, and a sheet of dielectric material 5003 (e.g., coated on conductive material). The frame (e.g., tensioning frame 5004) and the sheet including a dielectric material 5005 may also be included, and the film secured in place by a second portion of the film frame 5006. The air gap 5009 maybe formed between the film 5005 and the bottom surface 5003 of the top piece (which may include the return electrode(s)).

Figure 50B:
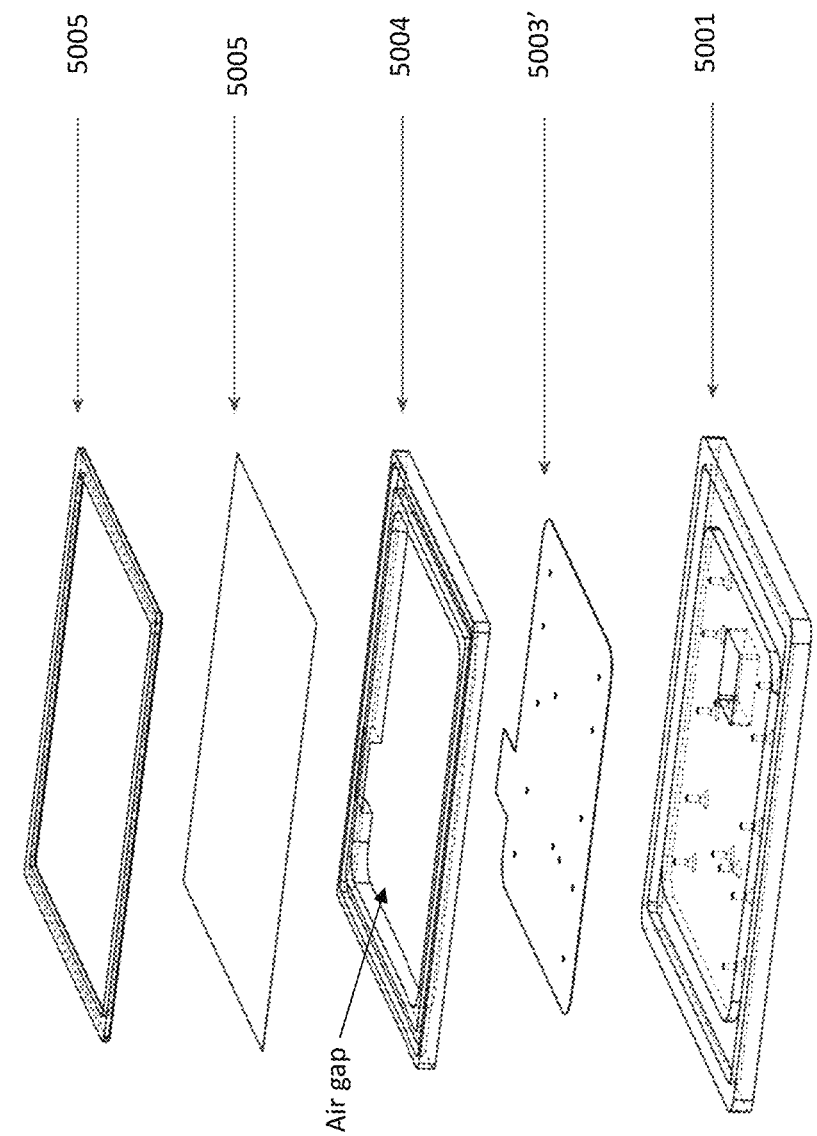
FIG. 50B is another example of an exploded view of a cartridge.

FIG. 50B depicts the individual components in the cartridge and film tensioning assembly after assembling the optically clear double-sided adhesive and the dielectric and/or hydrophobic material coated on conductive material. Conductive material can be any conductive material such as ITO, aluminum film, copper and others.

Figure 51:
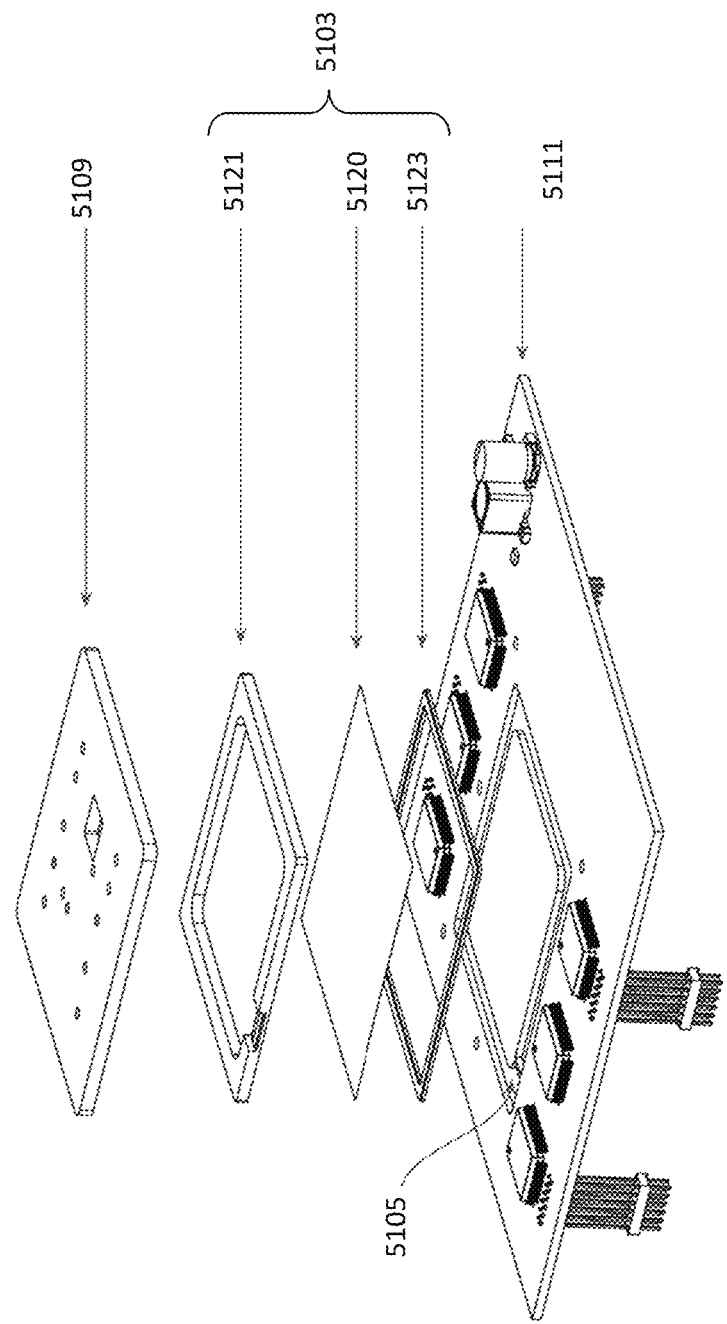
FIG. 51 is an exploded view of an example of a cartridge and a cartridge seating portion of a reader.

The film/cartridge and PCB interface may include a film tensioning frame as described above and a groove drilled out (trough) of the top surface of the PCB may form a boundary around the electrode grid of the reader. FIG. 51 shows an isometric, exploded view of an example of an assembly of a cartridge, including a film 5120 and film tensioning frame (outer frame 5121 and inner frame 5123), and an upper (top) portion of the cartridge 5109; FIG. 51 also shows a portion of a reader, including a PCB 5111 forming a seating surface for the cartridge. The seating surface also includes a trough 5105 to accept the lip around the bottom film of the cartridge (in this example, formed by the tensioning frame 5103). The trough may be a groove that is drilled out around the perimeter of the electrode grid. As the assembly arrangement in this embodiment shows, the film tensioning frame 5103 may slot into this trough 5105 around the electrode grid. Once assembled, the film tensioning frame 5103 may tension the film in X and Y, but also pulled downward in the Z direction at the edges of the film. The film may wrap over filleted edges of the trough, just slightly outside the boundaries of the electrode grid (not shown).

Figure 53:
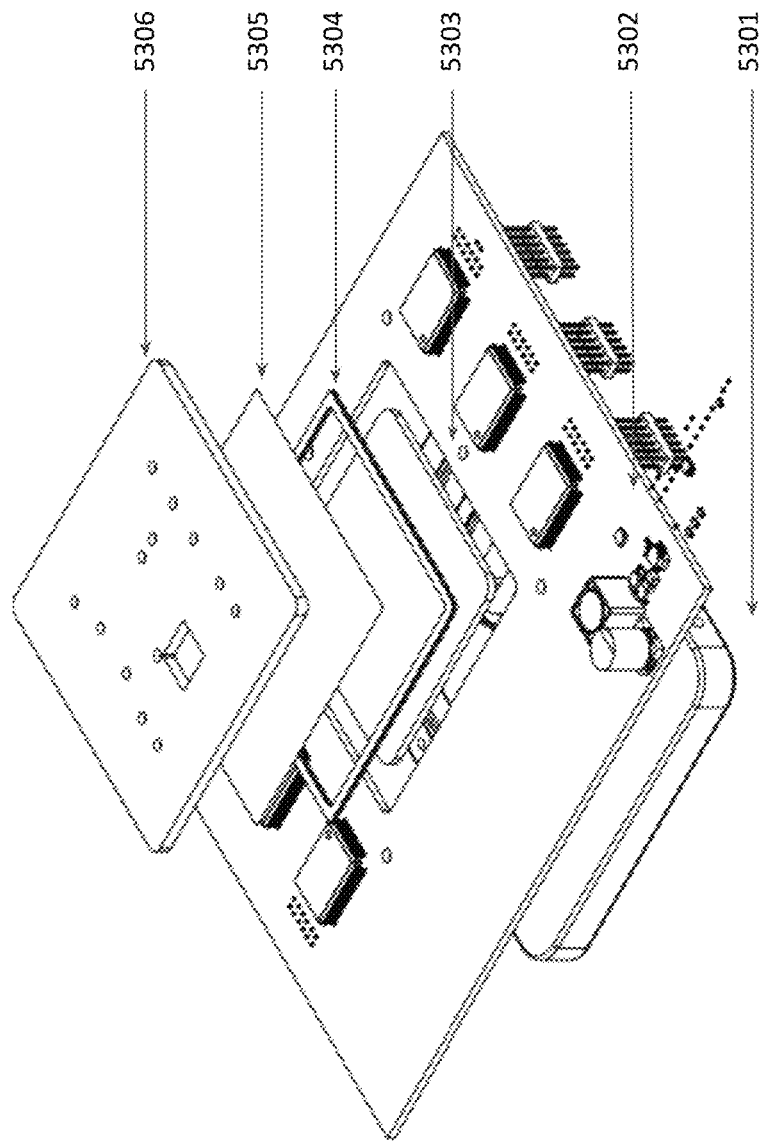
FIG. 53 is an exploded view of a cartridge and seating surface/region of a reader.

FIGS. 52A and 52B show top and cross-section views, respectively, of one example of a cartridge, including a bottom dielectric (and hydrophobic or hydrophobically coated) film, and film tensioning frames seated on a PCB assembly portion of a reader. The cross-section in FIG. 52B highlights how the dielectric and/or hydrophobic film may be pulled taught across the electrodes, and sealed down using the vacuum ports through at least some of the electrodes (drive electrodes) of the PCB, and also illustrates seating of an edge (extending proud of the film) in a trough formed in the PCB seating surface to seat the film. When fully assembled, these components may allow for a secure, fully tensioned, and planar dielectric (and/or hydrophobic) film to be secured to the driving electrode grid on the PCB. FIG. 53 is an exploded view showing individual components and their arrangement in assembly, including a cartridge upper body frame 5306, a dielectric film 5305 held in tension by a tensioning frame 5304, a PCB 5302 forming a seating surface on the reader, a groove or channel on the seating surface around the perimeter of the array of drive electrodes (driving electrodes) on the PCB, and a vacuum chuck 5301.

FIGS. 54A and 54B shows a top view of the assembly and a cross sectional view, respectively. The cross section view highlights the relationship of the vacuum chuck 5411 on the cartridge 5413 and film assembly, as well as on the PCB 5415. The section in FIG. 54B also highlights a few different effects of this system. The arrows 5405 depict the flow path for vacuum originating from a diaphragm vacuum pump 5407 on the outside of the chuck. This may be the same flow path as is described above in FIG. 35B. The arrows outline the force downward being applied to the film by the vacuum through the via holes in the PCB. The vacuum chuck and interface with the PCB securely adhere the film to the electrodes and apply downward force in Z. The film tensioning mechanism and PCB trough ensure the film remains planar by applying force in X and Y, while maintaining contact around the edges due to a fillet along the internal edge of the trough.

Reader Features

In general, any of the readers described herein may include a PCB portion, that may include the electrode array, active thermal control (e.g., heater, cooling, etc.), magnetic field applicator(s), etc., and a chuck (e.g., vacuum chuck) that may be mounted to the PCB. This portion of the reader may form the seating surface for the bottom of the cartridge, so that it may sit on the reader securely and in a predetermined orientation. For example, the cartridge may be keyed to fit onto the seating surface in a predetermined manner (e.g., by including one or more orientation slots, pins, etc.). The reader may also include one or more control units, including one or more processors, that may control the activity of the reader and may be configured to drive droplets and analyze information from the cartridge. The controller may also include memory, one or more datastores.

The seating surface of the reader may be configured both to seat a cartridge, but also to prevent arcing, sparking or shorting between the plurality of electrodes on the seating surface. For example, the seating surface may coated with an additional dielectric (onto which the dielectric bottom surface of the cartridge may sit) such as paralyene and/or alternative or additional materials. The dielectric bottom surface may prevent arcing between the electrodes in the array or electrodes (driving electrodes) on the seating surface. The spacing between the driving electrodes may be between about 50-120 micrometers. This close packing between electrodes on the otherwise flat surface may otherwise be susceptible to arcing/shorting between electrodes, thus the use of an outer dielectric coating (in addition to the dielectric layer of the cartridge) may limit sparking/arcing between electrodes.

As discussed and described above, some or all of the electrodes may include an opening through them which may be connected to a vacuum source for seating the electrodes onto the device. For example, in some variation every electrode in the array includes an opening therethrough; in other variations every other electrode may include an opening (e.g., alternating). In some variations every third electrode, every fourth electrode, etc. In some variations only corner electrodes may include an opening.

Droplet Detection

Figure 33A:
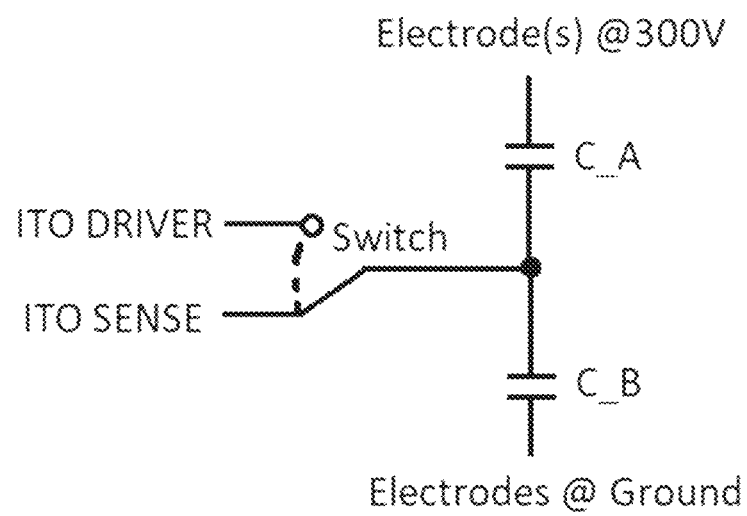
FIG. 33A shows an ITO sensing circuit with a switch.

Any of the apparatuses described herein may include droplet detection. As described above, droplet detection may be performed based on the capacitance of the electrode(s) in the array of driving electrodes by monitoring the current through the electrode(s). Also described herein are apparatuses (e.g., systems or devices, including readers) in which droplet detection is based on a capacitance measurement by creating a capacitor divider. In this example, the top plate may form a reference frame (e.g., reference electrode, such an ITO electrode) and may be usually driven between 0 and 300V to create the AC signal; during droplet detection the reference electrode (top electrode) may be disconnected from the driving signal and its voltage sensed by the controller (e.g., microprocessor), referred to in FIGS. 33A and 33B as "ITO sense" as it may act as a sensing electrode, and may be electrically coupled to one or more reference capacitors. One or a group of electrodes may be activated at a higher known voltage (e.g., 300V DC), while all other electrodes are grounded. This creates the divider as shown in FIG. 33A. FIG. 33A shows an ITO sensing circuit with a switch to toggle between sensing (e.g., capacitive sensing from the reference/top plate) and driving, e.g., to move one or more droplets.

In FIG. 33A, the voltage at the ITO sense node (the ITO sense electrode) is driven by the ratio of C_A to the total capacitance (C_A+C_B). The capacitance of C_A changes based on the material permittivity in between the plates of the capacitor (electrode to ITO). The capacitance of C_B also changes relative to what is present between the ITO and the remaining electrodes. Air, wax, water and reagents have different permittivity, and thus changing the capacitance and the voltage at ITO sense. This enables this droplet detection method to not only detect droplets (e.g., the presence/absence of a droplet) but also to differentiate between droplets and identify specific reagents within the electrode grid.

Figure 33B:
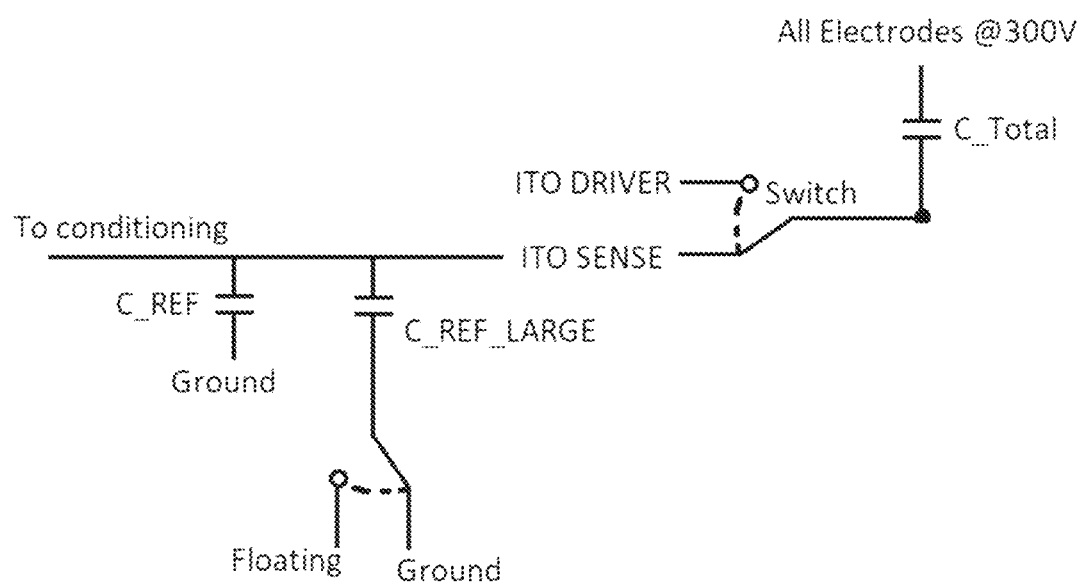
FIG. 33B illustrates another example of a capacitive sensing circuit that includes multiple reference capacitors.

Due to the variability of base capacitance, two calibration capacitors may be included (e.g., in FIGS. 33B, C_REF and C_REF_LARGE). FIG. 33B illustrates another example of a capacitive sensing circuit that includes multiple reference capacitors. By driving all electrodes (e.g., all of the drive electrodes) to 300V, the total capacitance C_Total can be calculated by using the reference capacitors. The reference capacitance can be increased if there is a large enough C_Total to saturate the voltage at ITO SENSE. The conditioning circuitry for the ITO SENSE may isolate the voltage from minor leakage currents.

Figure 34A:
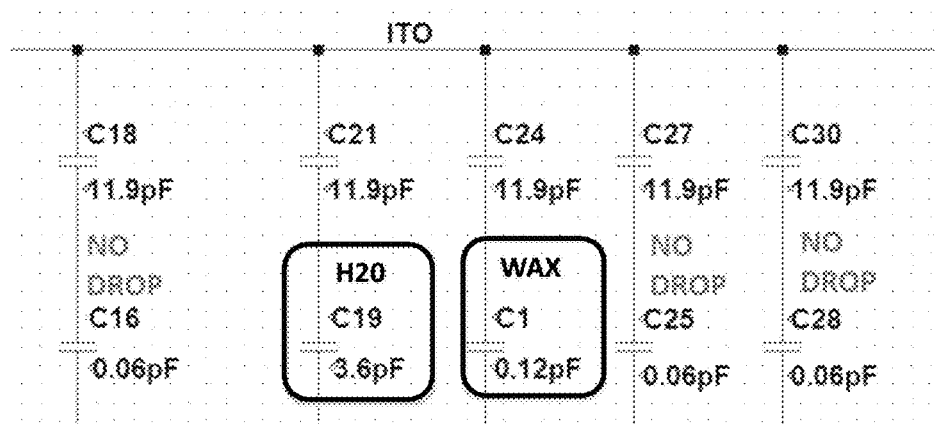
FIGS. 34A-34C illustrate one method of identifying and/or locating a droplet in the air gap as described herein.

FIG. 34A shows exemplary values for capacitance that may indicate the presence or absence (and/or identity of the material) of a droplet in one or more cells within the air gap. As discussed above, a 'cell' in the air gap may correspond to the region above a driving electrode when the cartridge including the air gap is placed into the DMF reader, which may have the array of drive electrodes on the cartridge seating region. In FIG. 34A, the "ITO" corresponds to the upper (e.g., retrun) electrode on the upper plate of the cartridge. In this example, C18, C21, C24, C27, C30 are the reference capacitor (e.g., 11.9 pF in this case) and C16, C19, C1, C25, C28 is the capacitance measured as described above, corresponding to the capacitance when different drive electrodes are measured (e.g., set to the high voltage, while grounding the other drive electrodes), either with or without a droplet. Water, wax and air (no droplet) have very different capacitances that can be used to identify the presence or absence of a droplet (e.g., capacitance greater than or equal to 0.09 pF, greater than or equal to 0.1 pF, etc.). In this example, a capacitance above this threshold (e.g., above 0.06 pF, 0.07 pF, 0.08 pF, 0.09 pF, 0.1 pF, 0.11 pF, etc.) indicates that the presence of a material in the air gap above the examined (set to high voltage, e.g., 300 V). Further, the range of the measured capacitance above this threshold may indicate the composition of the droplet, e.g., aqueous (water) and/or wax/oil. For example, a capacitance of greater than about 3 pF (e.g., 3 pF, 3.1 pF, 3.2 pF, 3.3 pF, 3.4 pF, 3.5 pF, etc.) may indicate that the droplet is aqueous, while a capacitance of between about 0.09 pF to about 3 pF may indicate that the droplet is wax or oil (e.g., between about 0.07 pF and about 3.3 pF, between about 0.09 pF and about 3.0 pF, etc.).

Figure 34B:
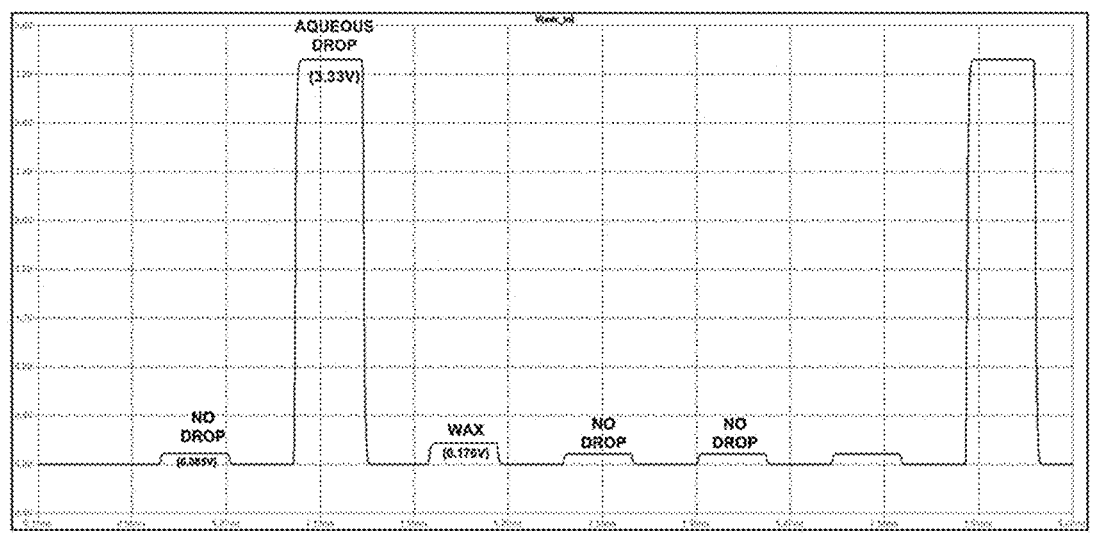
Figure 34C:
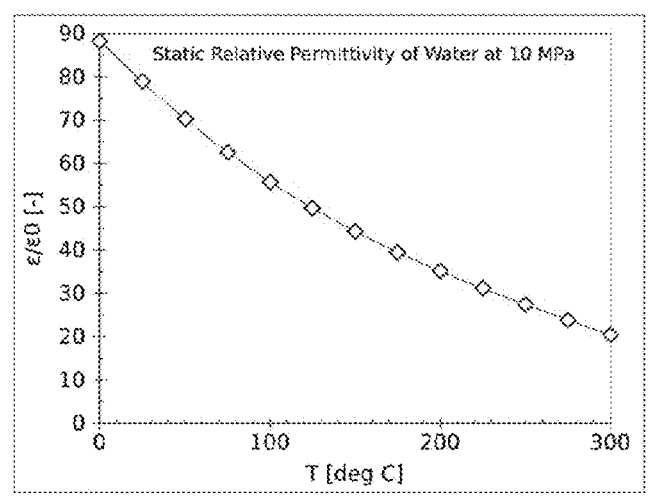

FIG. 34B is a graph showing example of measured voltages using this technique, based, showing the differences between different voltages measured with various droplets (water, wax) versus with no droplet (air) over a single test cell. In FIG. 34, the voltage detected when an aqueous droplet is present is about 3.3V, compared to 0.085V when there is no droplet present and 0.176V when wax is present. The measurement for wax is double that of air (no droplet/material), and water is much higher; in this example the circuit caps the value at 3.3V. Different materials can be detected by their differing permittivities. The permittivity of water may also be a function of temperature. Thus, in some variations, the capacitance may change as a function of temperature when a droplet is present. This property may be further used to identify water, and may also be used to estimate temperature. Thus, in some variations the capacitance measurement of the droplet may be used to estimate their temperature as well. For example, FIG. 34C is a graph showing the static relative permittivity of water, showing a change in relative permittivity with change in temperature (between 0-300 degrees C.).

Chuck Design

Any of the apparatuses described herein, e.g., the readers, may include a chuck (e.g., a vacuum chuck) that may form part of the seating surface, as mentioned above. The vacuum chuck may be attached to the electrode array (e.g., the drive electrodes that may be part of a printed circuit board) and may also be integrated with a magnet and/or heat dissipation features. Any of these elements or portions of these elements may be include or omitted, and may be used in any combination.

The vacuum chuck design may help ensure a reliable and effective vacuum adheres the bottom of the cartridge (e.g., in some variations a Dielectric and/or hydrophobic forming the dielectric layer) to the electrode grid. The vacuum may be applied through one or more (e.g., a manifold) of vias (e.g., copper vias).

In addition, any of the readers described herein may include a magnet that is integrated into the base, including the chuck and/or the seating surface. The integrated magnet (s) may be configured to allow an actuatable magnet to engage with material in the cartridge (e.g., magnetic beads in the liquid droplets in the air gap) through the vacuum chuck. The magnet(s) may rest slightly below the PCB forming the seating surface of the reader, without impacting the vacuum performance or function.

Any of the reads described herein may also or alternatively include one or more thermal regulators, including one or more heat dissipation elements that may quickly and accurately dissipate heat from the heater(s) in the reader that control the temperature of one or more cells in the cartridge when it is seated and retained on the seating surface of the reader. For example, described herein are two designs for heat dissipation elements that may be used separately or tighter. One exemplary thermal dissipation designs is configured to dissipate heat from a thermoelectric heater and another design is configured to dissipate heat from an embedded heater.

FIGS. 35A-48 illustrate a vacuum chuck portion of the reader that may be used with any of the reader apparatuses described herein. In general, the vacuum chuck may be configured such that negative pressure is applied through the chuck (e.g., from a vacuum pump), and is directed underneath the seating surface (e.g., the PCB forming part of the seating surface) in an area that is pneumatically isolated, e.g., by an O-ring. The seating surface may have via holes (e.g., in the PCB) that allow for the negative pressure to act directly on the bottom of the cartridge (e.g., a dielectric and/or hydrophobic film) that is seated on the topside of the seating surface (e.g., the PCB forming the seating surface), pulling the cartridge bottom down in the Z direction, and adhering it onto the electrode grid.

The vacuum chuck may include one or more of: a vacuum channel with ports on either end, a groove for an O-ring, threaded holes to attach the PCB, and a recess under the electrode grid. For example, FIG. 35A is a top view and FIG. 35B is a cross sectional view of one example of a vacuum chuck 3500. Section A-A highlights the vacuum channel and its accompanying ports. The pneumatic flow 3505 follows the path of the arrows shown in FIG. 35B: first pulling through at least one inlet port, then flowing through the channel 3507, and finally flowing out of the side port 3509. A portion of the chuck (over which the seating surface formed by the PCB will be placed) is surrounded by an O-ring 3503.

Figure 37:
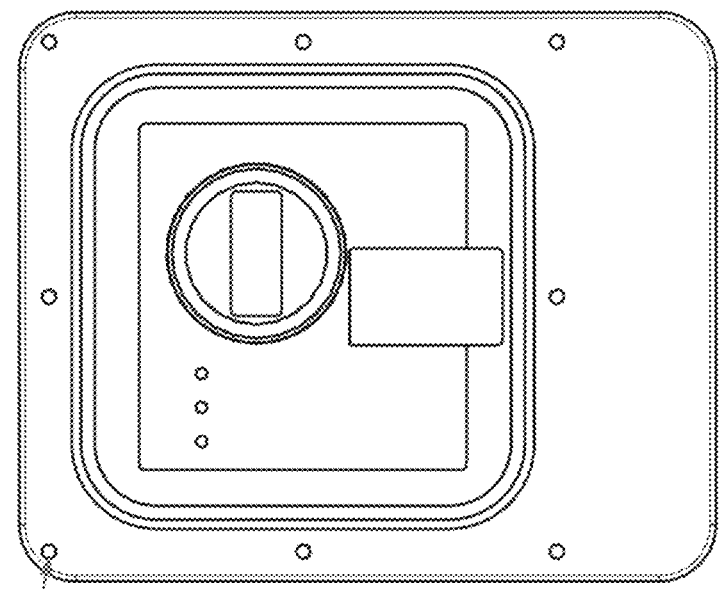
FIG. 37 shows a top view of a chuck similar to the one shown in FIGS. 35A-35B.
Figure 36:
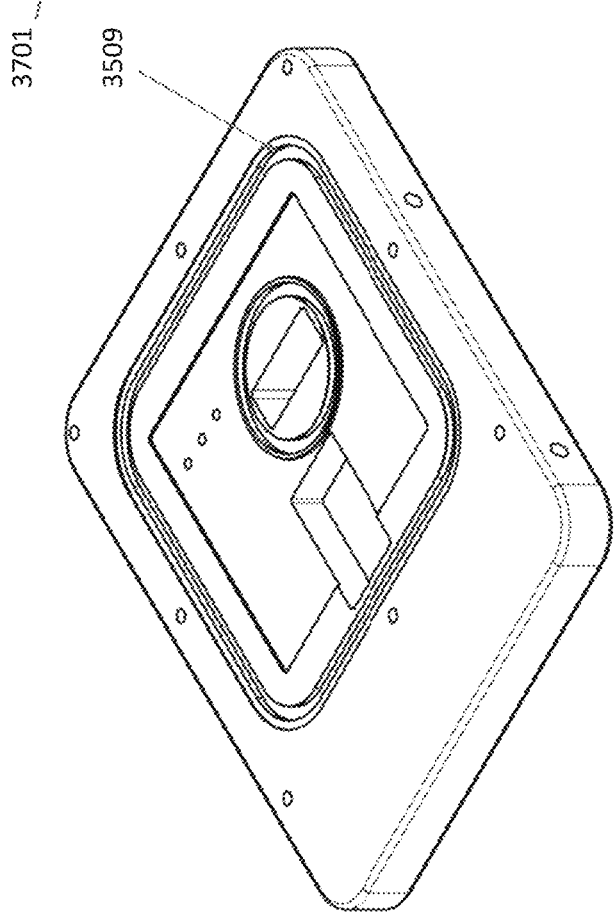
FIG. 36 shows an isometric view of the chuck shown in FIGS. 35A-35B.

For example, FIG. 36 shows an isometric view of the chuck shown in FIGS. 35A-35B. The groove 3509 (that may be designed using, e.g., a Parker O-Ring design standard) is configured to fit an O-ring. Once in place, and with the chuck fastened to the PCB, the O-ring may pneumatically isolate the vacuum directly under the electrode grid. The seating surface may be formed by securing a PCB having the electrodes (not shown) to the chuck. For example, as shown in FIG. 37, the chuck may include multiple threaded holes 3701 for attaching the seating surface (e.g., PCB). FIG. 37 shows a top view of a chuck similar to the one shown in FIGS. 35A-35B. In some variations the chuck includes a minimum of four threaded holes (eight shown in FIG. 37), each equidistant apart in at least the X or Y directions, and centered about the origin of the chuck. The screw holes may serve a dual-purpose: first to fasten the PCB to the chuck such that the interface of the two components is planar, second to apply a downward force in the Z direction about the perimeter of the O-ring, effectively creating a pneumatic seal.

FIG. 38A shows a top view of a chuck similar to the one shown in FIGS. 35A-35B and FIG. 38B shows a cross sectional and zoomed-in view of this chuck. FIG. 35B shows an enlarged image of section A-A, showing the boundaries of the recess 3801, 3803 (along the X axis) that may create space between the PCB and the surface of the chuck, but only in the isolated area where the vacuum is active. This space may optimize the pneumatic flow of the vacuum as described in the herein. In FIG. 38, an opening 3805 for a magnet is present on the upper region and may include sufficient space for the magnet to be moved to/from the cartridge (e.g., by moving up/down within the space, or in some variations laterally). The region around the magnet opening may include a gasket or sealing ring (e.g., O-ring) 3809 for isolating the magnet region from the vacuum region, similar to the outer O-ring.

As mentioned, any of the apparatuses described herein may include an integrated magnet. In FIGS. 35A-39, a recessed region 3905 may be used to hold an integrated magnet that may be moved up/down by the system to engage/disengage a magnetic field. Alternatively in some variations the magnet may be stationary, but may be toggled (on/off, and/or changing the intensity) by the reader's controller.

Thus, the vacuum chuck may include an integrated magnet and may therefore include one or both of: a cut-out that allows a magnet to travel through the chuck, and second an O-ring groove that isolates the magnet zone from the pneumatic flow of the vacuum. FIG. 39 shows a bottom view of a chuck similar to that shown in FIGS. 35A-35B. A throughcut region 3905 is shown, and can be sized to fit the desired magnet, and allows for uninterrupted travel of an actuatable magnet. A magnet can pass through the cut-out, landing directly below the PCB when engaged, or can be disengaged through the cut-out when not in use.

Figure 40:
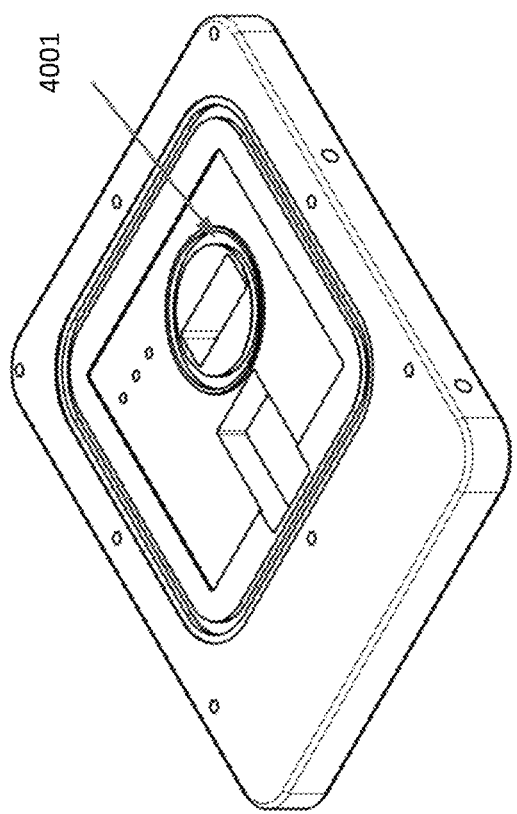
FIG. 40 shows an isometric view of a chuck similar to that shown in FIG. 35A.

FIG. 40 shows an isometric view of a chuck similar to that shown in FIG. 35A. A groove 4001 may fit an O-ring. Once in place, and with the chuck fastened to the PCB, the O-ring may pneumatically isolate the magnet cut-out zone from the rest of the vacuum chuck, specifically ensuring the vacuum is not compromised by the magnet cut-out.

Figure 41A:
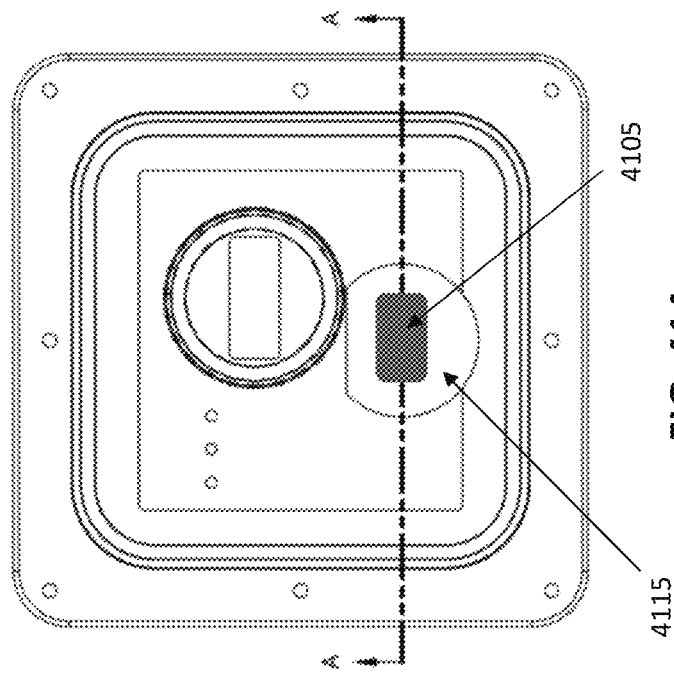
FIG. 41A shows one example of a heat dissipation system that may be included in any of the reader devices described herein.
Figure 41B:
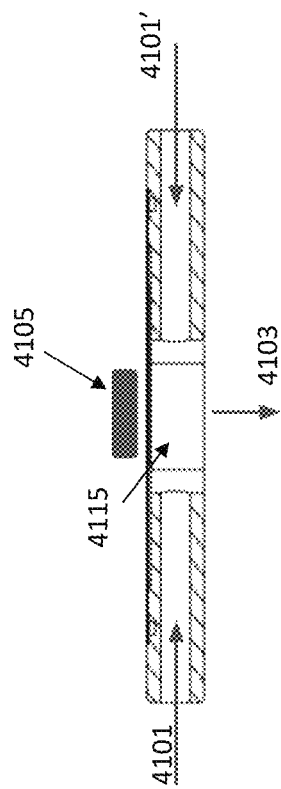
FIG. 41B is a sectional view through the chuck of FIG. 41A.

FIGS. 41A and 41B illustrate top and side sectional views, respectively, of a chuck similar to that shown in FIGS. 35A and 35B, but including a gap 4115 for thermally accessing a heating component, such as a heater (e.g., resistive heater) 4105. The heater 4105 is shown above the cavity 4115 in the chuck so that it may be easily thermally regulated (e.g., cooled). The resistive heater may be in the PCB (not shown in FIGS. 41A and 41B).

For example, FIG. 41A shows one example of a heat dissipation system that may be included in any of the reader devices described herein. This heat dissipation system may be built such that any thermal load created by a heater 4105 in the reader (e.g., in the PCB) may be dissipated properly and effectively. A first heat dissipation configuration may be built to dissipate heat generated by a heater embedded in the PCB and is described below as a heat dissipation of an embedded heater. The second heat dissipation design may be built to dissipate heat generated by a thermoelectric cooler embedded in the vacuum chuck and describe below as Heat Dissipation of Thermoelectric cooler. Both heat dissipation designs may employ unique features in the vacuum chuck, as well as accompanying components to dissipate the heat. Both designs can be used together or in the assembly, or independently.

For example, the heat dissipation of the embedded heater in the vacuum chuck may be configured as a vented chamber. In FIG. 41A, the top view of the chuck shows the heat dissipation aspects of the chuck; FIG. 41B shows a pair of air channels 4101 that feed into a cooling chamber 4103 that may be part of or below (or otherwise connected to) the region where the heater is positioned. In FIG. 41B, the flow path of the multiple air elements (channels 4101, 4101') acting in this system are shown. The air drawn in 4101 may be warmed by the heat, including residual heat, from the heater in the PCB (e.g., seating region, not shown), and may flow over the through-cut 4115 region in the vacuum chuck, which may be covered or partially covered, or open to the heater in the PCB (or to one or more thermal vias in thermal communication with the heater). Section A-A (shown in FIG. 41B) shows a pneumatic flow of two air elements, warm air 4105 and ambient air when a fan, fastened flush against the chuck and centered about the through-cut 4115, is turned on. The fan (not shown) may push the warm air generated by the heater out of the through-cut of the vacuum chuck. Simultaneously, the fan may pull ambient air into the chuck and through-cut via two channels in the chuck 4101, 4101'. The system can continuously or intermittently cycle ambient air into and warm air out of the chuck, effectively dissipating any heat generated by the PCB heater.

Also described herein are systems for heat dissipation of an embedded heater. For example, the assembly shown in FIG. 42 may be configured to include both the chuck 4203 and a fan 4205. The pneumatic flow described in the previous above may be controlled by a fan 4205 fastened to the bottom of the chuck 42031. FIG. 42 shows a front view of the chuck 4203 and the fan 4205. The first arrow 4221 points to the vacuum chuck (top structure) and the second set of arrows 4201, 4201' depict the airflow path. FIG. 43 shows an example of an arrangement of the chuck 4303, a fan 4307, a PCB 4305 forming a seating surface (e.g., including the array of electrodes, not shown) and a cartridge 4311. The cartridge may be held down by the vacuum through the openings (e.g., in some of the electrodes).

FIG. 44 shows an example of a heat dissipation system for regulating the temperature of a thermoelectric cooler through a vacuum chuck. In FIG. 45, an isometric view of a chuck (similar to that shown in FIG. 35A) is shown in FIG. 45B. The chuck shown includes a recess 4509 designed such that a thermoelectric cooler (TEC) can slot into it.

FIGS. 45A-45B show top and sectional views, respectively, of a chuck similar to that shown in FIG. 35A. The section (though A-A) shown in FIG. 45B highlights the thermal path of the heat generated by a thermoelectric cooling element 4525. The rectangle 4525 represents the TEC, and the arrows within the chuck depict the heat spreading throughout the chuck. The apparatus may include one or more heat sink of a desired size, that may be fastened to the bottom of the chuck and below the TEC, then absorbs the heat. Lastly, two fans, fastened to either side of the heat sink (shown in FIG. 46), may act in unison to push the hot air away from the entire system and funnel ambient air into the system.

Figure 48:
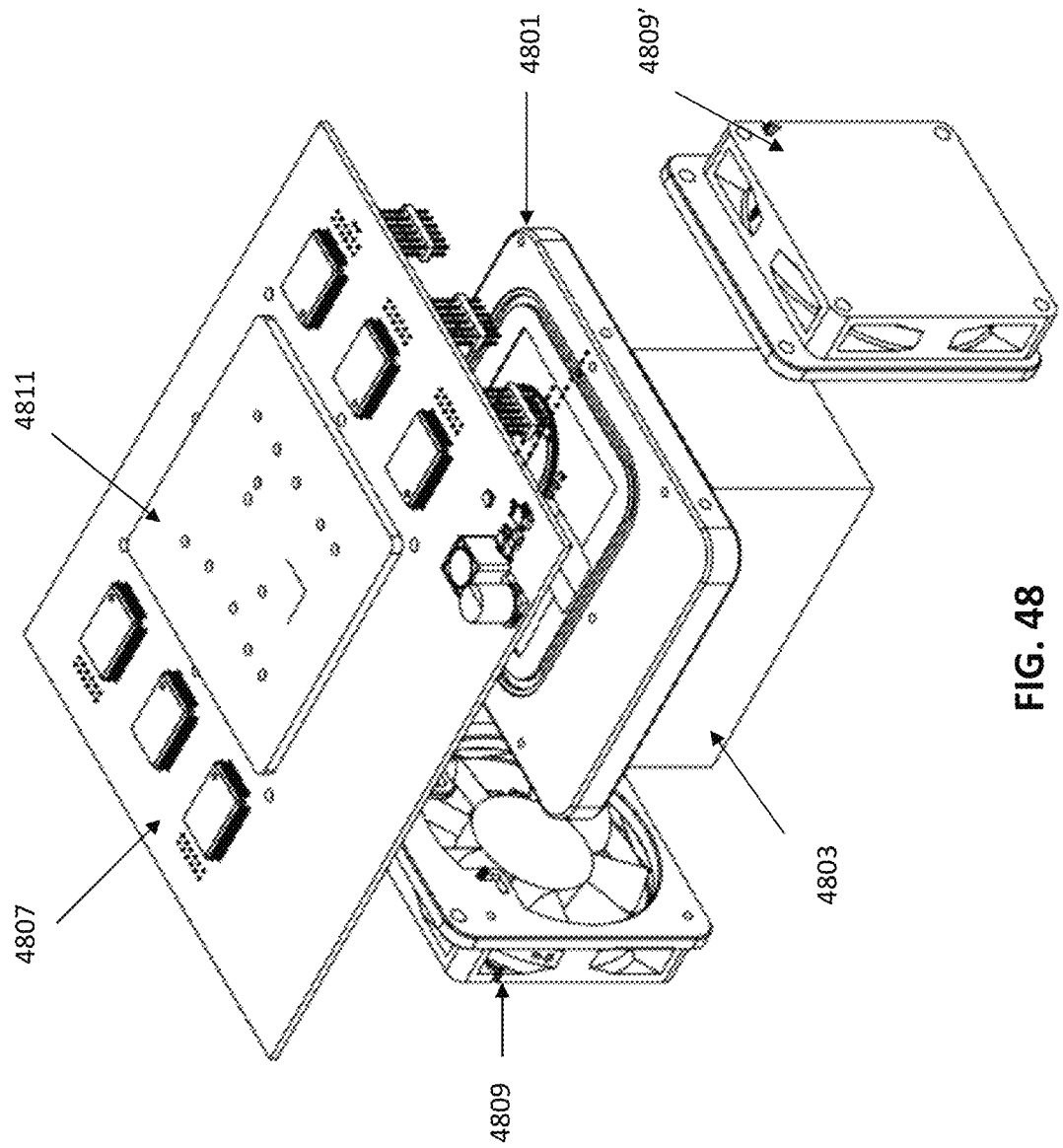
FIG. 48 illustrates one example of an assembly for a reader including a PCB with an array of electrodes for applying DMF to a cartridge (not shown), a vacuum block for holding the cartridge bottom onto the PCB and a thermal regulator sub-system including a heat sink/heat block and a pair of cooling fans.
Figure 49B:
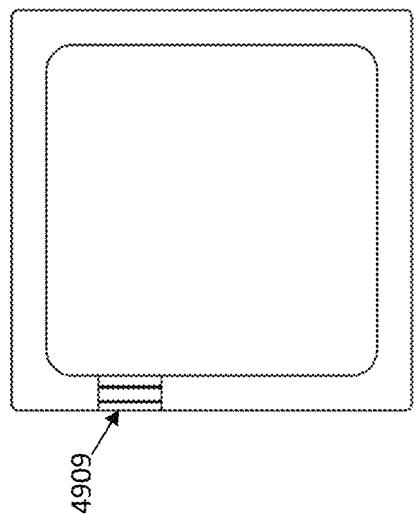
FIGS. 49A and 49B illustrate a tensioning frame and a film frame, respectively, for securing and holding smooth a film (e.g., dielectric film) that may form the bottom of a cartridge.
Figure 49D:
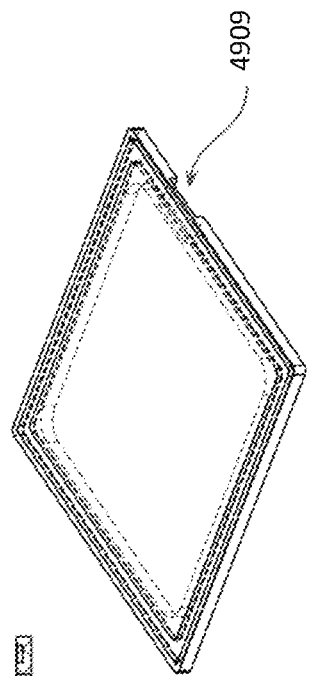
FIG. 49D is a perspective view of an assembled tensioning frame.
Figure 49A:
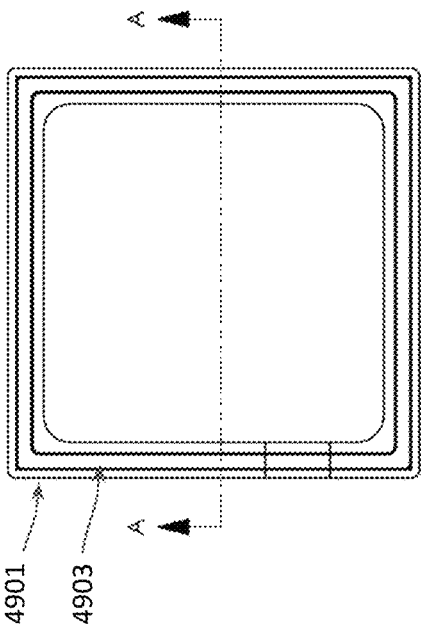
Figure 49C:
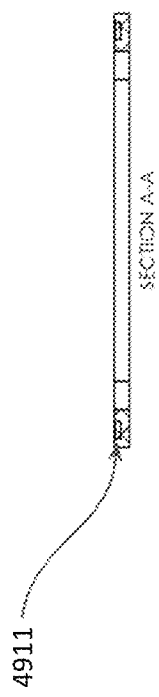
FIG. 49C is a side view of an assembled tensioning frame.

FIGS. 47A-47C illustrate assembly of one or more devices configured for heat dissipation of a thermoelectric cooler. For example, FIG. 46 shows the front view of a chuck. The arrows 4613 in FIG. 46 directed downwards show a thermal path of the heat in the chuck as described in FIG. 45. The arrows 4611, 4611' depict the flow path of air being pushed into the heatsink by a fan as well as the path of air being pulled out of the heatsink by a fan. The fans act in the same direction, simultaneously. FIGS. 47A-47C show an assembly process as well as multiple components that may be included in this apparatus and method of using it. For example, FIG. 47A shows a chuck 4701, FIG. 47B shows a chuck 4701 plus a heatsink 4703, and FIG. 47C shows the chuck 4701, plus the heatsink 4703, plus two fans 4709, 4709'. FIG. 48 depicts an exploded view of a partial arrangement of a reader assembly, including the assembly in FIG. 47 (e.g., chuck 4801, heat sink 4803, fans 4809, 4809') as well as the PCB 4807 including the driving electrodes and a heater (not visible); in addition a cartridge 4811 is attached via vacuum to the seating surface of the PCB.

Action Zones

Any of the apparatuses described herein may include one or more action zones that strategically position the different possible actions that a droplet can be subjected to for protocol execution. The goal of the plexing strategy is to adapt to different laboratory requirements in a more flexible, modular way. Different stages of the protocol to be executed may be grouped strategically into action zones to allow the protocol designer define abstract targets on the board. The action zones may be fixed regions under or over the electrode board used for reactions (i.e. mixing, merging, heating, cooling, thermocycling, magnet capture, waste, optical detection, etc.).

Figure 55:
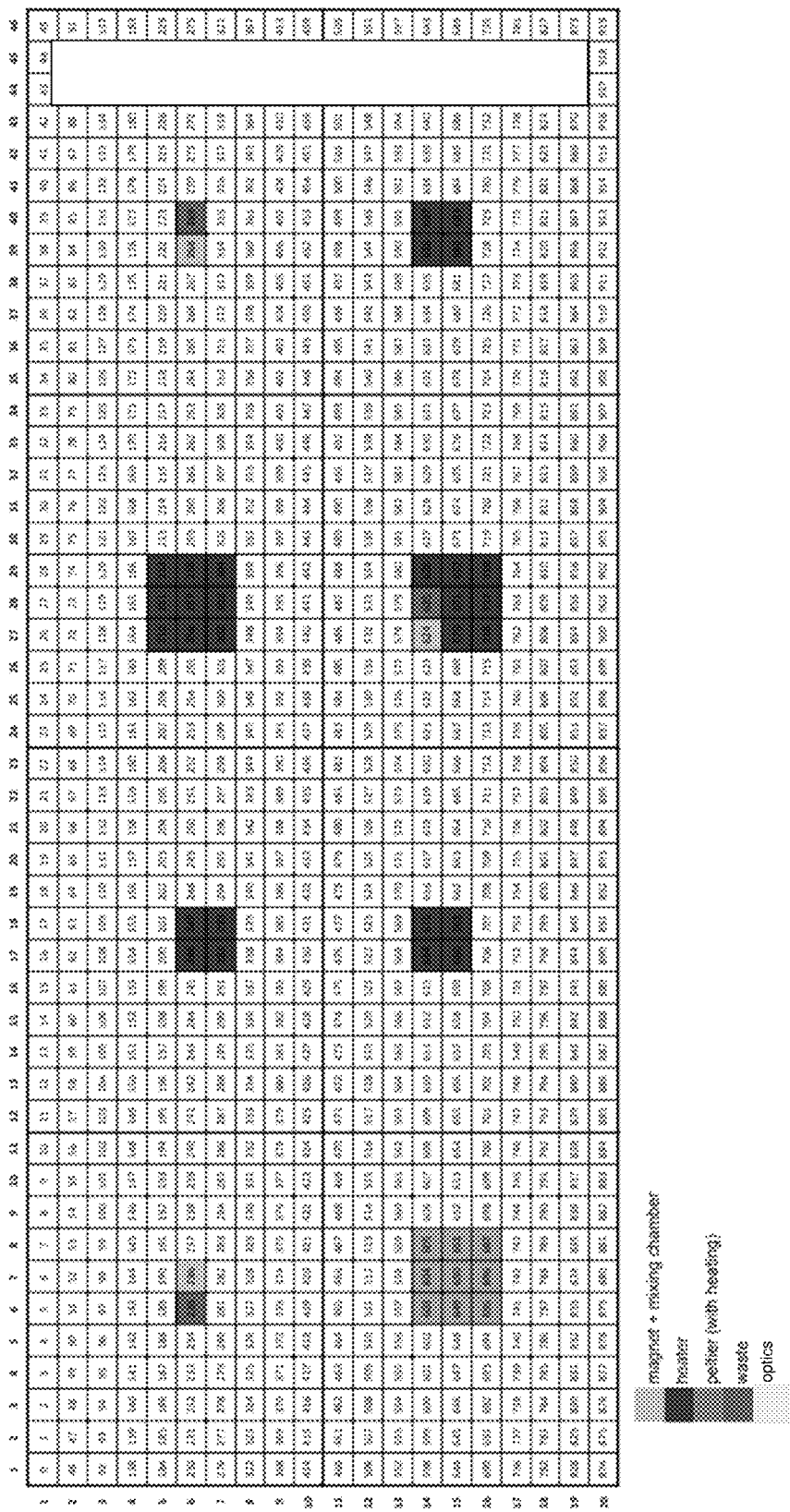
FIG. 55 shows an example of an electrode grid setup with independent action zones.

FIG. 55 shows an example of an electrode grid setup with independent action zones for either magnet capture, a heater which can be isothermal or thermocycler, a peltier which is an active cooling zone down to 4° C., a waste connection to the top plate through a channel and into a waste chamber, a mix connection to the top plate through a channel and optical detection. Thus, FIG. 55 shows an electrode grid with distinct action zones In order to better adapt to different user needs and laboratory space, independent single modules, each with its own power, environmentals, internal computer and connection to console unit for user interface may be multiplexed together. Additionally, a console unit for user interface can be integrated to control the different modules as well as other laboratory required functions such as scan the sample ID as well as the cartridge ID and integrate that information to the local laboratory or sample management system. Connection to console unit can be wireless or by cable. FIG. 56 schematically shows four independently controlled 1-plex modules with a console unit.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A cartridge for use with a digital microfluidics (DMF) reader apparatus, the cartridge having a bottom and a top, the cartridge comprising:
   a flexible sheet of dielectric material having a first side and a second side, the first side forming an exposed bottom outer surface of the bottom of the cartridge and configured to removably contact the DMF reader apparatus, wherein at least the second side of the sheet of dielectric material comprises a first hydrophobic layer;
   a tensioning frame applying tension to hold the flexible sheet of dielectric material flat over the exposed bottom outer surface of the bottom of the cartridge so that the flexible sheet of dielectric material flexes under a vacuum of at least 50 kPa applied by the DMF reader apparatus to secure the flexible sheet of dielectric material against a plurality of drive electrodes on the DMF reader apparatus;
   a top plate having a first side and a second side and a thickness therebetween;
   a ground electrode on the first side of the top plate;
   a second hydrophobic layer on the first side of the top plate covering the ground electrode; and
   an air gap separating the first hydrophobic layer and the second hydrophobic layer, wherein the air gap comprises a separation of greater than 280 micrometers.

2. The cartridge of claim 1, wherein the ground electrode comprises a grid pattern forming a plurality of open cells.

3. The cartridge of claim 2, wherein the grid pattern of the ground electrode is formed of a non-transparent material.

4. The cartridge of claim 1, wherein the ground electrode is formed of a conductive ink.

5. The cartridge of claim 1, wherein the ground electrode is formed of silver nanoparticles.

6. The cartridge of claim 2, wherein the minimum width of the grid pattern between the open cells is greater than 50 micrometers.

7. The cartridge of claim 2, wherein the open cells of the plurality of open cells comprise a quadrilateral shape or an elliptical shape.

8. The cartridge of claim 1, wherein the ground electrode extends over more than 50% of the first side of the top plate.

9. The cartridge of claim 1, wherein the top plate comprises a plurality of cavities within the thickness of the top plate, further wherein the cavities are filed with an insulating material having a low thermal mass and low thermal conductivity.

10. The cartridge of claim 9, wherein the insulating material comprises air.

11. The cartridge of claim 1, further comprising a microfluidics channel formed on or in the second side of the top plate, wherein the microfluidics channel extends along the second side of the top plate and at least one opening between the microfluidics channel and the air gap.

12. The cartridge of claim 1, wherein the top plate comprises polycarbonate and/or acrylic.

13. The cartridge of claim 1, wherein the sheet of dielectric is less than 30 microns thick.

14. The cartridge of claim 1, wherein the first hydrophobic layer of the second side of the dielectric material comprises a hydrophobic coating.

15. The cartridge of claim 1, wherein the air gap comprises a separation of greater than 400 micrometers.

16. The cartridge of claim 1, wherein the cartridge does not include a drive electrode on the flexible sheet of dielectric material.

17. A cartridge for use with a digital microfluidics (DMF) reader apparatus, the cartridge having a bottom and a top, the cartridge comprising:
   a flexible sheet of dielectric material having a first side and a second side, the first side forming an exposed bottom outer surface of the bottom of the cartridge, configured to removably contact the DMF reader apparatus;
   a tensioning frame applying tension to hold the flexible sheet of dielectric material flat over the exposed bottom outer surface of the bottom of the cartridge so that the flexible sheet of dielectric material flexes under a vacuum of at least 50 kPa applied by the DMF reader apparatus to secure the flexible sheet of dielectric material against a plurality of drive electrodes on the DMF reader apparatus;
   a first hydrophobic layer on the second side of the sheet of dielectric material;
   a top plate having a first side and a second side and a thickness therebetween;
   a ground electrode on the first side of the top plate;
   a second hydrophobic layer on the first side of the top plate covering the ground electrode;
   an air gap separating the first hydrophobic layer and the second hydrophobic layer;
   a microfluidics channel formed in or on the second side of the top plate, wherein the microfluidics channel extends along the second side of the top plate;
   an opening between the microfluidics channel and the air gap; and
   a cover covering the microfluidics channel, wherein the cover includes one or more access ports for accessing the microfluidics channel.

18. The cartridge of claim 17, wherein the microfluidics channel is configured to contain more than 1 ml of fluid within the microfluidics channel.

19. The cartridge of claim 17 wherein the air gap comprises a separation of greater than 500 micrometers.

20. The cartridge of claim 17, wherein the microfluidics channel comprises a first microfluidics channel and the opening between the microfluidics channel and the air gap comprises a first opening, further comprising a second microfluidics channel formed in the second side of the top plate, wherein the second microfluidics channel extends along the second side of the top plate, and a second opening between the second microfluidics channel and the air gap, wherein the first and second openings are adjacent to each other.

21. The cartridge of claim 20, wherein the first and second openings are within about 2 cm of each other.

22. The cartridge of claim 17, further comprising a window from the top of the cartridge to the air gap through which the air gap is visible.

23. The cartridge of claim 22, wherein the window forms between 2 and 50% of the top of the cartridge.

24. The cartridge of claim 17, wherein the bottom of the cartridge is formed by the first side of the sheet of dielectric material.

25. The cartridge of claim 17, further comprising a plurality of openings into the air gap from the top of the cartridge.

26. The cartridge of claim 17, wherein the top plate comprises polycarbonate and/or acrylic.

27. The cartridge of claim 17, further comprising one or more reagent reservoirs on the second side of the top plate.

28. The cartridge of claim 17, further comprising one or more freeze-dried reagent reservoirs on the second side of the top plate.

29. The cartridge of claim 17, wherein the sheet of dielectric material is flexible.

30. The cartridge of claim 17, wherein the top plate comprises a plurality of cavities within the thickness of the top plate, further wherein the cavities are filed with an insulating material having a low thermal mass and low thermal conductivity.

31. A cartridge for use with a digital microfluidics (DMF) reader apparatus, the cartridge having a bottom and a top, the cartridge comprising:
   a flexible sheet of dielectric material having a first side and a second side, the first side forming an exposed bottom outer surface of the bottom of the cartridge and configured to removably contact the DMF reader apparatus;
   a tensioning frame applying tension to hold the flexible sheet of dielectric material flat over the exposed bottom outer surface of the bottom of the cartridge so that the flexible sheet may be secured by vacuum to the DMF reader apparatus;
   a top plate having a first side and a second side;
   a ground electrode on the first side of the top plate;
   a second hydrophobic layer covering the ground electrode; and
   an air gap separating a first hydrophobic layer and the second hydrophobic layer, wherein the cartridge does not include a drive electrode on the flexible sheet of dielectric.

* * * * *